(12) United States Patent
Xu et al.

(10) Patent No.: US 9,745,320 B2
(45) Date of Patent: Aug. 29, 2017

(54) FIVE-AND-SIX-MEMBERED HETEROCYCLIC COMPOUND, AND PREPARATION METHOD, PHARMACEUTICAL COMPOSITION AND USE THEREOF

(71) Applicant: SHANGHAI CHEMEXPLORER CO., LTD., Shanghai (CN)

(72) Inventors: Zusheng Xu, Shanghai (CN); Nong Zhang, Shanghai (CN); Qingrui Sun, Shanghai (CN); Tinghan Wang, Shanghai (CN)

(73) Assignee: GUANGZHOU MAXINOVEL PHARMACEUTICALS CO., LTD., Guangzhou (CN)

( * ) Notice: Subject to any disclaimer, the term of this patent is extended or adjusted under 35 U.S.C. 154(b) by 0 days.

(21) Appl. No.: 14/761,772

(22) PCT Filed: Jan. 17, 2014

(86) PCT No.: PCT/CN2014/070778
§ 371 (c)(1),
(2) Date: Jul. 17, 2015

(87) PCT Pub. No.: WO2014/111037
PCT Pub. Date: Jul. 24, 2014

(65) Prior Publication Data
US 2015/0336982 A1 Nov. 26, 2015

(30) Foreign Application Priority Data
Jan. 18, 2013 (CN) .......................... 2013 1 0019856

(51) Int. Cl.
*C07D 495/04* (2006.01)
*C07D 491/048* (2006.01)
*A61K 31/519* (2006.01)
*A61P 35/00* (2006.01)
*C07D 487/04* (2006.01)

(52) U.S. Cl.
CPC .......... *C07D 495/04* (2013.01); *A61K 31/519* (2013.01); *C07D 487/04* (2013.01); *C07D 491/048* (2013.01)

(58) Field of Classification Search
CPC .. C07D 487/04; C07D 491/04; C07D 495/04; C07D 498/04; C07D 513/04; A61K 31/519
USPC ................. 544/253, 254, 280, 25; 514/258.1
See application file for complete search history.

(56) References Cited

U.S. PATENT DOCUMENTS 7,384,949 B2 * 6/2008 Gillespie .............. C07D 491/04
514/260.1
2007/0219186 A1 9/2007 Gopalsamy et al.

2010/0113420 A1 5/2010 Salas Solana et al.
2010/0204221 A1 * 8/2010 Vankayalapati ..... C07D 495/04
514/234.2
2011/0160185 A9 6/2011 Salas Solana et al.
2012/0309773 A1 12/2012 Babu et al.

FOREIGN PATENT DOCUMENTS

| CN | 101405289 A | 4/2009 |
|---|---|---|
| CN | 101679440 A | 3/2010 |
| CN | 102307875 A | 1/2012 |
| CN | 102762571 A | 10/2012 |
| CN | 103936757 A | 7/2014 |

OTHER PUBLICATIONS

Meyer et al. Clin Cancer Res. Apr. 15, 2014; 20(8): 2051-2059.*
Verstovsek S., American Society of Hematology, 636-642, 2009.*
Cornejo et al., Int J Biochem Cell Biol. 41 (12): 2376-2379, 2009.*
Mass, R. D., Int. J. Radiation Oncology Bio. Phys. vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition, vol. 1, 1004-1010, 1996.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
International Search Report dated Apr. 28, 2014 issued in corresponding PCT/CN2014/070778 application (pp. 1-2).
English Translation Abstract of CN 101405289 published Apr. 8, 2009.
English Translation Abstract of CN 101679440 published Mar. 24, 2010.
English Translation Abstract of CN 102307875 published Jan. 4, 2012.

(Continued)

*Primary Examiner* — Venkataraman Balasubramanian
(74) *Attorney, Agent, or Firm* — Millen White Zelano and Branigan, PC; John Sopp; Anthony Zelano

(57) ABSTRACT

A five-and-six-membered heterocyclic compound as represented by general formula I, pharmaceutically acceptable salt, metabolite, metabolic precursors or drug precursors thereof, preparation method, pharmaceutical composition, and use thereof; the five-and-six-membered heterocyclic compound has activity as a Janus kinase (JAK) inhibitor, and can be used to prepare drugs for treating diseases caused by the abnormal activity of kinase, such as cell proliferation diseases like cancer.

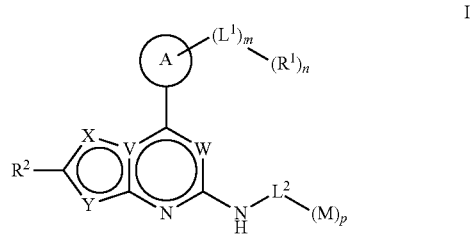

19 Claims, No Drawings

(56) References Cited

OTHER PUBLICATIONS

English Translation Abstract of CN 102762571 published Oct. 31, 2012.
Written Opinion dated Apr. 28, 2014 issued in corresponding PCT/CN2014/070778 application (pp. 1-12).
D.S. Aaronson et al., "A Road Map for Those Who Don't Know JAK-STAT", Science, vol. 296 (May 31, 2002) pp. 1653-1655.
J.J. O'Shea et al., "A New Modality for Immunosuppression: Targeting the JAK/STAT Pathway", Nature Reviews Drug Discovery, vol. 3 (Jul. 2004) pp. 555-564.
J.N. Ihle, "Cytokine Receptor Signalling", Nature, vol. 377 (Oct. 19, 1995) pp. 591-594.
T. Kisseleva et al., "Signaling Through the JAK/STAT Pathway, Recent Advances and Future Challenges", Gene, vol. 285 (2002) pp. 1-24.
J.M. Kremer et al., "The Safety and Efficacy of a JAK Inhibitor in Patients With Active Rheumatoid Arthritis", Arthritis & Rheumatism, vol. 60, No. 7 (Jul. 2009) pp. 1895-1905.
R. Buettner et al., "Activated STAT Signaling in Human Tumors Provides Novel Molecular Targets for Therapeutic Intervention", Clinical Cancer Research, vol. 8 (2002) pp. 945-954.
G. Niu et al., "Constitutive Stat3 Activity Up-Regulates VEGF Expression and Tumor Angiogenesis", Oncogene, vol. 21 (2002) pp. 2000-2008.
L.B. Mora et al., "Constitutive Activation of Stat3 in Human Prostate Tumors and Cell Lines: Direct Inhibition of Stat3 Signaling Induces Apoptosis of Prostate Cancer Cells", The Journal of Cancer Research, vol. 62 (2002) pp. 6659-6666.
J. K. Riley et al., "Interleukin-10 Receptor Signaling Through the JAK-STAT Pathway", The Journal of Biological Chemistry, vol. 274, No. 23 (1999) pp. 16513-16521.

\* cited by examiner

FIVE-AND-SIX-MEMBERED HETEROCYCLIC COMPOUND, AND PREPARATION METHOD, PHARMACEUTICAL COMPOSITION AND USE THEREOF

CROSS REFERENCE TO RELATED APPLICATION

The present application is the U.S. national stage application of International Application PCT/CN2014/070778, filed Jan. 17, 2014, which international application was published on Jul. 24, 2014, as International Publication WO2014/111037. The International Application claims priority of Chinese Patent Application 201310019856.9, filed Jan. 18, 2013, the contents of which are incorporated herein by reference in their entireties.

FIELD OF INVENTION

The present invention relates to a five-and-six-membered heterocyclic compound, and preparation method, pharmaceutical composition, and use thereof.

PRIOR ARTS

JAK-STAT (Janus kinase-signal transducer and activator of transcription) signaling pathway is a signal transduction pathway which is found in recent years caused by cytokines, and is involved in many important biological processes such as cell proliferation, differentiation, apoptosis and immune regulation (Aaronson, D. S. et al. *Science* 2002, 296, 1653-1655; O'Shea, J. J. et al. *Nat. Rev. Drug Discovery* 2004, 3, 555-564). Compared with other signaling pathway, this pathway transfer process is relatively simple, which is mainly composed of three components: tyrosine kinase receptor, tyrosine kinase JAK and transcription factor STAT.

There are corresponding receptors of cytokines (such as interferon IFN and interleukin (IL) and growth factors (such as epidermal growth factor EGF, platelet-derived growth factor PDGF etc.) on the cell membrane. The common feature of these receptors is that the receptor itself does not have kinase activity, but the intracellular segment has a binding site for tyrosine kinase JAK. After the receptor and ligand are combined, the tyrosine residues of the target proteins are phosphorylated by the JAK activation to achieve the signal from the extracellular to the intracellular delivery. The JAK family is a non receptor tyrosine kinase (PTK), and four JAK family kinases, including JAK1, JAK2, JAK3 and TYK2 have been so far identified. There are 7 JAK domains (JAK homology domain JH) in the structure, wherein JH1 domain is a kinase region and JH2 domain is a "pseudo" kinase region, JH6 and JH7 are receptor regions.

STAT in signal transduction and transcriptional activation play a key role. STAT is a DNA binding protein, is an important JAK substrate. There are seven members: STAT1, STAT2, STAT3, STAT4, STAT5a, STAT5b, and STAT6. The structure of STAT protein can be divided into several functional regions: N-terminal domain, helix domain, DNA binding domain, linker region, SH3 domain, SH2 domain and C-terminal transcriptional activator region. Among them, the most conservative and functionally important segment of the sequence is the SH2 domain, which has the same core sequence "GTFLLRFSS", as the SH2 domain of the Src tyrosine kinase.

The transmission of JAK-STAT signaling pathway is relatively simple. Signal transfer process is as follows: binding of cytokine and its receptor induces dimerization of the receptor molecule, which makes the JAK kinase coupling to the receptor gather near to each other and be activated by the interaction of tyrosine phosphorylation. After the activation of JAK, phosphorylation of tyrosine residues on the receptor is catalysed to occur, then these phosphorylated tyrosine sites and the surrounding amino acid sequences form "docking sites", at the same time, STAT proteins which contains SH2 domain are recruited to the "docking sites". Finally, JAK kinase catalyses the STAT proteins combined with the receptor to perform the phosphorylation, activated STAT proteins with a form of dimer enter the nucleus to combine with target genes and regulate the gene transcription (Ihie, J. J. *Nature* 1995, 377, 591-594). It is worth mentioning that a kind of JAK kinase may be involved in the signal transduction process of many kinds of cytokines, a kind of cytokine signaling pathways can also activate many JAK kinases, but cytokines, has certain selectivity on the activated STAT molecules. For example, IL-4 activates STAT6, while IL-12 activates specifically STAT4.

The JAK-STAT pathway exists widely in all tissues of histiocyte, it plays especially an important role in differentiation, proliferation, anti-infection of lymphoid, and it participates in a variety of inflammatory cytokines interactions and signal transduction (Kiesseleva T. et al. *J. Gene*, 2002, 285, 1-24). The abnormal activation of the pathway is closely related with a variety of diseases, searching and screening JAK inhibitor can contribute to in-depth study of the regulation mechanism of the JAK-STAT, so as to provide new drugs and methods for prevention and treatment of related diseases. Interleukin IL-6, IL-15, interferon (IFN), granulocyte macrophage set colony stimulating factor (GM-CSF) and other expression levels of synovial tissue in rheumatoid arthritis are significantly increased. They play an important role in the occurrence and development of diseases, and the cytokines play an important role through the JAK-STAT signal transduction pathway. Therefore, the inhibition of the JAK-STAT pathway on purpose can improve the pathophysiological process of rheumatoid arthritis (Joel M. K. et al. *Arthritis Rheum.* 2009, 60, 1859-1905).

The occurrence, growth, invasion and metastasis of tumor are related to the signal transduction pathway of JAK-STAT. The activation of STATs in normal signal transduction is fast and transient, and the STATs persistent activation is closely related to the malignant transformation of cells (Buettner R. et al. *Clin. Cancer Res.* 2002, 8(4), 945-954). STAT3 is the key position of EGFR, IL-6/JAK, Src and other signal pathways of carcinogenic tyrosine kinase, which is activated in a variety of tumor cells and tissues, such as breast cancer, ovarian cancer, head and neck squamous cell carcinoma, prostate cancer, malignant melanoma, multiple myeloma, lymphoma, brain tumors, non small cell lung cancer and leukemia etc (Niu G. et al. *Oncogene* 2002, 21(13), 2000-2008). JAK-STAT pathway inhibitors belong to PTK inhibitors, and this enzyme is a member of the oncogene proteins and family members, and plays an important role in normal and abnormal cell proliferation. The occurrence and growth of tumor can't be separated from PTK, therefore, JAK-STAT pathway inhibitor can inhibit tumor growth by inhibiting PTK, and has obvious anti-tumor effect (Mora L. B. et al. *J. Cancer Res.* 2002, 62(22), 6659-6666).

Inflammatory bowel disease is closely related to autoimmunity. JAK-STAT pathway is involved in a variety of important pathogenic inflammatory and anti-inflammatory cytokine signal transduction and regulation process, especially closely related to IFN-γ, IL-1, IL-6, IL-10 and IL-4. And inflammatory mediators and cytokines can also induce the activation of multiple signal pathways, so that directly or indirectly result in the expression of inflammatory mediators, which leads to damage to intestinal mucosa, but many intricate signaling mechanisms still remains to be elucidated. In theory, inhibition of excessive activation of the JAK-STAT signal transduction pathway can inhibit the expression of many inflammatory cytokines from upstream, so as to achieve the prevention and treatment of inflammation enteropathy (Riley, J. K. et al. *J. Biol. Chem.* 1999, 274, 16513-16521).

In addition, the latest studies show that rejection in organ transplantation, psoriasis, tissue and organ fibrosis, bronchial asthma, ischemic cardiomyopathy, congestive heart failure, myocardial infarction, blood system diseases and diseases of the immune system are closely related with the JAK-STAT signal transduction pathway, this signaling pathway is not only important for the maintenance of normal physiological function of the cells, but also has important regulatory effect on the occurrence and development of the diseases.

CONTENT OF THE PRESENT INVENTION

The technical problem to be solved in the present invention is to provide a five-and-six-membered heterocyclic compound represented by formula I, which is completely different from prior arts, and a pharmaceutically acceptable salt, a metabolite, a metabolic precursor or a prodrug thereof. The five-and-six-membered heterocyclic compound represented by formula I in the present invention is an efficient Janus kinase (JAK) inhibitor which can be used for preventing or treating cell proliferation diseases such as cancer, infections, inflammation and autoimmune diseases.

The present invention provides a five-and-six-membered heterocyclic compound represented by formula I, a pharmaceutically acceptable salt, a metabolite, a metabolic precursor or a prodrug thereof.

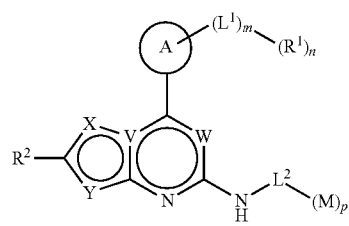

I wherein:

V is N or C;

W is N or $CR^3$;

X is O, S, N or $CR^4$;

Y is S or $CR^5$;

Ring A is an aryl (preferably a $C_{5-10}$ aryl, more preferably a phenyl (such as

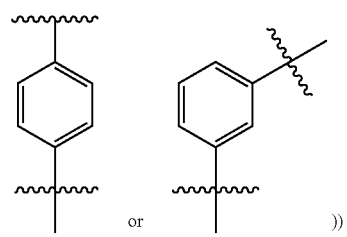 [SMILES: *c1ccc(*)cc1 ; *c1cccc(*)c1]

or a heteroaryl (preferably a $C_{2-5}$ heteroaryl containing 1 to 3 nitrogen atoms more preferably a pyrazole (such as

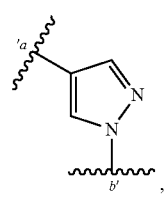 [SMILES: *c1cnn(*)c1]

a' is connected with a segment

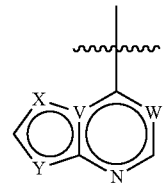

in formula I, b' is connected with $L^1$ in formula I), an imidazole, a pyrrole, a pyridine, a pyrimidine, a triazole, a azine a tetrazole, a pyridazine or a triazine; most preferably a pyrazole (such as

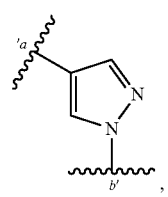

a' is connected with the segment

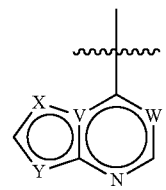

in formula I, b' is connected with $L^1$ in formula I));

$L^1$ is a chemical bond, an alkyl (preferably a $C_{1-4}$ alkyl), an alkylene, a cycloalkyl (preferably a $C_{3-6}$ cycloalkyl, more preferably a cyclopropyl) or a heterocycloalkyl (preferably a $C_{3-6}$ heterocycloalkyl containing 1 to 3 nitrogen atoms or a $C_{3-6}$ heterocycloalkyl containing 1 to 3 oxygen atoms);

Wherein the alkyl, alkylene, cycloalkyl or heterocycloalkyl can be independently substituted by the substituents selected from the group consisting of a halogen (such as F, Cl, Br or I, preferably F), a cyano, a sulfonyl (preferably a $C_{1-6}$ alkylsulfonyl or a $C_{3-6}$ cycloalkylsulfonyl, wherein the $C_{1-6}$ alkylsulfonyl is preferably a $C_{1-3}$ alkylsulfonyl, more preferably

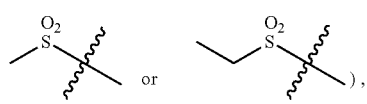

an acyl (preferably a formyl or a $C_{1-4}$ alkylacyl, wherein the $C_{1-4}$ alkylacyl is preferably a $C_2$ alkylacyl), a cycloalkyl (preferably a $C_{3-6}$ cycloalkyl, more preferably a cyclopentyl) and a heterocycloalkyl;

$L^2$ is an alkyl (preferably a $C_1$-4 alkyl, more preferably a methyl), an acyl (a formyl or a carbonyl), a cycloalkyl (preferably a $C_{3-6}$ cycloalkyl, more preferably a cyclopropyl or a cyclopentyl), a heterocycloalkyl (preferably a $C_{3-6}$ heterocycloalkyl containing 1 to 4 oxygen and/or nitrogen atoms; more preferably a $C_{3-6}$ heterocycloalkyl containing 1 to 3 oxygen atoms, the most preferably tetrahydropyranyl (such as

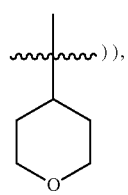

an aryl (preferably a $C_{6-10}$ aryl, more preferably a phenyl (such as

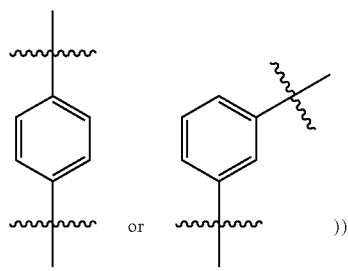 [SMILES: *c1ccc(*)cc1 ; *c1cccc(*)c1]

or a heteroaryl (preferably a $C_{3-10}$ heteroaryl containing 1 to 4 nitrogen atoms; more preferably a $C_{4-8}$ heteroaryl containing 1 to 4 nitrogen atoms; the most preferably a pyrazolyl (such as

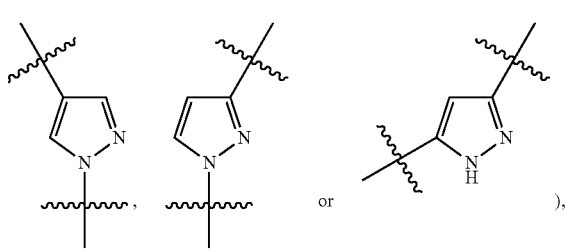

an imidazolyl, a pyridyl (such as

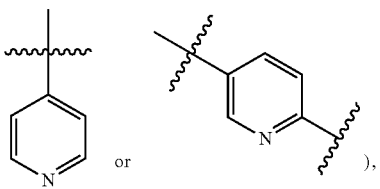 [SMILES: *c1ccncc1 ; *c1ccc(*)nc1]

a benzimidazolyl (such as

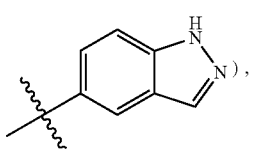 [SMILES: *c1ccc2[nH]ncc2c1]

a benzopyrazolyl (such as

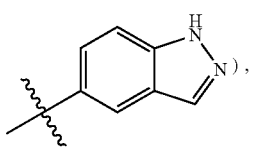 [SMILES: *c1ccc2[nH]ncc2c1]

a pyridazinyl (such as

or a pyrimidinyl (such as

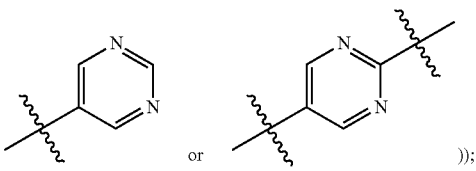 [SMILES: *c1cncnc1 ; *c1cnc(*)nc1]

M is a halogen (preferably fluorine), an alkyl (preferably a $C_{1-6}$ alkyl, more preferably a methyl, an ethyl, a propyl or an isopropyl), an alkylene, a cycloalkyl (preferably a $C_{3-6}$ cycloalkyl, more preferably a cyclopropyl), an alkoxy (preferably a $C_{1-4}$ alkoxy substituted by a heterocycloalkyl, more preferably a $C_2$ alkoxy substituted by a heterocycloalkyl; wherein the heterocycloalkyl of "a $C_{1-4}$ alkoxy substituted by a heterocycloalkyl" is preferably a $C_{2-10}$ heterocylcoalkyl containing 1 to 4 oxygen and/or nitrogen atoms; more preferably a morpholinyl (such as

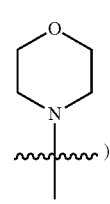

or a pyrrolidinyl), a heterocycloalkyl (preferably a $C_{3-8}$ heterocycloalkyl containing 1 to 4 oxygen and/or nitrogen atoms; more preferably a $C_{4-6}$ heterocycloalkyl containing 1 to 4 oxygen and/or nitrogen atoms; the most preferably a morpholinyl (such as

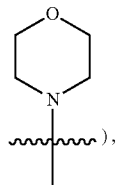 [SMILES: *N1CCOCC1]

a tetrahydropyranyl (such as

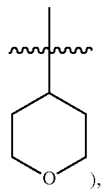

an azetidinyl (such as

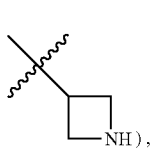

a piperidyl (such as

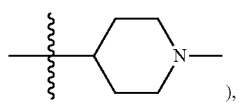 [SMILES: *C1CCN(C)CC1]

an oxetanyl (such as

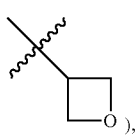

a tetrazolyl (such as

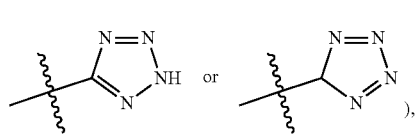 [SMILES: *c1nn[nH]n1 ; *C1N=NN=N1]

a piperazinyl or a pyrrolidinyl), an aryl (preferably a $C_{6-10}$ aryl, more preferably a phenyl), a heteroaryl, a cyano, a sulfonyl or an acyl; wherein the alkyl, alkylene, alkoxy, heterocycloalkyl, aryl, heteroaryl, sulfonyl or acyl defined in M can be optionally substituted by the substituents selected from the group consisting of a halogen (F, Cl, Br or I, preferably F; the $C_{1-6}$ alkyl substituted by the halogen is preferably a trifluoromethyl or

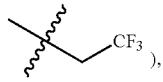

a hydroxyl (the $C_{1-6}$ alkyl substituted by the hydroxyl is preferably

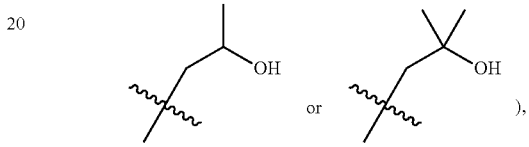

a cyano (the $C_{1-6}$ alkyl substituted by the cyano is preferably

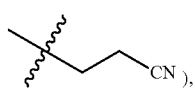 [SMILES: *CCC#N]

an amino, an acylamino, a nitro, a carboxyl, a sulfonyl, a methylsulfonyl (the $C_{1-6}$ alkyl substituted by the methylsulfonyl is preferably

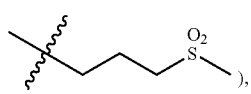 [SMILES: *CCCS(C)(=O)=O]

an acyl, an alkoxy (preferably a $C_{1-6}$ alkoxy, more preferably a $C_{1-3}$ alkoxy, such as a methoxy, an ethoxy, a propoxy or an isopropoxy; the $C_{1-6}$ alkyl substituted by the alkoxy is preferably

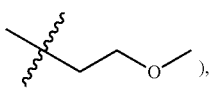 [SMILES: *CCOC]

a cycloalkyl (preferable a $C_{3-6}$ cycloalkyl, more preferably a cyclopropyl), a heterocycloalkyl (preferably a $C_{3-8}$ heterocycloalkyl containing 1 to 4 oxygen and/or nitrogen atoms; more preferably a $C_{4-6}$ heterocycloalkyl containing 1 to 4 oxygen and/or nitrogen atoms; the most preferably a morpholinyl (such as

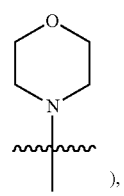 [SMILES: *N1CCOCC1]

a tetrahydropyranyl (such as

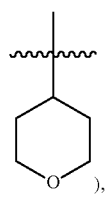 ), an azetidinyl (such as

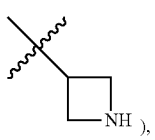 ), a piperidyl (such as

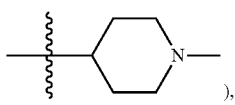 [SMILES: *C1CCN(C)CC1] ), an oxetanyl (such as

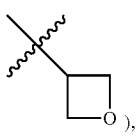 ), a piperazinyl, a pyrrolidinyl or a tetrazolyl (such as

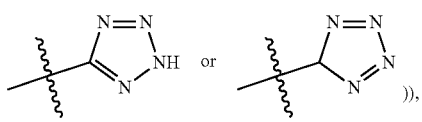 [SMILES: *c1nn[nH]n1 ; *C1N=NN=N1] )), an aryl and a heteroaryl;

$R^1$ is a hydrogen, a deuterium, a halogen (such as F, Cl, Br or I, preferably F), a cyano, an alkyl (preferably a $C_{1-4}$ alkyl), a cycloalkyl, a sulfonyl, an "alkyl-NH—CO—" or an "alkyl-NHSO$_2$—"; wherein the alkyl defined in $R^1$ can be optionally substituted by the substituents selected from the group consisting of a halogen, a hydroxyl, a cyano, an amino, a nitro, a carboxyl, a sulfonyl, an acyl, an alkoxy, a cycloalkyl, an alkenyl and an alkynyl;

Each of $R^2$, $R^3$, $R^4$ and $R^5$ is independently selected from a hydrogen, a deuterium, a halogen and an alkyl (preferably a $C_{1-4}$ alkyl);

m is 0, 1, 2 or 3; n is 1, 2, 3 or 4;

p is 0, 1, 2, 3, 4 or 5.

Each substituent in the compound represented by formula I is preferably as following groups: wherein, V is N or C;
W is N or CH;
X is O, S, N or CH;
Y is S or CH;

$R^2$ is a hydrogen, a deuterium, a halogen (such as F, Cl, Br or I) or an alkyl;

m is 0 or 1; n is 1 or 2;

p is 0 or 1.

In the present invention, the five-and-six-membered heterocyclic compound represented by formula I is preferably having the structure represented by formula II:

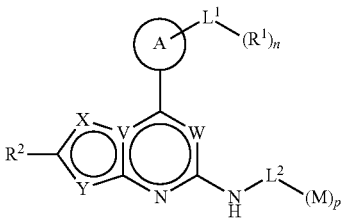

II wherein, each letter and substituent has the meaning given above.

In the present invention, the five-and-six-membered heterocyclic compound represented by formula I is more preferably having the structure represented by formula III-1, III-2 or III-3:

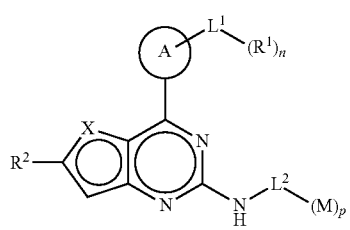

III-1

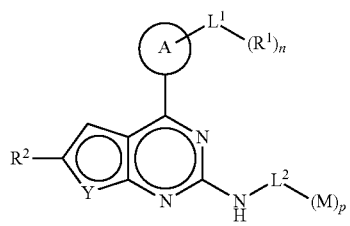

III-2

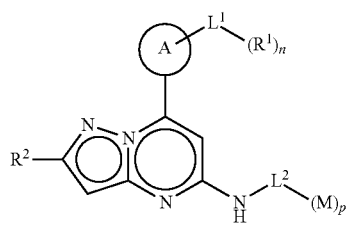

III-3 wherein, each letter and substituent has the meaning given above.

In the present invention, the compound represented by formula III-1 is preferably having the structure represented by formula IV-1-1 or IV-1-2:

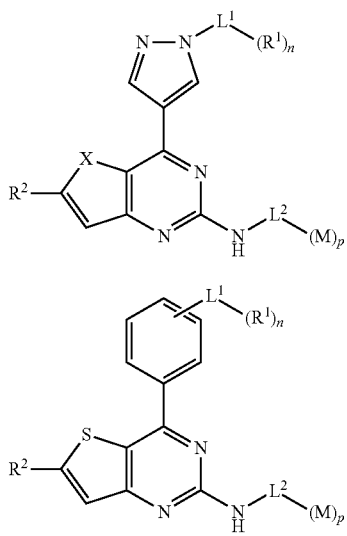

IV-1-1

IV-1-2 wherein, letters and substituents have the meanings given above, except that X is S or O.

In the present invention, the compound represented by formula III-2 is preferably having the structure represented by formula IV-2:

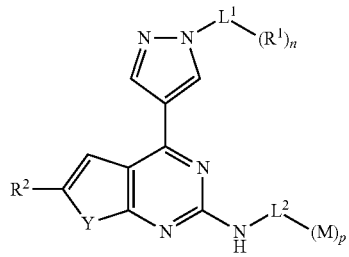

IV-2 wherein, each letter and substituent has the meaning given above.

In the present invention, the compound represented by formula III-3 is preferably having the structure represented by formula IV-3:

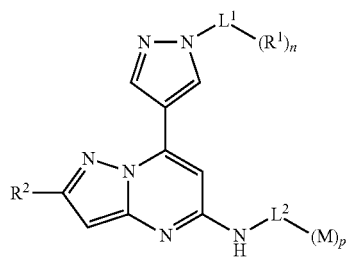

IV-3 wherein, each letter and substituent has the meaning given above.

In the present invention, the compound represented by formula IV-1-1 is preferably having the structure represented by formula V-1-1:

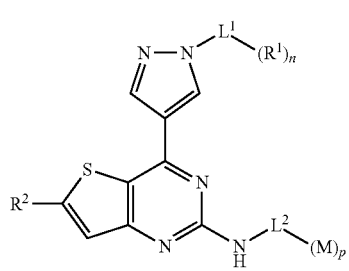

V-1-1 wherein, each letter and substituent has the meaning given above.

In the present invention, the five-and-six-membered heterocyclic compound represented by formula I is more preferably selected from the group consisting of:

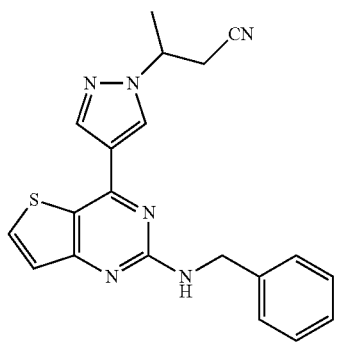

T-01

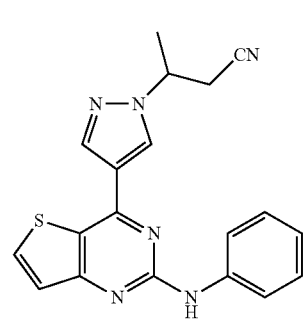

T-02

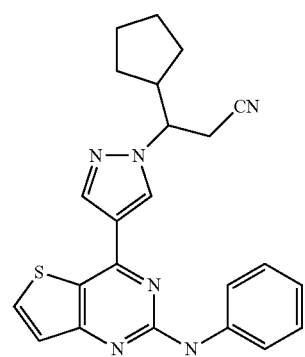

T-03

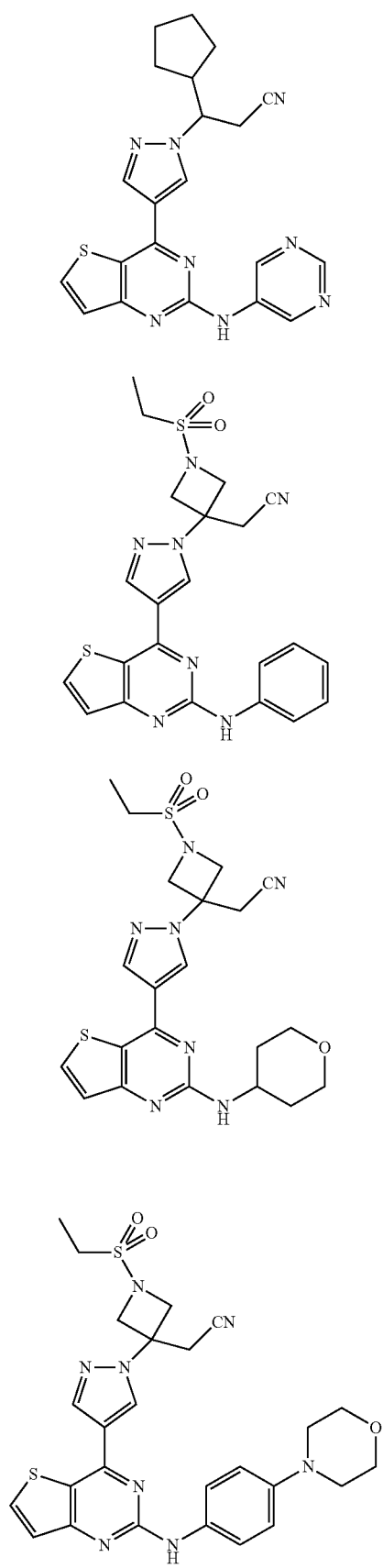
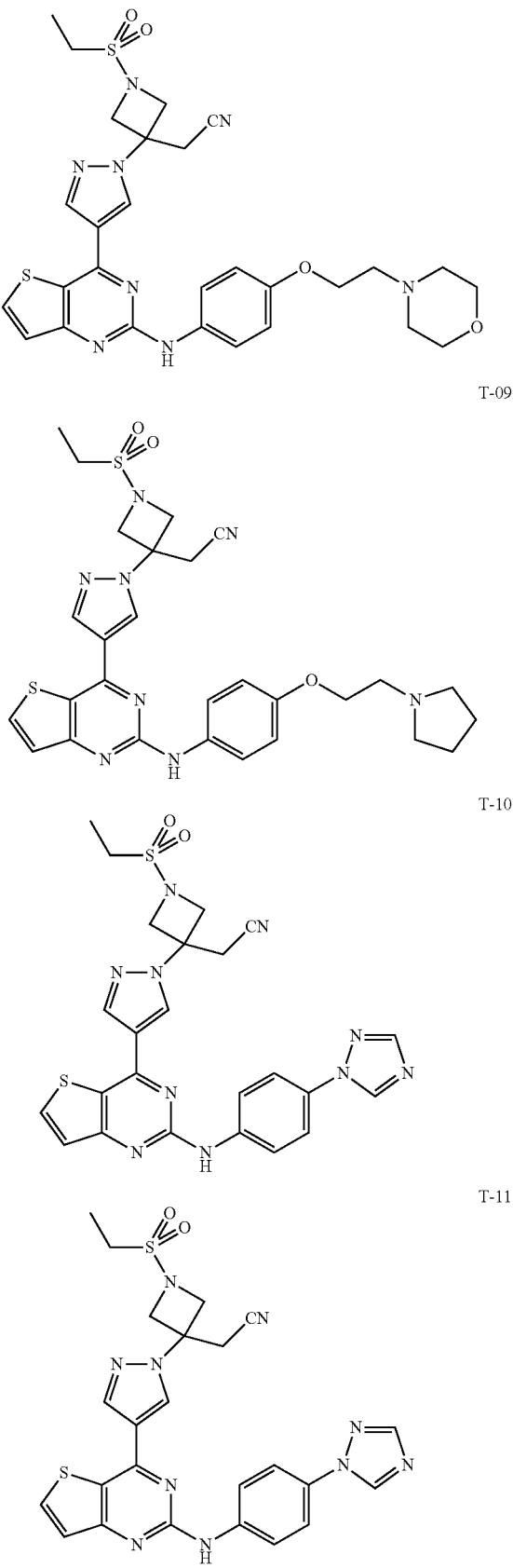

T-12 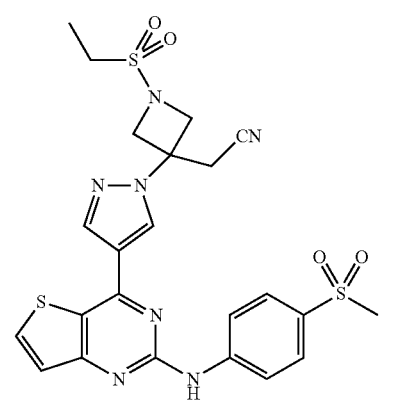
T-13 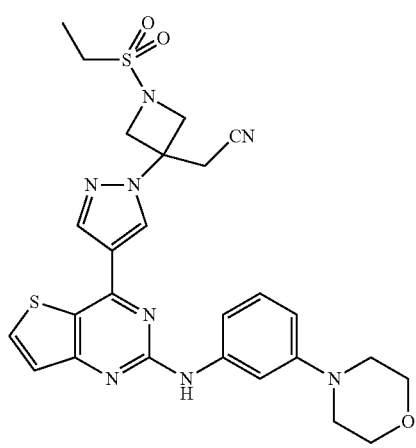
T-14 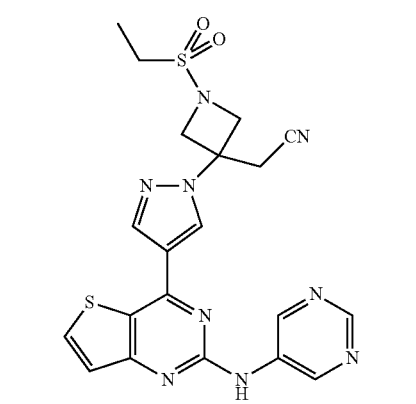
T-15 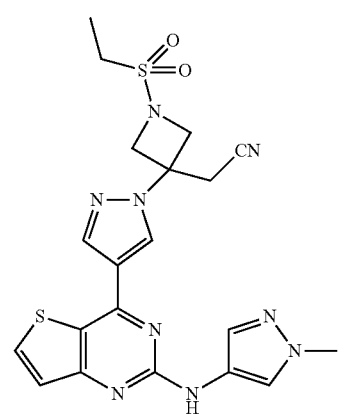
T-16 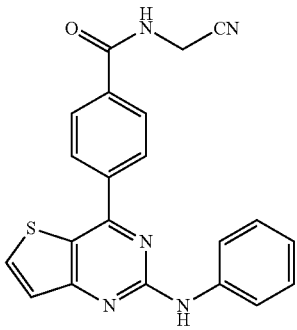
T-17 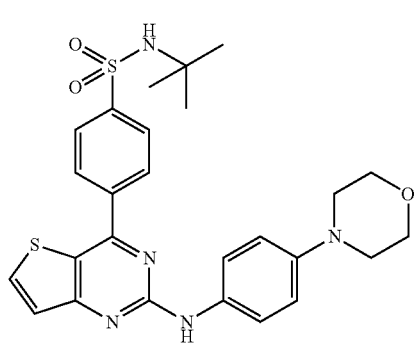
T-18 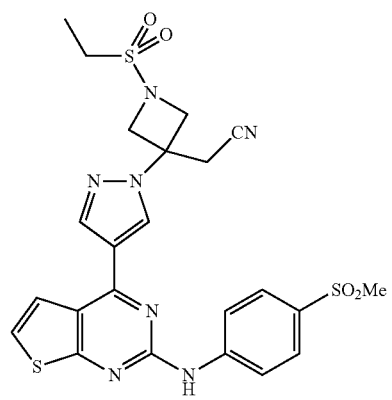
T-19 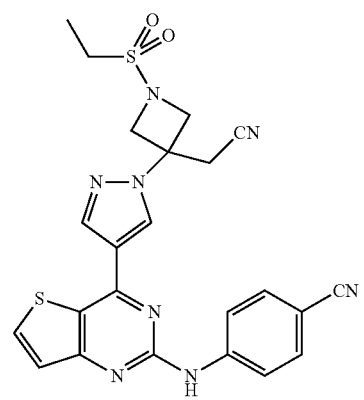

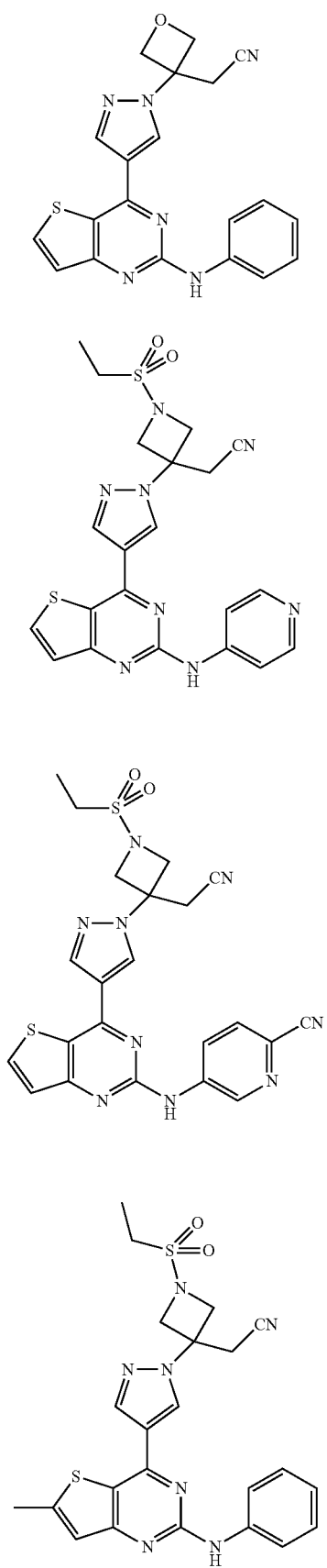
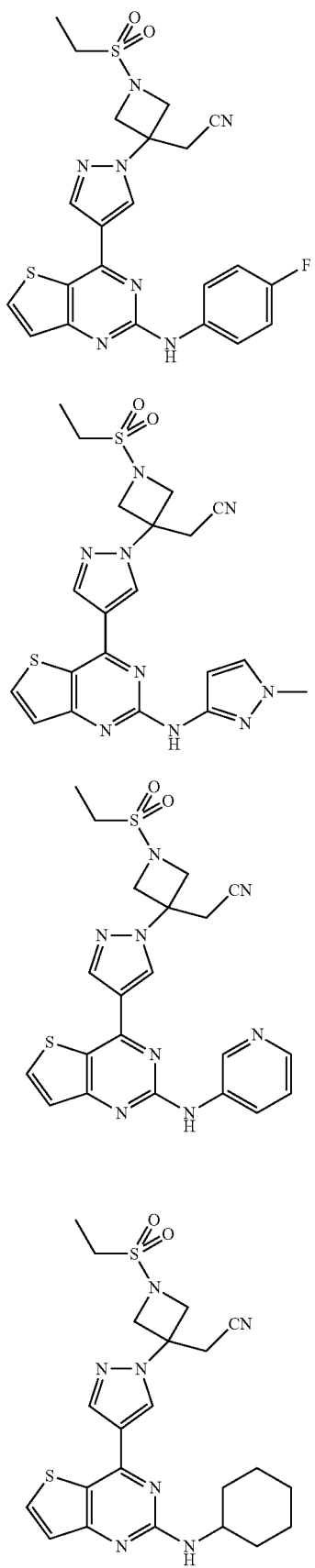

T-28 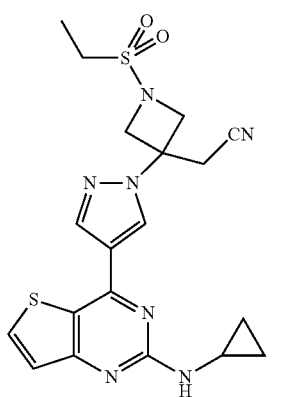
T-29 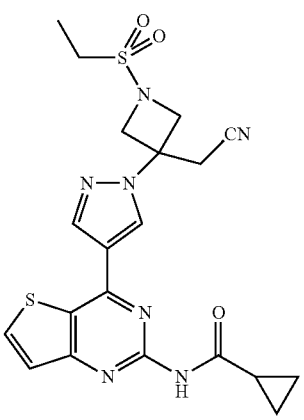
T-30 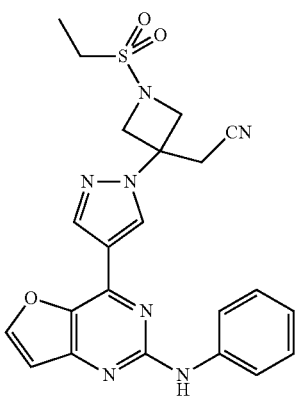
T-31 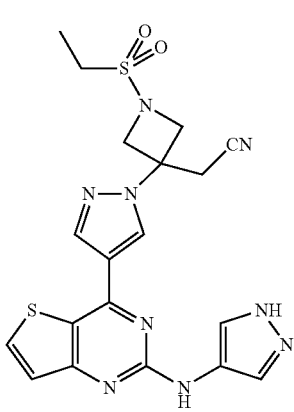
T-32 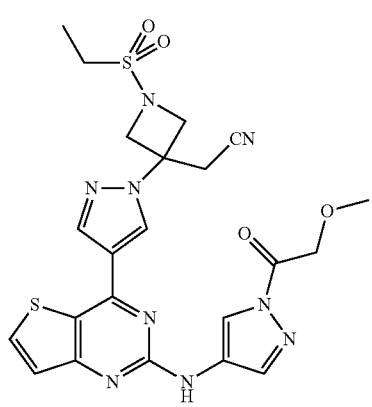
T-33 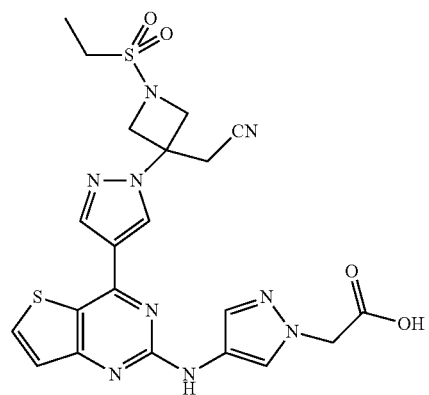
T-34 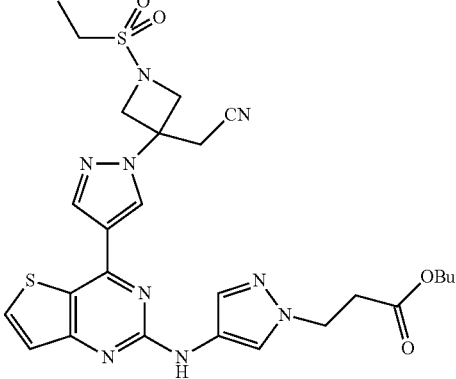
T-35 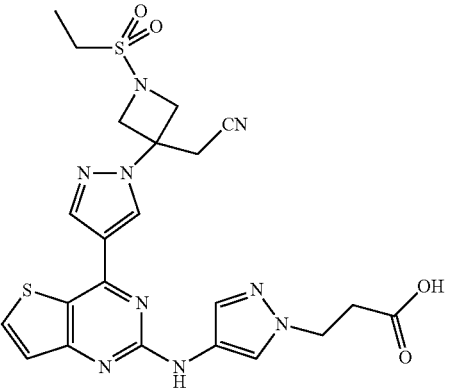

T-36
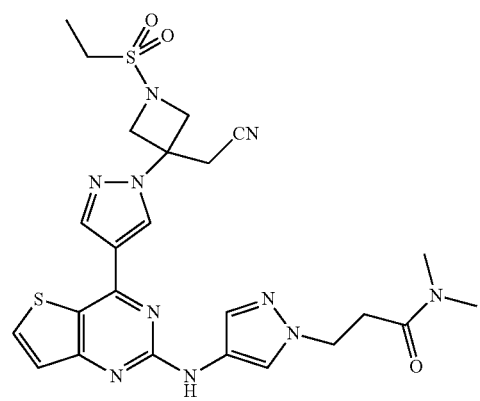
T-40
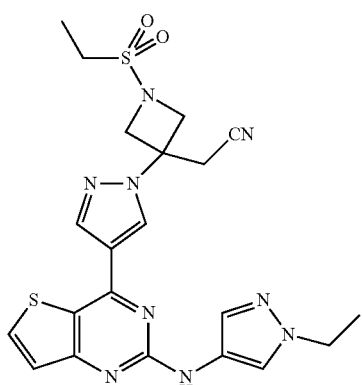
T-37
T-41
T-38
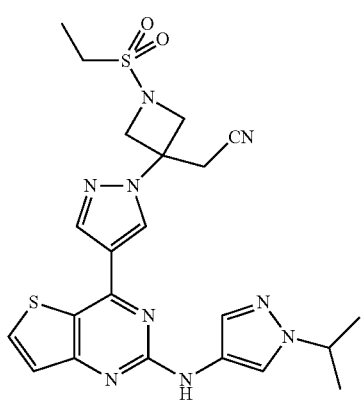
T-42
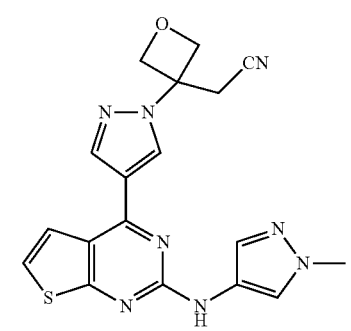
T-39
T-43
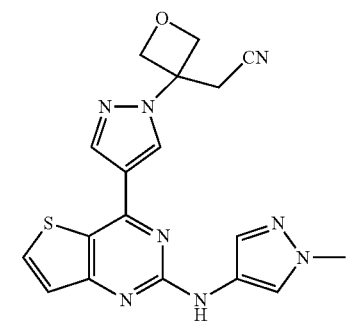

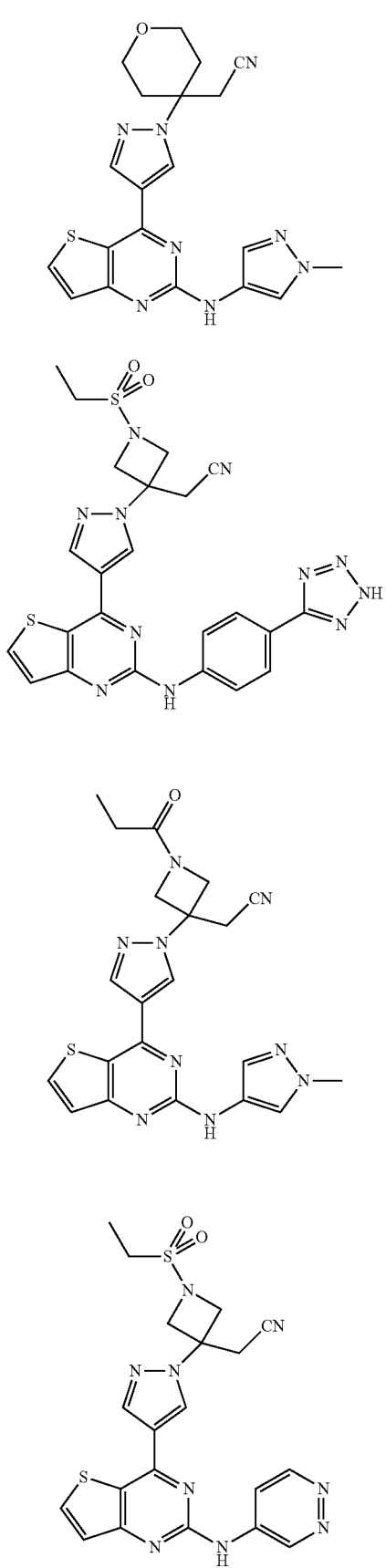
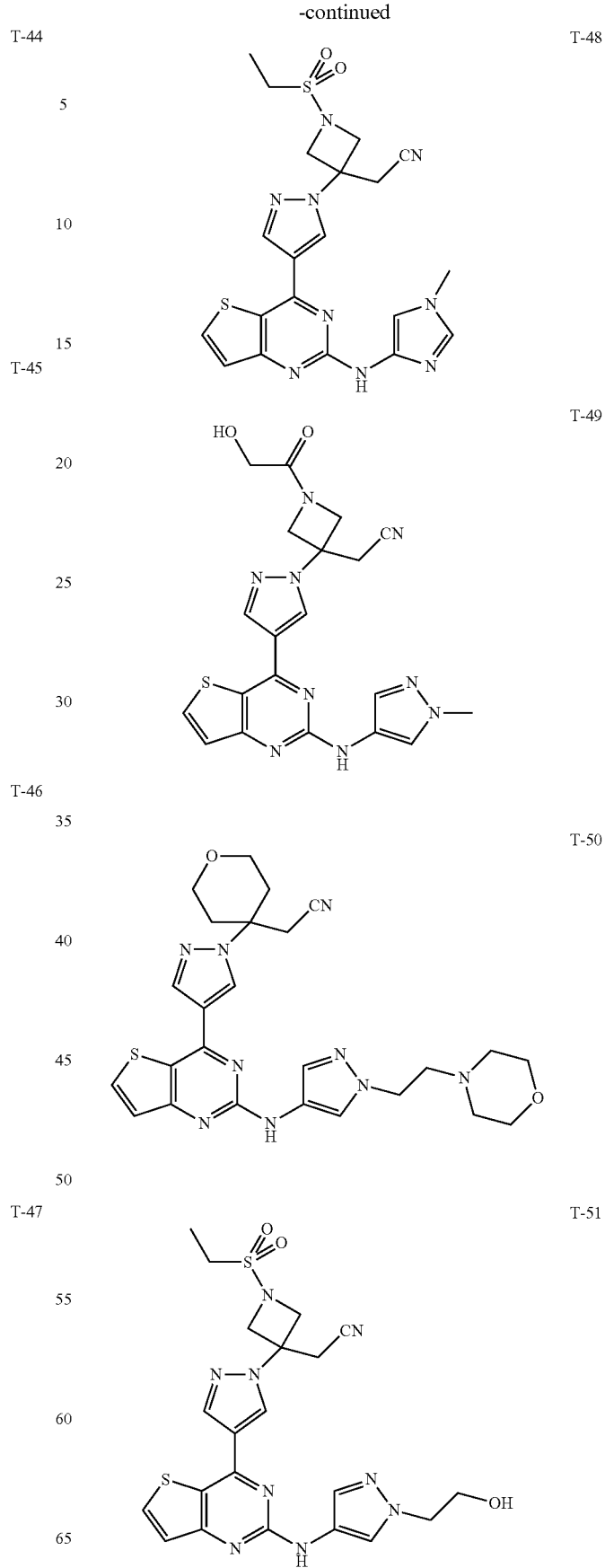

T-52 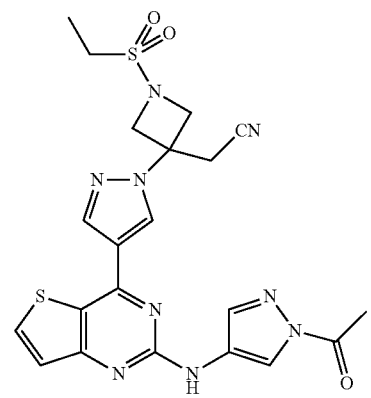
T-53 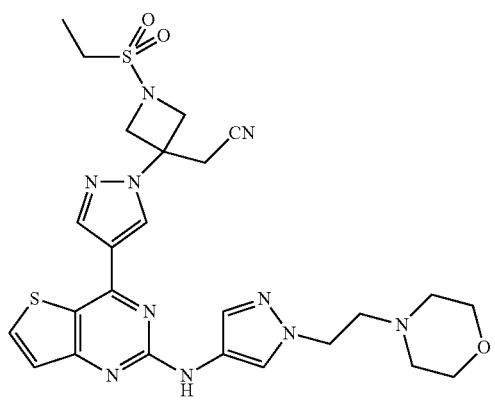
T-54 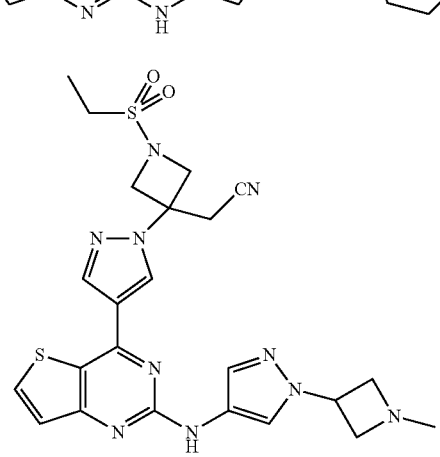
T-55 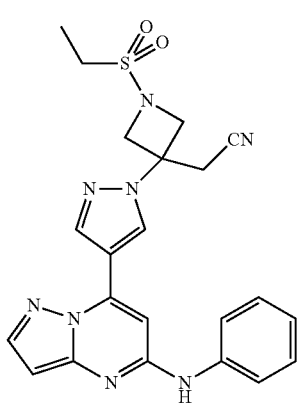
T-56 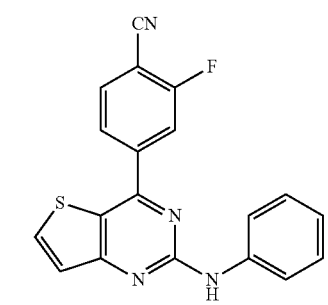
T-57 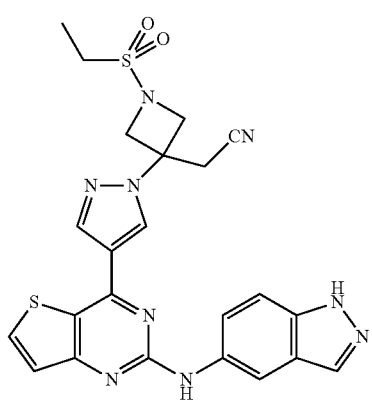
T-58 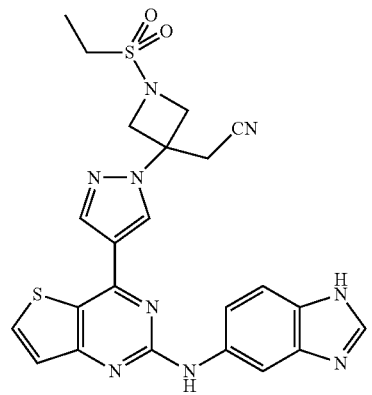
T-59 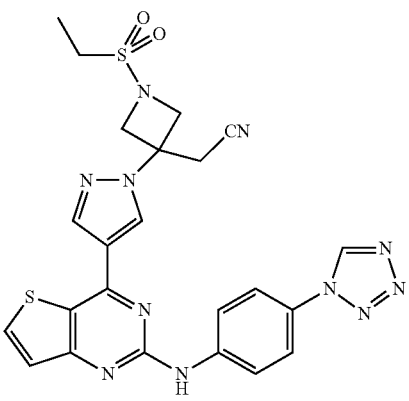

-continued
T-60
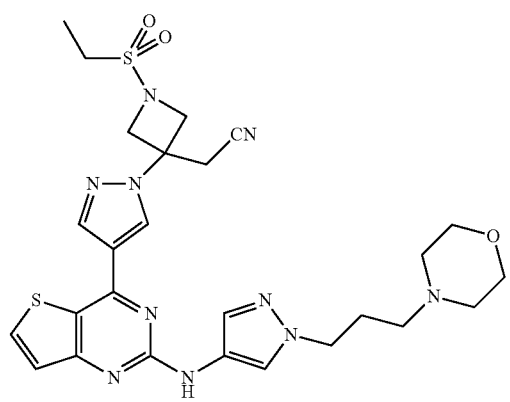
T-61
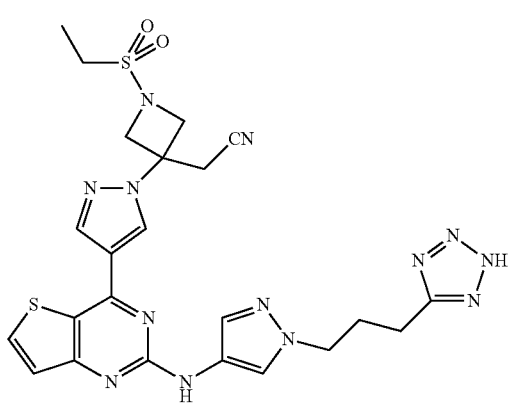
T-62
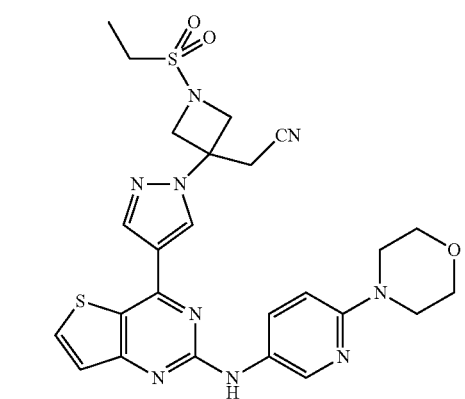
T-63
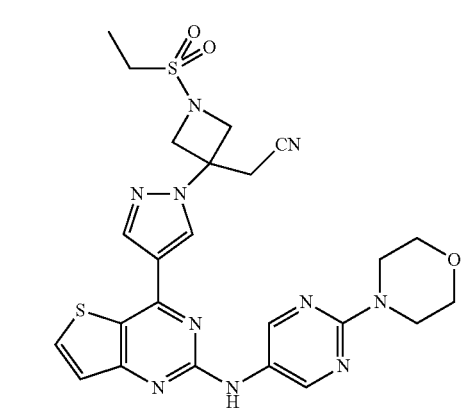
-continued
T-64
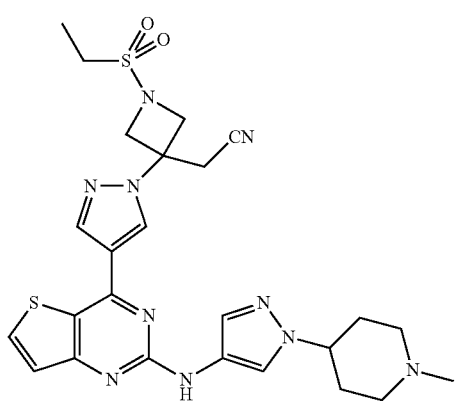
T-65
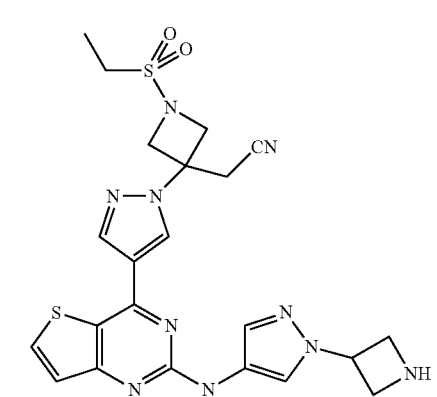
T-66
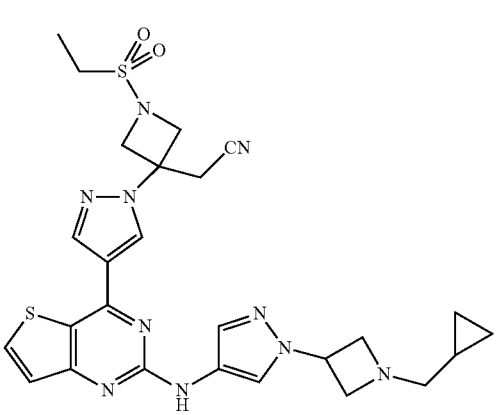
T-67
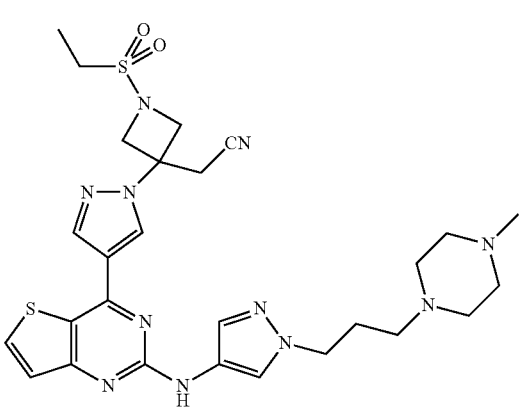

-continued
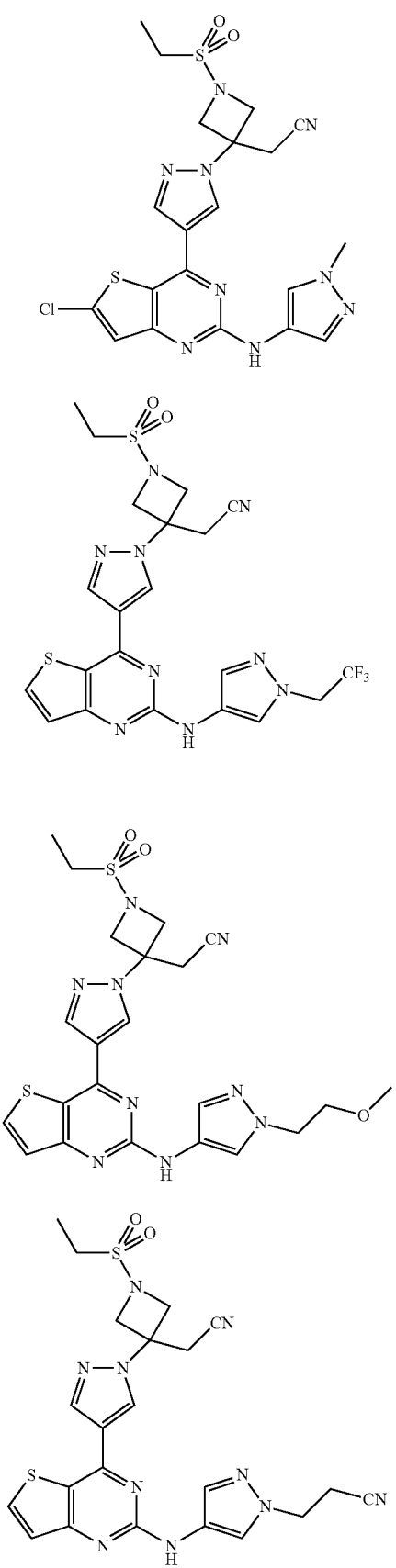
T-68
T-69
T-70
T-71
-continued
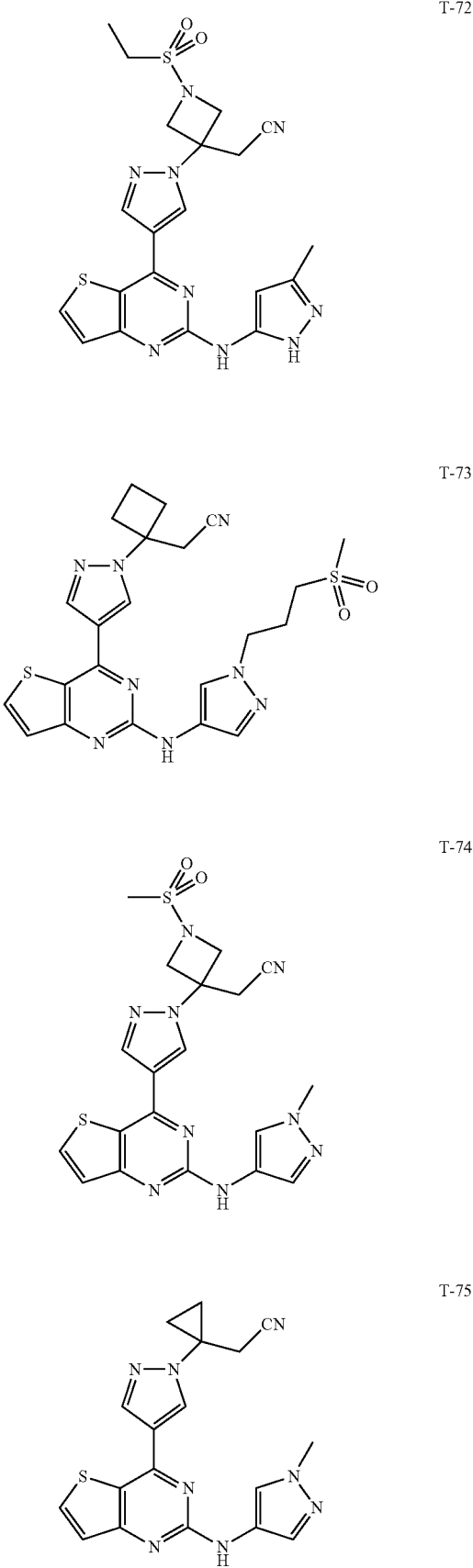
T-72
T-73
T-74
T-75

T-76
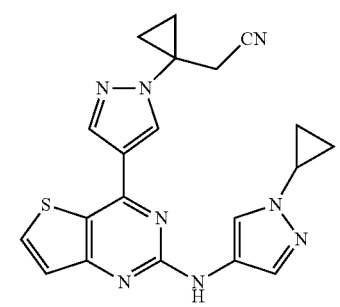
T-77
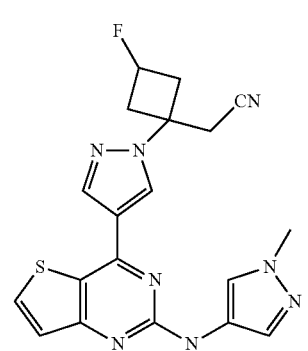
T-78
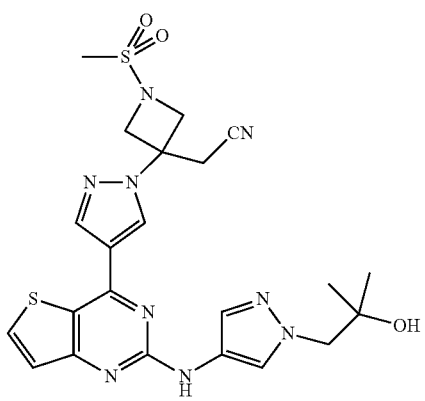
T-79
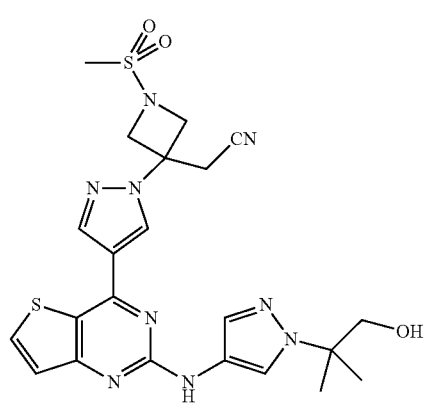
T-80
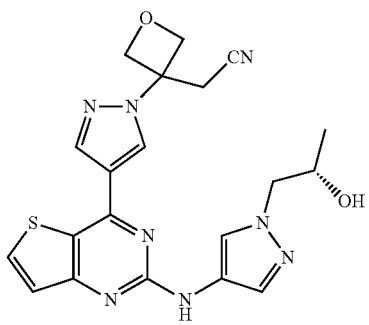
T-81
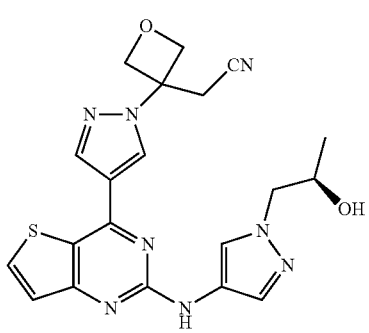
T-82
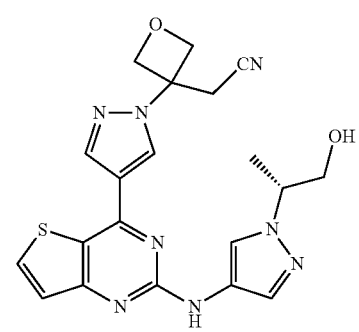
T-83
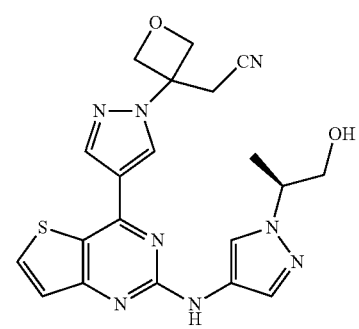

-continued

T-84
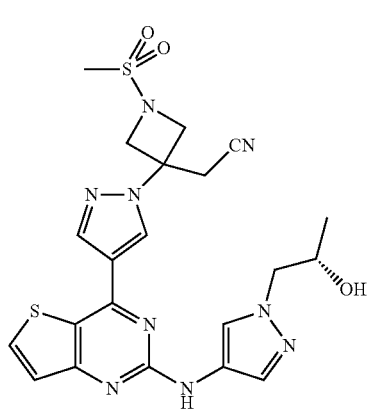

T-85
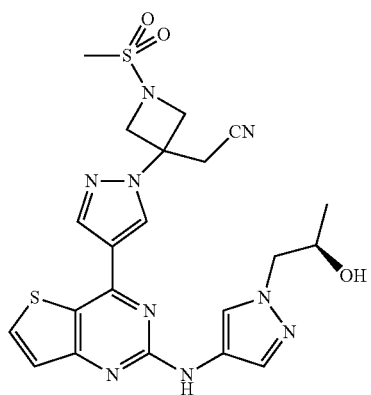

T-86
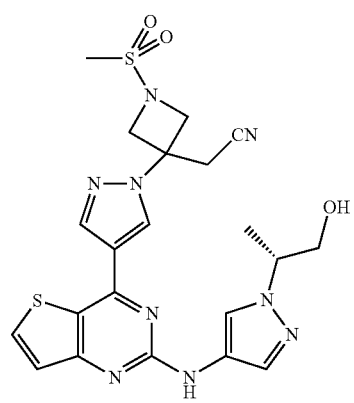

T-87
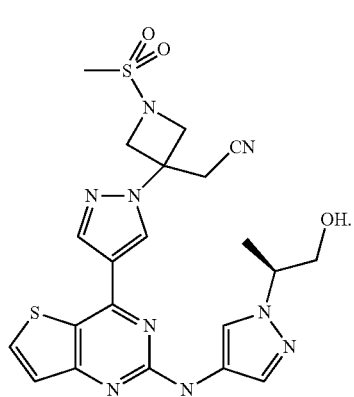

The present invention also provides a method for preparing the compound represented by formula I, which is selected from the group consisting of:

Method 1: under a basic condition, performing a nucleophilic substitution reaction between a compound represented by formula I-A and a compound represented by formula I-B,

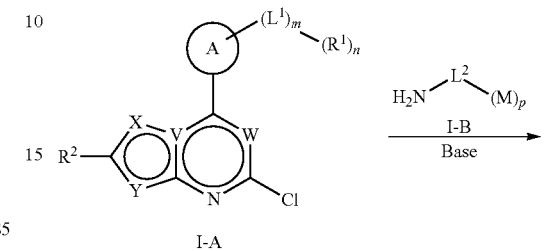

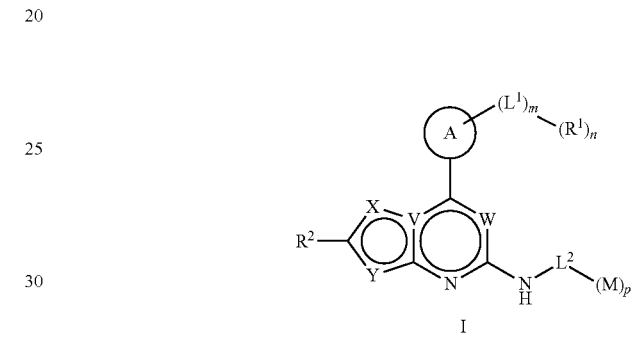

Method 2: under an acidic condition, performing a nucleophilic substitution reaction between a compound represented by formula I-A and a compound represented by formula I-B; or

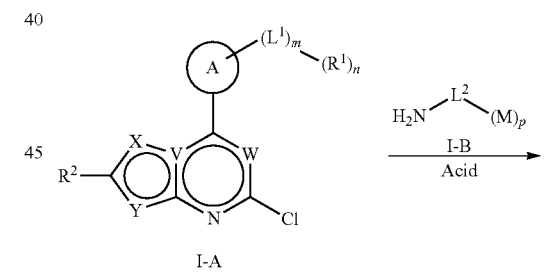

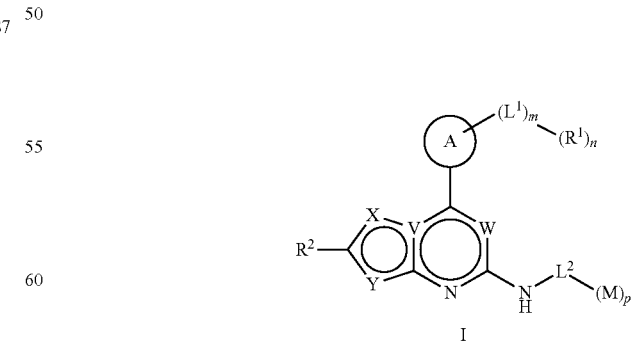

Method 3: performing a coupling reaction between a compound represented by formula I-A and a compound represented by formula I-B,

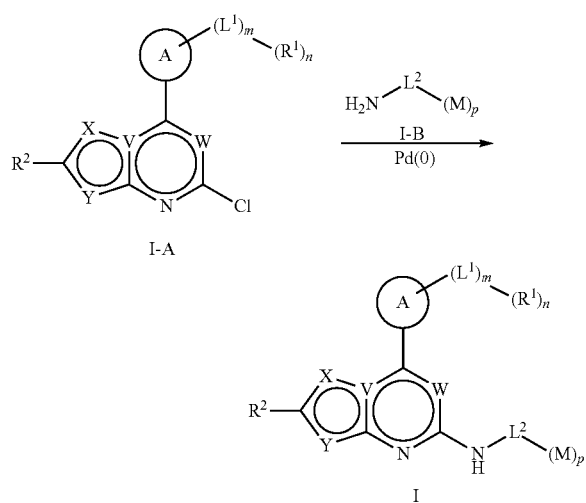

In method 1, 2 and 3, except special explanation, each letter and substituent has the meaning given above.

In method 1, the method and conditions for the nucleophilic substitution reaction are conventional in the art, the preferred method and conditions in the present invention are: in a solvent, performing the nucleophilic substitution reaction between the compound represented by formula I-A and the compound represented by formula I-B under a basic condition. The solvent is preferably selected from the group consisting of DMSO, 1,4-dioxane and DMF, more preferably DMSO. The base condition is preferably provided by an inorganic base, which is preferably selected from the group consisting of KF, NaF, $Cs_2CO_3$ and $K_2CO_3$, more preferably KF. A volume mass ratio of the solvent and the compound represented by formula I-A is preferably 10 mL/g-100 mL/g. The molar ratio of the compound represented by formula I-A to the compound represented by formula I-B is preferably 0.1:1-1:1, more preferably 0.3:1-0.9:1. The molar ratio of the base to the compound represented by formula I-B is preferably 1:1-10:1, more preferably 1:1-2:1. The nucleophilic substitution reaction is preferably carried out at 50° C.-150° C., more preferably 70° C.-110° C. The nucleophilic substitution reaction is preferably carried out till when the completion of the reaction is detected, 5 h-24 h is preferred in the present invention.

In method 2, the method and conditions for the nucleophilic substitution reaction are conventional in the art, the preferred method and conditions in the present invention are: in a solvent, performing the nucleophilic substitution reaction between the compound represented by formula I-A and the compound represented by formula I-B under an acidic condition. The solvent is preferably an organic solvent, which is preferably selected from the group consisting of isobutanol, n-butanol, DMSO and DMF, more preferably isobutanol. The acid condition is preferably provided by an organic acid and an inorganic acid, more preferably an organic acid. The organic acid is preferably p-toluenesulfonic acid, while the inorganic acid is preferably HCl and/or $H_2SO_4$. The volume mass ratio of the solvent and the compound represented by formula I-A is preferably 10 mL/g-100 mL/g. The molar ratio of the compound represented by formula I-A to the compound represented by formula I-B is preferably 0.1:1-1:1, more preferably 0.3:1-0.9:1. The molar ratio of the acid to the compound represented by formula I-B is preferably 0.1:1-3:1, more preferably 0.6:1-1.2:1. The nucleophilic substitution reaction is preferably carried out at 50° C.-150° C., more preferably 80° C.-120° C. The nucleophilic substitution reaction is preferably carried out till when the completion of the reaction is detected, 5 h-24 h is preferred in the present invention.

In method 3, the method and conditions for the coupling reaction is conventional in the art, the preferred method and conditions in the present invention are: in a solvent, at an atmosphere of inert gas, performing a coupling reaction between the compound represented by formula I-A and the compound represented by formula I-B at presence of a base and a Pd-catalyst, wherein the inert gas is preferably argon and/or nitrogen; the solvent is preferably an organic solvent and/or water, the organic solvent is preferably selected from the group consisting of 1,4-dioxane, toluene and glycoldimethylether, more preferably 1,4-dioxane. The volume mass ratio of the solvent and the compound represented by formula I-A is preferably 20 mL/g-100 mL/g. The base is preferably an inorganic base, and the inorganic base is preferably selected from the group consisting of $K_2CO_3$, $Cs_2CO_3$, $Na_2CO_3$ and $K_3PO_4$. The molar ratio of the base and the compound represented by formula I-A is preferably 1:1-10:1, more preferably 3:1-5:1. The Pd-catalyst is conventional in the art, which is preferably selected from the group consisting of $Pd_2(dba)_3$, $Pd(OAc)_2$, $Pd(Pph_3)_4$ and $Pd(dppf)Cl_2$. $Pd_2(dba)_3$ is more preferably. The molar ratio of the Pd-catalyst to the compound represented by formula I-A is preferably 0.005:1-0.5:1, more preferably 0.01:1-0.10:1. The molar ratio of the compound represented by formula I-A to the compound represented by formula I-B is preferably 0.5:1-2:1, more preferably 0.9:1-1.5:1. The coupling reaction is preferably carried out at 50° C.-150° C., more preferably 90° C.-130° C. The coupling reaction is preferably carried out till when the completion of the reaction is detected, 0.5 h-3 h is preferred in the present invention.

In the present invention, a preferred reaction route for preparing the compound represented by formula I is shown below:

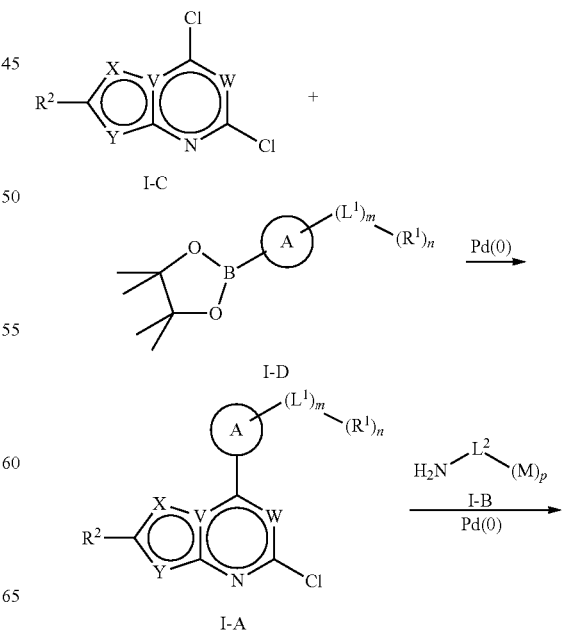

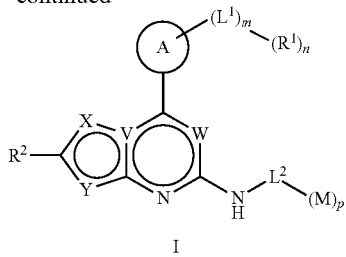

Persons skilled in the art may understand, according to the above compounds disclosed in the present invention, people may use well-known materials through kinds of familiar methods to prepare the compounds disclosed in the present invention, such as through chemical synthesis or extracting from plants, all of these methods are included in the present invention. Unless otherwise described or provided a preparation method, all the materials used in preparing the compounds or intermediates thereof in the present invention are known in the art or commercially available.

Each preferred condition for the methods in the present invention may be free combined to give better examples.

The present invention also provides a five-and-six-membered heterocyclic compound represented by formula I-A,

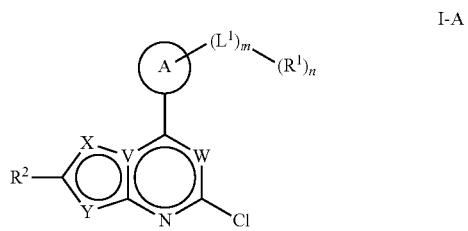

wherein,
V is N or C;
W is N or $CR^3$;
Each of X, Y is independently O, S, N or $CR^4$;
ring A is an aryl or a heteroaryl;
$L^1$ is a chemical bond, an alkyl (preferably a $C_{1-4}$ alkyl), an alkylene, a cycloalkyl (preferably a $C_{3-6}$ cycloalkyl, more preferably a cyclopropyl) or a heterocycloalkyl (preferably a $C_{3-6}$ heterocycloalkyl containing 1 to 3 nitrogen atoms or a $C_{3-6}$ heterocycloalkyl containing 1 to 3 oxygen atoms); wherein the alkyl, alkylene, cycloalkyl or heterocycloalkyl defined in $L^1$ can be optionally independently substituted by the substituents selected from the group consisting of a halogen (such as F, Cl, Br or I, preferably F), a cyano, a sulfonyl (preferably a sulfonyl substituted by a $C_{1-6}$ alkyl or a sulfonyl substituted by a $C_{3-6}$ cycloalkyl, wherein the sulfonyl substituted by a $C_{1-6}$ alkyl is preferably a sulfonyl substituted by a $C_{1-3}$ alkyl, more preferably

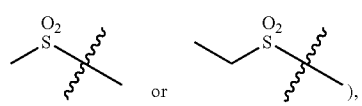

an acyl (preferably a formyl or an acyl substituted by a $C_{1-4}$ alkyl, wherein the acyl substituted by a $C_{1-4}$ alkyl is preferably an acyl substituted by a $C_2$ alkyl), a cycloalkyl (preferably a $C_{3-6}$ cycloalkyl, more preferably a cyclopentyl) and a heterocycloalkyl;

$R^1$ is a hydrogen, a deuterium, a halogen (such as F, Cl, Br or I, preferably F), a cyano, an alkyl (preferably a $C_{1-4}$ alkyl), a cycloalkyl, a sulfonyl, an "alkyl-NH—CO—" or an "alkyl-NHSO$_2$—"; wherein the alkyl defined in $R^1$ can be optionally substituted by the substituents selected from the group consisting of a halogen, a hydroxyl, a cyano, an amino, a nitro, a carboxyl, a sulfonyl, an acyl, an alkoxy, a cycloalkyl, an alkenyl and an alkynyl;

Each of $R^2$, $R^3$ and $R^4$ is independently selected from a hydrogen, a deuterium, a halogen and an alkyl;

m is 0, 1, 2, or 3;

n is 1, 2, 3 or 4.

In the present invention, the five-and-six-membered heterocyclic compound represented by formula I-A is preferably as follows:

when V is N, X is N and both W and Y are CH; or when V is C, W is N; each of X and Y is independently O, S or CH;

$R^2$ is a hydrogen, a halogen (such as F, Cl, Br or I) or an alkyl; m is 0, 1, or 2;

n is 1 or 2.

In the present invention, the five-and-six-membered heterocyclic compound represented by formula I-A is more preferably having the structure represented by formula III-A:

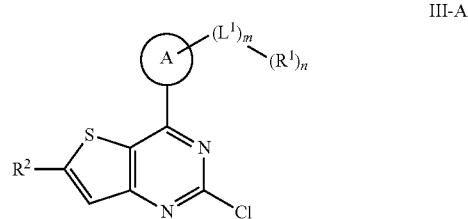

wherein, each of letter and substituent has the meaning given above.

In the present invention, the compound represented by general formula III-A is more preferably having the structure represented by formula IV-A:

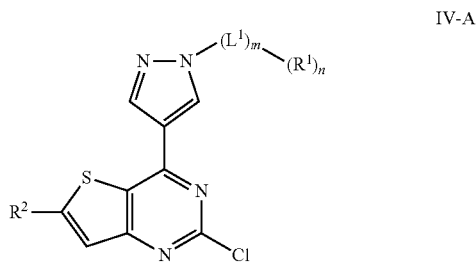

wherein, each of letter and substituent has the meaning given above.

In the present invention, the five-and-six-membered heterocyclic compound represented by formula I-A is more preferably selected from the group consisting of:

| | |
|---|---|
| 1 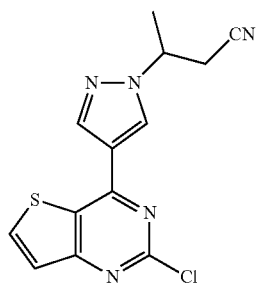 | 17a 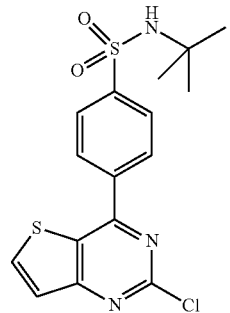 |
| 3 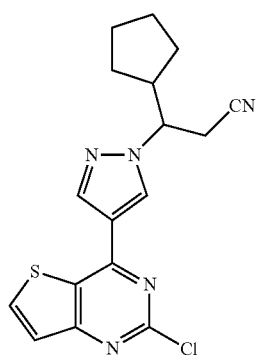 | 18 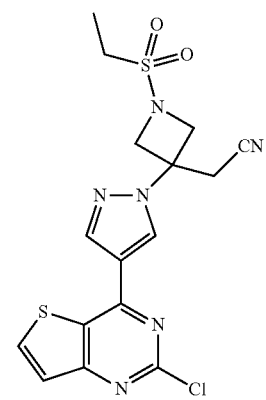 |
| 5 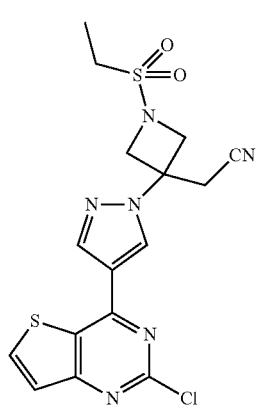 | 20 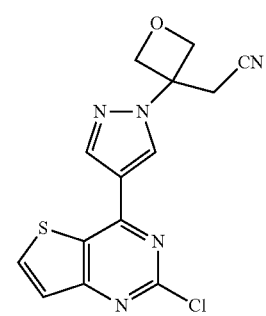 |
| 16-b 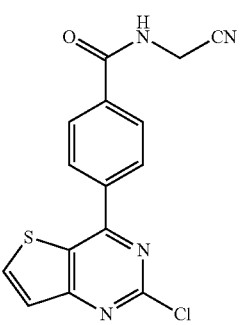 | 44 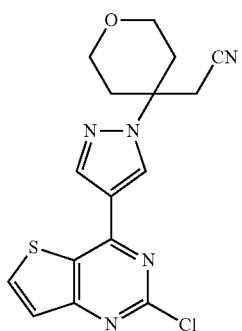 |

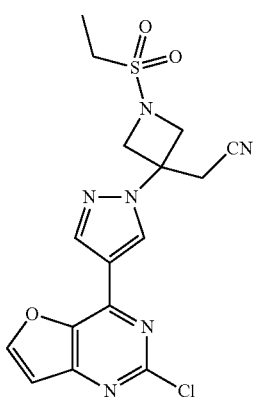
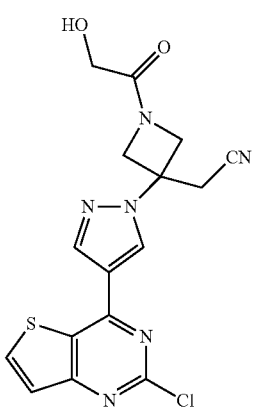
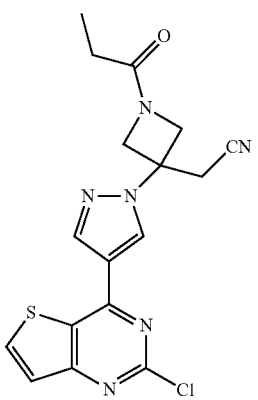
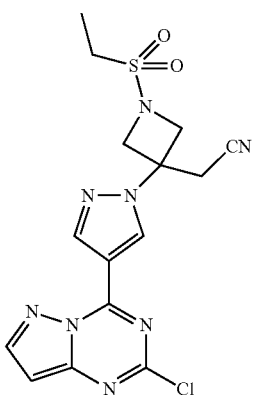
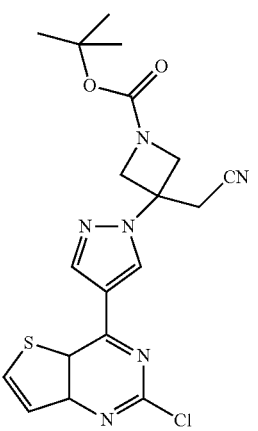

68

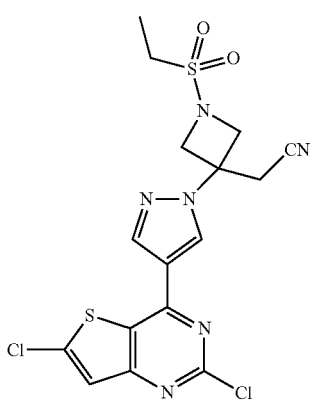

73

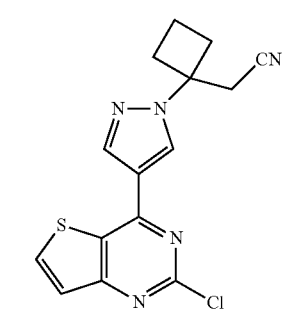

74

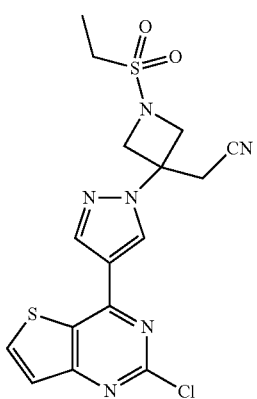

75

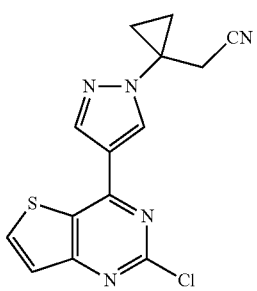

77

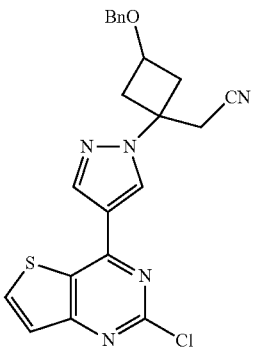

81

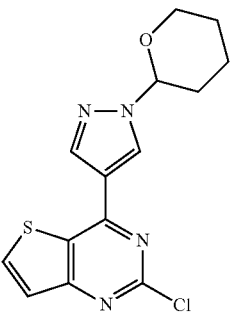

The present invention also provides a method for preparing the compound represented by formula I-A, comprising: performing a coupling reaction between a compound represented by formula I-C and a compound represented by formula I-D;

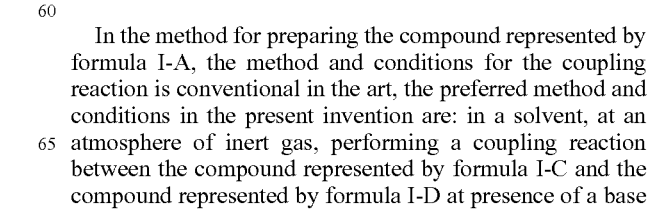

In the method for preparing the compound represented by formula I-A, the method and conditions for the coupling reaction is conventional in the art, the preferred method and conditions in the present invention are: in a solvent, at an atmosphere of inert gas, performing a coupling reaction between the compound represented by formula I-C and the compound represented by formula I-D at presence of a base and a Pd-catalyst. Wherein the inert gas is preferably argon and/or nitrogen; the solvent is preferably an organic solvent and/or water, the organic solvent is preferably selected from the group consisting of 1,4-dioxane, toluene and glycoldimethylether, more preferably 1,4-dioxane. The volume mass ratio of the solvent and the compound represented by formula I-C is preferably 20 mL/g-100 mL/g. The base is preferably an inorganic base, and the inorganic base is preferably selected from the group consisting of $K_2CO_3$, $Cs_2CO_3$, $Na_2CO_3$ and $K_3PO_4$. The molar ratio of the base to the compound represented by formula I-C is preferably 1:1-10:1, more preferably 3:1-5:1. The Pd-catalyst is conventional in the art, which is preferably selected from the group consisting of $Pd_2(dba)_3$, $Pd(OAc)_2$, $Pd(Pph_3)_4$ and $Pd(dppf)Cl_2$, more preferably $Pd(dppf)Cl_2$. The molar ratio of the Pd-catalyst to the compound represented by formula I-C is preferably 0.005:1-0.5:1, more preferably 0.01:1-0.10:1. The molar ratio of the compound represented by formula I-C to the compound represented by formula I-D is preferably 0.5:1-2:1, more preferably 0.9:1-1.5:1. The coupling reaction is preferably carried out at 20° C.-120° C., more preferably 70° C.-110° C. The coupling reaction is preferably carried out till when the completion of the reaction is detected, 4 h-18 h is preferred in the present invention.

The present invention also provides a use of the five-and-six-membered heterocyclic compound represented by formula I, a pharmaceutically acceptable salt, a metabolite, a metabolic precursor or a prodrug thereof in preparing a medicament as a Janus kinase (JAK) inhibitor.

The present invention also provides a use of the five-and-six-membered heterocyclic compound represented by formula I, a pharmaceutically acceptable salt, a metabolite, a metabolic precursor or a prodrug thereof in preparing a medicament for treating and/or preventing cell proliferation diseases. Wherein the cell proliferation diseases are conventional diseases caused by cell proliferation in the art, the preferred diseases in the present invention are cancer, injection, inflammation and autoimmune diseases.

The present invention also provides a pharmaceutical composition, which contains a therapeutically effective dosage of the five-and-six-membered heterocyclic compound represented by formula I, a pharmaceutically acceptable salt, a metabolite, a metabolic precursor or a prodrug thereof, and a variety of pharmaceutically acceptable carriers and/or attenuant.

The present invention provides a use of the pharmaceutical composition in preparing a medicament as a Janus kinase (JAK) inhibitor.

The present invention provides a use of the pharmaceutical composition in preparing a medicament for treating and/or preventing cell proliferation diseases. Wherein the cell proliferation diseases are conventional diseases caused by cell proliferation in the art, the preferred diseases in the present invention are cancer, injection, inflammation and autoimmune diseases.

The pharmaceutical composition in the present invention may be in a form suitable for an oral administration, may also be in a form of a sterile injectable aqueous solution. The oral administration or injectable aqueous solution may be prepared according to any known methods for preparing a pharmaceutical composition in the art.

Unless otherwise indicated, the following terms when used in the descriptions and the claims of the present invention have the following meanings:

As used herein, the term "alkyl" refers to a saturated linear or branched-chain aliphatic hydrocarbyl containing 1 to 20 carbon atoms, preferably 1 to 10 carbon atoms, more preferably 1 to 8 carbon atoms, such as a methyl, an ethyl, a n-propyl, an isopropyl, a n-butyl, a tert-butyl, an isobutyl, a pentyl, a hexyl, a heptyl, an octyl, a nonyl, a decyl, a 4,4-dimethylpentyl, a 2,2,4-trimethylpentyl, an undecyl, a dodecyl, and various isomers thereof etc.; as well as the alkyl containing 1 to 4 substituents selected from the group consisting of: a deuterium, a halogen (preferred F, Br, Cl or I), an alkyl, an alkoxy, an aryl, an aryloxy, an aryl or a diaryl substituted by an aryl, an arylalkyl, an arylalkoxy, an alkenyl, an alkynyl, a cycloalkyl, a cycloalkenyl, a cycloalkylalkyl, a cycloalkylalkoxy, an amino, a hydroxyl, a hydroxyalkyl, an acyl, an aldehyde group, a heteroaryl, a heteroaryloxy, a heterocycloalkyl, a heterocycloalkoxy, an arylheteroaryl, an arylalkoxycarbonyl, a heteroarylalkyl, a heteroarylalkoxy, an aryloxyalkyl, an aryloxyaryl, an alkylamino, an acylamino, an arylcarbonylamino, a nitro, a cyano, a thiol, a haloalkyl, a trihaloalkyl and/or an alkylthio.

As used herein, the term "alkylene" (used alone or as a part of other groups) refers to a subsaturated linear or branched-chain aliphatic hydrocarbyl containing 1 to 20 carbon atoms, preferably 1 to 10 carbon atoms, more preferably 1 to 8 carbon atoms, such as a methylene, an ethylene, a n-propylene, an isopropylene, a n-butylene, a tert-butylene, an isobutylene, a pentylene, a hexylene, a heptylene, an octylene, a nonylene, a decylene, a 4,4-dimethylpentylene, a 2,2,4-trimethylpentylene, an undecylene, a dodecylene, and various isomers thereof etc.; as well as the alkylene containing 1 to 4 substituents selected from the group consisting of: a deuterium, a halogen (preferred F, Br, Cl or I), an alkyl, an alkoxy, an aryl, an aryloxy, an aryl or a diaryl substituted by an aryl, an arylalkyl, an arylalkoxy, an alkenyl, an alkynyl, a cycloalkyl, an cycloalkenyl, a cycloalkylalkyl, a cycloalkylalkoxy, an amino, a hydroxyl, a hydroxyalkyl, an acyl, an aldehyde group, a heteroaryl, a heteroaryloxy, a heterocycloalkyl, a heterocycloalkoxy, an arylheteroaryl, an arylalkoxycarbonyl, a heteroarylalkyl, a heteroarylalkoxy, an aryloxyalkyl, an aryloxyaryl, an alkylamino, an acylamino, an arylcarbonylamino, a nitro, a cyano, a thiol, a haloalkyl, a trihaloalkyl and/or an alkylthio; the substituents selected from the group mentioned above may also form a ring together with the alkylene group, thereby forming a fused ring or a spiro ring.

The term "alicyclo" or "cycloalkyl" refers to a group having a single ring or multiple rings with only carbon atoms, wherein each ring can contain one or more than one double bonds without a conjugated π electronic system. Preferably, a cycloalkyl containing 1 to 3 rings with a total of 3 to 20 carbon atoms, more preferably 3 to 10 carbon atoms, for example: a cyclopropyl, a cyclobutyl, a cyclopentyl, a cyclohexyl, a cycloheptyl, a cyclooctyl, a cyclodecyl and a cyclododecyl, a cyclohexenyl; the cycloalkyl may be optionally substituted by 1 to 4 substituents selected from the group consisting of: a deuterium, a halogen, an alkyl, an alkoxy, a hydroxyl, an aryl, an aryloxy, an arylalkyl, a cycloalkyl, an alkylamino, an acylamino, an oxo, an acyl, an arylcarbonylamino, an amino, a nitro, a cyano, a thiol and/or an alkylthio and/or any alkyl defined in the present invention.

The term "alkoxy" refers to a cyclic or non-cyclic alkyl group containing an indicated number of carbon atoms and having a connection through an oxygen bridge. Thus, "alkoxy" includes the definition of the term "alkyl" and the term"cycloalkyl" mentioned above.

The term "alkenyl" refers to a straight-chain, branched-chain or cyclic non-aromatic hydrocarbyl having an indicated number of carbon atoms and at least one carbon-carbon double bond. Preferably there is one carbon-carbon double bond, and may have up to four non-aromatic carbon-carbon double bonds. Thus, "$C_{2-12}$ alkenyl" refers to an alkenyl group having 2 to 12 carbon atoms. "$C_{2-6}$ alkenyl" refers to an alkenyl group having 2 to 6 carbon atoms, including a vinyl, a propenyl, a butenyl, a 2-methyl-butenyl and a cyclohexenyl. A double bond may locate at a segment of straight chain, branched chain or cyclic portion of the alkenyl group and, where specified, the alkenyl group may be substituted, the alkenyl may be optionally substituted by the substituents selected from the group consisting of: an alkyl, a halogen, an alkoxy, a hydroxyl, an aryl, an aryloxy, an arylalkyl, a cycloalkyl, an alkylamino, an acylamino, an acyl, an arylcarbonylamino, an amino, a nitro, a cyano, a thiol and/or an alkylthio and/or any alkyl defined in the present invention.

The term "alkynyl" refers to a straight-chain, branched-chain or cyclic hydrocarbyl having an indicated number of carbon atoms and at least one carbon-carbon triple bond. It may have up to three carbon-carbon triple bonds. Thus, "$C_{2-12}$ alkynyl" refers to an alkynyl group having 2 to 12 carbon atoms. "$C_{2-6}$ alkynyl" refers to an alkynyl group having 2 to 6 carbon atoms, including an ethynyl, a propynyl, a butynyl and a 3-methyl-1-butynyl and the like.

As used herein, the term "aryl" refers to any stable monocyclic or bicyclic carbocyclic ring containing up to 7 atoms in each ring, wherein at least one ring is an aromatic ring. Examples of the above mentioned aryl group include a phenyl, a naphthyl, a tetrahydronaphthyl, a 2,3-indanyl, a biphenyl, a phenanthryl, an anthryl or an acenaphthyl. It can be understood that if an aryl substituent is a bicyclic ring having one non-aromatic ring, the connection is through the aromatic ring. It also includes the aryl optionally substituted by 1 to 4 substituents selected from the group consisting of: a deuterium, a halogen (preferred F, Br, Cl or I), an alkyl, an alkoxy, an aryl, an aryloxy, an aryl or a diaryl substituted by an aryl, an arylalkyl, an arylalkoxy, an alkenyl, an alkynyl, a cycloalkyl, a cycloalkenyl, a cycloalkylalkyl, a cycloalkylalkoxy, an optionally substituted amino, a hydroxyl, a hydroxyalkyl, an acyl, an aldehyde group, a heteroaryl, a heteroaryloxy, a heterocycloalkyl, a heterocycloalkyloxy, an arylheteroaryl, an arylalkoxycarbonyl, a heteroarylalkyl, a heteroarylalkoxy, an aryloxyalkyl, an aryloxyaryl, an alkylamino, an acylamino, an arylcarbonylamino, a nitro, a cyano, a thiol, a haloalkyl, a trihaloalkyl, and/or an alkylthio.

The term "aromatic ring" refers to any stable monocyclic or bicyclic carbocyclic ring containing up to 7 atoms in each ring, wherein at least one ring is an aromatic ring. Examples of the above mentioned aromatic ring group include a phenyl, a naphthyl, a tetrahydronaphthyl, a 2,3-indanyl, a biphenyl, a phenanthryl, an anthryl or an acenaphthyl. It can be understood that if an aryl substituent is a bicyclic ring having one non-aromatic ring, the connection is through the aromatic ring. It also includes the aromatic ring optionally substituted by 1 to 4 substituents selected from the group consisting of: a deuterium, a halogen (preferred F, Br, Cl or I), an alkyl, an alkoxy, an aryl, an aryloxy, an aryl or a diaryl substituted by an aryl, an arylalkyl, an arylalkoxy, an alkenyl, an alkynyl, a cycloalkyl, a cycloalkenyl, a cycloalkylalkyl, a cycloalkylalkoxy, an amino, a hydroxyl, a hydroxyalkyl, an acyl, an aldehyde group, a heteroaryl, a heteroaryloxy, a heterocycloalkyl, a heterocycloalkyloxy, an arylheteroaryl, an arylalkoxycarbonyl, a heteroarylalkyl, a heteroarylalkoxy, an aryloxyalkyl, an aryloxyaryl, an alkylamino, an acylamino, an arylcarbonylamino, a nitro, a cyano, a thiol, a haloalkyl, a trihaloalkyl, and/or an alkylthio.

As used herein, the term "arylheterocyclo" or "heteroarylcyclo" refers to any stable monocyclic or bicyclic ring containing up to 7 atoms in each ring, wherein at least one ring is an aromatic ring containing 1 to 4 heteroatoms selected from the group consisting of O, N, and S. The term "arylheterocyclo" or "heteroarylcyclo" groups within the scope of this definition include, but are not limited to, an acridinyl, a carbazolyl, a cinnolinyl, a carbolinyl, a quinoxalinyl, a imidazolyl, a pyrazolyl, a pyrrolyl, an indolyl, an indolinyl, a benzotriazolyl, a benzimidazolyl, a furyl, a thienyl, an isothiazolyl, a benzothienyl, a dihydrobenzothienyl, a benzofuranyl, an isobenzofuranyl, a benzoxazolyl, a benzofuroxanyl, a benzopyrazolyl, a quinolinyl, an isoindolyl, an isoquinolinyl, an oxazolyl, an oxadiazolyl, an isoxazolyl, an indolyl, a pyrazinyl, a pyridinopyridinyl, a pyridinotetrazolyl, a pyridazinyl, a pyridinyl, a naphthalene pyrimidyl, a pyrimidinyl, a pyrrolyl, a tetrazolyl, a thiadiazolyl, a thiazolyl, a thiophenyl, a triazolyl, a quinazolinyl, a tetrahydroquinolinyl, a dihydrobenzimidazolyl, a dihydrobenzofuranyl, a dihydrobenzoxazolyl, a dihydroquinolinyl. As the heterocycle defined below, the term "heteroarylcyclo" should also be understood to include N-oxide derivatives of any nitrogen-containing heteroaromatic group. It can be understood that if a heteroaryl substituent is a bicyclic ring having one non-aromatic ring or one ring without heteroatom, then the connection is through the aromatic ring or the heteroatom containing in the ring. The term "heteroarylcyclo" or "arylheterocyclo" groups can be optionally substituted by 1 to 4 substituents selected from the group consisting of a deuterium, a halogen, an alkyl, an alkoxy, a hydroxyl, an aryl, an aryloxy, an arylalkyl, a cycloalkyl, an alkylamino, an acylamino, an acyl, an arylcarbonylamino, an amino, a nitro, a cyano, a thiol and/or an alkylthio and/or any alkyl defined in the present invention.

The term "halogen" refers to a fluorine, a chlorine, a bromine, an iodine, or an astatine.

The term "hydroxyl" refers to

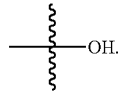

The term "amino" refers to

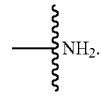

The term "cyano" refers to

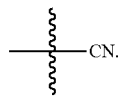 [SMILES: *C#N]

The term "carboxyl" refers to

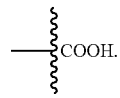

The term "sulfonyl" refers to

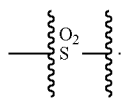

The term "acyl" refers to a carbonyl or a formyl, the term "carbonyl" refers that there are substituents on both sides of an acyl, and the term "formyl" refers that there is a substituent on only one side.

The term "acylamino" refers to a carbonyl amide or a formyl amide, the term "carbonyl amide" refers that there are substituents on both sides of an acylamino, and the term "formyl amide" refers that there is a substituent on only one side.

The term "haloalkyl" refers to an alkyl substituted by a halogen at optionally position. Thus, the "haloalkyl" includes the definition of the term "halogen" and the term "alkyl".

The term "haloalkoxy" refers to an alkoxy substituted by a halogen at optionally position. Thus, the "haloalkoxy" includes the definition of the term "halogen" and the term"alkoxy".

The term "aryloxy" refers to an aryl group containing the indicated number of carbon atoms and having a connection through an oxygen bridge. Thus, the "aryloxy" includes the definition of the term "aryl".

As used herein, the term "arylhetero" or "heteroaryl" refers to any stable monocyclic or bicyclic ring containing up to 7 atoms in each ring, wherein at least one ring is an aromatic ring containing 1 to 4 heteroatoms selected from the group consisting of O, N, and S. The term "heteroaryl" or "arylhetero" groups within the scope of this definition include, but are not limited to, an acridinyl, a carbazolyl, a cinnolinyl, a carbolinyl, a quinoxalinyl, a imidazolyl, a pyrazolyl, a pyrrolyl, an indolyl, an indolinyl, a benzotriazolyl, a benzimidazolyl, a furyl, a thienyl, an isothiazolyl, a benzothienyl, a dihydrobenzothienyl, a benzofuranyl, an isobenzofuranyl, a benzoxazolyl, a benzofuroxanyl, a benzopyrazolyl, a quinolinyl, an isoindolyl, an isoquinolinyl, an oxazolyl, an oxadiazolyl, an isoxazolyl, an indolyl, a pyrazinyl, a pyridinopyridinyl, a pyridinotetrazolyl, a pyridazinyl, a pyridinyl, a naphthalene pyrimidyl, a pyrimidinyl, a pyrrolyl, a tetrazolyl, a thiadiazolyl, a thiazolyl, a thiophenyl, a triazolyl, a quinazolinyl, a quinoxalinyl, a tetrahydroquinolinyl, a dihydrobenzimidazolyl, a dihydrobenzofuranyl, a dihydrobenzoxazolyl, a dihydroquinolinyl, a methylenedioxybenzoyl. As the heterocycle defined below, the term "heteroaryl" should also be understood to include N-oxide derivatives of any nitrogen-containing heteroaromatic group. It can be understood that if a heteroaryl substituent is a bicyclic ring having one non-aromatic ring or one ring without hetero atom, then the connection is through the aromatic ring. The term "heteroaryl" or "arylhetero" groups can be optionally substituted by 1 to 4 substituents selected from the group consisting of a deuterium, a halogen, an alkyl, an alkoxy, a hydroxyl, an aryl, an aryloxy, an arylalkyl, a cycloalkyl, an alkylamino, an acylamino, an acyl, an arylcarbonylamino, an amino, a nitro, a cyano, a thiol and/or an alkylthio and/or any alkyl defined in the present invention.

The term "heteroalicyclo" or "heterocycloalkyl" used herein alone or as a part of other groups refers to a 4 to 12 membered monocyclic or polycyclic group containing 1 to 4 heteroatoms (such as nitrogen, oxygen and/or sulphur) with may be one or more than one double bond in each ring but without a conjugated π electronic system in a ring. The term "heterocycloalkyl" groups may include 1 to 4 substituents, such as an alkyl, a halogen, an oxo and/or any alkyl set out above. In addition, any heterocycloalkyl rings can be fused to a cycloalkyl, an aryl, a heteroaryl or a heterocycloalkyl ring, and to form a fused ring. The term "heterocycloalkyl" groups within the scope of this definition include, but are not limited to, an oxazolinyl, an oxetanyl, a pyranyl, a tetrahydropyranyl, an azetidinyl, a 1,4-dioxanyl, a hexahydroazepanyl, a piperazinyl, a piperidinyl, a pyrrolidinyl, a morpholinyl, a thiomorpholinyl, a dihydrofuranyl, a dihydroimidazolyl, a dihydroindolyl, a dihydroisoxazolyl, a dihydroisothiazolyl, a dihydroxadiazolyl, a dihydroxazolyl, a dihydropyrazinyl, a dihydropyrazolyl, a dihydropyridyl, a dihydropyrimidinyl, a dihydropyrrolyl, a dihydrotetrazolyl, a dihydrothiadiazolyl, a dihydrothiazolyl, a dihydrothienyl, a dihydrotriazolyl, a dihydroazetidinyl, a tetrahydrofuranyl and a tetrahydrothienyl and N-oxides thereof. A heterocycloalkyl substituent can be linked with other groups through a carbon atom or a hetero atom.

In the present invention, all of the alkyl, cycloalkyl, heterocycloalkyl, aryl and heteroaryl having indicated carbon numbers as "$C_{x1\text{-}y1}$" (x1 and y1 are integer), for example "$C_{1\text{-}12}$ alkyl", indicate that these groups are not further substituted by substituents, such as that "$C_{1\text{-}12}$ alkyl" means an alkyl having 1 to 12 carbon atoms without further substituted.

On the basis of not to violate common sense of the field, all above preferred conditions can be combined in any way to provide preferred embodiments of the present invention.

The materials and reagents used in the present invention are all commercial available.

The positive effect of the present invention is that: the five-and-six-membered heterocyclic compound represented by formula I, a pharmaceutically acceptable salt, a metabolite, a metabolic precursor or a prodrug thereof in the present invention is a kind of efficient Janus kinase (JAK) inhibitor which can be used for treating or preventing cell proliferation diseases such as cancer, infections, inflammation and autoimmune diseases etc.

DETAILED DESCRIPTION OF THE PREFERRED EMBODIMENT

Below in conjunction with specific embodiments, the present invention is further elaborated. But the present invention is not therefore limited within the scope of the embodiments. The specific conditions of experiments for the following embodiments, when not indicated, are usually in accordance with conventional methods and conditions, or product manual.

The structures of compounds are identified by Nuclear Magnetic Resonance (NMR) or Mass Spectrum (MS). NMR spectrum was obtained by Bruker Avance-500, using deuterated dimethyl sulphoxide, deuterated chloroform and deuterated methanol etc. as a solvent, tetramethyl silane (TMS) as an internal standard. LC-MS spectrum was obtained by liquid chromatography mass (LC-MS) spectrometry Agilent Technologies 6110, and the ESI ion source was used. Microwave reaction was performed in the Explorer full automatic microwave synthesizer produced by CEM, the magnetron frequency was 2450 MHz, continuous microwave output power was 300 W. Gilson 281 was used for the preparation HPLC, and the column was Shimadazu Shim-Pack, PRC-ODS, 20×250 mm, 15 μm.

Example 1

3-(4-(2-(Benzylamino)thieno[3,2-d]pyrimidin-4-yl)-1H-pyrazol-1-yl)butanenitrile T-01

Synthetic Route:

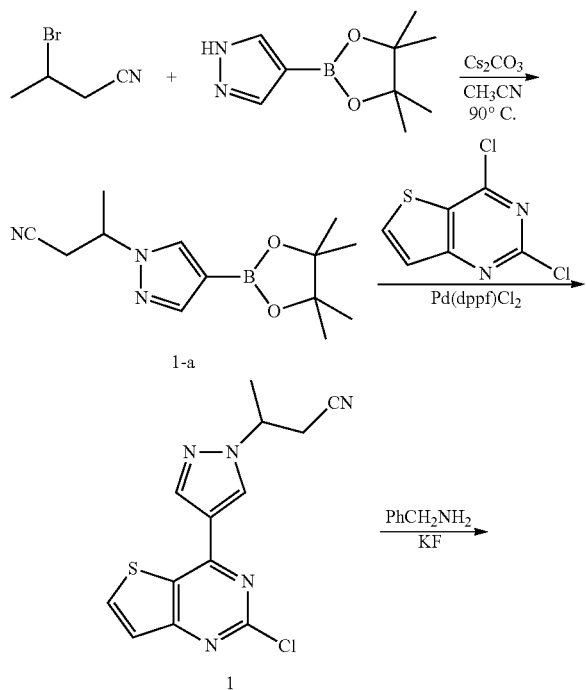

Preparation of Compound 1-a

To a solution of 3-Bromobutanenitrile (2.0 g, 10.3 mmol) and 4-(4,4,5,5-tetramethyl-1,3,2-dioxaborolan-2-yl)-1H-pyrazole (2.3 g, 15.5 mmol) in acetonitrile (100 mL) was added cesium carbonate (13.3 g, 41.2 mmol). The mixture was warmed to 90° C. and stirred for 3 hours. After cooled to the room temperature, the reaction was quenched with water (100 mL). Ethyl acetate (100 mL×3) was used to extract the mixture, the organic layers were combined and washed with water (60 mL×3) and saturated brine (60 mL) in sequence. After dried over anhydrous sodium sulfate, the organic layer was filtrated, the filtrate was concentrated in vacuum to give colorless oil 1-a (2.3 g), the crude product was used directly for the next step. LC-MS (ESI): m/z=262 [M+H]$^+$.

Preparation of Compound 1

Under nitrogen, to a solution of 2,4-dichlorothieno[3,2-d]pyrimidine (265 mg, 1.29 mmol), compound 1-a (261 mg, 1.0 mmol) and Pd(dppf)Cl$_2$ (80 mg, 0.1 mmol) in 1,4-dioxane (10 mL) was added sodium carbonate (318 mg, 3.0 mmol), the mixture was warmed to 65° C. and stirred for 18 hours. The mixture was concentrated in vacuum, the residue was purified by silica column chromatography (petroleum ether:ethyl acetate=2:1) to give compound 1 (250 mg, yield: 82%). LC-MS (ESI): m/z=304 [M+H]$^+$.

Preparation of Compound T-01

A mixture of compound 1 (30 mg, 0.1 mmol), benzylamine (32 mg, 0.3 mmol), potassium fluoride (17 mg, 0.3 mmol), 1,4-dioxane (5 mL) and DMSO (1 mL) was heated to 110° C. and stirred for 20 hours. The mixture was concentrated in vacuum, the residue was diluted with water (50 mL), then extracted with ethyl acetate (50 mL). The organic layer was washed with water (20 mL×2) and saturated brine (20 mL) in sequence, then dried over anhydrous sodium sulfate. After filtration, the filtrate was concentrated in vacuum and the residue was purified by silica column chromatography (dichloromethane:methanol=100:1) to give compound T-01 (20 mg, yield: 53%). LC-MS (ESI): m/z=375 [M+H]$^+$.

$^1$H-NMR (400 MHz, CDCl$_3$) δ: 8.29 (s, 1H), 8.24 (s, 1H), 7.80 (d, J=5.6 Hz, 1H), 7.41-7.42 (m, 2H), 7.31-7.35 (m, 2H), 7.24-7.28 (m, 2H), 5.63 (br, 1H), 4.75 (d, J=6.0 Hz, 2H), 4.73 (m, 1H), 2.93-3.06 (m, 2H), 1.76 (d, J=6.8 Hz, 3H) ppm

Example 2

3-(4-(2-(Phenylamino)thieno[3,2-d]pyrimidin-4-yl)-1H-pyrazol-1-yl)butanenitrile T-02

Synthetic Route:

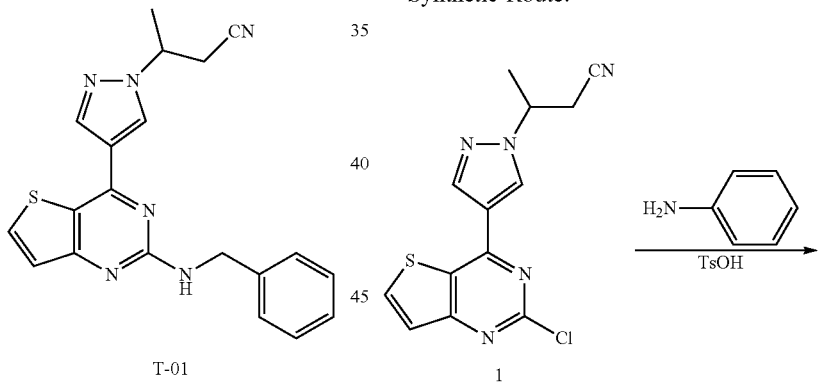

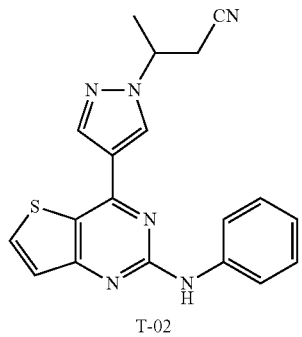

Compound 1 (30 mg, 0.1 mmol), aniline (55 mg, 0.6 mmol) and p-toluene sulfonic acidmonohydrate (76 mg, 0.4 mmol) were dissolved in isobutanol (8 mL), the mixture was heated to 110° C. and stirred for 16 hours. The mixture was concentrated in vacuum, and the residue was diluted with ethanol (30 mL), then washed with saturated aqueous sodium dicarbonate (30 mL), water (30 mL) and saturated brine (30 mL) in sequence. After dried over anhydrous sodium sulfate, the mixture was filtrated, and the filtrate was concentrated in vacuum, the residue was purified by silica column chromatography (petroleum ether:ethyl acetate=1:1) to give compound T-02 (20 mg, yield: 55%). LC-MS (ESI): m/z=361 [M+H]$^+$.

$^1$H-NMR (400 MHz, CDCl$_3$) δ: 8.35 (s, 1H), 8.32 (s, 1H), 7.88 (d, J=5.6 Hz, 1H), 7.75 (d, J=8.0 Hz, 1H), 7.33~7.39 (m, 4H), 7.03~7.06 (m, 1H), 4.75~4.80 (m, 1H), 2.96-3.09 (m, 2H), 1.76 (d, J=6.8 Hz, 3H) ppm Example 3

3-Cyclopentyl-3-(4-(2-(phenylamino)thieno[3,2-d]pyrimidin-4-yl)-1H-pyrazol-1-yl)propanenitrile T-03

Synthetic Route:

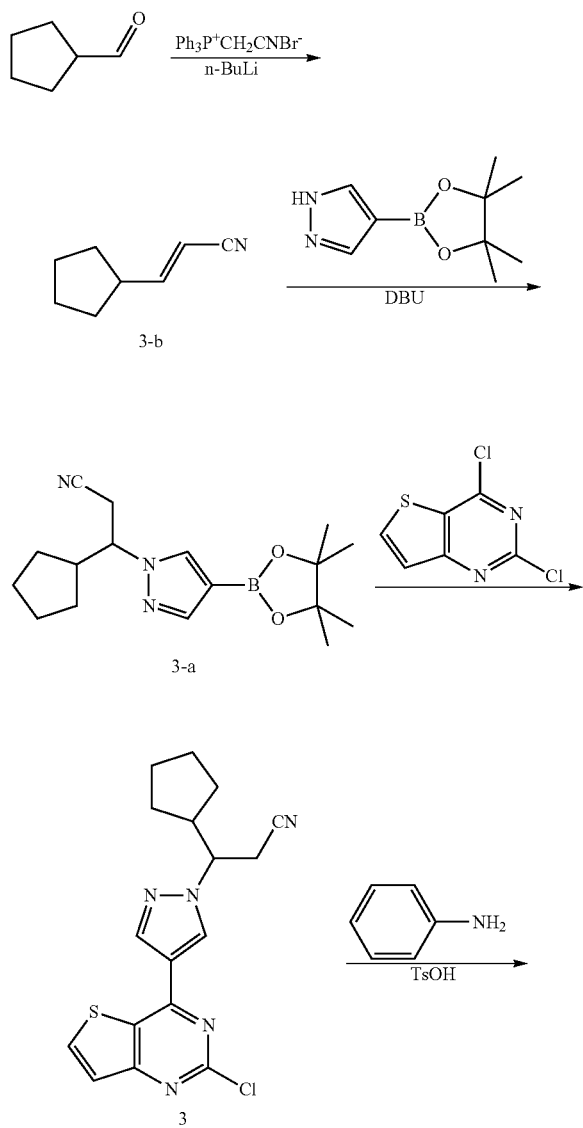

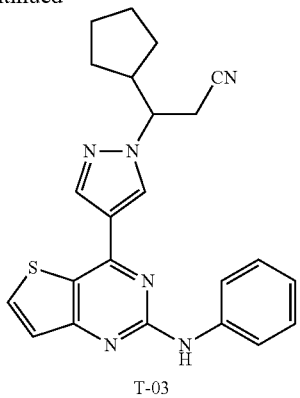

Preparation of Compound 3-b

Under nitrogen, a suspension of (cyanomethyl)triphenylphosphanium bromide (12 g, 31.49 mmol) in anhydrous THF (100 mL) was cooled to 0° C., a solution of 2.5 M n-BuLi in n-hexane (13 mL, 34.64 mmol) was added dropwise. The mixture was stirred at 0° C. for another 30 minutes, then cyclopentane-carbaldehyde (3.1 g, 31.49 mmol) was added, and the mixture was warmed to the room temperature and stirred for further 1 hour. The reaction was quenched with saturated aqueous ammonium chloride solution (50 mL), extracted with ethyl acetate (100 mL×3). The organic layers were combined, washed with water (60 mL×3) and saturated brine (60 mL) in sequence, dried over anhydrous sodium sulfate. The mixture was filtrated, the filtrate was concentrated in vacuum, the residue was purified by silica column chromatography (petroleum ether:ethyl acetate=10:1) to give colorless oil 3-b (1.0 g, yield: 26.2%). LC-MS (ESI): m/z=122 [M+H]$^+$.

Preparation of Compound 3-a

To a solution of compound 3-b (1 g, 8.26 mmol) and 4-(4,4,5,5-tetramethyl-1,3,2-dioxaborolan-2-yl)-1H-pyrazole (2.4 g, 12.39 mmol) in acetonitril (10 mL) was added 1,8-diazabicyclo[5.4.0]undec-7-ene (2.5 g, 16.52 mmol). The mixture was stirred at 60° C. for 18 hours. The mixture was concentrated in vacuum. To the residue was added water (50 mL), then the mixture was extracted with ethyl acetate (100 mL×3). The organic layers were combined, washed with water (60 mL×3) and saturated brine (60 mL) in sequence, dried over anhydrous sodium sulfate. The mixture was filtrated, the filtrate was concentrated in vacuum, the residue was purified by silica column chromatography (petroleum ether:ethyl acetate=3:1) to give yellow oil 3-a (715 mg, yield: 27.5%). LC-MS (ESI): m/z=316 [M+H]$^+$.

Preparation of Compound 3

Under nitrogen, to a suspension of compound 3-a (715 mg, 2.27 mmol), 2,4-dichlorotheino[3,2-d]pyrimidine (465 mg, 2.27 mmol) and sodium carbonate (72 mg, 6.80 mmol) in 1,4-dioxane (4 mL) and water (4 mL) was added Pd(dppf)Cl$_2$ (233 mg, 0.28 mmol). The mixture was stirred at 80° C. for 16 hours. The mixture was concentrated, and to the residue was added water (20 mL). Then the mixture was extracted with methylene chloride (20 mL×3), the organic layers were combined, washed with water (60 mL×3) and saturated brine (60 mL) in sequence, and then dried over anhydrous sodium sulfate, filtrated. The filtrate was concentrated in vacuum, and the residue was purified by silica column chromatography (petroleum ether:ethyl acetate=2:1) to give light yellow solid 3 (330 mg, yield: 40.7%). LC-MS (ESI): m/z=358 [M+H]$^+$.

Preparation of Compound T-03

To a solution of compound 3 (50 mg, 0.14 mmol) and aniline (39 mg, 0.42 mmol) in isobutanol (0.5 mL) was added p-toluene sulfonic acid monohydrate (54 mg, 0.28 mmol). The mixture was heated to 110° C. and stirred for 16 hours. The mixture was then cooled to room temperature, and stirred for further 2 hours. The mixture was filtrated and the solid was purified by preparation HPLC (mobile phase: acetonitrile, water (0.05% trifluoroacetic acid); gradient: 40%-70%-10%) to give compound T-03 (23 mg, yield: 39.7%). LC-MS (ESI): m/z=415 [M+H]⁺.

$^1$H-NMR (400 MHz, CDCl$_3$) δ: 8.37 (d, J=6 Hz, 2H), 7.90 (d, J=6 Hz, 1H), 7.76 (d, J=8 Hz, 2H), 7.37 (m, 3H), 7.05 (t, J=7 Hz, 1H), 4.28 (m, 1H), 3.17 (m, 1H), 2.97 (m, 1H), 2.61 (m, 1H), 1.99 (m, 1H), 1.71 (m, 7H) ppm Example 4

3-Cyclopentyl-3-(4-(2-(pyrimidin-5-ylamino)thieno[3,2-d]pyrimidin-4-yl)-1H-pyrazol-1-yl)propanenitrile T-04

Synthetic Route:

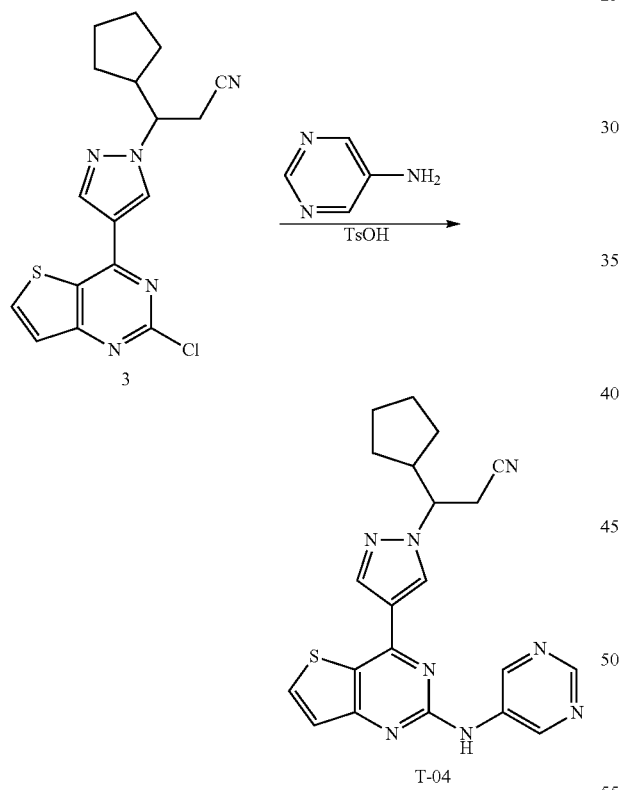

Preparation of Compound T-04

To a solution of compound 3 (50 mg, 0.14 mmol) and 5-aminopyrimidine (40 mg, 0.42 mmol) in isobutanol (0.5 mL) was added p-toluene sulfonic acid monohydrate (53 mg, 0.28 mmol). The mixture was heated to 110° C. and stirred for 16 hours. The mixture was then concentrated in vacuum and the residue was purified by preparation HPLC (mobile phase:acetonitrile, water (0.05% trifluoroacetic acid); gradient: 60%-90%-10%) to give compound T-04 (7 mg, yield: 12%) as a yellow solid. LC-MS (ESI): m/z=417 [M+H]⁺.

$^1$H-NMR (400 MHz, CD$_3$OD) δ: 9.37 (s, 2H), 8.76 (s, 1H), 8.65 (s, 1H), 8.41 (s, 1H), 8.21 (d, J=6 Hz, 1H), 7.43 (d, J=6 Hz, 1H), 4.53 (m, 1H), 3.12~3.28 (m, 2H), 2.56 (m, 1H), 1.97 (m, 1H), 1.41~1.72 (m, 7H) ppm Example 5

2-(1-(Ethylsulfonyl)-3-(4-(2-(phenylamino)thieno[3,2-d]pyrimidin-4-yl)-1H-pyrazol-1-yl)azetidin-3-yl)acetonitrile T-05

Synthetic Route:

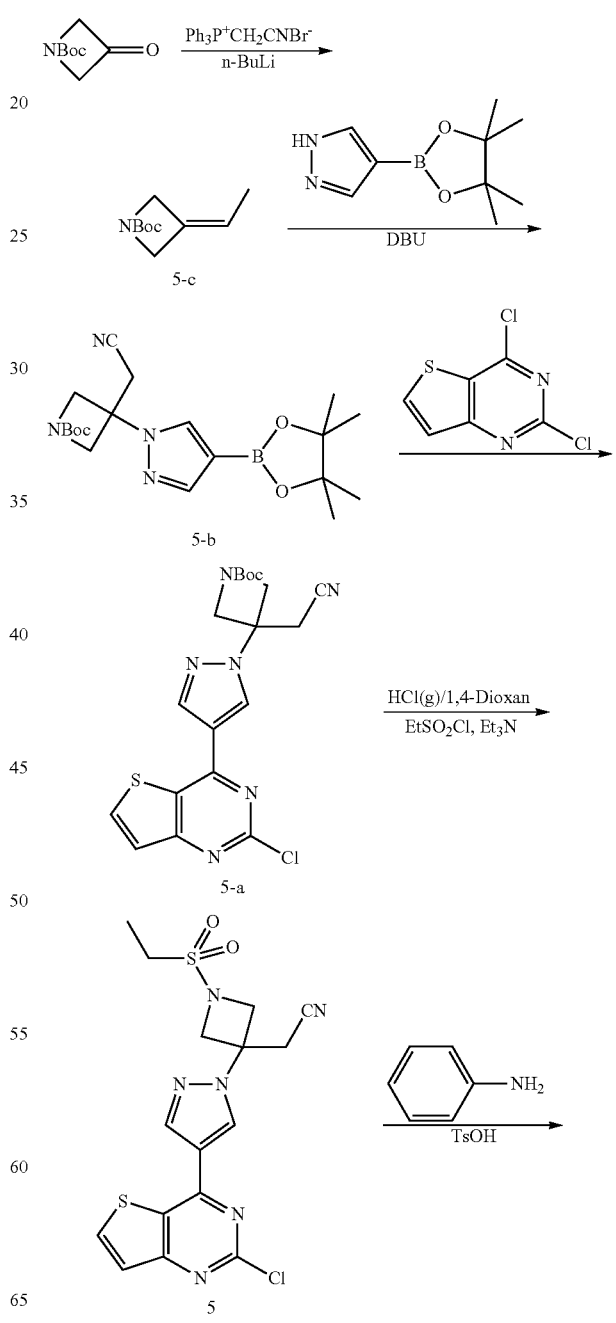

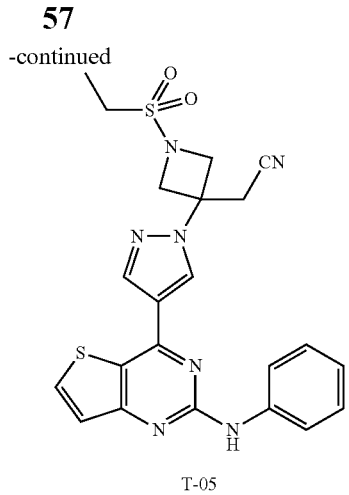

T-05

Preparation of Compound 5-c

Under nitrogen, a suspension of (cyanomethyl)triphenylphosphanium bromide (13.4 g, 35.09 mmol) in anhydrous THF (100 mL) was cooled to 0° C., a solution of 2.5 M n-BuLi in n-hexane (15.5 mL, 38.59 mmol) was added dropwise. The mixture tert-butyl-3-oxoazetidine-1-carboxylate (6.0 g, 35.09 mmol) was added, and the mixture was warmed to room temperature and stirred for further 1 hour. The reaction was quenched with saturated aqueous ammonium chloride solution (50 mL), extracted with ethyl acetate (150 mL×3). The organic layers were combined, washed with water (100 mL×3) and saturated brine (100 mL) in sequence, dried over anhydrous sodium sulfate. The resultant mixture was filtrated, the filtrate was concentrated in vacuum, and the residue was purified by silica column chromatography (petroleum ether:ethyl acetate=5:1) to give a white solid 5-c (2.5 g, yield: 37%). LC-MS (ESI): m/z=217 [M+Na]$^+$.

Preparation of Compound 5-b

To a solution of compound 5-c (6.0 g, 30.93 mmol) and 4-(4,4,5,5-tetramethyl-1,3,2-dioxaborolan-2-yl)-1H-pyrazole (9.2 g, 47.42 mmol) in acetonitril (60 mL) was added 1,8-diazabicyclo[5.4.0]undec-7-ene (10.0 g, 65.79 mmol). The mixture was stirred at 60° C. for 18 hours. The mixture was concentrated in vacuum. To the residue was added 1 N aqueous hydrogen chloride solution (100 mL), then the mixture was extracted with ethyl acetate (100 mL×3). The organic layers were combined, washed with water (60 mL×3) and saturated brine (60 mL) in sequence, dried over anhydrous sodium sulfate. The resultant mixture was filtrated, the filtrate was concentrated in vacuum, and the residue was purified by silica column chromatography (petroleum ether:ethyl acetate=3:1) to give a white solid 5-b (7.1 g, yield: 59.2%). LC-MS (ESI): m/z=389 [M+H]$^+$.

Preparation of Compound 5-a

Under nitrogen, to a suspension of compound 5-b (4.0 g, 10.3 mmol), 2,4-dichlorotheino[3,2-d]pyrimidine (2.52 g, 12.4 mmol) and sodium carbonate (3.3 g, 31.2 mmol) in 1,4-dioxane (25 mL) and water (25 mL) was added Pd(dppf)Cl$_2$ (1.1 g, 1.5 mmol). The mixture was stirred at 80° C. for 16 hours. The mixture was concentrated in vacuum. To the residue was added water (200 mL), then the mixture was extracted with methylene chloride (200 mL×3). The organic layers were combined, washed with water (100 mL×3) and saturated brine (100 mL) in sequence, and then dried over anhydrous sodium sulfate, filtrated. The filtrate was concentrated in vacuum, and the residue was purified by silica column chromatography (petroleum ether:ethyl acetate=2:1) to give a light yellow solid 5-a (3.2 g, yield: 63%). LC-MS (ESI): m/z=43 [M+H]$^+$.

Preparation of Compound 5

To a solution of compound 5-a (310 mg, 0.72 mmol) in dichloromethane (2 mL) was added a solution of hydrogen chloride in 1,4-dioxane (4 N, 1 mL), the mixture was stirred at room temperature for 16 hours. The resultant mixture was concentrated and to the residue was added dichloromethane (10 mL) and triethylamine (2 mL). The mixture was then cooled to 0° C., ethanesulfonyl chloride (154 mg, 1.37 mmol) was added dropwise, and after completion of dropping, the mixture was stirred at 0° C. for further 30 minutes. To the resultant mixture was added water (5 mL), and the mixture was extracted with dichloromethane (10 mL×3). The organic layers were combined, washed with water (10 mL×3) and saturated brine (10 mL) in sequence, dried over anhydrous sodium sulfate. The mixture was filtrated, the filtrate was concentrated in vacuum, the residue was purified by silica column chromatography (petroleum ether:ethyl acetate=2:1) to give compound 5 (108 mg, yield: 34%). LC-MS (ESI): m/z=423 [M+H]$^+$.

Preparation of Compound T-05

To a solution of compound 5 (50 mg, 0.12 mmol) and aniline (33 mg, 0.36 mmol) in isobutanol (1 mL) was added p-toluene sulfonic acid monohydrate (45 mg, 0.24 mmol). The mixture was heated to 110° C. and stirred for 16 hours. The mixture was then concentrated under reduced pressure and the residue was purified by preparation HPLC (mobile phase:acetonitrile, water (0.05% trifluoroacetic acid); gradient: 60%-90%-10%) to give a yellow solid T-05 (21 mg, yield: 37%). LC-MS (ESI): m/z=480 [M+H]$^+$.

$^1$H-NMR (400 MHz, CDCl$_3$) δ: 8.47 (s, 1H), 8.39 (s, 1H), 7.92 (d, J=5 Hz, 1H), 7.75 (d, J=8 Hz, 2H), 7.38 (m, 3H), 7.06 (t, J=7 Hz, 1H), 4.64 (d, J=9 Hz, 2H), 4.26 (d, J=9 Hz, 2H), 3.39 (s, 2H), 3.10 (q, J=7 Hz, 2H), 1.43 (t, J=7 Hz, 3H) ppm Example 6

2-(1-(Ethylsulfonyl)-3-(4-(2-((tetrahydro-2H-pyran-4-yl)amino)thieno[3,2-d]pyrimidin-4-yl)-1H-pyrazol-1-yl)azetidin-3-yl)acetonitrile T-06

Synthetic Route:

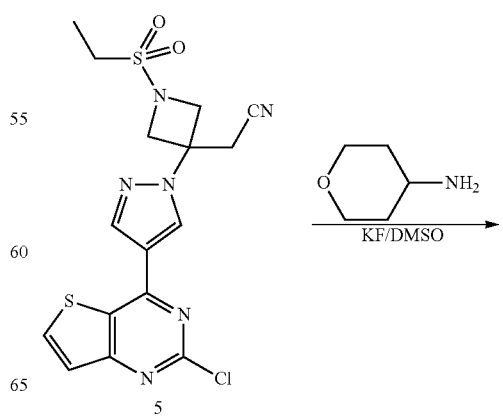

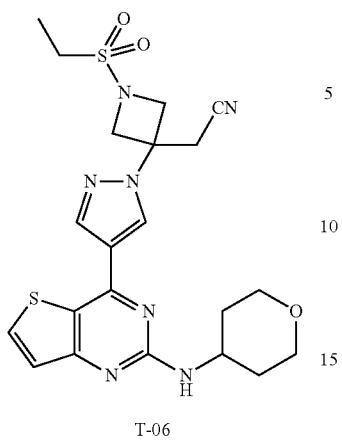

T-06

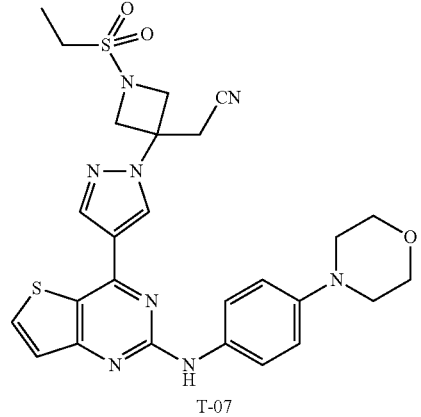

T-07

Compound 5 (150 mg, 0.36 mmol), 4-aminotetrahydropyran (90 mg, 0.89 mmol) and anhydrouspotassium fluoride (31 mg, 0.54 mmol) were suspended in DMSO (2 mL), the mixture was stirred at 80° C. for 16 hours. The mixture was then cooled to room temperature and diluted with dichloromethane (50 mL), after washed with water (20 mL×2), the organic layer was dried over anhydrous sodium sulfate. The mixture was filtered, the filtrate was concentrated in vacuum, and the residue was purified by preparation TLC (petroleum ether:ethyl acetate=2:1) to give compound T-06 (18 mg, yield: 11%). LC-MS (ESI): m/z=488 [M+H]$^+$.

$^1$H-NMR (400 MHz, CDCl$_3$) δ: 8.41 (s, 1H), 8.34 (s, 1H), 7.83 (d, J=5 Hz, 1H), 7.25 (d, J=5 Hz, 1H), 5.10 (br, 1H), 4.63 (d, J=9 Hz, 2H), 4.24 (d, J=9 Hz, 2H), 4.19 (m, 1H), 4.05 (m, 2H), 3.55 (m, 2H), 3.41 (s, 2H), 3.11 (q, J=7 Hz, 2H), 2.10 (m, 2H), 1.61 (m, 2H), 1.42 (t, J=7 Hz, 3H) ppm Example 7

2-(1-(Ethylsulfonyl)-3-(4-(2-((4-morpholinophenyl)amino)thieno[3,2-d]pyrimidin-4-yl)-1H-pyrazol-1-yl)azetidin-3-yl)acetonitrile T-07

Synthetic Route:

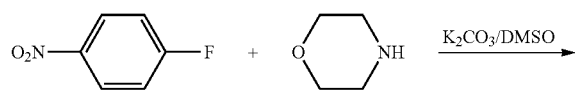

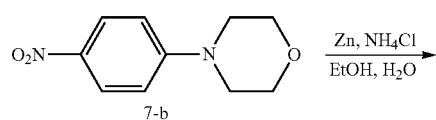

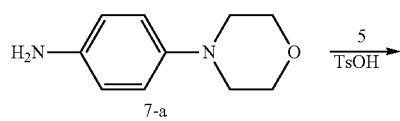

Preparation of Compound 7-b

1-Flouro-4-nitrobenzene (2.9 g, 20.56 mmol) and morpholine (3.6 g, 41.13 mmol) were dissolved in DMSO (15 mL), potassium carbonate was added and the mixture was stirred at 80° C. for 18 hours. After cooled to room temperature, the mixture was poured into water (100 mL), there was yellow solid precipitated. After filtration, the filter cake was washed with water. The filter cake was then dried in vacuum for 24 hours to give compound 7-b (3.5 g, yield: 82%), which was used directly for the next step without purification.

Preparation of Compound 7-a

Compound 7-b (1.5 g, 7.21 mmol) and ammonium chloride (1.0 g, 18.03 mmol) were dissolved in 50% ethanol-water (20 mL), Zn-powder (1.2 g, 18.03 mmol) was then added. The mixture was refluxed for 30 minutes. After cooled to room temperature, the mixture was filtrated. The filter cake was washed with ethanol (10 mL), the combined filtrate were concentrated under reduced pressure. The residue was diluted with water (50 mL) and extracted with ethyl acetate (50 mL×3), the organic layer was dried over anhydrous sodium sulfate. After filtration, the filtrate was concentrated under reduced pressure to give light brown solid 7-a (1.1 g, yield: 86%), which was used directly for the next step without purification. LC-MS (ESI): m/z=179 [M+H]$^+$.

Preparation of Compound T-07

Compound 5 (150 mg, 0.36 mmol) and compound 7-a (190 mg, 1.07 mmol) were dissolved in isobutanol (2 mL), p-toluene sulfonic acid monohydrate (135 mg, 0.71 mmol) was added. The mixture was heated to 110° C. and stirred for 16 hours. After cooled to room temperature, the mixture was stirred for further 30 minutes. There was solid precipitated, after filtration, the solid was purified by preparation HPLC (mobile phase:acetonitrile, water (0.05% trifluoroacetic acid); gradient: 50%-80%-10%) to give yellow solid T-07 (21 mg, yield: 26%). LC-MS (ESI): m/z=565 [M+H]$^+$.

$^1$H-NMR (400 MHz, CDCl$_3$) δ: 8.44 (s, 1H), 8.35 (s, 1H), 7.89 (d, J=5 Hz, 1H), 7.61 (d, J=9 Hz, 2H), 7.32 (d, J=5 Hz, 1H), 6.96 (d, J=9 Hz, 2H), 4.64 (d, J=9 Hz, 2H), 4.24 (d, J=9 Hz, 2H), 3.89 (m, 4H), 3.41 (s, 2H), 3.08~3.16 (m, 61H), 1.43 (t, J=7 Hz, 3H) ppm

Example 8

2-(1-(Ethylsulfonyl)-3-(4-(2-((4-(2-morpholinoethoxy)phenyl)amino)thieno[3,2-d]pyrimidin-4-yl)-1H-pyrazol-1-yl)azetidin-3-yl)acetonitrile T-08

Synthetic Route:

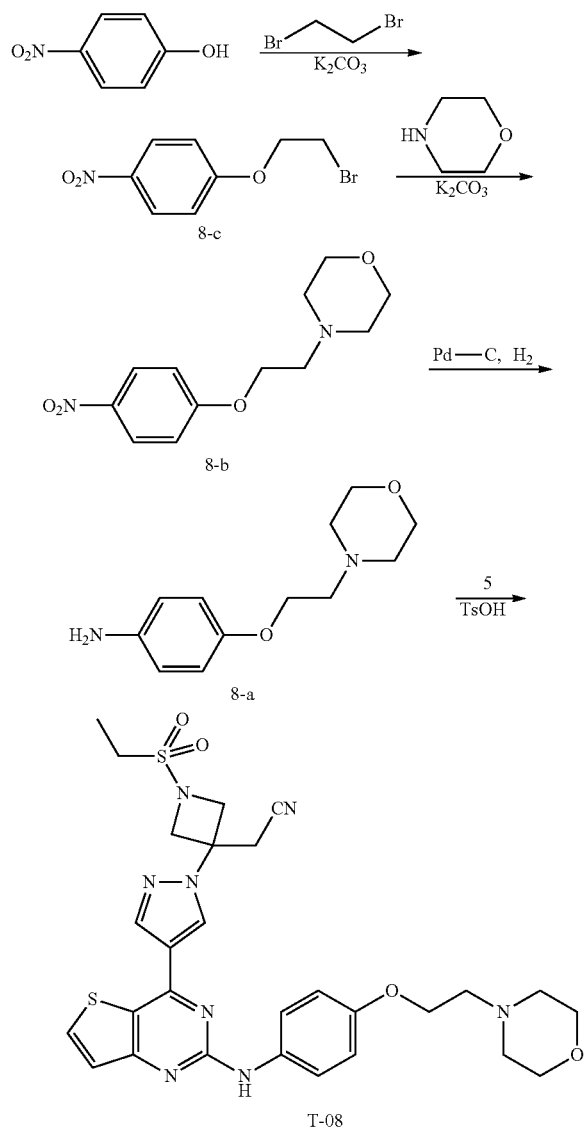

Preparation of Compound 8-c p-Nitrophenol (6.0 g, 43.16 mmol) and 1,2-dibromoethane (16.0 g, 86.02 mmol) were dissolved in acetone (60 mL), potassium carbonate (9.0 g, 65.22 mmol) was then added. The mixture was refluxed for 3 hours, then cooled to room temperature. The resultant mixture was filtrated and the filter cake was washed with acetone (30 mL). The filtrate was concentrated under reduced pressure, and the residue was diluted with water (50 mL), then extracted with ethyl acetate (50 mL×3). The organic layers were combined, washed with water (50 mL×3) and saturated brine (50 mL). After dried over anhydrous sodium sulfate, the mixture was filtrated, and the filtrate was concentrated in vacuum, the residue was purified by silica column chromatography (petroleum ether: ethyl acetate=5:1) to give light yellow solid 8-c (2.1 g, yield: 19%).

Preparation of Compound 8-b

Compound 8-c (1.0 g, 4.08 mmol) and morpholine (702 mg, 8.16 mmol) were dissolved in acetonitrile (5 mL), potassium carbonate (1.2 g, 8.16 mmol) was added. The mixture was refluxed for 3 hours, and then cooled to room temperature, after filtration, the filter cake was washed with ethyl acetate (30 mL). The filtrate was concentrated under reduced pressure, the residue was diluted with water (50 mL) and extracted with ethyl acetate (50 mL×3). The organic layers were combined and washed with water (50 mL×3) and saturated brine (50 mL) in sequence. After dried over anhydrous sodium sulfate, the mixture was filtrated, and the filtrate was concentrated in vacuum to give light yellow solid 8-b (900 mg), which was used directly for the next step without further purification.

Preparation of Compound 8-a

Under hydrogen (1 atm), to a solution of compound 8-b (900 mg, 3.57 mmol) in ethanol (50 mL) was added 10% Pd—C (0.5 g). The mixture was stirred at 25° C. for 18 hours, and then filtrated. The filtrate was concentrated under reduced pressure to give light yellow oil 8-a (760 mg, yield: 96%), which was used directly for the next step without purification.

Preparation of Compound T-08

Compound 8-a (105 mg, 0.47 mmol) and compound 5 (100 mg, 0.24 mmol) were dissolved in n-butanol (2 mL), p-toluene sulfonic acid monohydrate (68 mg, 0.36 mmol) was added. The mixture was heated to 110° C. and stirred for 16 hours, after cooled to room temperature, the mixture was stirred for further 30 minutes. The resultant mixture was filtered, the solid was purified by preparation HPLC (mobile phase:acetonitrile, water (0.05% trifluoroacetic acid); gradient: 40%-70%-10%) to give yellow solid T-08 (51 mg, yield: 35%). LC-MS (ESI): m/z=609 [M+H]$^+$.

$^1$H-NMR (400 MHz, CDCl$_3$) δ: 8.43 (s, 1H), 8.35 (s, 1H), 7.86 (d, J=5 Hz, 1H), 7.61 (d; J=9 Hz, 2H), 7.31 (d, J=5 Hz, 1H), 7.19 (s, 1H), 6.93 (d, J=9 Hz, 2H), 4.63 (d, J=9 Hz, 2H), 4.16 (t, J=5 Hz, 2H), 3.78 (t, J=4 Hz, 4H), 3.39 (s, 2H), 3.09 (q, J=6 Hz, 2H), 2.89 (t, J=4 Hz, 2H), 2.69 (s, 4H), 1.43 (t, J=6 Hz, 3H) ppm

Example 9

2-(1-(Ethylsulfonyl)-3-(4-(2-((4-(2-(pyrrolidin-1-yl)ethoxy)phenyl)amino)thieno[3,2-d]pyrimidin-4-yl)-1H-pyrazol-1-yl)azetidin-3-yl)acetonitrile T-09

Synthetic Route:

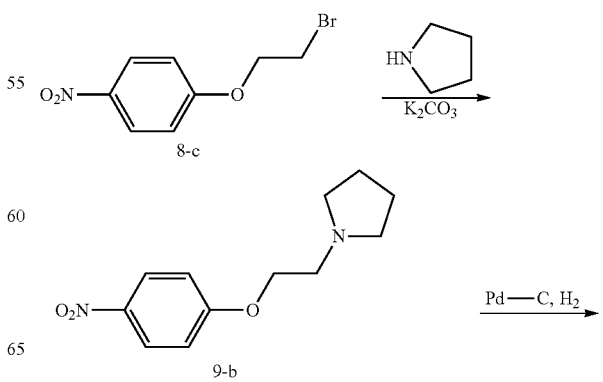

-continued

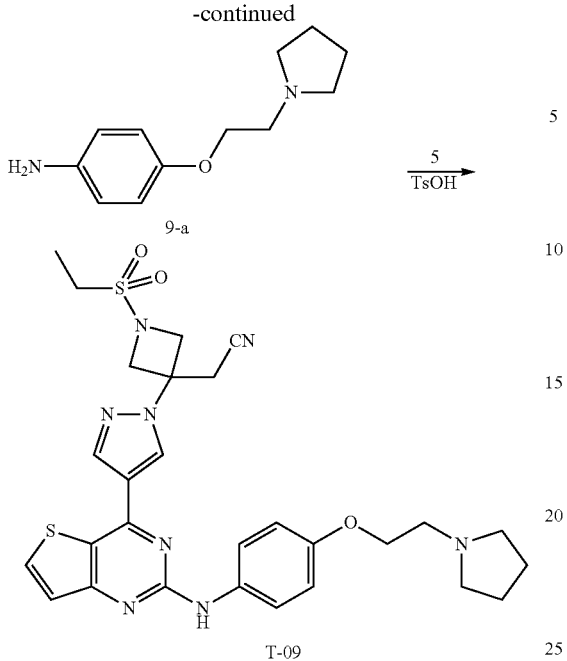

T-09

Preparation of Compound 9-b

Compound 8-c (1.0 g, 4.08 mmol) and pyrrolidine (580 mg, 8.16 mmol) were dissolved in acetonitrile (50 mL), potassium carbonate (1.2 g, 8.16 mmol) was added. The mixture was refluxed for 3 hours, and then cooled to room temperature. After filtration, the filter cake was washed with ethyl acetate (30 mL). The filtrate was concentrated under reduced pressure, and the residue was diluted with water (50 mL) and extracted with ethyl acetate (50 mL×3). The organic layers were combined and washed with water (50 mL×3) and saturated brine (50 mL) in sequence. After dried over anhydrous sodium sulfate, the mixture was filtrated, and the filtrate was concentrated in vacuum to give yellow oil 9-b (1.0 g), which was used directly for the next step without further purification.

Preparation of Compound 9-a

Under hydrogen (1 atm), to a solution of compound 9-b (1.0 g, 4.24 mmol) in ethanol (50 mL) was added 10% Pd—C (0.5 g). The mixture was stirred at 25° C. for 18 hours, and then filtrated, the filtrate was concentrated under reduced pressure to give light yellow oil 9-a (780 mg, yield: 90%), which was used directly for the next step without purification.

Preparation of Compound T-09

Compound 9-a (73 mg, 0.35 mmol) and compound 5 (50 mg, 0.12 mmol) were dissolved in n-butanol (2 mL), p-toluene sulfonic acid monohydrate (45 mg, 0.24 mmol) was added. The mixture was heated to 110° C. and stirred for 16 hours. After cooled to room temperature, the mixture was stirred for further 30 minutes. The resultant mixture was filtrated, and the solid was purified by preparation HPLC (mobile phase:acetonitrile, water (0.05% trifluoroacetic acid); gradient: 50%-80%-10%) to give yellow solid T-09 (51 mg, yield: 36%). LC-MS (ESI): m/z=593 [M+H]$^+$.

$^1$H-NMR (400 MHz, MeOD) δ: 8.60 (m, 1H), 8.20 (m, 2H), 7.55 (m, 1H), 7.22 (m, 1H), 7.02 (m, 2H), 4.61 (d, J=9 Hz, 2H), 4.34 (m, 2H), 4.26 (d, J=9 Hz, 2H), 3.77 (m, 2H), 3.68 (m, 2H), 3.60 (s, 2H), 3.17~3.24 (m, 4H), 2.04~2.20 (m, 4H), 1.38 (t, J=6 Hz, 3H) ppm Example 10

2-(3-(4-(2-((4-(1H-1,2,4-Triazol-1-yl)phenyl)amino)thieno[3,2-d]pyrimidin-4-yl)-1H-pyrazol-1-yl)-1-(ethylsulfonyl)azetidin-3-yl)acetonitrile T-10

Synthetic Route:

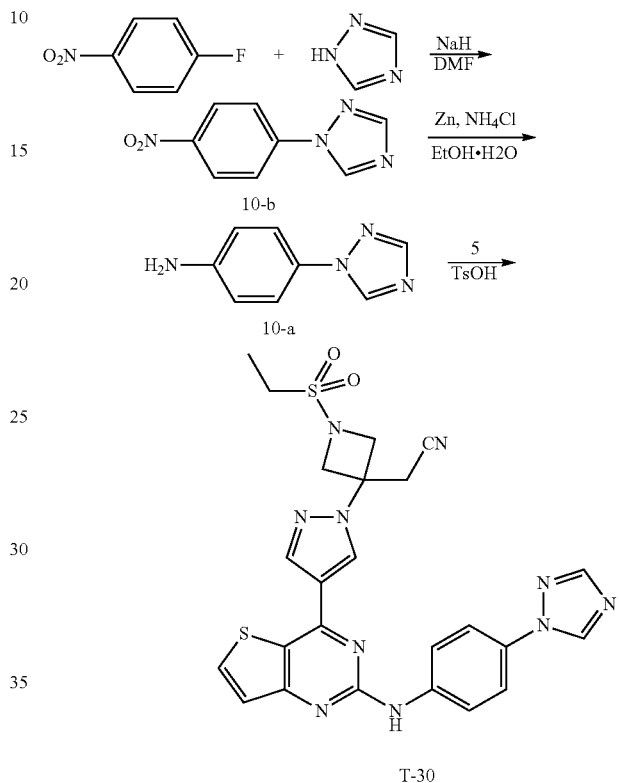

T-30

Preparation of Compound 10-b

At 0° C., to a solution of 1,2,4-triazole (2.7 g, 39.01 mmol) in DMF (50 mL) was added sodium hydride (1.6 g, 39.01 mmol). The mixture was stirred for 30 minutes and 1-flouro-4-nitrobenzene (5.0 g, 35.46 mmol) was added, and the resultant mixture was stirred for further 2 hours. Water (150 mL) was added slowly to the mixture, there was solid precipitated. After filtration, the filter cake was washed with water (50 mL×3), and the solid was dried in vacuum for 8 hours to give yellow solid 10-b (6.2 g, yield: 91%), which was used for the next step without further purification. LC-MS (ESI): m/z=191 [M+H]$^+$.

Preparation of Compound 10-a

Compound 10-b (3.0 g, 15.78 mmol) and ammonium chloride (2.1 g, 39.62 mmol) were dissolved in 50% ethanol-water (60 mL). Zn-powder (2.6 g, 40 mmol) was then added. The mixture was refluxed for 30 minutes. After cooled to room temperature, the mixture was filtrated, and the filter cake was washed with ethanol (10 mL). The combined filtrate were concentrated under reduced pressure, and the residue was diluted with water (100 mL) and extracted with ethyl acetate (100 mL×3). The organic layer was dried over anhydrous sodium sulfate. After filtration, the filtrate was concentrated under reduced pressure to give yellow solid 10-a (1.1 g, yield: 81%), which was used directly for the next step without purification. LC-MS (ESI): m/z=161 [M+H]$^+$.

Preparation of Compound T-10

Compound 10-a (114 mg, 0.71 mmol) and compound 5 (100 mg, 0.24 mmol) were dissolved in n-butanol (2 mL), p-toluene sulfonic acid monohydrate (180 mg, 0.95 mmol) was added. The mixture was heated to 110° C. and stirred for 16 hours. After cooled to room temperature, the mixture was stirred for further 30 minutes, and there was solid precipitated. After filtration, the solid was purified by preparation HPLC (mobile phase:acetonitrile, water (0.05% trifluoroacetic acid); gradient: 60%-90%-10%) to give yellow solid T-10 (25 mg, yield: 19%). LC-MS (ESI): m/z=547 [M+H]$^+$.

$^1$H-NMR (400 MHz, CDCl$_3$) δ: 8.58 (d, J=4 Hz, 2H), 8.41 (s, 1H), 8.13 (s, 1H), 8.09 (d, J=6 Hz, 1H), 7.92 (d, J=9 Hz, 2H), 7.71 (d, J=9 Hz, 2H), 7.49 (d, J=6 Hz, 1H), 4.66 (d, J=9 Hz, 2H), 4.25 (d, J=9 Hz, 2H), 3.45 (s, 2H), 3.10 (q, J=6 Hz, 2H), 1.43 (t, J=6 Hz, 3H) ppm Example 11

2-(3-(4-(2-((4-(1H-Pyrazol-1-yl)phenyl)amino)thieno[3,2-d]pyrimidin-4-yl)-1H-pyrazol-1-yl)-1-(ethylsulfonyl)azetidin-3-yl)acetonitrile T-11

Synthetic Route:

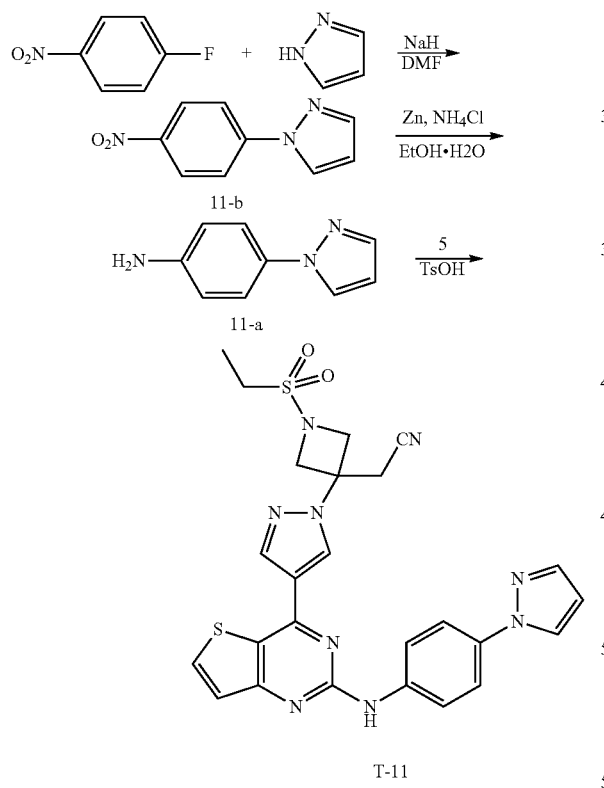

T-11

Preparation of Compound 11-b

At 0° C., to a solution of pyrazole (2.7 g, 39.01 mmol) in DMF (50 mL) was added sodium hydride (1.6 g, 39.01 mmol), the mixture was stirred for 30 minutes. Then 1-flouro-4-nitrobenzene (5.0 g, 35.46 mmol) was added, and the resultant mixture was stirred for further 2 hours. Water (250 mL) was added slowly to the mixture, and there was solid precipitated. After filtration, the filter cake was washed with water (50 mL×3), and the solid was dried in vacuum for 8 hours to give yellow solid 11-b (6 g, yield: 90%), which was used for the next step without further purification.

Preparation of Compound 11-a

Compound 11-b (1.0 g, 5.29 mmol) and ammonium chloride (0.7 g, 13.23 mmol) were dissolved in 50% ethanol-water (20 mL). Zn-powder (0.9 g, 13.23 mmol) was then added. The mixture was refluxed for 30 minutes. After cooled to room temperature, the mixture was filtrated, and the filter cake was washed with ethanol (10 mL). The combined filtrate were concentrated under reduced pressure, and the residue was diluted with water (50 mL) and extracted with ethyl acetate (50 mL×3). The organic layer was dried over anhydrous sodium sulfate. After filtration, the filtrate was concentrated under reduced pressure to give yellow solid 11-a (670 mg, yield: 80%), which was used directly for the next step without purification. LC-MS (ESI): m/z=160 [M+H]$^+$.

Preparation of Compound T-11

Compound 11-a (79 mg, 0.50 mmol) and compound 5 (70 mg, 0.17 mmol) were dissolved in n-butanol (2 mL), p-toluene sulfonic acid monohydrate (95 mg, 0.50 mmol) was added. The mixture was heated to 110° C. and stirred for 16 hours. After cooled to room temperature, the mixture was stirred for further 30 minutes, and there was solid precipitated. After filtration, the solid was purified by preparation HPLC (mobile phase:acetonitrile, water (0.05% trifluoroacetic acid); gradient: 60%-90%-10%) to give yellow solid T-11 (31 mg, yield: 34%). LC-MS (ESI): m/z=546 [M+H]$^+$.

$^1$H-NMR (400 MHz, CDCl$_3$) δ: 8.49 (s, 1H), 8.40 (s, 1H), 7.94 (d, J=6 Hz, 1H), 7.91 (d, J=2 Hz, 1H), 7.84 (d, J=9 Hz, 2H), 7.68~7.73 (m, 3H), 7.40 (d, J=6 Hz, 2H), 6.47 (t, J=2 Hz, 1H), 4.65 (d, J=9 Hz, 2H), 4.26 (d, J=9 Hz, 2H), 3.43 (s, 2H), 3.10 (q, J=6 Hz, 2H), 1.43 (t, J=6 Hz, 3H) ppm Example 12

2-(1-(Ethylsulfonyl)-3-(4-(2-((4-(methylsulfonyl)phenyl)amino)thieno[3,2-d]pyrimidin-4-yl)-1H-pyrazol-1-yl)azetidin-3-yl)acetonitrile T-12

Synthetic Route:

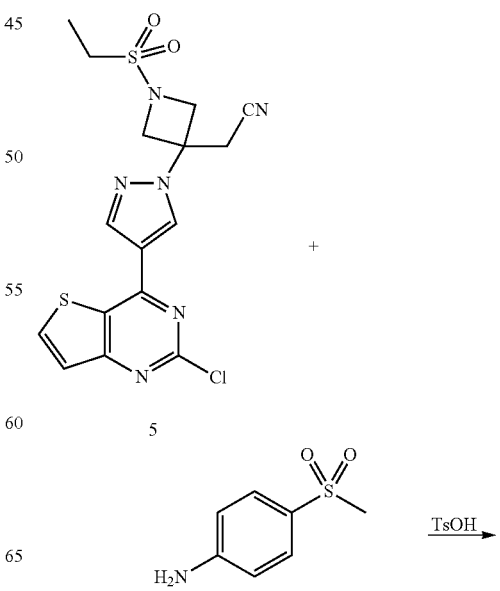

-continued

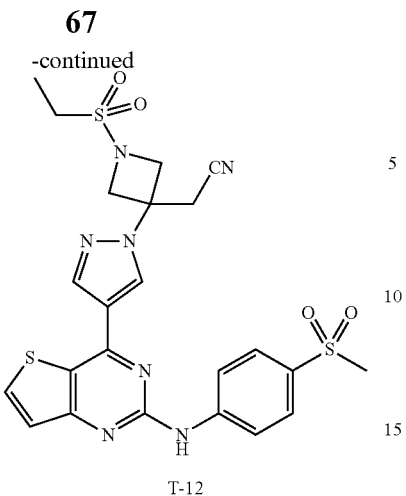

T-12

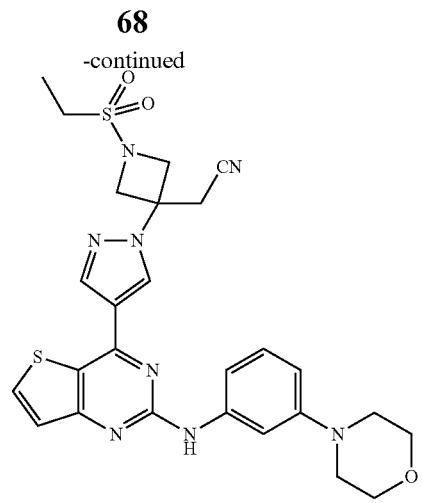

T-13

4-Methylsulfonylaniline (98 mg, 0.57 mmol) and compound 5 (80 mg, 0.19 mmol) were dissolved in n-butanol (2 mL), p-toluene sulfonic acid monohydrate (72 mg, 0.38 mmol) was added. The mixture was heated to 110° C. and stirred for 16 hours. After cooled to room temperature, the mixture was stirred for further 30 minutes, and there was solid precipitated. After filtration, the solid was purified by preparation HPLC (mobile phase:acetonitrile, water (0.05% trifluoroacetic acid); gradient: 65%-95%-10%) to give white solid T-12 (30 mg, yield: 28%). LC-MS (ESI): m/z=558 [M+H]$^+$.

$^1$H-NMR (400 MHz, CDCl$_3$) δ: 8.51 (s, 1H), 8.40 (s, 1H), 7.92~8.00 (m, 6H), 7.44 (d, J=6 Hz, 1H), 4.66 (d, J=9 Hz, 2H), 4.26 (d, J=9 Hz, 2H), 3.44 (s, 2H), 3.13 (q, J=6 Hz, 2H), 3.07 (m, 3H), 1.44 (t, J=6 Hz, 3H) ppm Example 13

2-(1-(Ethylsulfonyl)-3-(4-(2-((3-morpholinophenyl)amino)thieno[3,2-d]pyrimidin-4-yl)-1H-pyrazol-1-yl)azetidin-3-yl)acetonitrile T-13

Synthetic Route:

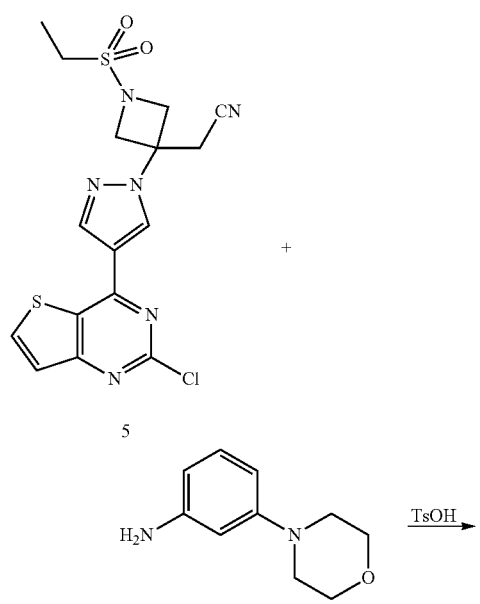

3-(4-Morpholinyl)aniline (102 mg, 0.57 mmol) and compound 5 (80 mg, 0.19 mmol) were dissolved in n-butanol (2 mL), p-toluene sulfonic acid monohydrate (180 mg, 0.95 mmol) was added. The mixture was heated to 110° C. and stirred for 16 hours. After cooled to room temperature, the mixture was stirred for further 30 minutes, and there was solid precipitated. After filtration, the solid was purified by preparation HPLC (mobile phase:acetonitrile, water (0.05% trifluoroacetic acid); gradient: 60%-90%-10%) to give white solid T-13 (15 mg, yield: 14%). LC-MS (ESI): m/z=565 [M+H]$^+$.

$^1$H-NMR (400 MHz, CDCl$_3$) δ: 10.2 (br, 1H), 8.56 (s, 1H), 8.36 (s, 1H), 8.04 (d, J=6 Hz, 1H), 7.61 (d, J=6 Hz, 2H), 7.28~7.36 (m, 3H), 6.75 (m, 1H), 4.63 (d, J=9 Hz, 2H), 4.25 (d, J=9 Hz, 2H), 3.90 (m, 4H), 3.41 (s, 2H), 3.24 (m, 2H), 3.08 (q, J=6 Hz, 2H), 1.43 (t, J=7 Hz, 3H) ppm Example 14

2-(1-(Ethylsulfonyl)-3-(4-(2-(pyrimidin-5-ylamino)thieno[3,2-d]pyrimidin-4-yl)-1H-pyrazol-1-yl)azetidin-3-yl)acetonitrile T-14

Synthetic Route:

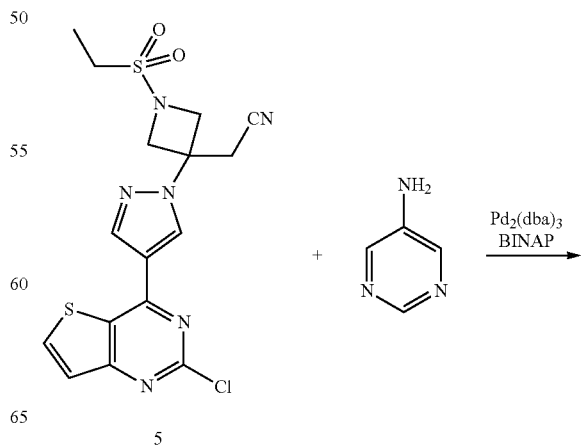

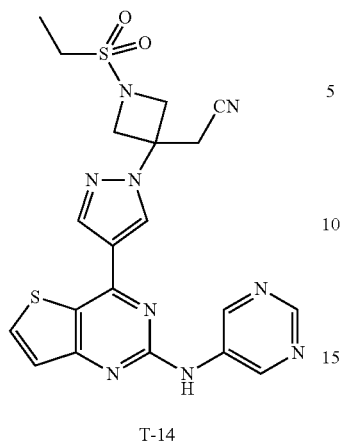

T-14

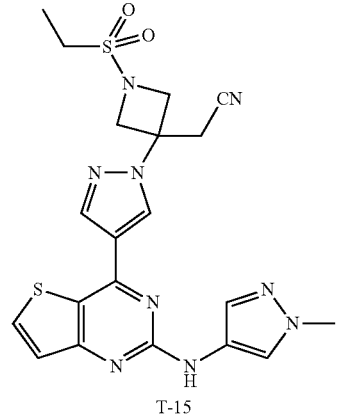

T-15

Under nitrogen, to a suspension of compound 5 (130 mg, 0.31 mmol), 5-amino pyrimidine (89 mg, 0.94 mmol) and cesium carbonate (102 mg, 0.32 mmol) in 1,4-dioxane (4 mL) were added $Pd_2(dba)_3$ (47 mg, 0.05 mmol) and BINAP (34 mg, 0.05 mmol). The mixture was heated to 120° C. by microwave and stirred for 60 minutes. After cooled to room temperature, the mixture was diluted with dichoromethane (20 mL), and then was filtrated, the filtrate was concentrated under reduced pressure. The residue was diluted with methanol (5 mL), and there was solid precipitated. After filtration, the solid was purified by preparation HPLC (mobile phase: acetonitrile, water (0.05% trifluoroacetic acid); gradient: 40%-70%-10%) to give light yellow solid T-14 (16 mg, yield: 10%). LC-MS (ESI): m/z=482 [M+H]$^+$.

$^1$H-NMR (400 MHz, CDCl$_3$) δ: 9.29 (s, 2H), 8.94 (s, 1H), 8.55 (s, 1H), 8.40 (br, 1H), 8.39 (s, 1H), 8.02 (d, J=6 Hz, 1H), 7.42 (d, J=6 Hz, 1H), 4.67 (d, J=9 Hz, 2H), 4.27 (d, J=9 Hz, 2H), 3.44 (s, 2H), 3.11 (q, J=7 Hz, 2H), 1.43 (t, J=7 Hz, 3H) ppm Example 15

2-(1-(Ethylsulfonyl)-3-(4-(2-((1-methyl-1H-pyrazol-4-yl)amino)thieno[3,2-d]pyrimidin-4-yl)-1H-pyrazol-1-yl)azetidin-3-yl)acetonitrile T-15

Synthetic Route:

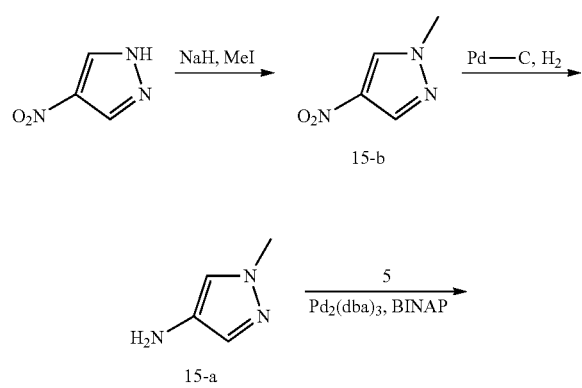

Preparation of Compound 15-b

At 0° C., to a solution of 4-nitropyrazole (3.3 g, 29.2 mmol) in anhydrous THF (30 mL) was added sodium hydride (1.3 g, 32.1 mmol). After the mixture was stirred for 1 hour, iodomethane (2 mL) was added slowly, and the resultant mixture was stirred for further 2 hours. Then the mixture was poured into ice water (100 mL), extracted with ethyl acetate (50 mL×3), and the organic layer was dried over anhydrous sodium sulfate. The mixture was filtrated, the filtrate was concentrated under reduced pressure. The residue was added into a component solvent (20 mL) of petroleum ether and ethyl acetate (20:1), stirred, and there was solid precipitated. After filtration, the solid was dried in vacuum for 8 hours to give white solid 15-b (2.6 g, yield: 70%), which was used directly for the next step without further purification. LC-MS (ESI): m/z=128 [M+H]$^+$.

Preparation of Compound 15-a

Under hydrogen (1 atm), to a solution of compound 15-b (1.0 g, 7.87 mmol) in ethanol (15 mL) was added 10% Pd—C (0.2 g). The mixture was stirred at 25° C. for 18 hours, and then filtrated, the filtrate was concentrated under reduced pressure, the residue was purified by silica column chromatography (petroleum ether:ethyl acetate=1:1) to give red oil 15-a (700 mg, yield: 92%).

Preparation of Compound T-15

Under nitrogen, to a suspension of compound 5 (200 mg, 0.47 mmol), compound 15-a (138 mg, 1.42 mmol) and cesium carbonate (309 mg, 0.95 mmol) in 1,4-dioxane (4 mL) were added $Pd_2(dba)_3$ (55 mg, 0.06 mmol) and BINAP (40 mg, 0.06 mmol). The mixture was heated to 120° C. by microwave and stirred for 60 minutes. After cooled to room temperature, the mixture was diluted with dichoromethane (20 mL), and then filtrated, the filtrate was concentrated under reduced pressure, the residue was purified by preparation HPLC (mobile phase:acetonitrile, water (0.05% trifluoroacetic acid); gradient: 60%-90%-10%) to give light yellow solid T-15 (23 mg, yield: 14%). LC-MS (ESI): m/z=484[M+H]$^+$.

$^1$H-NMR (400 MHz, CDCl$_3$) δ: 8.44 (s, 1H), 8.34 (s, 1H), 8.55 (s, 1H), 7.97 (s, 1H), 7.86 (d, J=6 Hz, 1H), 7.53 (s, 1H), 7.31 (d, J=6 Hz, 1H), 7.19 (s, 1H), 4.63 (d, J=9 Hz, 2H), 4.24 (d, J=9 Hz, 2H), 3.93 (s, 3H), 3.39 (s, 2H), 3.09 (q, J=7 Hz, 2H), 1.41 (t, J=7 Hz, 3H) ppm

Example 16

N-(Cyanomethyl)-4-(2-(phenylamino)thieno[3,2-d]pyrimidin-4-yl)benzamide T-16

Synthetic Route:

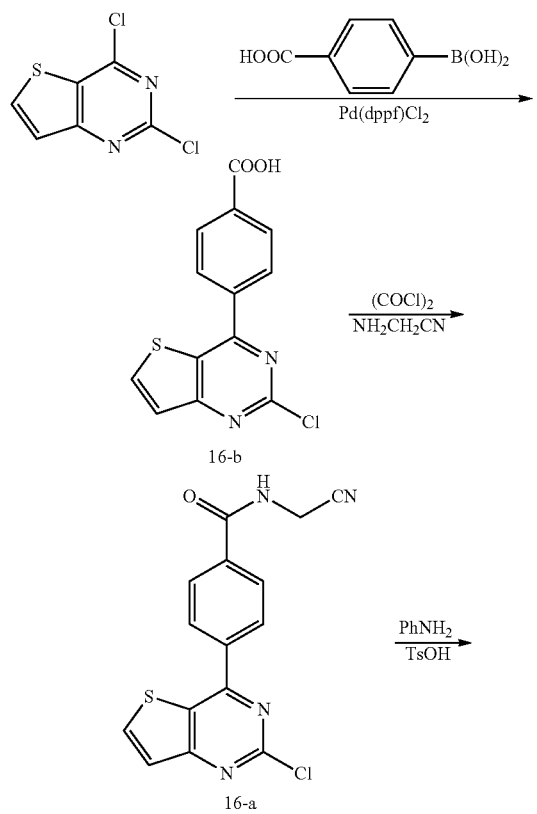

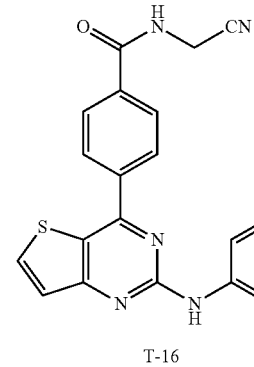

T-16

Preparation of Compound 16-b

Under nitrogen, to a suspension of 2,4-dichlorotheino[3,2-d]pyrimidine (1.0 g, 4.9 mmol), 4-boronobenzoic acid (542 mg, 3.3 mmol) and sodium carbonate (2.1 g, 19.6 mmol) in 1,4-dioxane (10 mL) and water (10 mL) was added Pd(dppf)Cl$_2$ (400 mg, 0.5 mmol). The mixture was stirred at 80° C. for 16 hours, then was cooled to room temperature. Hydrochloric acid (1.0 N) was added slowly to adjust pH=3. The mixture was then extracted with ethyl acetate (20 mL×3), the organic layer was washed with aqueous saturated sodium dicarbonate (50 mL) and saturated brine (50 mL). After dried over anhydrous sodium sulfate, the mixture was filtrated, and the filtrate was concentrated under reduced pressure to give yellow solid 16-b (160 mg, yield: 20%), which was used directly for the next step without further purification. LC-MS (ESI): m/z=291 [M+H]$^+$.

Preparation of Compound 16-a

To a suspension of compound 16-b in dichloromethane were added oxalyl chloride (4 mL) and DMF (0.1 m w) respectively, stirred at room temperature for 3 hours. The mixture was then concentrated under reduced pressure, the residue was diluted with dichloromethane (50 mL) and cooled to 0° C. Aminoacetonitrile hydrochloride (75 mg, 0.81 mmol) and triethylamine (0.6 mL) were added slowly to the mixture in sequence. After warmed slowly to room temperature, the mixture was stirred for further 2 hours, dichloromethane (50 mL) and water (20 mL) were added. The organic layer was washed with aqueous hydrochloride (1 N, 10 mL) and water (20 mL), and then dried over anhydrous sodium sulfate. The mixture was filtrated, the filtrate was concentrated under reduced pressure, the residue was purified by preparation HPLC (mobile phase:acetonitrile, water (0.05% trifluoroacetic acid); gradient: 40%-70%-10%) to give 16-a (125 mg, yield: 68%). LC-MS (ESI): m/z=329 [M+H]$^+$.

Preparation of Compound T-16

Aniline (108 mg, 1.16 mmol) and compound 16-a (125 mg, 0.38 mmol) were dissolved in n-butanol (0.5 mL), p-toluene sulfonic acid monohydrate (133 mg, 0.7 mmol) was added. The mixture was heated to 110° C. and stirred for 16 hours. The mixture was concentrated under reduced pressure, the residue was purified by preparation HPLC (mobile phase:acetonitrile, water (0.05% trifluoroacetic acid); gradient: 60%-90%-10%) to give yellow solid T-16 (33 mg, yield: 23%). LC-MS (ESI): m/z=386 [M+H]$^+$.

$^1$H-NMR (400 MHz, MeOD) δ: 8.31~8.34 (m, 2H), 8.19 (d, J=5 Hz, 1H), 8.08 (dd, J=2 Hz, J=6 Hz, 2H), 7.82 (dd, J=2 Hz, J=8 Hz, 3H), 7.40 (d, J=6 Hz, 1H), 7.33 (t, J=8 Hz, 2H), 7.01 (t, J=8 Hz, 1H), 4.39 (s, 2H) ppm

Example 17

N-(Tert-butyl)-4-(2-((4-morpholinophenyl)amino)thieno[3,2-d]pyrimidin-4-yl)benzenesulfonamide T-17

Synthetic Route:

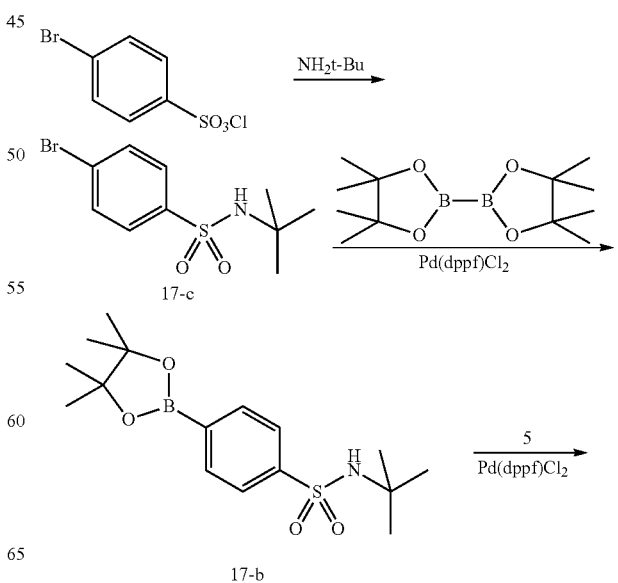

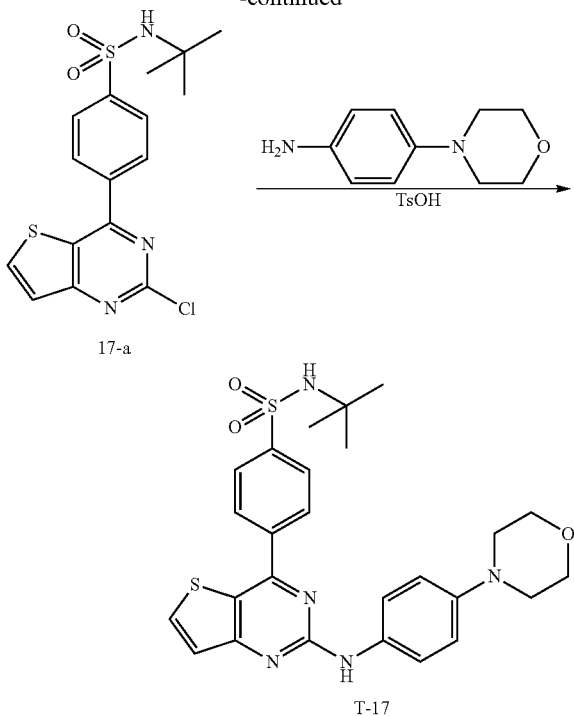

brine (50 mL) in sequence. After dried over anhydrous sodium sulfate, the mixture was filtrated, the filtrate was concentrated under reduced pressure. The residue was purified by silica column chromatography (petroleum ether: ethyl acetate=5:1) to give light yellow solid 17-a (105 mg, yield: 32%). LC-MS (ESI): m/z=382 [M+H]$^+$.

Preparation of Compound T-17

Compound 17-a (100 mg, 0.26 mmol) and 4-(4-morpholinyl)aniline (140 mg, 0.79 mmol) were dissolved in n-butanol (2 mL), p-toluene sulfonic acid monohydrate (180 mg, 0.95 mmol) was added. The mixture was heated to 110° C. and stirred for 16 hours. After cooled to room temperature, the mixture was stirred for another 30 minutes and there was solid precipitated. After filtration, the solid was purified by preparation HPLC (mobile phase:acetonitrile, water (0.05% trifluoroacetic acid); gradient: 60%-90%-10%) to give yellow solid T-17 (15 mg, yield: 25%). LC-MS (ESI): m/z=524 [M+H]$^+$.

$^1$H-NMR (400 MHz, CDCl$_3$) δ: 8.26 (d, J=9 Hz, 2H), 8.08 (d, J=9 Hz, 1H), 7.89 (d, J=5 Hz, 1H), 7.94 (d, J=5 Hz, 1H), 7.70 (br, 2H), 7.3, 8 (d, J=5 Hz, 1H), 7.04 (br, 2H), 4.82 (s, 1H), 3.90 (m, 4H), 3.20 (br, 4H), 1.27 (s, 9H) ppm Example 18

2-(1-(Ethylsulfonyl)-3-(4-(2-((4-(methylsulfonyl)phenyl)amino)thieno[2,3-d]pyrimidin-4-yl)-1H-pyrazol-1-yl)azetidin-3-yl)acetonitrile T-18

Synthetic Route:

Preparation of Compound 17-c

At 0° C., 4-bromobenzenesulfonyl chloride (3.0 g, 11.8 mml) was added to a solution of t-butyl amine (2.0 g, 29.6 mmol) in dichloromethane (30 mL) and stirred for 30 minutes. The reaction mixture was washed with aqueous hydrochloride (1 N, 20 mL) and water (30 mL×3) in sequence. The organic layer was dried over anhydrous sodium sulfate. After filtration, the filtrate was concentrated under reduced pressure to give white solid 17-c (3.6 g, yield: 100%), which was used directly for the next step without further purification.

Preparation of Compound 17-b

Under nitrogen, to a suspension of compound 17-c (500 mg, 1.72 mmol), bis(pinacolato)diboron (524 mg, 2.06 mmol) and potassium acetate (505 mg, 5.15 mmol) in 1,4-dioxane (5 mL) was added Pd(dppf)Cl$_2$ (130 mg, 0.17 mmol). The mixture was stirred at 80° C. for 16 hours. After concentration of the mixture under reduced pressure, the residue was diluted with water (50 mL), then extracted with ethyl acetate (50 mL×3). The organic layers were combined and washed with water (50 mL×3) and saturated brine (50 mL) in sequence. After dried over anhydrous sodium sulfate, the mixture was filtrated, the filtrate was concentrated under reduced pressure. The residue was purified by silica column chromatography (petroleum ether:ethyl acetate=5:1) to give white solid 17-b (350 mg, yield: 60%). LC-MS (ESI): m/z=340 [M+H]$^+$.

Preparation of Compound 17-a

Under nitrogen, to a suspension of compound 17-b (300 mg, 0.89 mmol), compound 5 (181 mg, 0.89 mmol) and sodium carbonate (281 mg, 2.67 mmol) in ethanol (2 mL) and water (2 mL) was added Pd(dppf)Cl$_2$ (74 mg, 0.1 mmol). The mixture was stirred at 80° C. for 16 hours. After concentration of the mixture under reduced pressure, the residue was diluted with water (50 mL), and then extracted with ethyl acetate (50 mL×3). The organic layers were combined and washed with water (50 mL×3) and saturated

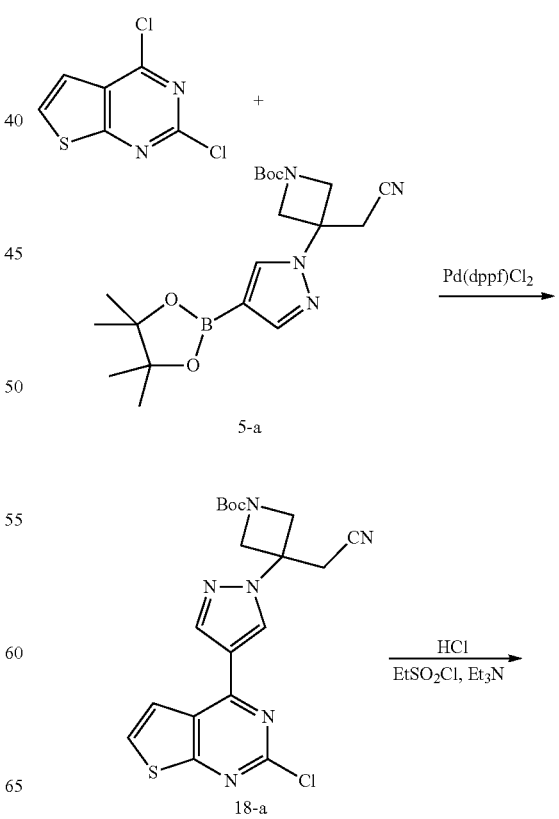

-continued

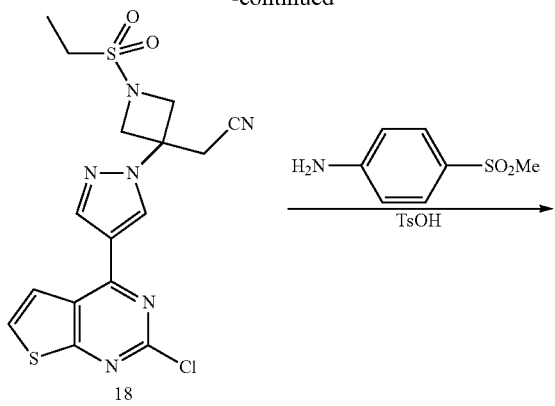

Preparation of Compound 18-a

Under nitrogen, to a suspension of 2,4-dichlorotheino[2,3-d]pyrimidine (500 mg, 2.45 mmol), compound 5-a (633 mg, 1.63 mmol) and sodium carbonate (779 mg, 7.35 mmol) in 1,4-dioxane (5 mL) was added Pd(dppf)Cl$_2$ (250 mg, 0.3 mmol). The mixture was stirred at 80° C. for 4 hours, then cooled to room temperature. Dichloromethane (50 mL) was added, the resultant mixture was filtered, the filtrate was concentrated under reduced pressure. The residue was purified by silica column chromatography (petroleum ether:ethyl acetate=1:1 to dichloromethane:methanol=10:1) to give gray solid 18-a (360 mg, yield: 52%). LC-MS (ESI): m/z=431 [M+H]$^+$.

Preparation of Compound 18

Compound 18-a (360 mg, 0.84 mmol) was dissolved in dichloromethane (2 mL), a solution of 4N hydrochloride in 1,4-dioxane (4 mL) was added. The mixture was stirred at room temperature for 16 hours, and then was concentrated under reduced pressure. The residue was diluted with dichloromethane (10 mL) and triethylamine (2 mL). The mixture was cooled to 0° C., ethylsulfonyl chloride (141 mg, 1.26 mmol) was added dropwise. After completion of dropping, the mixture was stirred at 0° C. for further 30 minutes. Water (5 mL) was added, and the mixture was extracted with dichloromethane (10 mL×3). The organic layers were combined, washed with water (10 mL×3) and saturated brine (10 mL) in sequence, dried over anhydrous sodium sulfate, then filtrated, and the filtrate was concentrated under reduced pressure. The residue was purified by silica column, chromatography (petroleum ether:ethyl acetate=2:1) to give compound 18 (90 mg, yield: 26%). LC-MS (ESI): m/z=423 [M+H]$^+$.

Preparation of Compound T-18

Compound 18 (80 mg, 0.19 mmol) and 4-methylsulfonylaniline (98 mg, 0.57 mmol) were dissolved in n-butanol (2 mL), p-toluene sulfonic acid monohydrate (72 mg, 0.38 mmol) was added. The mixture was heated to 110° C. and stirred for 16 hours. The mixture was concentrated under reduced pressure, the residue was purified by preparation HPLC (mobile phase:acetonitrile, water (0.05% trifluoroacetic acid); gradient: 50%-80%-10%) to give light yellow solid T-18 (13 mg, yield: 13%). LC-MS (ESI): m/z=558 [M+H]$^+$.

$^1$H-NMR (400 MHz, CDCl$_3$) δ: 9.70 (br, 1H), 8.75 (s, 1H), 8.29 (s, 1H), 8.99 (d, J=9 Hz, 2H), 7.93 (d, J=9 Hz, 2H), 7.51 (d, J=6 Hz, 1H), 7.43 (d, J=6 Hz, 1H), 4.66 (d, J=9 Hz, 2H), 4.28 (d, J=9 Hz, 2H), 3.44 (s, 2H), 3.10 (q, J=7H, 2H), 3.06 (s, 31H), 1.43 (t, J=7 Hz, 3H) ppm

Example 19

4-((4-(1-(3-(Cyanomethyl)-1-(ethylsulfonyl)azetidin-3-yl)-1H-pyrazol-4-yl)thieno[3,2-d]pyrimidin-2-yl)amino)benzonitrile T-19

Synthetic Route:

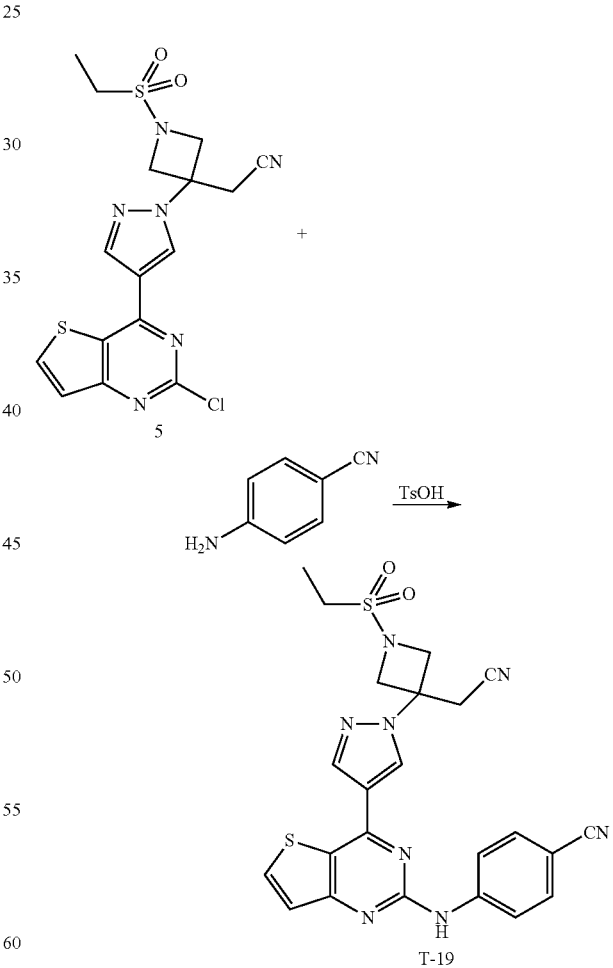

Preparation of Compound T-19

Compound 5 (50 mg, 0.12 mmol) and 4-aminobenzonitrile (42 mg, 0.36 mmol) were dissolved in n-butanol (2 mL), p-toluene sulfonic acid monohydrate (45 mg, 0.24 mmol) was added. The mixture was heated to 110° C. and stirred for 16 hours, then concentrated under reduced pressure. The residue was purified by preparation HPLC (mobile phase:acetonitrile, water (0.05% trifluoroacetic acid); gradient: 65%-95%-10%) to give light yellow solid T-19 (13 mg, yield: 13%). LC-MS (ESI): m/z=505 [M+H]$^+$.

$^1$H-NMR (400 MHz, CDCl$_3$) δ: 8.49 (s, 1H), 8.39 (s, 1H), 7.98 (d, J=6 Hz, 1H), 7.90 (d, J=9 Hz, 2H), 7.65 (d, J=9 Hz, 2H), 7.43 (d, J=6 Hz, 1H), 4.66 (d, J=9 Hz, 2H), 4.26 (d, J=9 Hz, 2H), 3.44 (s, 2H), 3.11 (q, J=7 Hz, 2H), 1.43 (t, J=7 Hz, 3H) ppm Example 20

2-(3-(4-(2-(Phenylamino)thieno[3,2-d]pyrimidin-4-yl)-1H-pyrazol-1-yl)oxetan-3-yl)acetonitrile T-20

Synthetic Route:

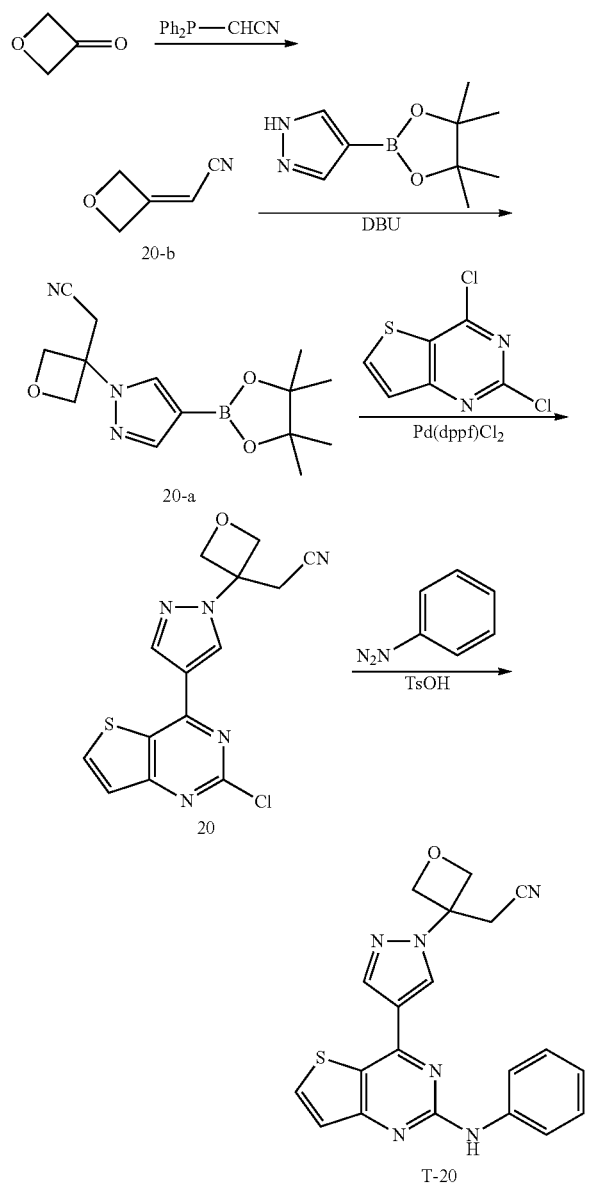

Preparation of Compound 20-b

At room temperature, (cyanomethyl)triphenylphosphanium bromide (10.0 g, 33.2 mmol) and 3-oxetanone (1.2 g, 16.7 mmol) were dissolved in dichloromethane (100 mL), the mixture was stirred for 16 hours, then concentrated under reduced pressure. The residue was added into a component solvent (50 mL) of petroleum ether and ethyl acetate (10:1), and there was white solid precipitated. After filtration, the filtrate was concentrated under reduced pressure, the residue was purified by silica column chromatography (petroleum ether:ethyl acetate=5:1) to give compound 20-b (1.0 g, yield: 63%).

$^1$H-NMR (400 MHz, CDCl$_3$) δ: 5.39 (m, 2H), 5.30 (m, 2H), 5.25 (m, 1H) ppm

Preparation of Compound 20-a

To a solution of compound 20-b (500 mg, 5.26 mmol) and 4-(4,4,5,5-tetramethyl-1,3,2-dioxaborolan-2-yl)-1H-pyrazole (1.3 g, 6.7 mmol) in acetonitrile (10 mL) was added 1,8-diazabicyclo[5.4.0]undec-7-ene (1.6 g, 10.53 mmol). The mixture was stirred at 60° C. for 18 hours, then concentrated under reduced pressure. 1 N Aqueous hydrochloride solution was added into the residue to adjust pH=3-4, then the mixture was extracted with ethyl acetate (20 mL×3). The organic layers were combined, washed with water (20 mL×3) and saturated brine (20 mL) in sequence, dried over anhydrous sodium sulfate, filtrated, and the filtrate was concentrated under reduced pressure to give yellow oil 20-a (900 mg, yield: 59%), which was used directly for the next step without further purification. LC-MS (ESI): m/z=290 [M+H]$^+$.

Preparation of Compound 20

Under nitrogen, compound 20-a (300 mg, 1.04 mmol), 2,4-dichlorotheino[3,2-d]pyrimidine (317 mg, 1.56 mmol) and sodium carbonate (331 mg, 3.12 mmol) were suspended in 1,4-dioxane (0.5 mL) and water (0.5 mL), Pd(dppf)Cl$_2$ (82 mg, 0.1 mmol) was added. The mixture was stirred at 80° C. for 4 hours, then concentrated under reduced pressure. To the residue was added water (20 mL), the mixture was extracted with dichloromethane (20 mL×3). The organic layers were combined, washed with water (10 mL×3) and saturated brine (10 mL) in sequence, dried over anhydrous sodium sulfate, filtrated, the filtrate was concentrated under reduced pressure. The residue was purified by silica column chromatography (petroleum ether:ethyl acetate=2:1) to give light yellow solid 20 (102 mg, yield: 30%). LC-MS (ESI): m/z=332 [M+H]$^+$.

Preparation of Compound T-20

Compound 20 (50 mg, 0.15 mmol) and aniline (42 mg, 0.45 mmol) were dissolved in n-butanol (2 mL), p-toluene sulfonic acid monohydrate (58 mg, 0.3 mmol) was added. The mixture was heated to 110° C. and stirred for 16 hours, then concentrated under reduced pressure. The residue was purified by preparation HPLC (mobile phase:acetonitrile, water (0.05% trifluoroacetic acid); gradient: 60%-90%-10%) to give light yellow solid T-20 (23 mg, yield: 40%). LC-MS (ESI): m/z=389 [M+H]$^+$.

$^1$H-NMR (400 MHz, CDCl$_3$) δ: 8.45 (s, 1H), 8.40 (s, 1H), 7.89 (d, J=5 Hz, 1H), 7.75 (d, J=8 Hz, 2H), 7.37 (m, 31H), 7.20 (s, 1H), 7.05 (t, J=7 Hz, 1H), 5.20 (d, J=8 Hz, 2H), 4.89 (d, J=8 Hz, 2H), 3.46 (s, 2H) ppm

Example 21

2-(1-(Ethylsulfonyl)-3-(4-(2-(pyridin-4-ylamino)thieno[3,2-d]pyrimidin-4-yl)-1H-pyrazol-1-yl)azetidin-3-yl)acetonitrile T-21

Synthetic Route:

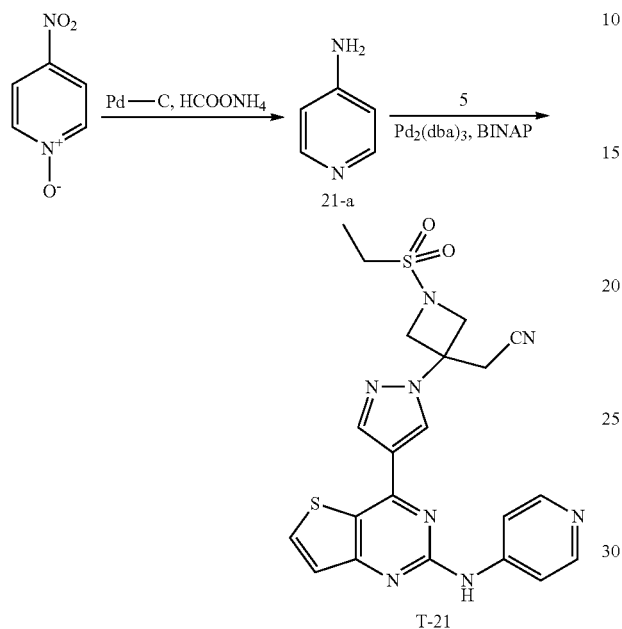

Preparation of Compound 21-a

To a solution of 4-nitropyridine 1-oxide (600 mg, 6.46 mmol) and ammonium formate (622 mg, 10.92 mmol) in ethanol (10 mL) was added slowly 10% Pd—C (0.6 g). The mixture was stirred at room temperature for 16 hours. After filtration, the filtrate was concentrated under reduced pressure. To the residue was added water (20 mL), the mixture was extracted with ethyl acetate (20 mL×3). The organic layers were combined, washed with water (10 mL×3) and saturated brine (10 mL) in sequence, dried over anhydrous sodium sulfate, then filtrated, the filtrate was concentrated under reduced pressure to give light yellow solid 21-a (380 mg, yield: 94%), which was used directly for the next step without purification.

Preparation of Compound T-21

Under nitrogen, to a suspension of compound 5 (100 mg, 0.24 mmol), compound 21-a (45 mg, 0.48 mmol) and cesium carbonate (155 mg, 0.48 mmol) in 1,4-dioxane (2 mL) were added $Pd_2(dba)_3$ (22 mg, 0.03 mmol) and BINAP (20 mg, 0.03 mmol). The mixture was heated to 120° C. by microwave and stirred for 60 minutes. After cooled to room temperature, the mixture was diluted with dichloromethane (20 mL), and then filtrated, the filtrate was concentrated under reduced pressure. The residue was purified by preparation HPLC (mobile phase:acetonitrile, water (0.05% trifluoroacetic acid); gradient: 40%-70%-10%) to give yellow solid T-21 (8 mg, yield: 7%). LC-MS (ESI): m/z=481 [M+H]$^+$.

$^1$H-NMR (400 MHz, CDCl$_3$) δ: 8.72 (s, 1H), 8.37 (m, 4H), 8.30 (br, 1H), 8.23 (d, J=6 Hz, 1H), 7.42 (d, J=6 Hz, 1H), 4.57 (d, J=9 Hz, 2H), 4.22 (d, J=9 Hz, 2H), 3.55 (s, 2H), 3.10 (q, J=7 Hz, 2H), 1.31 (t, J=7 Hz, 3H) ppm

Example 22

5-((4-(1-(3-(Cyanomethyl)-1-(ethylsulfonyl)azetidin-3-yl)-1H-pyrazol-4-yl)thieno[3,2-d]pyrimidin-2-yl)amino)picolinonitrile T-22

Synthetic Route:

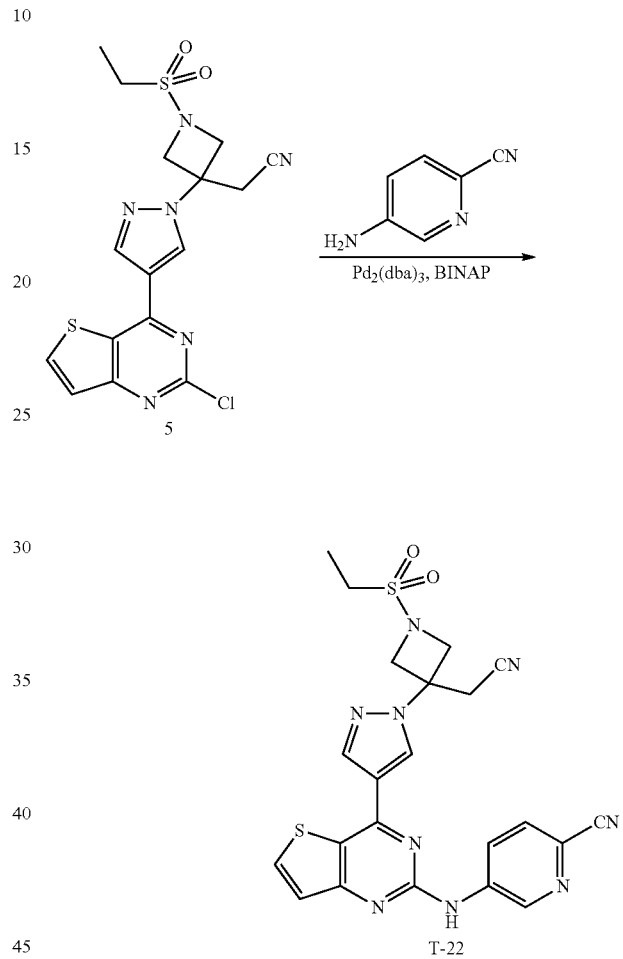

Under nitrogen, to a suspension of compound 5 (100 mg, 0.24 mmol), 2-cyano-5-aminopyridine (56 mg, 0.48 mmol) and cesium carbonate (155 mg, 0.48 mmol) in 1,4-dioxane (2 mL) were added $Pd_2(dba)_3$ (22 mg, 0.03 mmol) and BINAP (20 mg, 0.03 mmol). The mixture was heated to 120° C. by microwave and stirred for 60 minutes. After cooled to room temperature, the mixture was diluted with dichloromethane (20 mL), and then filtrated, the filtrate was concentrated under reduced pressure. The residue was purified by preparation HPLC (mobile phase:acetonitrile, water (0.05% trifluoroacetic acid); gradient: 50%-80%-10%) to give yellow solid T-22 (33 mg, yield: 28%). LC-MS (ESI): m/z=506 [M+H]$^+$.

$^1$H-NMR (400 MHz, CDCl$_3$) δ: 10.49 (s, 1H), 9.10 (d, J=2 Hz, 1H), 8.89 (s, 1H), 8.66 (dd, J=9 Hz, J=2 Hz, 1H), 7.97 (s, 1H), 8.49 (d, J=6 Hz, 1H), 8.45 (s, 1H), 7.96 (d, J=9 Hz, 1H), 7.54 (d, J=5 Hz, 1H), 4.58 (d, J=9 Hz, 2H), 4.29 (d, J=9 Hz, 2H), 3.73 (s, 2H), 3.25 (q, J=7 Hz, 2H), 1.26 (t, J=7 Hz, 3H) ppm

Example 23

2-(1-(Ethylsulfonyl)-3-(4-(6-methyl-2-(phenylamino)thieno[3,2-d]pyrimidin-4-yl)-1H-pyrazol-1-yl)azetidin-3-yl)acetonitrile T-23

Synthetic Route:

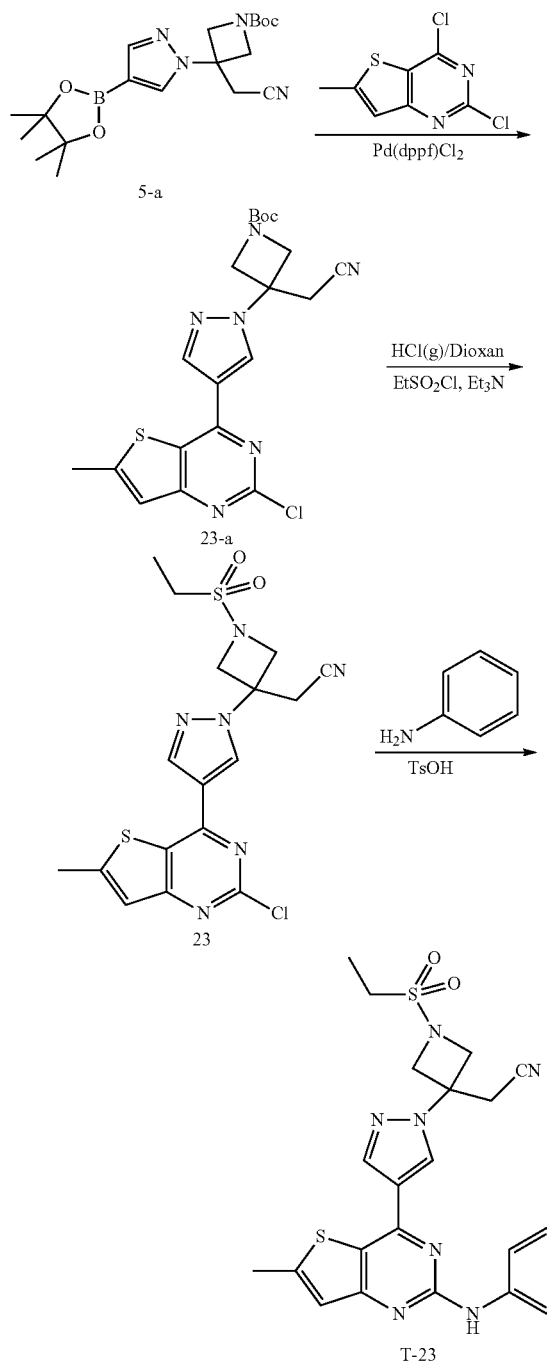

Preparation of Compound 23-a

Under nitrogen, to a suspension of compound 5-a (194 mg, 0.5 mmol), 2,4-dichloro-6-methyltheino[3,2-d]pyrimidine (149 mg, 0.5 mmol) and aqueous sodium carbonate (2.0 N, 0.75 mL) in 1,4-dioxane (7.5 mL) was added Pd(dppf)Cl₂ (18 mg, 0.025 mmol). The mixture was stirred at 80° C. for 4 hours, then concentrated, and the residue was diluted with ethyl acetate (50 mL), filtrated through celite. Then the organic layer was washed with water (10 mL×3) and saturated brine (10 mL) in sequence, dried over anhydrous sodium sulfate, filtrated, the filtrate was concentrated under reduced pressure, and the residue was purified by preparation TLC (dichloromethane:methanol=30:1) to give compound 23-a (165 mg, yield: 74%). LC-MS (ESI): m/z=445 [M+H]⁺.

Preparation of Compound 23

To a solution of compound 23-a (165 mg, 0.37 mmol) in 1,4-dioxane (4 mL) was added a solution of hydrochloride in 1,4-dioxane (4 N, 0.93 mL). The mixture was stirred at room temperature for 16 hours, then concentrated. To the residue was added dichloromethane (10 mL) and triethylamine (0.16 mL, 1.12 mmol). The mixture was then cooled to 0° C., ethylsulfonyl chloride (62 mg, 0.56 mmol) was added dropwise. After the completion of dropping, the mixture was stirred at 0° C. for further 30 minutes. Water (5 mL) was added, and the mixture was extracted with dichloromethane (10 mL×3). The organic layers were combined, washed with water (10 mL×3) and saturated brine (10 mL) in sequence, dried over anhydrous sodium sulfate, filtrated, and the filtrate was concentrated under reduced pressure. The residue was purified by preparation TLC (petroleum ether:ethyl acetate=1:1) to give compound 23 (60 mg, yield: 37%). LC-MS (ESI): m/z=437 [M+H]⁺.

Preparation of Compound T-23

Compound 23 (60 mg, 0.14 mmol) and aniline (39 mg, 0.42 mmol) were dissolved in isobutanol (10 mL), p-toluene sulfonic acid monohydrate (53 mg, 0.28 mmol) was added. The mixture was heated to 110° C. and stirred for 16 hours, then concentrated under reduced pressure, and the residue was purified by preparation TLC (petroleum ether:ethyl acetate=1:1) to give compound T-23 (20 mg, yield: 29%). LC-MS (ESI): m/z=494 [M+H]⁺.

¹H-NMR (400 MHz, DMSO-d₆) δ: 9.56 (s, 1H), 8.78 (s, 1H), 8.35 (s, 1H), 7.88 (d, J=8.4 Hz, 2H), 7.31 (t, J=7.8 Hz, 2H), 7.18 (s, 1H), 6.94 (t, J=7.4 Hz, 1H), 4.57 (d, J=9.2 Hz, 2H), 4.27 (d, J=9.2 Hz, 2H), 3.72 (s, 2H), 3.22~3.28 (m, 2H), 2.67 (s, 3H), 1.25 (t, J=7.4 Hz, 3H) ppm

Example 24

2-(1-(Ethylsulfonyl)-3-(4-(2-((4-fluorophenyl)amino)thieno[3,2-d]pyrimidin-4-yl)-1H-pyrazol-1-yl)azetidin-3-yl)acetonitrile T-24

Synthetic Route:

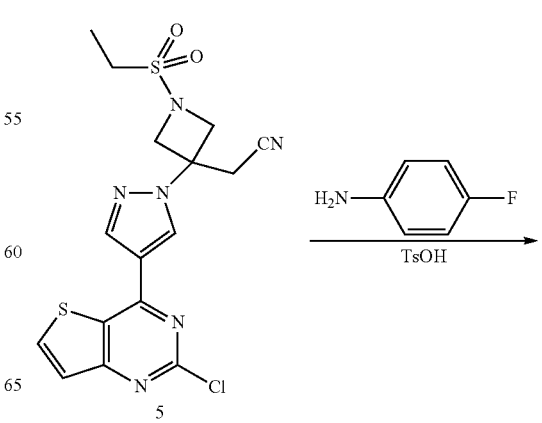

-continued

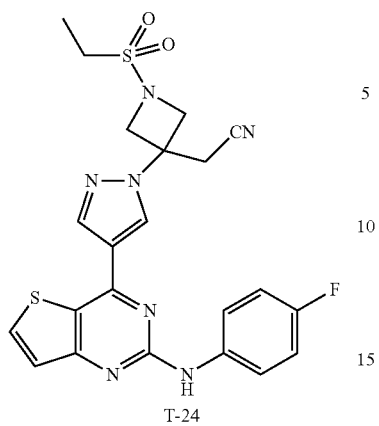
T-24

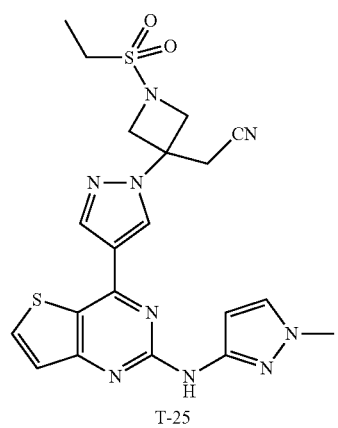
T-25

Compound 5 (208 mg, 0.49 mmol) and 4-fluoroaniline (164 mg, 1.48 mmol) were dissolved in isobutanol (12 mL), p-toluene sulfonic acid monohydrate (188 mg, 0.98 mmol) was added. The mixture was heated to 110° C. and stirred for 16 hours, then concentrated under reduced pressure, and the residue was dissolved in dichloromethane (100 mL), washed with water (20 mL×3) and saturated brine (20 mL) in sequence, dried over anhydrous sodium sulfate, filtrated, the filtrate was concentrated under reduced pressure, and there was solid formed. The solid was washed with dichloromethane (5 mL) and ethyl acetate (25 mL) to give compound T-24 (30 mg, yield: 12%). LC-MS (ESI): m/z=498 [M+H]$^+$.

$^1$H-NMR (400 MHz, DMSO-d$_6$) δ: 9.66 (s, 1H), 8.83 (s, 1H), 8.39-8.40 (m, 2H), 7.89-7.92 (m, 2H), 7.42 (d, J=5.5 Hz, 1H), 7.16 (t, J=9.0 Hz, 2H), 4.58 (d, J=9.0 Hz, 2H), 4.28 (d, J=9.5 Hz, 2H), 3.73 (s, 2H), 3.23-3.27 (m, 2H), 1.26 (t, J=7.5 Hz, 3H) ppm Under nitrogen, to a suspension of compound 5 (150 mg, 0.35 mmol), 3-amino-1-methylpyrazole (104 mg, 1.48 mmol) and cesium carbonate (228 mg, 0.7 mmol) in 1,4-dioxane (4 mL) were added Pd$_2$(dba)$_3$ (32 mg, 0.035 mmol) and BINAP (22 mg, 0.035 mmol). The mixture was heated to 120° C. by microwave and stirred for 60 minutes. After cooled to room temperature, the mixture was diluted with dichloromethane (100 mL), washed with water (20 mL×3) and saturated brine (20 mL) in sequence, dried over anhydrous sodium sulfate, then filtrated, and the filtrate was concentrated under reduced pressure. There was solid formed and the solid was washed with THF (20 mL) and methanol (10 mL) to give compound T-25 (80 mg, yield: 46%). LC-MS (ESI): m/z=484 [M+H]$^+$.

$^1$H-NMR (400 MHz, DMSO) δ: 9.58 (s, 1H), 8.80 (s, 1H), 8.36-8.37 (m, 2H), 7.57 (d, J=1.5 Hz, 1H), 7.38 (d, J=5.0 Hz, 1H), 6.77 (d, J=2.0 Hz, 1H), 4.57 (d, J=9.0 Hz, 2H), 4.27 (d, J=9.5 Hz, 2H), 3.76 (s, 3H), 3.72 (s, 2H), 3.23-3.27 (m, 2H), 1.25 (t, J=7.5 Hz, 3H) ppm Example 25

2-(1-(Ethylsulfonyl)-3-(4-(2-((1-methyl-1H-pyrazol-3-yl)amino)thieno[3,2-d]pyrimidin-4-yl)-1H-pyrazol-1-yl)azetidin-3-yl)acetonitrile T-25

Synthetic Route:

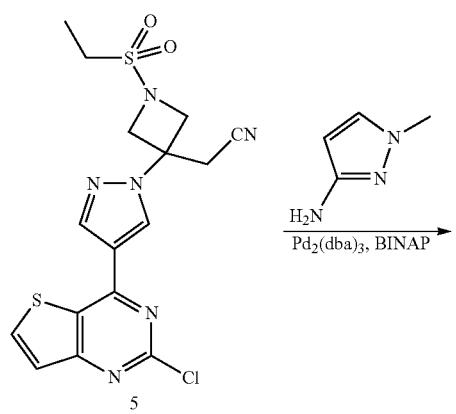

Example 26

2-(1-(Ethylsulfonyl)-3-(4-(2-(pyridin-3-ylamino)thieno[3,2-d]pyrimidin-4-yl)-1-pyrazol-1-yl)azetidin-3-yl)acetonitrile T-26

Synthetic Route:

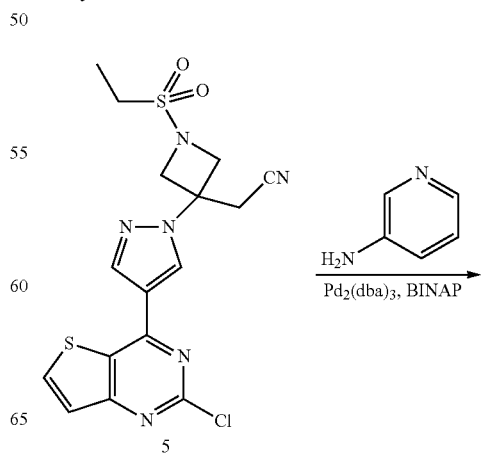

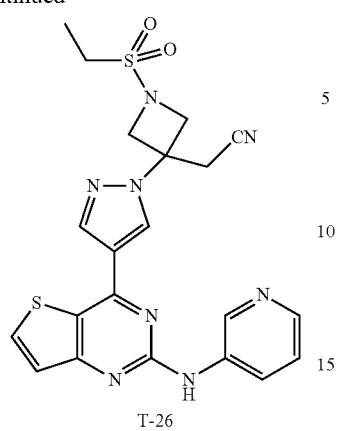

T-26

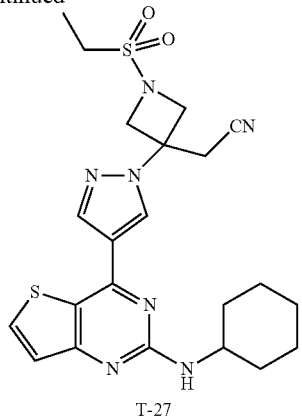

T-27

Under nitrogen, to a suspension of compound 5 (100 mg, 0.23 mmol), 3-aminopyridine (22 mg, 0.23 mmol) and cesium carbonate (154 mg, 0.47 mmol) in 1,4-dioxane (4 mL) were added Pd$_2$(dba)$_3$ (22 mg, 0.023 mmol) and BINAP (15 mg, 0.023 mmol). The mixture was heated to 125° C. by microwave and stirred for 30 minutes. After cooled to room temperature, the mixture was diluted with dichloromethane (100 mL), washed with water (20 mL×3) and saturated brine (20 mL) in sequence, dried over anhydrous sodium sulfate, then filtrated, and the filtrate was concentrated under reduced pressure. The residue was purified by preparation HPLC (mobile phase:acetonitrile, water (0.05% trifluoroacetic acid); gradient: 40%-70%-10%) to give compound T-26 (18 mg, yield: 16%). LC-MS (ESI): m/z=481 [M+H]$^+$.

$^1$H-NMR (400 MHz, CDCl$_3$) δ: 8.91 (d, J=2.4 Hz, 1H), 8.45 (s, 1H), 8.33 (s, 1H), 8.27-8.31 (m, 2H), 7.90 (d, J=7.0 Hz, 1H), 7.51 (s, 1H), 7.29-7.34 (m, 2H), 4.66 (d, J=9.2 Hz, 2H), 4.25 (d, J=9.6 Hz, 2H), 3.42 (s, 2H), 3.08-3.14 (m, 2H), 1.42 (t, J=7.2 Hz, 3H) ppm Under nitrogen, to a suspension of compound 5 (200 mg, 0.47 mmol), cyclohexylamine (141 mg, 1.42 mmol) and cesium carbonate (463 mg, 1.42 mmol) in 1,4-dioxane (4 mL) were added Pd$_2$(dba)$_3$ (43 mg, 0.047 mmol) and BINAP (30 mg, 0.047 mmol). The mixture was heated to 125° C. by microwave and stirred for 60 minutes. After cooled to room temperature, the mixture was diluted with ethyl acetate (100 mL), washed with water (20 mL×3) and saturated brine (20 mL) in sequence, dried over anhydrous sodium sulfate, then filtrated, and the filtrate was concentrated under reduced pressure. The residue was purified by preparation HPLC (mobile phase:acetonitrile, water (0.05% trifluoroacetic acid); gradient: 40%-70%-10%) to give compound T-27 (25 mg, yield: 11%). LC-MS (ESI): m/z=486 [M+H]$^+$.

$^1$H-NMR (500 MHz, CDCl$_3$) δ: 8.38 (s, 1H), 8.34 (s, 1H), 7.79 (d, J=5.5 Hz, 1H), 7.24 (d, J=5.0 Hz, 1H), 5.05 (d, J=8.5 Hz, 1H), 4.62 (d, J=9.5 Hz, 2H), 4.25 (d, J=9.5 Hz, 2H), 3.95-3.97 (m, 1H), 3.40 (s, 2H), 3.06-3.11 (m, 2H), 2.09-2.12 (m, 2H), 1.76-1.80 (m, 3H), 1.65-1.67 (m, 1H), 1.45-1.48 (m, 1H), 1.42 (t, J=7.0 Hz, 3H), 1.25-1.31 (m, 3H) ppm Example 27

2-(3-(4-(2-(Cyclohexylamino)thieno[3,2-d]pyrimidin-4-yl)-1H-pyrazol-1-yl)-1-(ethylsulfonyl)azetidin-3-yl)acetonitrile T-27

Synthetic Route:

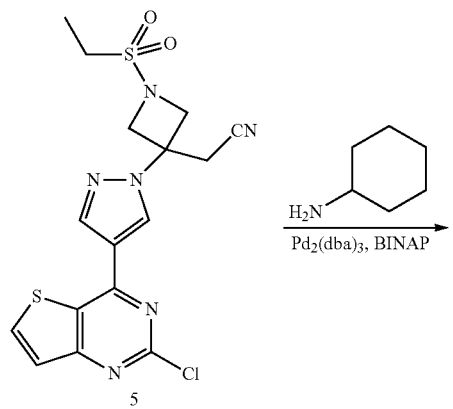

Example 28

2-(3-(4-(2-(Cyclopropylamino)thieno[3,2-d]pyrimidin-4-yl)-1H-pyrazol-1-yl)-1-(ethylsulfonyl)azetidin-3-yl)acetonitrile T-28

Synthetic Route:

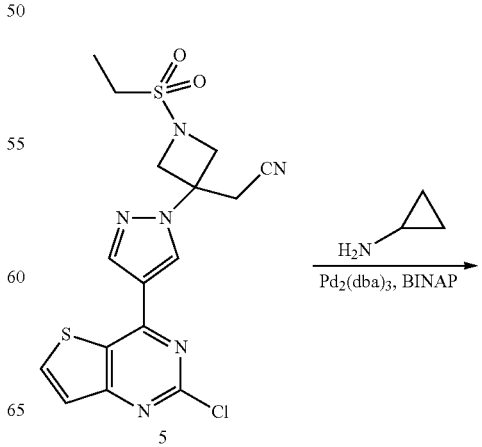

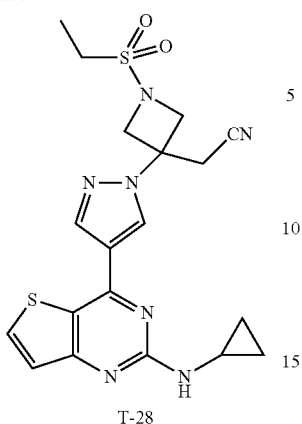

T-28

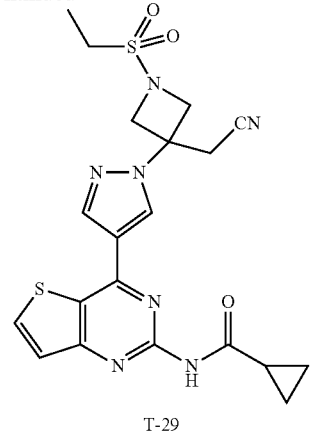

T-29

Under nitrogen, to a suspension of compound 5 (85 mg, 0.20 mmol), cyclopropyl amine (33 mg, 0.6 mmol) and cesium carbonate (196 mg, 0.6 mmol) in 1,4-dioxane (4 mL) were added Pd$_2$(dba)$_3$ (18 mg, 0.02 mmol) and BINAP (12 mg, 0.02 mmol). The mixture was heated to 125° C. by microwave and stirred for 40 minutes. After cooled to room temperature, the mixture was diluted with ethyl acetate (100 mL), washed with water (20 mL×3) and saturated brine (20 mL) in sequence, dried over anhydrous sodium sulfate, then filtrated, and the filtrate was concentrated under reduced pressure. The residue was purified by preparation TLC (dichloromethane:ethyl acetate=1:1) to give compound T-28 (8 mg, yield: 9%). LC-MS (ESI): m/z=444 [M+H]$^+$.

$^1$H-NMR (500 MHz, CDCl$_3$) δ: 8.33 (s, 1H), 8.28 (s, 1H), 7.76 (d, J=5.5 Hz, 1H), 7.26 (d, J=5.5 Hz, 1H), 5.33 (s, 1H), 4.55 (d, J=9.0 Hz, 2H), 4.18 (d, J=9.5 Hz, 2H), 3.33 (s, 2H), 3.00-3.04 (m, 2H), 2.80-2.84 (m, 1H), 1.34 (t, J=7.5 Hz, 3H), 0.78-0.82 (m, 2H), 0.52-0.55 (m, 2H) ppm Example 29

N-(4-(1-(3-(Cyanomethyl)-1-(ethylsulfonyl)azetidin-3-yl)-1H-pyrazol-4-yl)thieno[3,2-d]pyrimidin-2-yl)cyclopropanecarboxamide T-29

Synthetic Route:

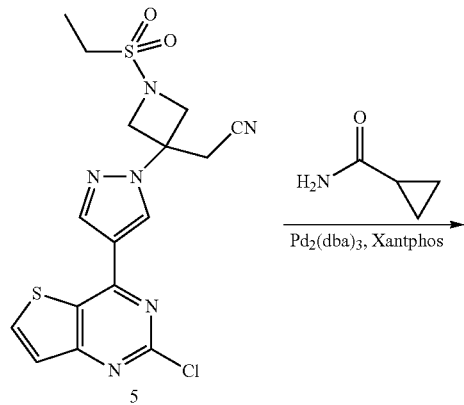

Under nitrogen, to a suspension of compound 5 (50 mg, 0.12 mmol), cyclopropanecarboxamide (30 mg, 0.36 mmol) and cesium carbonate (55 mg, 0.16 mmol) in 1,4-dioxane (4 mL) were added Pd$_2$(dba)$_3$ (11 mg, 0.012 mmol) and Xantphos (7 mg, 0.012 mmol). The mixture was heated to 125° C. by microwave and stirred for 30 minutes. After cooled to room temperature, the mixture was diluted with dichloromethane (100 mL), washed with water (20 mL×3) and saturated brine (20 mL), dried over anhydrous sodium sulfate, then filtrated, and the filtrate was concentrated under reduced pressure. The residue was purified by preparation HPLC (mobile phase:acetonitrile, water (0.05% trifluoroacetic acid); gradient: 50%-80%-10%) to give compound TI-29 (22 mg, yield: 39%). LC-MS (ESI): m/z=472 [M+H]$^+$.

$^1$H-NMR (400 MHz, CDCl$_3$) δ: 10.88 (s, 1H), 8.87 (s, 1H), 8.53 (d, J=5.2 Hz, 1H), 8.41 (s, 1H), 7.54 (d, J=5.2 Hz, 1H), 4.57 (d, J=8.8 Hz, 2H), 4.27 (d, J=9.2 Hz, 2H), 3.72 (s, 2H), 3.22-3.28 (m, 2H), 2.17-2.23 (m, 1H), 1.24 (t, J=7.2 Hz, 3H), 0.81-0.85 (m, 4H) ppm Example 30

2-(1-(Ethylsulfonyl)-3-(4-(2-(phenylamino)furo[3,2-d]pyrimidin-4-yl)-1H-pyrazol-1-yl)azetidin-3-yl)acetonitrile T-30

Synthetic Route:

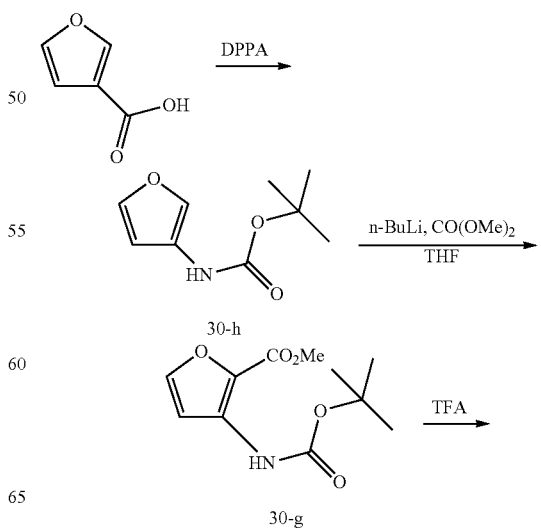

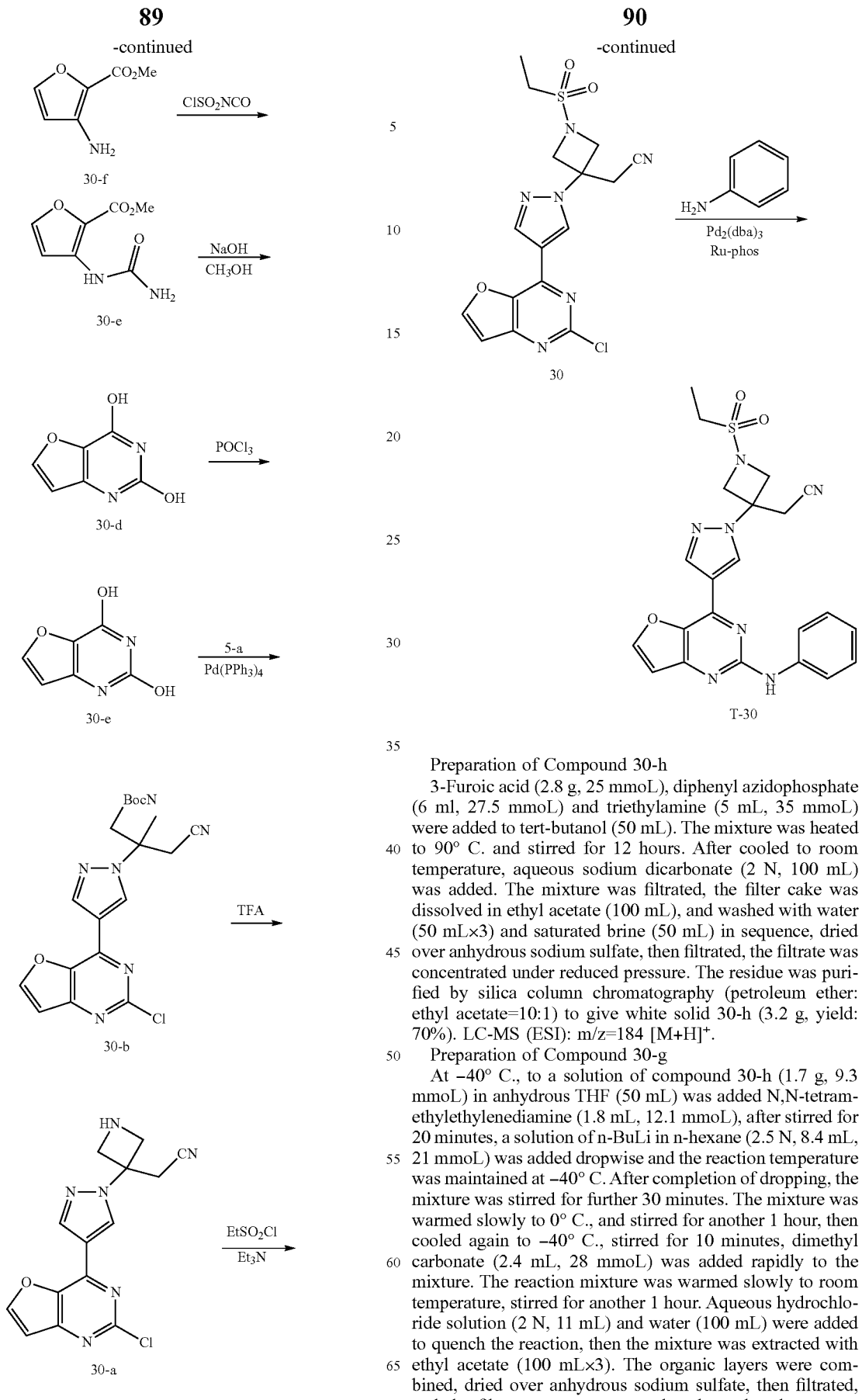

Preparation of Compound 30-h

3-Furoic acid (2.8 g, 25 mmoL), diphenyl azidophosphate (6 ml, 27.5 mmoL) and triethylamine (5 mL, 35 mmoL) were added to tert-butanol (50 mL). The mixture was heated to 90° C. and stirred for 12 hours. After cooled to room temperature, aqueous sodium dicarbonate (2 N, 100 mL) was added. The mixture was filtrated, the filter cake was dissolved in ethyl acetate (100 mL), and washed with water (50 mL×3) and saturated brine (50 mL) in sequence, dried over anhydrous sodium sulfate, then filtrated, the filtrate was concentrated under reduced pressure. The residue was purified by silica column chromatography (petroleum ether: ethyl acetate=10:1) to give white solid 30-h (3.2 g, yield: 70%). LC-MS (ESI): m/z=184 [M+H]$^+$.

Preparation of Compound 30-g

At −40° C., to a solution of compound 30-h (1.7 g, 9.3 mmoL) in anhydrous THF (50 mL) was added N,N-tetramethylethylenediamine (1.8 mL, 12.1 mmoL), after stirred for 20 minutes, a solution of n-BuLi in n-hexane (2.5 N, 8.4 mL, 21 mmoL) was added dropwise and the reaction temperature was maintained at −40° C. After completion of dropping, the mixture was stirred for further 30 minutes. The mixture was warmed slowly to 0° C., and stirred for another 1 hour, then cooled again to −40° C., stirred for 10 minutes, dimethyl carbonate (2.4 mL, 28 mmoL) was added rapidly to the mixture. The reaction mixture was warmed slowly to room temperature, stirred for another 1 hour. Aqueous hydrochloride solution (2 N, 11 mL) and water (100 mL) were added to quench the reaction, then the mixture was extracted with ethyl acetate (100 mL×3). The organic layers were combined, dried over anhydrous sodium sulfate, then filtrated, and the filtrate was concentrated under reduced pressure.

The residue was purified by silica column chromatography (petroleum ether:ethyl acetate=100:1) to give white solid 30-g (0.56 g, yield: 25%). LC-MS (ESI): m/z=142 [M+H]$^+$.

Preparation of Compound 30-f

To a solution of compound 30-g (0.56 g, 2.3 mmoL) in dichloromethane (4 mL) was added trifluoroacetic acid (2.5 mL), the mixture was stirred at room temperature for 2 hours. After the mixture was concentrated under reduced pressure, the residue was treated with aqueous sodium dicarbonate solution (2 N, 6 mL), then extracted with ethyl acetate (5 mL×3). The organic layers were combined, washed with water (10 mL×3) and saturated brine (20 mL) in sequence, dried over anhydrous sodium sulfate, then filtrated, the filtrate was concentrated under reduced pressure to give yellow liquid 30-f (0.35 g, yield: 100%), which was used directly for the next step without purification.

Preparation of Compound 30-e

At −78° C., to a solution of compound 30-f (0.35 g, 2.5 mmoL) in dichloromethane (5 mL) was added dropwise chlorosulfonyl isocyanate (0.49 g, 3.5 mmoL). After completion of dropping, the mixture was warmed to room temperature, and stirred for 40 minutes. The mixture was concentrated under reduced pressure, the residue was treated with HCl (6 N, 3 mL, 18 mmol), then warmed to 100° C., and stirred for 30 minutes. The mixture was cooled to room temperature, then concentrated under reduced pressure, the residue was treated with aqueous sodium dicarbonate solution (2 N, 6 mL), extracted with ethyl acetate (5 mL×3). The organic layers were combined, washed with water (10 mL×3) and saturated brine (20 mL) in sequence. After dried over anhydrous sodium sulfate, the mixture was filtrated, and the filtrate was concentrated under reduced pressure to give yellow solid 30-e (176 mg, yield: 38%), which was used directly for the next step without purification. LC-MS (ESI): m/z=185 [M+H]$^+$.

Preparation of Compound 30-d

To a solution of compound 30-e (0.176 g, 0.96 mmoL) in methanol (4 mL) was added aqueous sodium hydroxide solution (2 N, 2 mmoL), the mixture was refluxed for 2 hours. After cooled to room temperature, aqueous hydrochloride solution (6 N, 0.5 mL) was added to adjust pH=3. The mixture was concentrated under reduced pressure, to the residue was added methanol (5 mL), and there was gray solid precipitated. After filtration, the filter cake was dried in vacuum to give gray solid 30-d (110 mg, yield: 75%), which was used directly for the next step without purification. LC-MS (ESI): m/z=153 [M+H]$^+$.

Preparation of Compound 30-c

At −40° C., to a solution of compound 30-d (0.86 g, 5.6 mmoL) in phosphorus oxychloride (8 mL) was added N,N-diisopropylethylamine (2 mL), after stirred for 10 minutes, the mixture was refluxed for 24 hours. After cooled to room temperature, the mixture was poured into ice water to quench the reaction, and then extracted with ethyl acetate (50 mL×3). The organic layers were combined, washed with water (20 mL×3) and saturated brine (20 mL) in sequence, then dried over anhydrous sodium sulfate, filtrated, the filtrate was concentrated under reduced pressure. The residue was purified by silica column chromatography (petroleum ether:ethyl acetate-100:1) to give white solid 30-c (430 mg, yield: 41%). LC-MS (ESI): m/z=189 [M+H]$^+$.

Preparation of Compound 30-b

Under nitrogen, to a suspension of compound 5-a (640 mg, 1.65 mmol), compound 30-c (280 mg, 1.49 mmol) and potassium carbonate (720 mg, 5.2 mmol) in 1,4-dioxane (2 mL) and water (6 mL) was added Pd(PPh$_3$)$_4$ (57 mg, 0.05 mmol), the mixture was heated to 80° C. and stirred for 16 hours. The mixture was then concentrated under reduced pressure, the residue was diluted with water (20 mL), extracted with dichloromethane (20 mL×3). The organic layer were combined, washed with water (10 mL×3) and saturated brine (10 mL) in sequence, then dried over anhydrous sodium sulfate, filtrated, the filtrate was concentrated under reduced pressure. The residue was purified by silica column chromatography (petroleum ether:ethyl acetate=3:1) to give light yellow solid 30-b (620 mg, yield: 70%). LC-MS (ESI): nm/z=415 [M+H]$^+$.

Preparation of Compound 30-a

To a solution of compound 30-b (500 mg, 1.2 mmoL) in dichloromethane (4 mL) was added trifluoroacetic acid (1 mL), the mixture was stirred at room temperature for 2 hours. After the mixture was concentrated under reduced pressure, the residue was treated with aqueous sodium dicarbonate solution (2 N, 6 mL), extracted with ethyl acetate (5 mL×3). The organic layers were combined, washed with water (20 mL×3) and saturated brine (20 mL) in sequence, then dried over anhydrous sodium sulfate, filtrated, the filtrate was concentrated under reduced pressure to give light yellow liquid 30-a (370 mg, yield: 97%), which was used directly for the next step without purification. LC-MS (ESI): m/z=315 [M+H]$^+$.

Preparation of Compound 30

At 0° C., to a solution of compound 30-a (314 mg, 1.0 mmoL) and triethylamine (1 mL) in dichloromethane (4 mL) was added dropwise ethylsulfonyl chloride (154 mg, 1.2 mmoL). After stirred for 30 minutes, the mixture was concentrated under reduced pressure, and the residue was treated with aqueous sodium dicarbonate (2 N, 6 mL), extracted with ethyl acetate (5 mL×3). The organic layers were combined, washed with water (10 mL×3) and saturated brine (20 mL) in sequence, then dried over anhydrous sodium sulfate, filtrated, the filtrate was concentrated under reduced pressure to give yellow liquid 30 (280 mg, yield: 70%), which was used directly for the next step without purification. LC-MS (ESI): m/z=407 [M+H]$^+$.

Preparation of Compound T-30

Under nitrogen, to a suspension of compound 30 (70 mg, 0.17 mmol), aniline (25 mg, 0.26 mmol) and potassium carbonate (138 mg, 1.0 mmol) in 1,4-dioxane (4 mL) were added Pd$_2$(dba)$_3$ (15 mg, 0.017 mmol) and Ruphos (10 mg, 0.07 mmol), the mixture was heated to 130° C. by microwave and stirred for 3 hours. After cooled to room temperature, the mixture was diluted with ethyl acetate (10 mL), then filtrated, and the filtrate was concentrated under reduced pressure. The residue was purified by preparation HPLC (mobile phase:acetonitrile, water (0.05% trifluoroacetic acid); gradient: 50%-80%-10%) to give compound T-30 (16 mg, yield: 20%). LC-MS (ESI): m/z=464 [M+H]$^+$.

$^1$H-NMR (400 MHz, CDCl$_3$) δ: 9.48 (s, 1H), 8.86 (s, 1H), 8.42 (d, J=1.6 Hz, 1H), 8.40 (s, 1H), 7.88 (d, J=6.4 Hz, 2H), 7.30 (t, J=6.4 Hz, 1H), 7.04 (d, J=1.6 Hz, 1H), 6.93 (t, J=6.4 Hz, 1H), 4.56 (d, J=7.2 Hz, 2H), 4.27 (d, J=7.2 Hz, 2H), 3.72 (s, 2H), 3.25 (q, J=6 Hz, 2H), 1.25 (t, J=6 Hz, 3H) ppm

Example 31

2-(3-(4-(2-((1H-Pyrazol-4-yl)amino)thieno[3,2-d]pyrimidin-4-yl)-1H-pyrazol-1-yl)-1-(ethylsulfonyl)azetidin-3-yl)acetonitrile T-31

Synthetic Route:

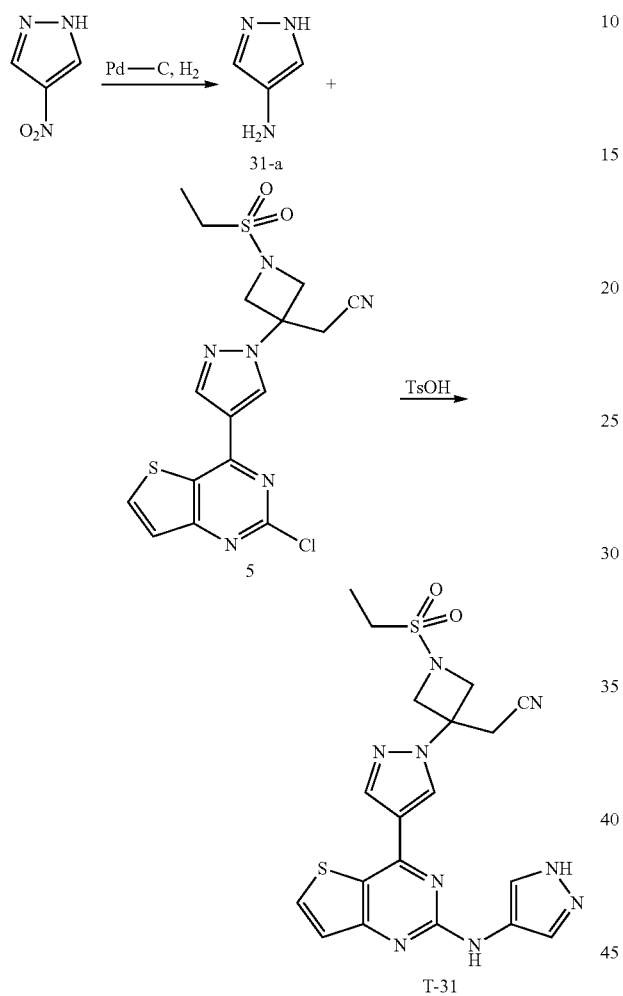

Preparation of Compound 31-a

Under hydrogen (1 atm), to a solution of 4-nitropyrazole (1.13 g, 10 mmol) in methanol (10 mL) was added 10% Pd—C (0.1 g). The mixture was stirred at 25° C. for 12 hours, and then filtrated, the filtrate was concentrated under reduced pressure to give compound 31-a (860 mg, yield: 100%), which was used directly for the next step without purification.

Preparation of Compound T-31

Compound 31-a (130 mg, 1.5 mmol) and compound 5 (222 mg, 0.5 mmol) were dissolved in n-butanol (10 mL), p-toluene sulfonic acid monohydrate (344 mg, 2.0 mmol) was added. The mixture was heated to 120° C. and stirred for 3 hours. After cooled to room temperature, the mixture was treated with saturated aqueous sodium bicarbonate solution (10 mL), then extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:water (0.04% trifluoroacetic acid), acetonitrile; gradient: 32%-62%) to give compound T-31 (143 mg, yield: 61%). LC-MS (ESI): m/z=470 [M+H]$^+$.

$^1$H-NMR (400 MHz, DMSO-d$_6$) δ: 9.43 (s, 1H), 8.81 (s, 1H), 8.37 (s, 1H), 8.34 (d, J=4.0 Hz, 1H), 7.87 (s, 2H), 739 (d, J=4.0 Hz, 1H), 4.57 (d, J=8 Hz, 2H), 4.27 (d, J=8 Hz, 2H), 3.91 (s, 4H), 3.24 (q, J=6 Hz, 2H), 1.25 (t, J=6 Hz, 3H) ppm

Example 32

2-(1-(Ethylsulfonyl)-3-(4-(2-((1-(2-methoxyacetyl)-1H-pyrazol-4-yl)amino)thieno[3,2-d]pyrimidin-4-yl)-1H-pyrazol-1-yl)azetidin-3-yl)acetonitrile T-32

Synthetic Route:

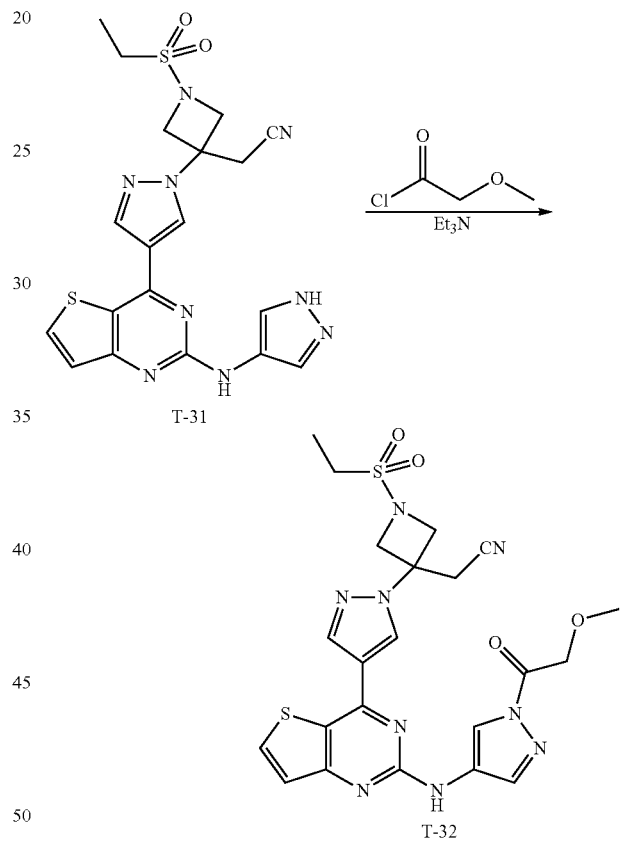

At 0° C., to a solution of compound T-31 (47 mg, 0.1 mmoL) and triethylamine (100 mg, 1.0 moL) in dichloromethane (10 mL) was added slowly methoxyacetyl chloride (11 mg, 0.2 mmol), and stirred for 1 hour. The mixture was concentrated under reduced pressure, the residue was treated with saturated aqueous sodium bicarbonate solution (5 mL), extracted with dichloromethane (5 mL×3). The organic layers were combined, dried over anhydrous sodium sulfate, then filtrated, the filtrate was concentrated under reduced pressure. The residue was purified by silica column chromatography (petroleum ether:ethyl acetate=3:1) to give compound T-32 (32 mg, yield: 59%/o). LC-MS (ESI): m/z=542 [M+H]$^+$.

$^1$H-NMR (400 MHz, DMSO-d$_6$) δ: 9.94 (s, 1H), 8.85 (s, 1H), 8.66 (s, 1H), 8.43 (d, J=5.2 Hz, 1H), 8.39 (s, 1H), 8.06

(s, 1H), 7.51 (d, J=5.2 Hz, 1H), 4.87 (s, 2H), 4.57 (d, J=9.2 Hz, 2H), 4.28 (d, J=9.2 Hz, 2H), 3.73 (s, 2H), 3.43 (s, 3H), 3.25 (q, J=7.2 Hz, 2H), 1.25 (t, J=7.2 Hz, 3H) ppm

Example 33

2-(4-((4-(1-(3-(Cyanomethyl)-1-(ethylsulfonyl)azetidin-3-yl)-1H-pyrazol-4-yl)thieno[3,2-d]pyrimidin-2-yl)amino)-1H-pyrazol-1-yl)acetic acid T-33

Synthetic Route:

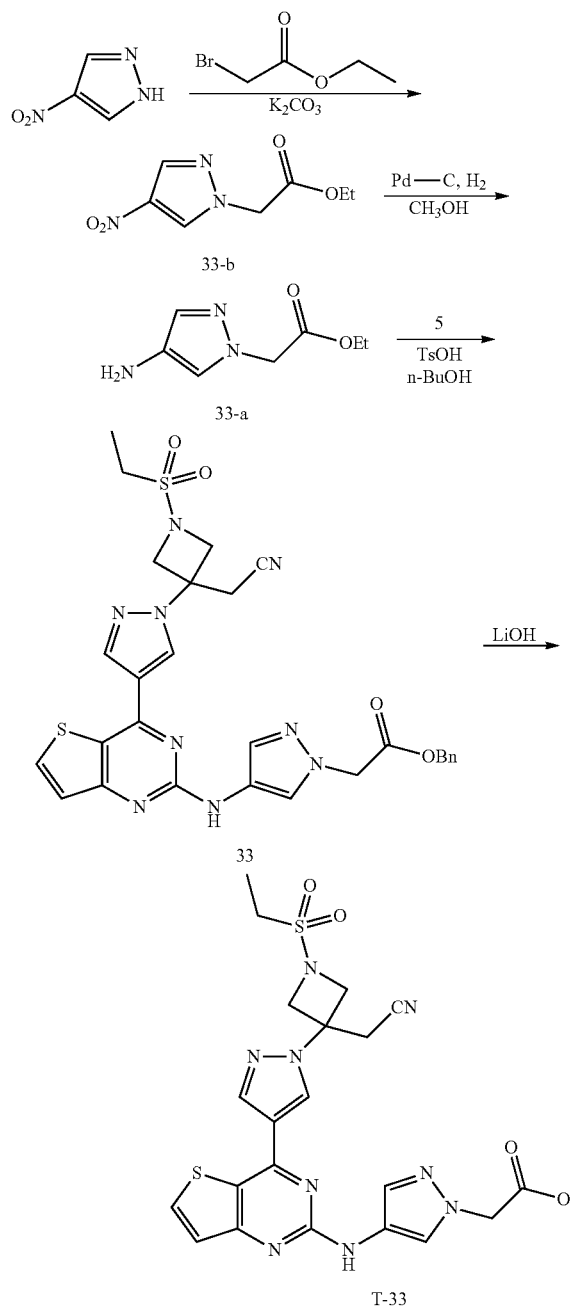

Preparation of Compound 33-b

Ethyl bromoacetate (1.67 g, 10 mmol) and potassium carbonate (2.76 g, 20 mmol) were added to a solution of 4-nitropyrazole (1.13 g, 10 mmol) in DMF (15 mL), the mixture was heated to 90° C. and stirred for 12 hours. After the mixture was cooled to room temperature, water (60 mL) was added, then the mixture was extracted with ethyl acetate (20 mL×3). The organic layers were combined, washed with water (10 mL) and saturated brine (10 mL) in sequence, dried over anhydrous sodium sulfate, then filtrated, the filtrate was concentrated under reduced pressure. The residue was purified by silica column chromatography (petroleum ether:ethyl acetate=5:1) to give compound 33-b (1.68 g, yield: 84%). LC-MS (ESI): m/z=200 [M+H]$^+$.

Preparation of Compound 33-a

Under hydrogen (1 atm), to a solution of compound 33-b (1.0 g, 5 mmol) in methanol (10 mL) was added 10% Pd—C (0.1 g). The mixture was stirred at 25° C. for 12 hours, and then filtrated, the filtrate was concentrated under reduced pressure to give compound 33-a (760 mg, yield: 90%), which was used directly for the next step without purification. LC-MS (ESI): m/z=170 [M+H]$^+$.

Preparation of Compound 33

Compound 33-a (170 mg, 1.0 mmol) and compound 5 (211 mg, 0.5 mmol) were dissolved in n-butanol (10 mL), p-toluene sulfonic acid monohydrate (344 mg, 2.0 mmol) was added. The mixture was heated to 120° C. and stirred for 3 hours, then cooled to room temperature. The mixture was treated with saturated aqueous sodium bicarbonate solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by silica column chromatography (petroleum ether: ethyl acetate=3:1) to give compound 33 (116 mg, yield: 21%). LC-MS (ESI): m/z=584 [M+H]$^+$.

Preparation of Compound T-33

Aqueous LiOH solution (2 N, 0.5 mL) was added to a solution of compound 33 (83 mg, 0.15 mmol) in MeOH (2 mL) and THF (6 mL), the mixture was stirred at 25° C. for 1 hour. Aqueous HCl solution (2 N, 0.5 mL) was added, the mixture was concentrated under reduced pressure to remove organic solvents. The residue was treated with water (2 mL), extracted with ethyl acetate (2-mL×3). The organic layers were combined, dried over anhydrous sodium sulfate, then filtrated, the filtrate was concentrated under reduced pressure to give compound T-33 (36 mg, yield: 47%). LC-MS (ESI): m/z=528 [M+H]$^+$.

$^1$H-NMR (400 MHz, DMSO-d$_6$) δ: 8.65 (s, 1H), 8.31 (s, 1H), 8.09 (s, 1H), 8.07 (d, J=4.4 Hz, 1H), 7.56 (s, 1H), 7.23 (d, J=4.4 Hz, 1H), 4.90 (s, 2H), 4.56 (d, J=7.2 Hz, 2H), 4.22 (d, J=7.2 Hz, 2H), 3.51 (s, 2H), 3.07 (q, J=5.6 Hz, 2H), 1.27 (t, J=5.6 Hz, 3H) ppm

Example 34

Butyl 3-(4-((4-(1-(3-(cyanomethyl)-1-(ethylsulfonyl) azetidin-3-yl)-1H-pyrazol-4-yl)thieno[3,2-d]pyrimidin-2-yl)amino)-1H-pyrazol-1-yl)propanoate T-34

Synthetic Route:

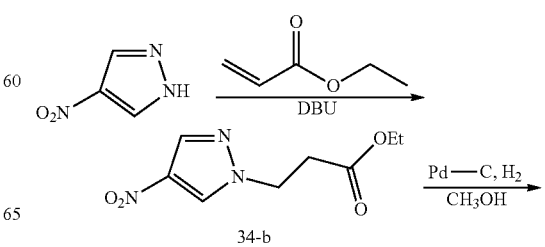

97
-continued

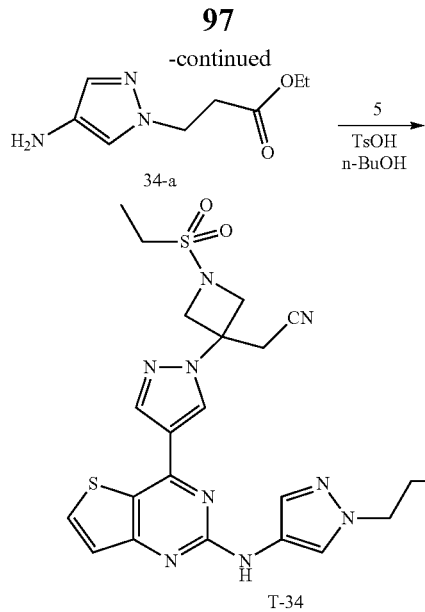

Preparation of Compound 34-b

4-Nitropyrazole (1.13 g, 10 mmol) and ethyl acrylate (1.72 g, 20 mmol) were dissolved in acetonitrile (30 mL), DBU (2 mL) was added. The mixture was stirred at 90° C. for 12 hours. Then the mixture was concentrated under reduced pressure, the residue was treated with water (50 mL), extracted with ethyl acetate (50 mL×3). The organic layers were combined, washed with water (50 mL×3) and saturated brine (50 mL) in sequence, dried over anhydrous sodium sulfate, then filtrated, the filtrate was concentrated under reduced pressure. The residue was purified by silica column chromatography (petroleum ether:ethyl acetate=3:1) to give compound 34-b (1.37 g, yield: 69%/c). LC-MS (ESI): m/z=214 [M+H]$^+$.

Preparation of Compound 34-a

Under hydrogen (1 atm), to a solution of compound 34-b (1.0 g, 5 mmol) in methanol (10 mL) was added 10% Pd—C (0.1 g). The mixture was stirred at 25° C. for 12 hours, and then filtrated, the filtrate was concentrated under reduced pressure to give compound 34-a (780 mg, yield: 92%), which was used directly for the next step without purification. LC-MS (ESI): m/z=184 [M+H]$^+$.

Preparation of Compound T-34

Compound 34-a (184 mg, 1.0 mmol) and compound 5 (211 mg, 0.5 mmol) were dissolved in n-butanol (10 mL), p-toluene sulfonic acid monohydrate (258 mg, 1.5 mmol) was added. The mixture was heated to 120° C. and stirred for 3 hours, then cooled to room temperature. The mixture was treated with saturated aqueous sodium bicarbonate solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by silica column chromatography (petroleum ether: ethyl acetate=3:1) to give compound T-34 (138 mg, yield: 24.8%). LC-MS (ESI): m/z=598 [M+H]$^+$.

$^1$H-NMR (400 MHz, CDCl$_3$) δ: 8.45 (s, 1H), 8.23 (s, 1H), 8.01 (s, 1H), 7.80 (d, J=5.6 Hz, 1H), 7.46 (s, 1H), 7.23 (d, J=5.6 Hz, 1H), 7.05 (s, 1H), 4.62 (d, J=9.6 Hz, 2H), 4.38 (t, J=6.4 Hz, 2H), 4.19 (d, J=9.6 Hz, 2H), 4.00 (t, J=6.4 Hz, 2H), 3.35 (s, 2H), 3.02 (q, J=7.2 Hz, 2H), 2.85 (t, J=6.4 Hz, 2H), 1.49 (q, J=7.2 Hz, 2H), 1.34 (t, J=7.2 Hz, 3H), 1.24 (m, 4H), 0.79 (t, J=7.2 Hz, 3H) ppm

98

Example 35

3-(4-((4-(1-(3-(Cyanomethyl)-1-(ethylsulfonyl)azetidin-3-yl)-1H-pyrazol-4-yl)thieno[3,2-d]pyrimidin-2-yl)amino)-1H-pyrazol-1-yl)propanoic acid T-35

Synthetic Route:

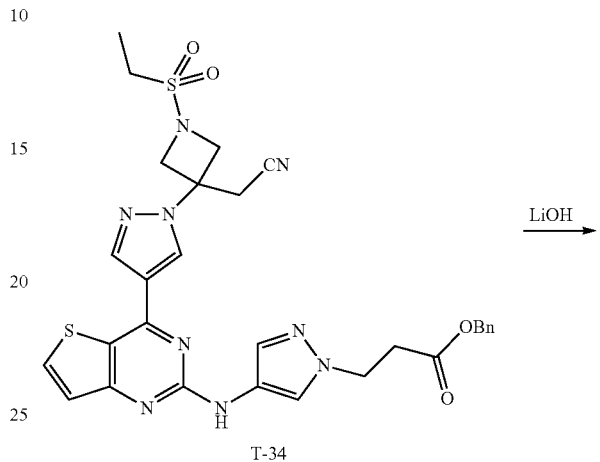

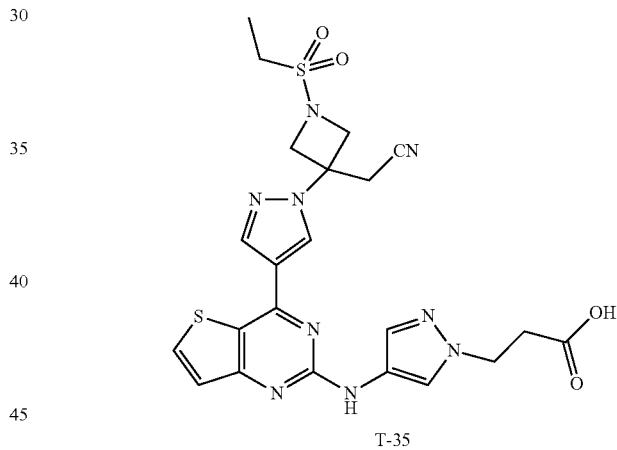

Aqueous LiOH solution (2 N, 0.5 mL) was added to a solution of compound T-34 (138 mg, 0.25 mmol) in MeOH (2 mL) and THF (6 mL), the mixture was stirred at 25° C. for 1 hour. Aqueous HCl solution (2 N, 0.5 mL) was added, the mixture was concentrated under reduced pressure to remove organic solvents. The residue was treated with water (2 mL), extracted with ethyl acetate (2 mL×3). The organic layers were combined, dried over anhydrous sodium sulfate, then filtrated, the filtrate was concentrated under reduced pressure. The residue was purified by preparation HPLC (mobile phase:water (0.04% trifluoroacetic acid), acetonitrile; gradient: 32%-62%) to give compound T-35 (98 mg, yield: 71%). LC-MS (ESI): m/z=542 [M+H]$^+$.

$^1$H-NMR (400 MHz, DMSO-d$_6$) δ: 9.44 (s, 1H), 8.81 (s, 1H), 8.41 (s, 1H), 8.34 (d, J=5.2 Hz, 1H), 8.09 (s, 1H), 7.57 (s, 1H), 7.37 (d, J=5.2 Hz, 1H), 4.59 (d, J=8.8 Hz, 2H), 4.32 (t, J=6.4 Hz, 2H), 4.27 (d, J=8.8 Hz, 2H), 3.73 (s, 2H), 3.25 (q, J=7.6 Hz, 2H), 2.79 (t, J=6.4 Hz, 2H), 1.25 (t, J=7.6 Hz, 3H) ppm

Example 36

3-(4-((4-(1-(3-(Cyanomethyl)-1-(ethylsulfonyl)azetidin-3-yl)-1H-pyrazol-4-yl)thieno[3,2-d]pyrimidin-2-yl)amino)-1H-pyrazol-1-yl)-N,N-dimethylpropanamide T-36

Synthetic Route:

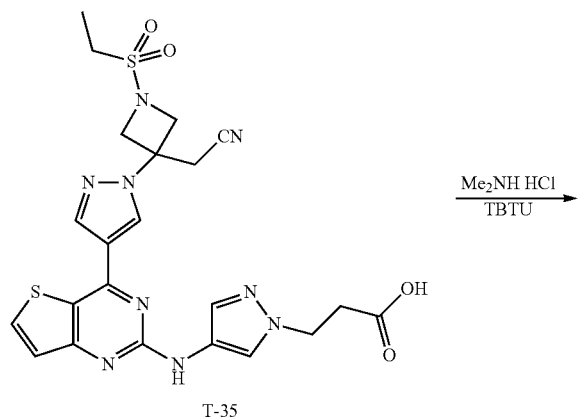

Example 37

4-(4-((4-(1-(3-(Cyanomethyl)-1-(ethylsulfonyl)azetidin-3-yl)-1H-pyrazol-4-yl)thieno[3,2-d]pyrimidin-2-yl)amino)-1H-pyrazol-1-yl)-N,N-dimethylbutanamide T-37

Synthetic Route:

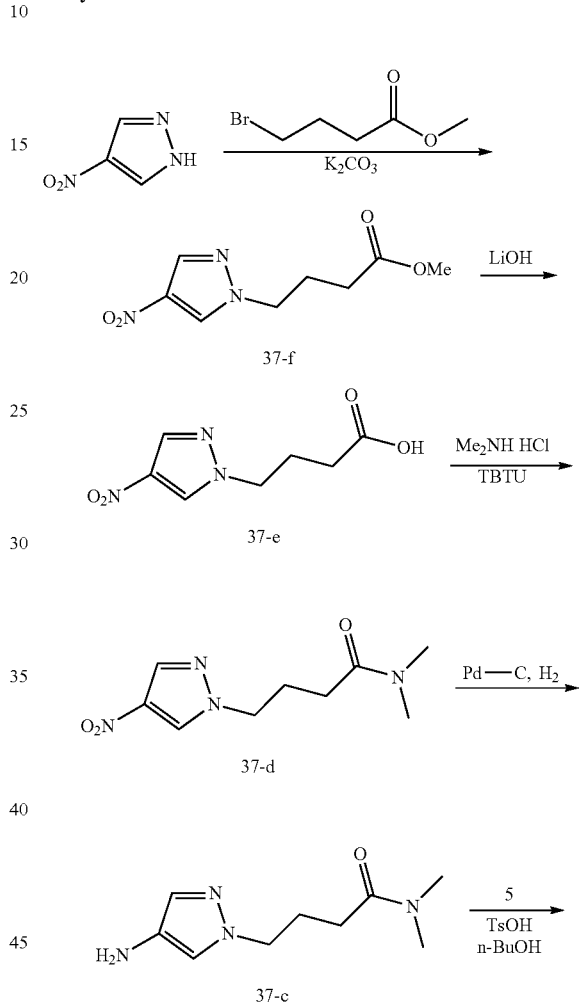

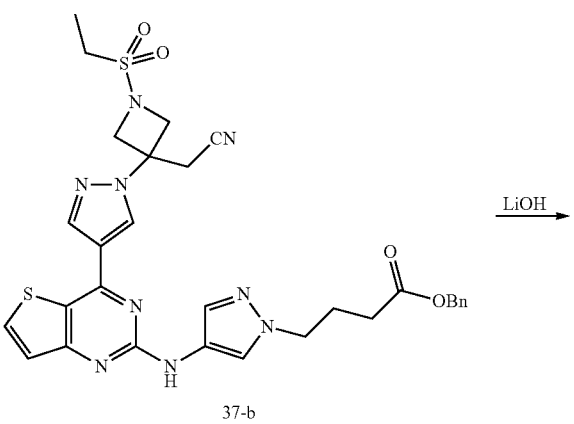

TBTU (200 mg, 0.62 mmol) and N,N-diisopropylethylamine (65 mg, 0.5 mmol) were added to a solution of compound T-35 (70 mg, 0.13 mmol) and dimethylamine hydrochloride (12 mg, 0.26 mmol) in dichloromethane (5 mL). After stirred at 25° C. for 1 hour, the mixture was treated with aqueous hydrochloride solution (1 N, 4 mL), then extracted with dichloromethane (3 mL×3). The organic layers were combined, dried over anhydrous sodium sulfate, then filtrated, the filtrate was concentrated under reduced pressure. The residue was purified by preparation HPLC (mobile phase:water (0.04% trifluoroacetic acid), acetonitrile; gradient: 30%-60%) to give compound T-36 (31 mg, yield: 42%). LC-MS (ESI): m/z=569 [M+H]$^+$.

$^1$H-NMR (400 MHz, CD$_3$OD) δ: 8.86 (s, 1H), 8.47 (s, 1H), 8.26 (d, J=5.2 Hz, 1H), 8.18 (s, 1H), 7.65 (s, 1H), 7.37 (d, J=5.2 Hz, 1H), 4.71 (d, J=8.8 Hz, 2H), 4.49 (t, J=6.0 Hz, 2H), 4.32 (d, J=8.8 Hz, 2H), 3.65 (s, 2H), 3.32 (q, J=7.2 Hz, 2H), 2.97 (m, 8H), 1.38 (t, J=7.2 Hz, 3H) ppm

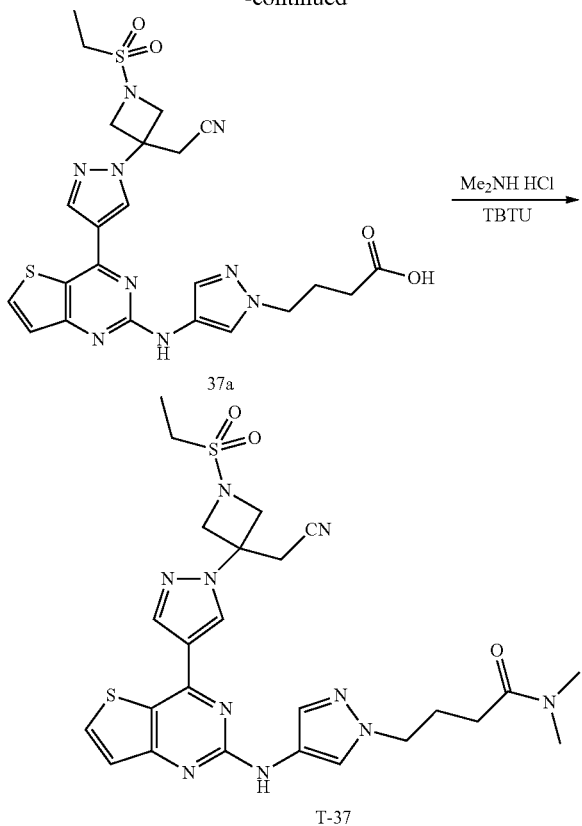

Preparation of Compound 37-f

4-Nitropyrazole (1.13 g, 10 mmol) and methyl 4-bromobutyrate (1.81 g, 10 mmol) were dissolved in DMF (15 mL), potassium carbonate (2.76 g, 2 mmol) was added. The mixture was stirred at 90° C. for 12 hours, then treated with water (60 mL), extracted with ethyl acetate (20 mL×3). The organic layers were combined, washed with water (20 mL×3) and saturated brine (20 mL) in sequence, dried over anhydrous sodium sulfate, then filtrated, the filtrate was concentrated under reduced pressure. The residue was purified by silica column chromatography (petroleum ether: ethyl acetate=5:1) to give compound 37-f (1.42 g, yield: 67%). LC-MS (ESI): m/z=214 [M+H]$^+$.

Preparation of Compound 37-e

Aqueous LiOH solution (2 N, 1.0 mL) was added to a solution of compound 37-f (426 mg, 2.0 mmol) in MeOH (2 mL) and THF (6 mL), the mixture was stirred at 25° C. for 1 hour. Aqueous HCl solution (2 N, 1.0 mL) was added, the mixture was concentrated under reduced pressure to remove organic solvents. The residue was treated with water (2 mL), extracted with ethyl acetate (2 mL×3). The organic layers were combined, dried over anhydrous sodium sulfate, then filtrated, the filtrate was concentrated under reduced pressure to give compound 37-e (368 mg, yield: 92%), which was used directly for the next step without purification. LC-MS (ESI): m/z=200 [M+H]$^+$.

Preparation of Compound 37-d

TBTU (800 mg, 2.4 mmol) and N,N-diisopropylethylamine (650 mg, 5 mmol) were added to a solution of compound 37-e (368 mg, 1.85 mmol) and dimethylamine hydrochloride (110 mg, 2.4 mmol) in dichloromethane (20 mL). After stirred at 25° C. for 1 hour, the mixture was treated with aqueous hydrochloride solution (1 N, 4 mL), extracted with dichloromethane (20 mL×3). The organic layers were combined, dried over anhydrous sodium sulfate, then filtrated, the filtrate was concentrated under reduced pressure to give compound 37-d (320 mg, yield: 76%), which was used directly for the next step without purification. LC-MS (ESI): m/z=227 [M+H]$^+$.

Preparation of Compound 37-c

Under hydrogen (1 atm), to a solution of compound 37-d (320 mg, 1.4 mmol) in methanol (10 mL) was added 10% Pd—C (0.1 g). The mixture was stirred at 25° C. for 12 hours, and then filtrated, the filtrate was concentrated under reduced pressure to give compound 37-c (280 mg, yield: 74%), which was used directly for the next step without purification. LC-MS (ESI): m/z=197 [M+H]$^+$.

Preparation of Compound 37-b

Compound 37-c (200 mg, 1.0 mmol) and compound 5 (221 mg, 0.5 mmol) were dissolved in n-butanol (10 mL), p-toluene sulfonic acid monohydrate (258 mg, 1.5 mmol) was added. The mixture was heated to 120° C. and stirred for 3 hours, then cooled to room temperature. The mixture was treated with saturated aqueous sodium bicarbonate solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by silica column chromatography (petroleum ether: ethyl acetate=3:1) to give compound 37-b (118 mg, yield: 41%). LC-MS (ESI): m/z=612 [M+H]$^+$.

Preparation of Compound 37-a

Aqueous LiOH solution (2 N, 0.5 mL) was added to a solution of compound 37-b (114 mg, 0.2 mmol) in MeOH (2 mL) and THF (6 mL), the mixture was stirred at 25° C. for 1 hour. Aqueous HCl solution (2 N, 0.5 mL) was added, the mixture was concentrated under reduced pressure to remove organic solvents. The residue was treated with water (2 mL), extracted with ethyl acetate (2 mL×3). The organic layers were combined, dried over anhydrous sodium sulfate, then filtrated, the filtrate was concentrated under reduced pressure to give compound 37-a (68 mg, yield: 61%), which was used directly for the next step without purification. LC-MS (ESI): m/z=556 [M+H]$^+$.

Preparation of Compound T-37

TBTU (200 mg, 0.62 mmol) and N,N-diisopropylethylamine (65 mg, 0.5 mmol) were added to a solution of compound 37-a (68 mg, 0.12 mmol) and dimethylamine hydrochloride (11 mg, 0.24 mmol) in dichloromethane (5 mL). After stirred at 25° C. for 1 hour, the mixture was treated with aqueous hydrochloride solution (1 N, 4 mL), extracted with dichloromethane (3 mL×3). The organic layers were combined, dried over anhydrous sodium sulfate, then filtrated, the filtrate was concentrated under reduced pressure. The residue was purified by preparation HPLC (mobile phase:water (0.04% trifluoroacetic acid), acetonitrile; gradient: 30%-60%) to give compound T-37 (21 mg, yield: 30%). LC-MS (ESI): m/z=583 [M+H]$^+$.

$^1$H-NMR (400 MHz, CD$_3$OD) δ: 8.79 (s, 1H), 8.44 (s, 1H), 8.23 (d, J=5.2 Hz, 1H), 8.12 (s, 1H), 7.66 (s, 1H), 7.36 (d, J=5.2 Hz, 1H), 4.67 (d, J=8.8 Hz, 2H), 4.32 (d, J=8.8 Hz, 2H), 4.25 (t, J=6.8 Hz, 2H), 3.64 (s, 2H), 3.20 (q, J=7.2 Hz, 2H), 2.97 (d, J=35.6 Hz, 6H), 2.42 (t, J=6.4 Hz, 2H), 2.19 (m, 2H), 1.38 (t, J=7.2 Hz, 3H) ppm

Example 38

2-(1-(Ethylsulfonyl)-3-(4-(2-((1-(tetrahydro-2H-pyran-4-yl)-1H-pyrazol-4-yl)amino)thieno[3,2-d]pyrimidin-4-yl)-1H-pyrazol-1-yl)azetidin-3-yl)acetonitrile T-38

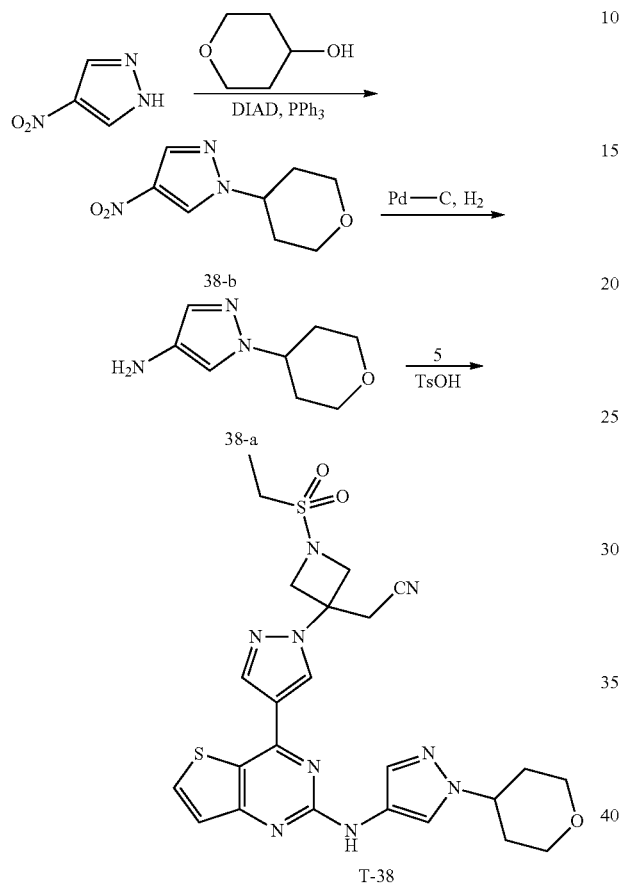

Preparation of Compound 38-b

At 25° C., DIAD (3.06 g, 15 mmol) was added slowly to a solution of 4-nitropyrazole (1.13 g, 10 mmol), tetrahydro-2H-pyran-4-ol (1.12 g, 11 mmol) and PPh$_3$ (3.93 g, 15 mmol) in anhydrous THF (50 mL). After stirred for 3 hours, the mixture was concentrated under reduced pressure, the residue was purified by silica column chromatography (petroleum ether:ethyl acetate=3:1) to give compound 38-b (990 mg, yield: 49%). LC-MS (ESI): m/z=198 [M+H]$^+$.

Preparation of Compound 38-a

Under hydrogen (1 atm), to a solution of compound 38-b (990 mg, 49 mmol) in methanol (10 mL) was added 10% Pd—C (0.1 g). The mixture was stirred at 25° C. for 12 hours, and then filtrated, the filtrate was concentrated under reduced pressure to give compound 38-a (620 mg, yield: 75%), which was used directly for the next step without purification.

Preparation of Compound T-38

Compound 38-a (170 mg, 1.0 mmol) and compound 5 (221 mg, 0.5 mmol) were dissolved in n-butanol (10 mL), p-toluene sulfonic acid monohydrate (258 mg, 1.5 mmol) was added. The mixture was heated to 120° C. and stirred for 3 hours, then cooled to room temperature. The mixture was treated with saturated aqueous sodium bicarbonate solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:water (0.04% trifluoroacetic acid), acetonitrile; gradient: 30%-60%) to give compound T-38 (38 mg, yield: 13.6%). LC-MS (ESI): m/z=554 [M+H]$^+$.

$^1$H-NMR (400 MHz, CD$_3$OD) δ: 8.76 (s, 1H), 8.44 (s, 1H), 8.22 (d, J=5.2 Hz, 1H), 8.14 (s, 1H), 7.69 (s, 1H), 7.35 (d, J=5.2 Hz, 1H), 4.66 (d, J=9.6 Hz, 2H), 4.51 (m, 1H), 4.31 (d, J=9.6 Hz, 2H), 4.10 (d, J=3.6 Hz, 2H), 3.64 (s, 2H), 3.62 (d, J=3.6 Hz, 2H), 3.20 (q, J=7.6 Hz, 2H), 2.11 (m, 3H), 1.38 (t, J=7.6 Hz, 3H) ppm

Example 39

2-(1-(Ethylsulfonyl)-3-(4-(2-((1-(oxetan-3-yl)-1H-pyrazol-4-yl)amino)thieno[3,2-d]pyrimidin-4-yl)-1H-pyrazol-1-yl)azetidin-3-yl)acetonitrile T-39

Synthetic Route:

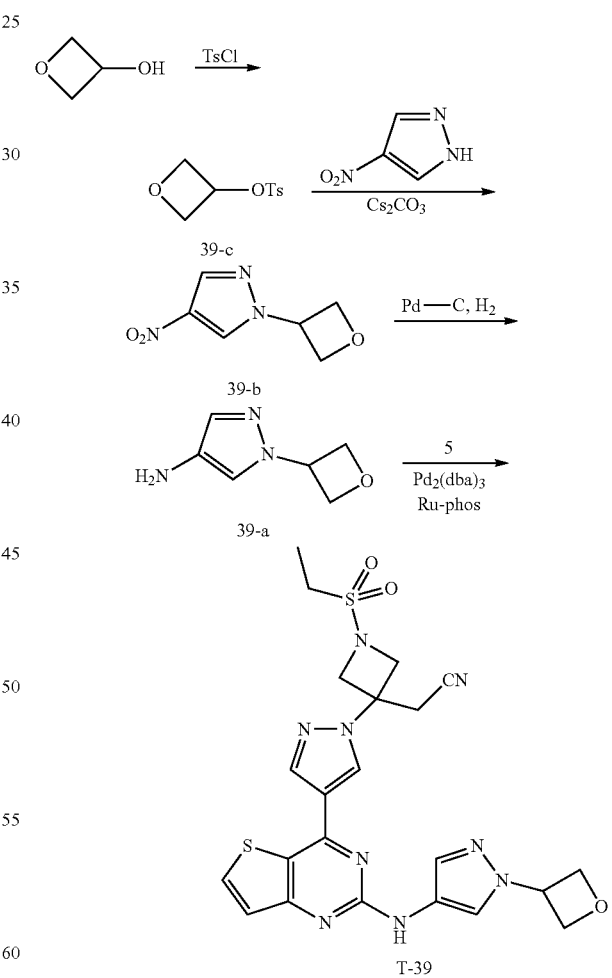

Preparation of Compound 39-c

At 0° C., aqueous NaOH solution (2 N, 15 mL) was added dropwise to a solution of oxetan-3-ol (1.48 g, 20 mmol) and p-toluene sulfonyl chloride (4.18 g, 22 mmol) in water (50 mL). After stirred for 3 hours, the mixture was treated with water (100 mL), extracted with dichloromethane (100 mL×3). The organic layers were combined, dried over anhydrous sodium sulfate, then filtrated, the filtrate was concentrated under reduced pressure. The residue was purified by silica column chromatography (petroleum ether: ethyl acetate=10:1) to give compound 39-c (3.9 g, yield: 85%). LC-MS (ESI): m/z=229 [M+H]+.

Preparation of Compound 39-b

Compound 39-c (3.9 g, 17 mmol) was added to a solution of 4-nitropyrazole (1.13 g, 10 mmol) and cesium carbonate (6.5 g, 20 mmol) in DMF (15 mL), and then was heated to 120° C. and stirred for 12 hours. After cooled to room temperature, the mixture was treated with water (60 mL), extracted with ethyl acetate (20 mL×3). The organic layers were combined, dried over anhydrous sodium sulfate, then filtrated, the filtrate was concentrated under reduced pressure. The residue was purified by silica column chromatography (petroleum ether:ethyl acetate=5:1) to give compound 39-b (1.3 g, yield: 77%). LC-MS (ESI): m/z=170 [M+H]+.

Preparation of Compound 39-a

Under hydrogen (1 atm), to a solution of compound 39-b (1.3 g, 7.7 mmol) in methanol (10 mL) was added 10% Pd—C (0.1 g). The mixture was stirred at 25° C. for 12 hours, and then filtrated, the filtrate was concentrated under reduced pressure to give compound 39-a (820 mg, yield: 76%), which was used directly for the next step without purification. LC-MS (ESI): m/z=140 [M+H]+.

Preparation of Compound T-39

Under nitrogen, to a suspension of compound 39-a (24 mg, 0.17 mmol), compound 5 (71 mg, 0.17 mmol) and potassium carbonate (138 mg, 1.0 mmol) in 1,4-dioxane (4 mL) were added Pd$_2$(dba)$_3$ (15 mg, 0.017 mmol) and Ruphos (10 mg, 0.07 mmol), the mixture was heated to 130° C. by microwave and stirred for 3 hours. After cooled to room temperature, the mixture was diluted with ethyl acetate (10 mL), then filtrated, and the filtrate was concentrated under reduced pressure. The residue was purified by preparation HPLC (mobile phase:acetonitrile, water (0.05% trifluoroacetic acid); gradient: 50%-80%-10%) to give compound T-39 (13 mg, yield: 14.5%). LC-MS (ESI): m/z=526 [M+H]+.

$^1$H-NMR (400 MHz, CDCl$_3$) δ: 8.74 (s, 1H), 8.43 (s, 1H), 8.31 (s, 1H), 8.13 (d, J=4.4 Hz, 1H), 7.77 (s, 1H), 7.34 (d, J=4.4 Hz, 2H), 5.60 (m, 1H), 5.10 (m, 4H), 4.77 (d, J=7.2 Hz, 2H), 4.33 (d, J=7.2 Hz, 2H), 3.64 (s, 2H), 3.21 (q, J=6.0 Hz, 2H), 2.51 (s, 3H), 1.40 (t, J=6.0 Hz, 3H) ppm Example 40

2-(3-(4-(2-((1-Ethyl-1H-pyrazol-4-yl)amino)thieno[3,2-d]pyrimidin-4-yl)-1H-pyrazol-1-yl)-1-(ethylsulfonyl)azetidin-3-yl)acetonitrile T-40

Synthetic Route:

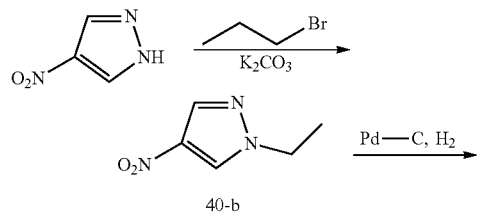

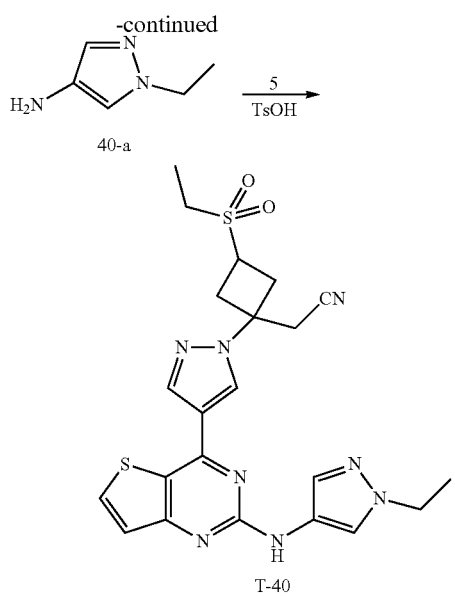

Preparation of Compound 40-b

Bromoethane (1.1 g, 10 mmol) and potassium carbonate (2.76 g, 20 mmol) were added to a solution of 4-nitropyrazole (1.13 g, 10 mmol) in DMF (15 mL) respectively, the mixture was heated to 90° C. and stirred for 12 hours. After cooled to room temperature, the mixture was treated with water (60 mL), extracted with ethyl acetate (20 mL×3). The organic layers were combined, dried over anhydrous sodium sulfate, then filtrated, the filtrate was concentrated under reduced pressure. The residue was purified by silica column chromatography (petroleum ether:ethyl acetate=5:1) to give compound 40-b (1.2 g, yield: 85%). LC-MS (ESI): m/z=142 [M+H]+.

Preparation of Compound 40-a

Under hydrogen (1 atm), to a solution of compound 40-b (1.0 g, 7.1 mmol) in methanol (10 mL) was added 10% Pd—C (0.1 g). The mixture was stirred at 25° C. for 12 hours, and then filtrated, the filtrate was concentrated under reduced pressure to give compound 40-a (760 mg, yield: 96%), which was used directly for the next step without purification. LC-MS (ESI): m/z=112 [M+H]+.

Preparation of Compound T-40

Compound 40-a (111 mg, 1.0 mmol) and compound 5 (221 mg, 0.5 mmol) were dissolved in n-butanol (10 mL), p-toluene sulfonic acid monohydrate (258 mg, 1.5 mmol) was added. The mixture was heated to 120° C. and stirred for 3 hours, then cooled to room temperature. The mixture was treated with saturated aqueous sodium bicarbonate solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:water (0.04% trifluoroacetic acid), acetonitrile; gradient: 40%-70%) to give compound T-40 (23 mg, yield: 9.2%). LC-MS (ESI): m/z=498 [M+H]+.

$^1$H-NMR (400 MHz, DMSO-d$_6$) δ: 9.44 (s, 1H), 8.82 (s, 1H), 8.39 (s, 1H), 8.34 (d, J=5.2, 1H), 8.06 (s, 1H), 7.58 (s, 1H), 7.38 (d, J=5.2 Hz, 1H), 4.58 (d, J=9.2 Hz, 2H), 4.27 (d, J=9.2 Hz, 2H), 4.14 (q, J=7.2 Hz, 2H), 3.24 (q, J=7.2 Hz, 2H), 1.39 (t, J=7.2 Hz, 3H), 1.25 (t, J=7.2 Hz, 3H) ppm

Example 41

2-(1-(Ethylsulfonyl)-3-(4-(2-((1-isopropyl-1H-pyrazol-4-yl)amino)thieno[3,2-d]pyrimidin-4-yl)-1H-pyrazol-1-yl)azetidin-3-yl)acetonitrile T-41

Preparation of Compound T-41
Synthetic Route:

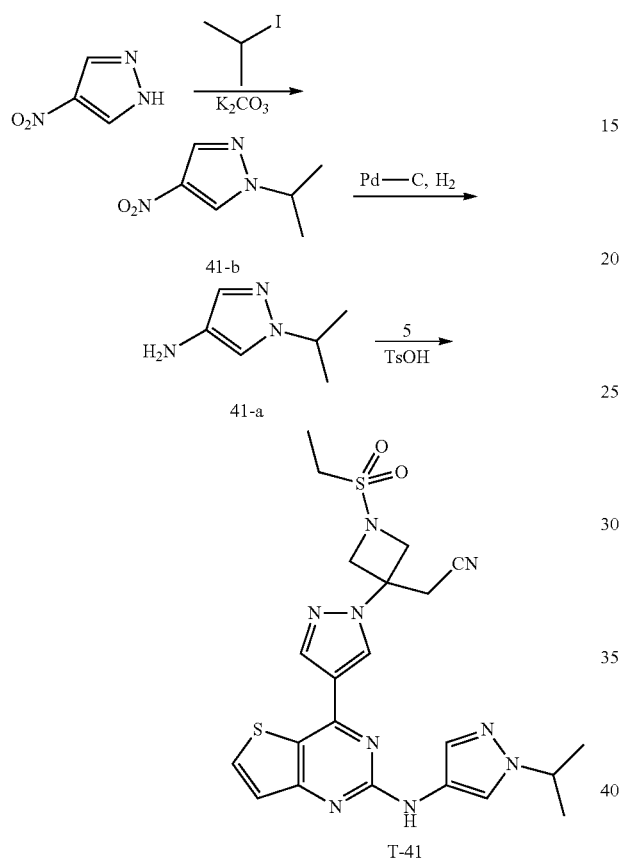

Preparation of Compound 41-b

2-Iodopropane (2.3 g, 13.27 mmol) and potassium carbonate (1.81 g, 13.27 mmol) were added to a solution of 4-nitropyrazole (1.0 g, 8.85 mmol) in DMF (10 mL) in sequence, the mixture was heated to 60° C. and stirred for 3 hours. The mixture was poured into ice water (100 mL), extracted with ethyl acetate (100 mL×3). The organic layers were combined, dried over anhydrous sodium sulfate, then filtrated, the filtrate was concentrated under reduced pressure to give yellow oil 41-b (1.1 g, yield: 81%), which was used for the next step without purification.

Preparation of Compound 41-a

Under hydrogen (1 atm), to a solution of compound 41-b (1.1 g, 8.8 mmol) in ethanol (20 mL) was added 10% Pd—C (0.2 g). The mixture was stirred at 25° C. for 12 hours, and then filtrated, the filtrate was concentrated under reduced pressure to give compound 41-a (830 mg, yield: 94%), which was used directly for the next step without purification. LC-MS (ESI): m/z=126 [M+H]$^+$.

Preparation of Compound T-41

Compound 41-a (71 mg, 0.57 mmol) and compound 5 (80 mg, 0.19 mmol) were dissolved in n-butanol (2 mL), p-toluene sulfonic acid monohydrate (71 mg, 0.38 mmol) was added. The mixture was heated to 115° C. and stirred for 18 hours, then cooled to room temperature. The mixture was treated with saturated aqueous sodium bicarbonate solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:acetonitrile/methanol (1:1), water (0.05% trifluoroacetic acid); gradient: 75%-95%-10%) to give compound T-41 (48 mg, yield: 49%). LC-MS (ESI): m/z=512 [M+H]$^+$.

$^1$H-NMR (400 MHz, CDCl$_3$) δ: 8.65 (s, 1H), 8.30 (d, J=3 Hz, 1H), 8.15 (d, J=5 Hz, 1H), 8.00 (d, J=3 Hz, 1H), 7.67 (d, J=3 Hz, 1H), 7.36 (d, J=6 Hz, 1H), 4.63 (t, J=6 Hz, 2H), 4.53 (m, 1H), 4.28 (d, J=9 Hz, 1H), 3.60 (s, 3H), 3.18 (q, J=7 Hz, 2H), 1.39 (t, J=7 Hz, 3H) ppm

Example 42

2-(3-(4-(2-((1-Methyl-1H-pyrazol-4-yl)amino)thieno[2,3-d]pyrimidin-4-yl)-1H-pyrazol-1-yl)oxetan-3-yl)acetonitrile T-42

Synthetic Route:

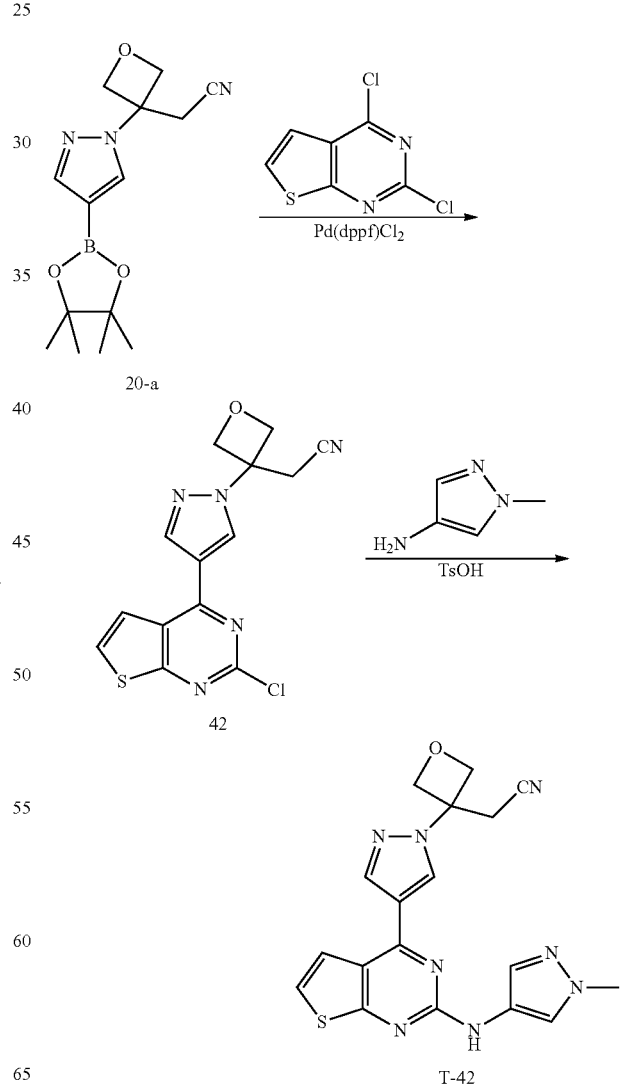

Preparation of Compound 42

Under nitrogen, 2,4-dichlorotheino[2,3-d]pyrimidine (317 mg, 1.56 mmol), compound 20-a (300 mg, 1.04 mmol) and sodium carbonate (331 mg, 3.12 mmol) were suspended in 1,4-dioxane (5 mL), Pd(dppf)Cl₂ (82 mg, 0.1 mmol) was added. The mixture was heated to 80° C. and stirred for 18 hours. After cooled to room temperature, the mixture was diluted with dichloromethane (50 mL), then filtrated, and the filtrate was concentrated under reduced pressure. The residue was purified by silica column chromatography (petroleum ether:ethyl acetate=1:1 to dichloromethane:methanol=10:1) to give gray solid 42 (120 mg, yield: 35%). LC-MS (ESI): m/z=332 [M+H]⁺.

Preparation of Compound T-42

Compound 42 (50 mg, 0.15 mmol) and 1-methyl-4-aminopyrazole (44 mg, 0.45 mmol) were dissolved in n-butanol (2 mL), p-toluene sulfonic acid monohydrate (58 mg, 0.31 mmol) was added. The mixture was heated to 110° C. and stirred for 16 hours, then cooled to room temperature. The mixture was treated with saturated aqueous sodium bicarbonate solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:acetonitrile, water (0.05% trifluoroacetic acid); gradient: 50%-80%-10%) to give compound T-42 (14 mg, yield: 24%). LC-MS (ESI): m/z=393 [M+H]⁺.

¹H-NMR (400 MHz, CDCl₃) δ: 8.59 (br, 1H), 8.25 (s, 1H), 7.92 (s, 1H), 7.66 (s, 1H), 7.42 (d, J=6 Hz, 1H), 7.24 (d, J=6 Hz, 1H), 5.21 (d, J=9 Hz, 2H), 4.87 (d, J=9 Hz, 2H), 3.93 (s, 3H), 3.45 (s, 2H) ppm Example 43

2-(3-(4-(2-((1-Methyl-1H-pyrazol-4-yl)amino)thieno[3,2-d]pyrimidin-4-yl)-1H-pyrazol-1-yl)oxetan-3-yl)acetonitrile T-43

Synthetic Route:

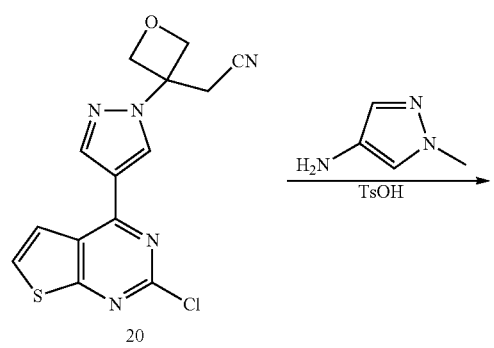

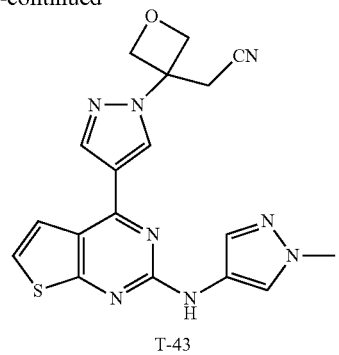

T-43

Compound 20 (108 mg, 0.33 mmol) and 1-methyl-4-aminopyrazole (95 mg, 0.98 mmol) were dissolved in n-butanol (3 mL), p-toluene sulfonic acid monohydrate (124 mg, 0.66 mmol) was added. The mixture was heated to 110° C. and stirred for 16 hours, then cooled to room temperature. The mixture was treated with saturated aqueous sodium bicarbonate solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation TLC (mobile phase:ethyl acetate) to give compound T-43 (75 mg, yield: 59%). LC-MS (ESI): m/z=393 [M+H]⁺.

¹H-NMR (400 MHz, CDCl₃) δ: 8.42 (s, 1H), 8.36 (s, 1H), 7.96 (s, 1H), 7.87 (d, J=6 Hz, 1H), 7.54 (s, 1H), 7.33 (d, J=6 Hz, 1H), 7.14 (s, 1H), 5.18 (d, J=9 Hz, 2H), 4.87 (d, J=9 Hz, 2H), 3.92 (s, 3H), 3.43 (s, 2H) ppm Example 44

2-(4-(4-(2-((1-Methyl-1H-pyrazol-4-yl)amino)thieno[3,2-d]pyrimidin-4-yl)-1H-pyrazol-1-yl)tetrahydro-2H-pyran-4-yl)acetonitrile T-44

Synthetic Route:

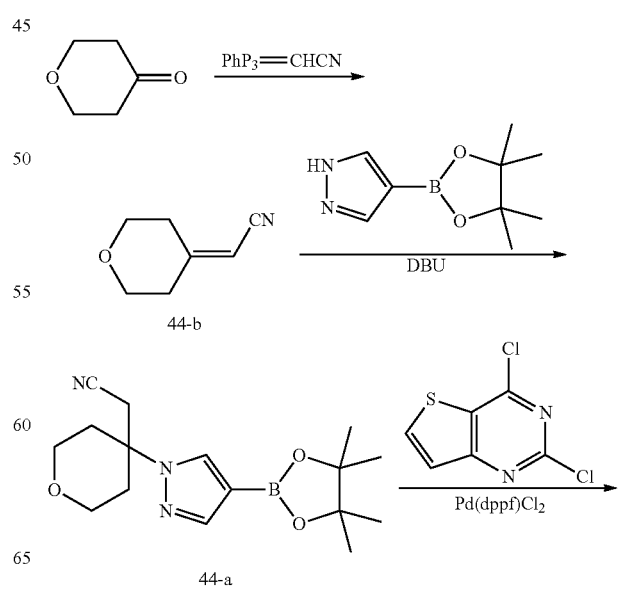

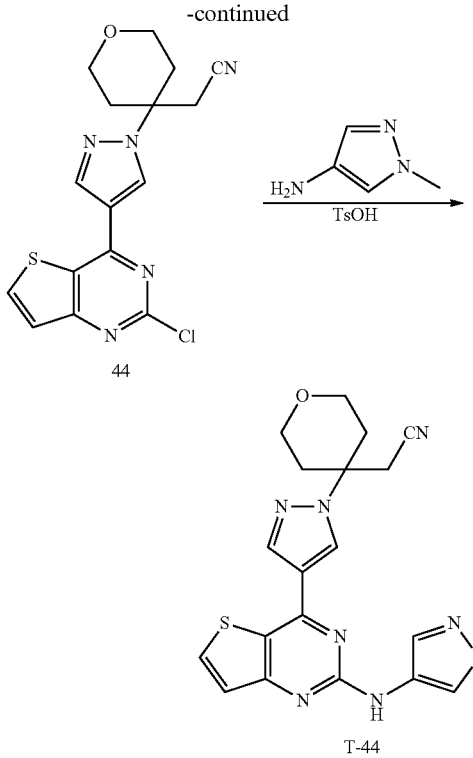

Preparation of Compound 44-b

At room temperature, cyanomethylene triphenylphosphorane (8.0 g, 20 mmol) and 4-oxotetrahydropyran (2.0 g, 20 mmol) were dissolved in dichloromethane (20 mL), the mixture was stirred for 16 hours. The mixture was concentrated under reduced pressure, and the residue was added to a component solvent (50 mL) of petroleum ether and ethyl acetate (10:1). There was white solid precipitated, and the mixture was filtered, the filtrate was concentrated under reduced pressure. The residue was purified by silica column chromatography (petroleum ether:ethyl acetate=5:1) to give compound 44-b (2.0 g, yield: 81%), which was used directly for the next step without purification.

Preparation of Compound 44-a

Compound 44-b (500 mg, 4.06 mmol) and 4-(4,4,5,5-tetramethyl-1,3,2-dioxaborolan-2-yl)-1H-pyrazole (1.2 g, 6.09 mmol) were dissolved in acetonitrile (10 mL), 1,8-diazabicyclo(5.4.0)undec-7-ene (1.23 g, 8.12 mmol) was added. The mixture was stirred at 60° C. for 18 hours. The mixture was then concentrated under reduced pressure, and the residue was treated with 1N aqueous hydrochloride solution to adjust pH=3-4, then extracted with ethyl acetate (20 mL×3). The organic layers were combined, washed with water (20 mL×3) and saturated brine (20 mL) in sequence, dried over anhydrous sodium sulfate, then filtrated, the filtrate was concentrated under reduced pressure to give yellow oil 44-a (700 mg, yield: 54%), which was used directly for the next step without purification. LC-MS (ESI): m/z=318 [M+H]+.

Preparation of Compound 44

Under nitrogen, compound 44-a (500 mg, 3.65 mmol), 2,4-dichlorotheino[3,2-d]pyrimidine (745 mg, 3.65 mmol) and sodium carbonate (1.2 g, 10.95 mmol) were suspended in 1,4-dioxane (0.5 mL) and water (0.5 mL), Pd(dppf)Cl$_2$ (330 mg, 0.4 mmol) was added. The mixture was heated to 80° C. and stirred for 4 hours. The mixture was concentrated under reduced pressure, the residue was treated with water (20 mL), extracted with dichloromethane (20 mL×3). The organic layers were combined, washed with water (10 mL×3) and saturated brine (10 mL) in sequence, dried over anhydrous sodium sulfate, then filtrated, the filtrate was concentrated under reduced pressure to give light yellow solid 44 (210 mg, yield: 38%). LC-MS (ESI): m/z=360 [M+H]+.

Preparation of Compound T-44

Compound 44 (120 mg, 0.34 mmol) and 1-methyl-4-aminopyrazole (97 mg, 10.03 mmol) were dissolved in n-butanol (5 mL), p-toluene sulfonic acid monohydrate (127 mg, 0.67 mmol) was added. The mixture was heated to 110° C. and stirred for 16 hours, then concentrated under reduced pressure. The residue was purified by preparation TLC (mobile phase:ethyl acetate) to give light yellow solid T-44 (121 mg, yield: 86%). LC-MS (ESI): m/z=421 [M+H]+.
$^1$H-NMR (400 MHz, CDCl$_3$) δ: 8.43 (s, 1H), 8.38 (s, 1H), 7.98 (s, 1H), 7.87 (d, J=6 Hz, 1H), 7.54 (s, 1H), 7.33 (d, J=6 Hz, 1H), 7.03 (s, 1H), 3.93 (s, 3H), 3.89 (m, 2H), 3.61 (m, 2H), 2.95 (s, 2H), 2.67 (m, 2H), 2.24 (m, 2H) ppm Example 45

2-(3-(4-(2-((4-(2H-Tetrazol-5-yl)phenyl)amino)thieno[3,2-d]pyrimidin-4-yl)-1H-pyrazol-1-yl)-1-(ethylsulfonyl)azetidin-3-yl)acetonitrile T-45

Synthetic Route:

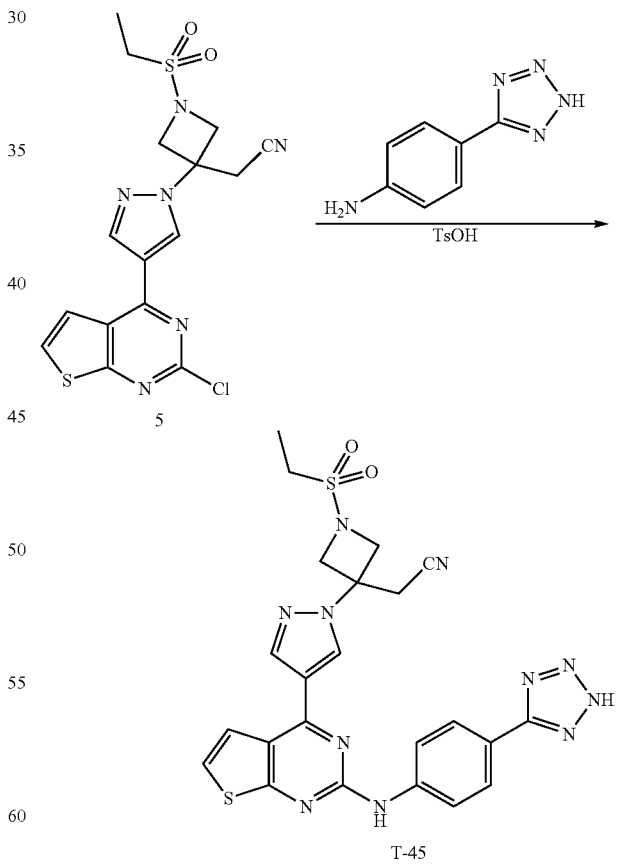

Compound 5 (422 mg, 1.0 mmol) and 4-(2H-tetrazole-5-yl)aniline (242 mg, 1.5 mmol) were dissolved in n-butanol (5 mL), p-toluene sulfonic acid monohydrate (285 mg, 1.5 mmol) was added. The mixture was heated to 110° C. and stirred for 16 hours, then concentrated under reduced pressure. The residue was purified by preparation HPLC (mobile phase:acetonitrile, water (0.05% trifluoroacetic acid); gradient: 60%-90%-10%) to give light yellow solid T-45 (52 mg, yield: 10%). LC-MS (ESI): m/z=548 [M+H]$^+$.

$^1$H-NMR (400 MHz, DMSO-d$_6$) δ: 10.08 (s, 1H), 8.88 (s, 1H), 8.45 (m, 2H), 8.13 (d, J=9 Hz, 1H), 7.99 (d, J=9 Hz, 1H), 7.50 (d, J=9 Hz, 1H), 4.59 (d, J=9 Hz, 2H), 4.29 (d, J=9 Hz, 2H), 3.74 (s, 2H), 3.24 (q, J=7 Hz, 2H), 1.25 (t, J=7 Hz, 3H) ppm Example 46

2-(3-(4-(2-((1-Methyl-1H-pyrazol-4-yl)amino)thieno[3,2-d]pyrimidin-4-yl)-1H-pyrazol-1-yl)-1-propionylazetidin-3-yl)acetonitrile T-46

Synthetic Route:

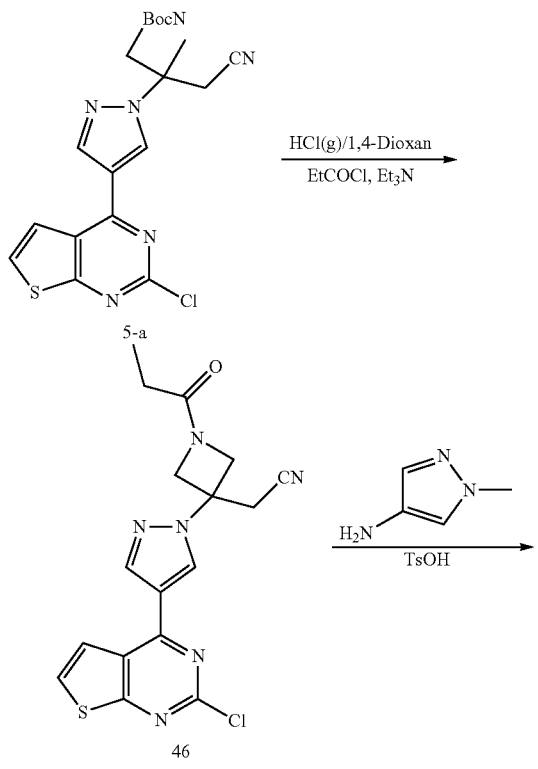

Preparation of Compound 46

To a solution of compound 5-a (250 mg, 0.58 mmol) in dichloromethane (2 mL) was added a solution of hydrochloride in 1,4-dioxane (4 N, 4 mL), the mixture was stirred at room temperature for 16 hours, then concentrated under reduced pressure, and the residue was treated with dichloromethane (5 mL) and triethylamine (0.4 mL). The mixture was then cooled to 0° C., propionyl chloride (100 mg, 1.09 mmol) was added dropwise, and the mixture was stirred at 0° C. for further 30 minutes after completion of dropping. Water (15 mL) was added, and the mixture was extracted with dichloromethane (10 mL×3). The organic layers were combined, washed with water (10 mL×3) and saturated brine (10 mL) in sequence, dried over anhydrous sodium sulfate, then filtrated, the filtrate was concentrated under reduced pressure. The residue was purified by silica column chromatography (petroleum ether:ethyl acetate=2:1) to give compound 46 (140 mg, yield: 63%). LC-MS (ESI): m/z=387 [M+H]$^+$.

Preparation of Compound T-46

Compound 46 (140 mg, 0.36 mmol) and 1-methyl-4-aminopyrazole (105 mg, 1.09 mmol) were dissolved in n-butanol (3 mL), p-toluene sulfonic acid monohydrate (137 mg, 0.73 mmol) was added. The mixture was heated to 110° C. and stirred for 16 hours, then concentrated under reduced pressure, and the residue was purified by preparation TLC (dichloromethane:methanol=10:1) to give yellow solid T-46 (65 mg, yield: 40%). LC-MS (ESI): m/z=448 [M+H]$^+$.

$^1$H-NMR (400 MHz, DMSO-d$_6$) δ: 9.46 (s, 1H), 8.79 (s, 1H), 8.37 (s, 1H), 8.34 (d, J=5 Hz, 1H), 8.05 (s, 1H), 7.56 (s, 1H), 7.37 (d, J=5 Hz, 1H), 4.78 (d, J=91 Hz, 1H), 4.78 (m, 2H), 4.24 (d, J=9 Hz, 1H), 3.84 (s, 3H), 3.72 (s, 2H), 2.15 (q, J=7 Hz, 2H), 0.99 (t, J=7 Hz, 3H) ppm Example 47

2-(1-(Ethylsulfonyl)-3-(4-(2-(pyridazin-4-ylamino)thieno[3,2-d]pyrimidin-4-yl)-1H-pyrazol-1-yl)azetidin-3-yl)acetonitrile T-47

Synthetic Route:

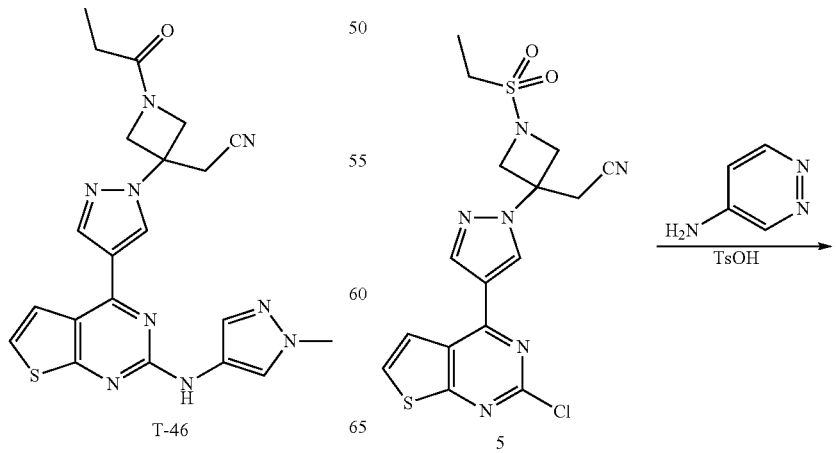

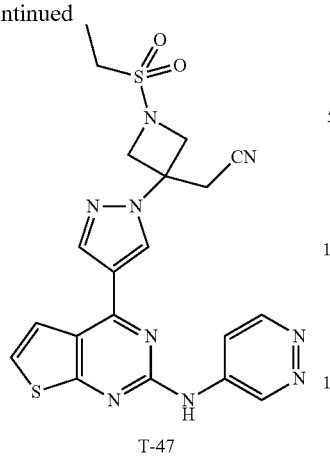

T-47

Compound 5 (50 mg, 0.12 mmol) and 4-aminopyridazine (34 mg, 0.36 mmol) were dissolved in n-butanol (3 mL), p-toluene sulfonic acid monohydrate (45 mg, 0.24 mmol) was added. The mixture was heated to 110° C. and stirred for 16 hours, then concentrated under reduced pressure, the residue was purified by preparation HPLC (mobile phase: acetonitrile, water (0.05% trifluoroacetic acid); gradient: 60%-90%-10%) to give yellow solid T-47 (6 mg, yield: 11%). LC-MS (ESI): m/z=482 [M+H]$^+$.

$^1$H-NMR (400 MHz, CDCl$_3$) δ: 8.79 (d, J=9 Hz, 1H), 8.54 (s, 1H), 8.45 (s, 1H), 8.08 (d, J=6 Hz, 1H), 7.92 (d, J=3 Hz, 1H), 7.66 (d, J=6 Hz, 1H), 6.32 (m, 1H), 4.66 (d, J=9 Hz, 2H), 4.26 (d, J=9 Hz, 2H), 3.44 (s, 2H), 3.12 (q, J=7 Hz, 2H), 1.43 (t, J=7 Hz, 3H) ppm Example 48

2-(1-(Ethylsulfonyl)-3-(4-(2-((1-methyl-1H-imidazol-4-yl)amino)thieno[3,2-d]pyrimidin-4-yl)-1H-pyrazol-1-yl)azetidin-3-yl)acetonitrile T-48

Synthetic Route:

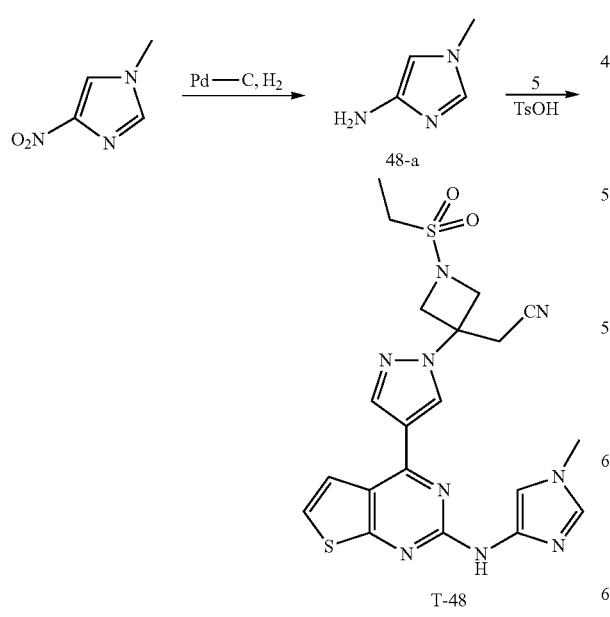

Preparation of Compound 48-a

Under hydrogen (1 atm), to a solution of compound 1-methyl-4-nitro-1H-imidazole (500 mg, 3.94 mmol) in ethanol (20 mL) was added 10% Pd—C (0.1 g). The mixture was stirred at 25° C. for 12 hours, and then filtrated, the filtrate was concentrated under reduced pressure to give compound 48-a (310 mg, yield: 82%), which was used directly for the next step without purification.

Preparation of Compound T-48

Compound 5 (70 mg, 0.17 mmol) and compound 48-a (48 mg, 0.5 mmol) were dissolved in n-butanol (3 mL), p-toluene sulfonic acid monohydrate (60 mg, 0.33 mmol) was added. The mixture was heated to 110° C. and stirred for 16 hours, then concentrated under reduced pressure, the residue was purified by preparation HPLC (mobile phase:acetonitrile, water (0.05% trifluoroacetic acid); gradient: 60%-90%-10%) to give yellow solid T-48 (5 mg, yield: 6%). LC-MS (ESI): m/z=484 [M+H]$^+$.

$^1$H-NMR (500 MHz, CD$_3$OD) δ: 8.80 (s, 1H), 8.64 (s, 1H), 8.47 (s, 1H), 8.28 (d, J=5 Hz, 1H), 7.49 (d, J=5 Hz, 1H), 7.45 (s, 1H), 4.67 (d, J=9 Hz, 2H), 4.32 (d, J=9 Hz, 2H), 3.99 (s, 2H), 3.65 (s, 2H), 3.20 (q, J=7 Hz, 2H), 1.39 (t, J=7 Hz, 3H) ppm Example 49

2-(1-(2-Hydroxyacetyl)-3-(4-(2-((1-methyl-1H-pyrazol-4-yl)amino)thieno[3,2-d]pyrimidin-4-yl)-1H-pyrazol-1-yl)azetidin-3-yl)acetonitrile T-49

Synthetic Route:

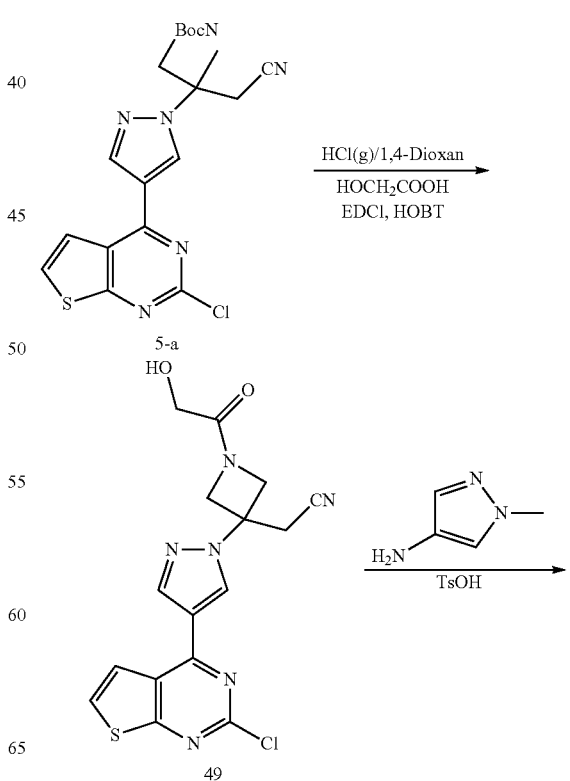

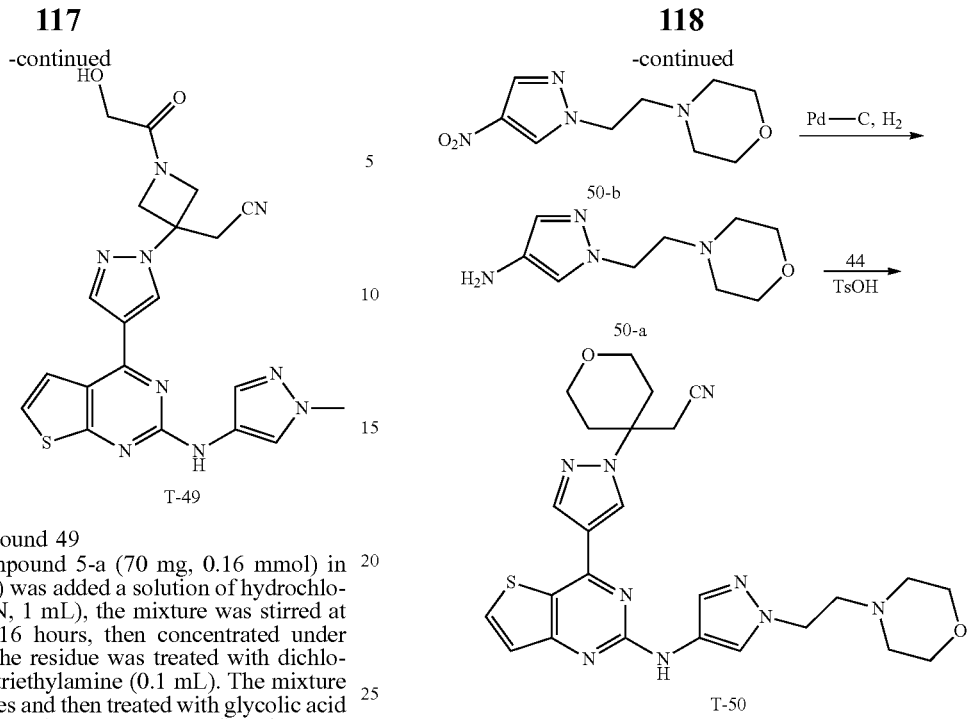

T-49

Preparation of Compound 49

To a solution of compound 5-a (70 mg, 0.16 mmol) in dichloromethane (1 mL) was added a solution of hydrochloride in 1,4-dioxane (4 N, 1 mL), the mixture was stirred at room temperature for 16 hours, then concentrated under reduced pressure, and the residue was treated with dichloromethane (5 mL) and triethylamine (0.1 mL). The mixture was stirred for 15 minutes and then treated with glycolic acid (16 mg, 0.21 mmol), EDCI (40 mg, 0.21 mmol) and HOBT (3 mg, 0.02 mmol) in sequence. The mixture was stirred at room temperature for further 16 hours, then water (15 mL) was added, and the mixture was extracted with dichloromethane (10 mL×3). The organic layers were combined, washed with aq. HCl solution (1 N, 50 mL) and saturated aq. NaHCO$_3$ solution (50 mL) in sequence, dried over anhydrous sodium sulfate, then filtrated, the filtrate was concentrated under reduced pressure. The residue was purified by preparation TLC (dichloromethane:methanol=10:1) to give compound 49 (20 mg, yield: 44%). LC-MS (ESI): m/z=389 [M+H]$^+$.

Preparation of Compound T-49

Compound 49 (20 mg, 0.05 mmol) and 1-methyl-4-aminopyrazole (15 mg, 0.16 mmol) were dissolved in n-butanol (2 mL), p-toluene sulfonic acid monohydrate (20 mg, 0.1 mmol) was added. The mixture was heated to 120° C. and stirred for 3 hours, then concentrated under reduced pressure, the residue was purified by preparation TLC (dichloromethane:methanol=10:1) to give yellow solid T-49 (5 mg, yield: 22%). LC-MS (ESI): m/z=450 [M+H]$^+$.

$^1$H-NMR (400 MHz, CD$_3$OD) δ: 8.77 (s, 1H), 8.43 (s, 1H), 8.25 (d, J=5 Hz, 1H), 8.02 (s, 1H), 7.65 (s, 1H), 7.35 (d, J=5 Hz, 1H), 4.99 (d, J=10 Hz, 1H), 4.76 (d, J=10 Hz, 1H), 4.69 (d, J=11 Hz, 1H), 4.46 (d, J=11 Hz, 1H), 4.21 (s, 2H), 3.93 (s, 3H), 3.62 (s, 2H) ppm

Example 50

2-(4-(4-(2-((1-(2-Morpholinoethyl)-1H-pyrazol-4-yl)amino)thieno[3,2-d]pyrimidin-4-yl)-1H-pyrazol-1-yl)tetrahydro-2H-pyran-4-yl)acetonitrile T-50

Synthetic Route:

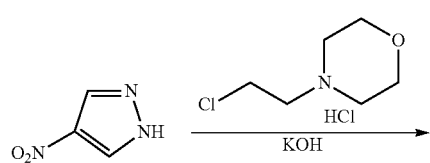

T-50

Preparation of Compound 50-b

N-(2-chloroethyl)morpholine hydrochloride (2.1 g, 11.06 mmol) and potassium hydroxide (1.24 g, 22.12 mmol) were added to a solution of 4-nitropyrazole (1.0 g, 8.85 mmol) in ethanol (20 mL) in sequence, the mixture was heated to 80° C. and stirred for 3 hours. The mixture was then concentrated under reduced pressure, the residue was treated with water (50 mL), extracted with ethyl acetate (50 mL×3). The organic layers were combined, dried over anhydrous sodium sulfate, then filtrated, the filtrate was concentrated under reduced pressure. The residue was purified by silica column chromatography (petroleum ether:ethyl acetate=1:1) to give compound 50-b (600 mg, yield: 30%). LC-MS (ESI): m/z=227 [M+H]$^+$.

Preparation of Compound 50-a

Under hydrogen (1 atm), to a solution of compound 50-b (600 mg, 2.66 mmol) in ethanol (20 mL) was added 10% Pd—C (0.1 g). The mixture was stirred at 25° C. for 12 hours, and then filtrated, the filtrate was concentrated under reduced pressure to give compound 50-a (450 mg, yield: 87%), which was used directly for the next step without purification. LC-MS (ESI): m/z=197 [M+H]$^+$.

Preparation of Compound T-50

Compound 50-a (80 mg, 0.41 mmol) and compound 44 (60 mg, 0.17 mmol) were dissolved in n-butanol (6 mL), p-toluene sulfonic acid monohydrate (210 mg, 1.11 mmol) was added. The mixture was heated to 130° C. and stirred for 3 hours, then concentrated under reduced pressure, the residue was purified by preparation HPLC (mobile phase: acetonitrile, water (0.05% trifluoroacetic acid); gradient: 60%-90%-10%) to give yellow solid T-50 (10 mg, yield: 12%). LC-MS (ESI): m/z=520 [M+H]$^+$.

$^1$H-NMR (400 MHz, CD$_3$OD) δ: 8.71 (s, 1H), 8.44 (s, 1H), 8.25 (s, 1H), 8.21 (d, J=6 Hz, 1H), 7.75 (s, 1H), 7.36 (d, J=6 Hz, 1H), 4.65 (t, J=6 Hz, 2H), 3.91 (m, 6H), 3.57 (m, 2H), 3.32 (br, 4H), 3.18 (s, 2H), 2.70 (m, 2H), 2.25 (m, 2H) ppm

Example 51

2-(1-(Ethylsulfonyl)-3-(4-(2-((1-(2-hydroxyethyl)-1H-pyrazol-4-yl)amino)thieno[3,2-d]pyrimidin-4-yl)-1H-pyrazol-1-yl)azetidin-3-yl)acetonitrile T-51

Synthetic Route:

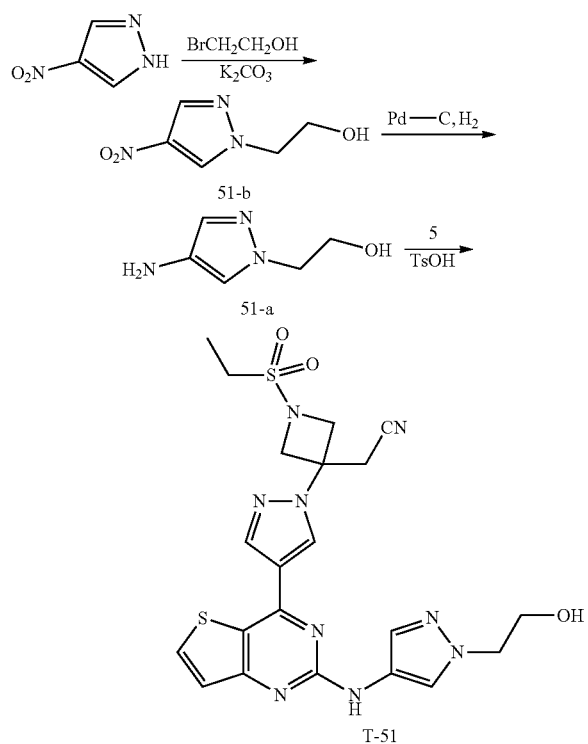

Preparation of Compound 51-b

2-Bromoethanol (1.9 g, 15.57 mmol) and potassium carbonate (2.9 g, 21.12 mmol) were added to a solution of 4-nitropyrazole (1.6 g, 14.16 mmol) in acetonitrile (20 mL) in sequence, the mixture was heated to 60° C. and stirred for 16 hours. After cooled to room temperature, the mixture was filtrated, the filtrate was concentrated under reduced pressure to give compound 51-b (1.1 g, yield: 49.5%), which was used directly for the next step without purification.

Preparation of Compound 51-a

Under hydrogen (1 atm), to a solution of compound 51-b (1.1 g, 7 mmol) in ethanol (20 mL) was added 10% Pd—C (0.2 g). The mixture was stirred at 25° C. for 12 hours, and then filtrated, the filtrate was concentrated under reduced pressure to give compound 51-a (740 mg, yield: 83%)), which was used directly for the next step without purification. LC-MS (ESI): m/z=128 [M+H]$^+$.

Preparation of Compound T-51

Compound 51-a (72 mg, 0.57 mmol) and compound 5 (80 mg, 0.19 mmol) were dissolved in n-butanol (2 m), p-toluene sulfonic acid monohydrate (72 mg, 0.38 mmol) was added. The mixture was heated to 115° C. and stirred for 18 hours, then concentrated under reduced pressure, the residue was purified by preparation HPLC (mobile phase:acetonitrile, water (0.05% trifluoroacetic acid); gradient: 40%-70%-10%) to give yellow solid T-51 (45 mg, yield: 46%). LC-MS (ESI): m/z=514 [M+H]$^+$.

$^1$H-NMR (400 MHz, CDCl$_3$) δ: 11.80 (s, 1H), 8.52 (s, 1H), 8.15 (s, 1H), 8.01 (d, J=6 Hz, 1H), 7.77 (s, 1H), 7.68 (s, 1H), 7.28 (s, 1H), 7.18 (d, J=6 Hz, 1H), 4.69 (d, J=9 Hz, 2H), 4.24 (d, J=9 Hz, 4H), 4.03 (s, 2H), 3.49 (s, 2H), 3.12 (q, J=7 Hz, 2H), 1.43 (t, J=7 Hz, 3H) ppm

Example 52

2-(3-(4-(2-((1-Acetyl-1H-pyrazol-4-yl)amino)thieno[3,2-d]pyrimidin-4-yl)-1H-pyrazol-1-yl)-1-(ethylsulfonyl)azetidin-3-yl)acetonitrile T-52

Synthetic Route:

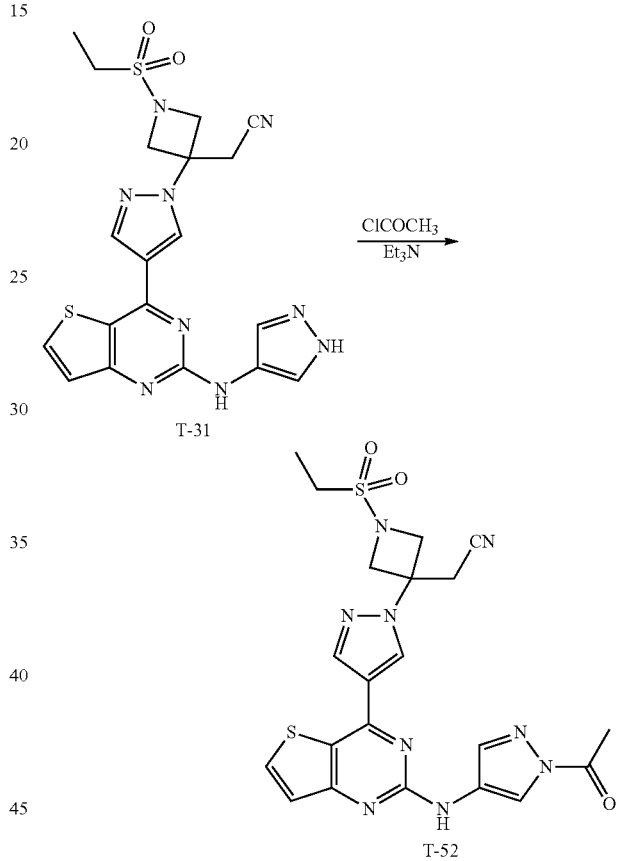

At 0° C., to a solution of compound T-31 (35 mg, 0.075 mmoL) and triethylamine (0.1 mL) in dichloromethane (5 mL) was added slowly acetyl chloride (7 mg, 0.089 mmol), and stirred for 30 minutes. The mixture was concentrated under reduced pressure, the residue was treated with saturated aqueous sodium bicarbonate solution (5 mL), extracted with dichloromethane (5 mL×3). The organic layers were combined, dried over anhydrous sodium sulfate, then filtrated, the filtrate was concentrated under reduced pressure. The residue was purified by preparation HPLC (mobile phase:acetonitrile, water (0.05% trifluoroacetic acid); gradient: 70%-95%-10%) to give compound T-52 (25 mg, yield: 66%). LC-MS (ESI): m/z=512 [M+H]$^+$.

$^1$H-NMR (400 MHz, CDCl$_3$) δ: 8.78 (s, 1H), 8.56 (s, 1H), 8.41 (s, 1H), 8.01 (d, J=5 Hz, 1H), 7.92 (s, 1H), 7.46 (d, J=5 Hz, 1H), 4.65 (d, J=9 Hz, 2H), 4.28 (d, J=9 Hz, 4H), 3.42 (s, 2H), 3.11 (q, J=7 Hz, 2H), 2.72 (s, 3H), 1.43 (t, J=7 Hz, 3H) ppm

Example 53

2-(1-(Ethylsulfonyl)-3-(4-(2-((1-(2-morpholino-ethyl)-1H-pyrazol-4-yl)amino)thieno[3,2-d]pyrimidin-4-yl)-1H-pyrazol-1-yl)azetidin-3-yl)acetonitrile
T-53

Synthetic Route:

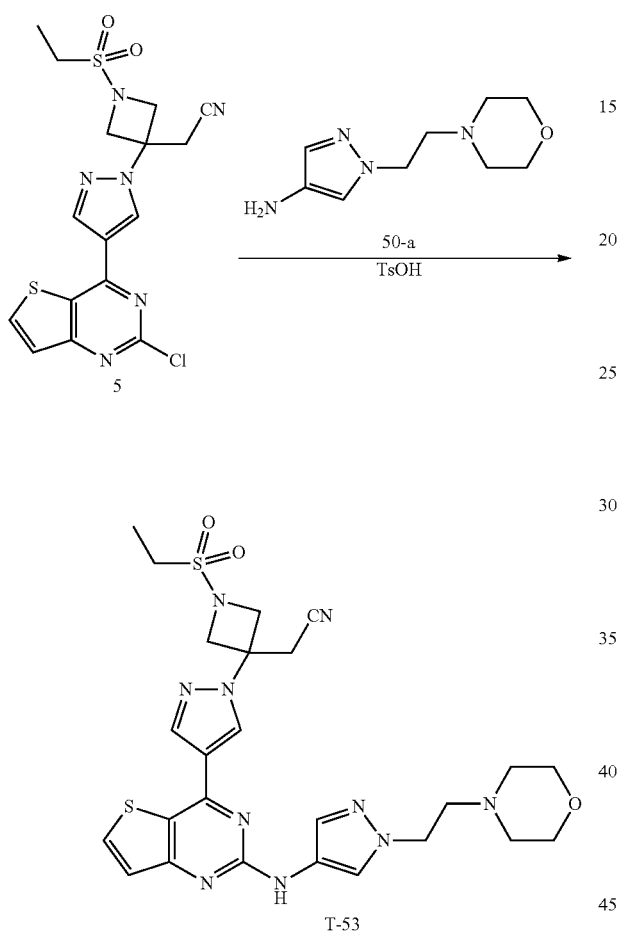

Example 54

2-(1-(Ethylsulfonyl)-3-(4-(2-((1-(1-methylazetidin-3-yl)-1H-pyrazol-4-yl)amino) thieno[3,2-d]pyrimidin-4-yl)-1H-pyrazol-1-yl)azetidin-3-yl)acetonitrile
T-54

Synthetic Route:

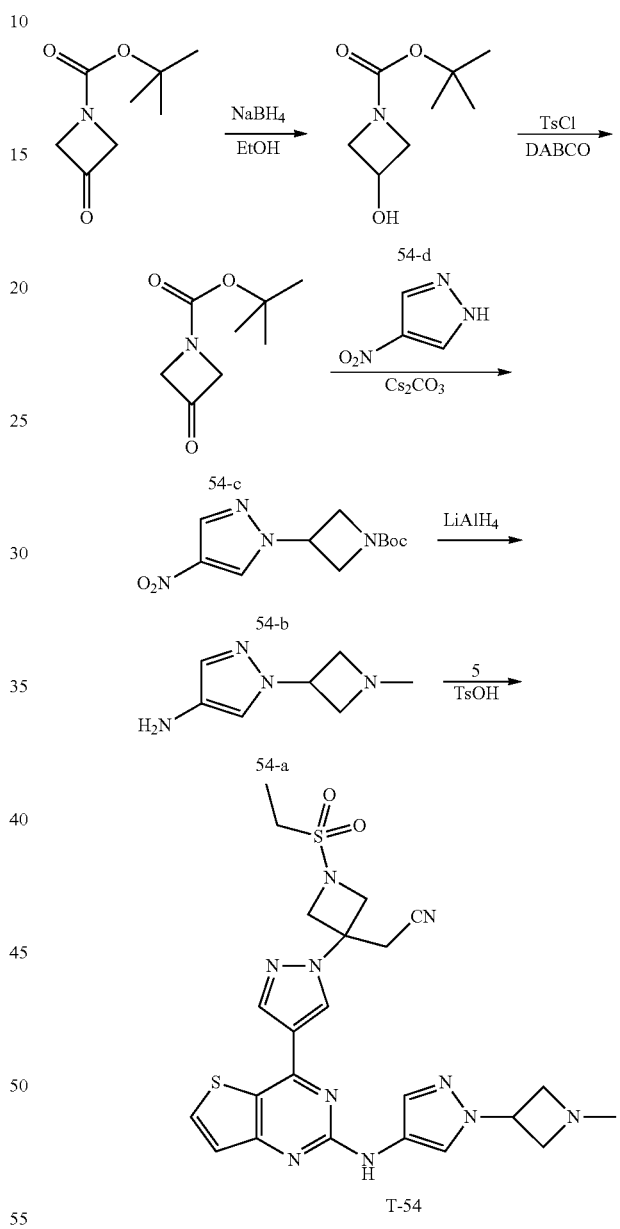

Compound 50-a (97 mg, 0.5 mmol) and compound 5 (70 mg, 0.17 mmol) were dissolved in n-butanol (2 mL), p-toluene sulfonic acid monohydrate (126 mg, 0.67 mmol) was added. The mixture was heated to 115° C. and stirred for 18 hours, then concentrated under reduced pressure, the residue was purified by preparation HPLC (mobile phase:acetonitrile, water (0.05% trifluoroacetic acid); gradient: 40%-70%-10%) to give yellow solid T-53 (41 mg, yield: 43%). LC-MS (ESI): m/z=583 [M+H]$^+$.

$^1$H-NMR (400 MHz, CDCl$_3$) δ: 12.09 (s, 1H), 8.94 (s, 1H), 8.39 (s, 1H), 8.21 (s, 1H), 8.14 (d, J=5 Hz, 1H), 7.72 (s, 1H), 7.47 (d, J=5 Hz, 1H), 4.74 (m, 4H), 4.26 (d, J=9 Hz, 4H), 3.93 (m, 4H), 3.71 (t, J=5 Hz, 2H), 3.51 (s, 2H), 3.11 (m, 4H), 3.09 (q, J=7 Hz, 2H), 1.43 (t, J=7 Hz, 31-1) ppm Preparation of Compound 54-d Sodium borohydride (1.01 g, 26.7 mmol) was added slowly to a solution of 1-Boc-3-azetidinone (2.28 g, 13.3 mmol) in ethanol (30 mL), stirred for 2 hours, the mixture was then concentrated under reduced pressure. The residue was treated with water (50 mL), extracted with ethyl acetate (50 mL×3). The organic layers were combined, dried over anhydrous sodium sulfate, then filtrated, the filtrate was concentrated under reduced pressure to give compound 54-d (2.28 g, yield: 99%), which was used directly for the next step without purification. LC-MS (ESI): m/z=175 [M+H]$^+$.

123

Preparation of Compound 54-c

At 0° C., p-toluene sulfonyl chloride (2.12 g, 11.1 mmol) was added slowly to a solution of compound 54-d (1.28 g, 7.4 mmoL) and DABCO (1.66 g, 14.8 mmoL) in dichloromethane (30 mL). After the temperature was raised to room temperature, the mixture was stirred for further 40 minutes. The mixture was diluted with dichloromethane (30 mL), washed with aqueous HCl solution (1 N, 50 mL), saturated aqueous NaHCO$_3$ solution (50 mL) and water (50 mL) in sequence. The organic layer was dried over anhydrous sodium sulfate, then filtrated, the filtrate was concentrated under reduced pressure to give compound 54-c (1.96 g, yield: 81%), which was used directly for the next step without purification. LC-MS (ESI): m/z=350 [M+Na]$^+$.

Preparation of Compound 54-b

Compound 54-c (4.9 g, 15 mmol) and cesium carbonate (6.5 g, 2 mmol) were added to a solution of 4-nitropyrazole (1.13 g, 10 mmol) in DMF (15 mL) in sequence, and then the mixture was heated to 120° C. and stirred for 12 hours. After cooled to room temperature, the mixture was treated with water (60 mL), extracted with ethyl acetate (30 mL×3). The organic layers were combined, dried over anhydrous sodium sulfate, then filtrated, the filtrate was concentrated under reduced pressure. The residue was purified by silica column chromatography (petroleum ether:ethyl acetate=5:1) to give compound 54-b (1.1 g, yield: 41%). LC-MS (ESI): m/z=291 [M+Na]$^+$.

Preparation of Compound 54-a

A solution of compound 54-b (1.1 g, 4.1 mmol) in anhydrous THF (10 mL) was added slowly to a suspension of lithium aluminium hydride (360 mg, 10 mmol) in anhydrous THF (10 mL). The mixture was refluxed for 3 hours, then cooled to room temperature, ethyl acetate (2 mL) was then added slowly dropwise. The mixture was filtrated, the filtrate was concentrated under reduced pressure to give compound 54-a (430 mg, yield: 69%), which was used directly for the next step without purification. LC-MS (ESI): m/z=153 [M+H]$^+$.

Preparation of Compound T-54

Compound 54-a (152 mg, 1 mmol) and compound 5 (221 mg, 0.5 mmol) were dissolved in n-butanol (10 mL), p-toluene sulfonic acid monohydrate (258 mg, 1.5 mmol) was added. The mixture was heated to 120° C. and stirred for 3 hours, then cooled to room temperature. The mixture was treated with saturated aqueous NaHCO$_3$ solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:acetonitrile, water (0.05% trifluoroacetic acid); gradient: 40%-70%-10%) to give yellow solid T-54 (28 mg, yield: 10.4%). LC-MS (ESI): m/z=554 [M+H]$^+$.

$^1$H-NMR (400 MHz, CD$_3$OD) δ: 8.74 (s, 1H), 8.43 (s, 1H), 8.25 (s, 1H), 8.13 (d, J=4.0 Hz, 1H), 7.74 (s, 1H), 7.35 (d, J=4.0 Hz, 1H), 5.05 (m, 1H), 4.67 (d, J=7.2 Hz, 2H), 4.33 (d, J=7.2 Hz, 2H), 3.90 (t, J=5.6 Hz, 2H), 3.66 (t, J=5.6 Hz, 2H), 3.64 (s, 2H), 3.21 (q, J=6.0 Hz, 2H), 2.51 (s, 3H), 1.38 (t, J=6.0 Hz, 3H) ppm

124

Example 55

2-(1-(Ethylsulfonyl)-3-(4-(5-(phenylamino)pyrazolo[1,5-a]pyrimidin-7-yl)-1H-pyrazol-1-yl)azetidin-3-yl)acetonitrile T-55

Synthetic Route:

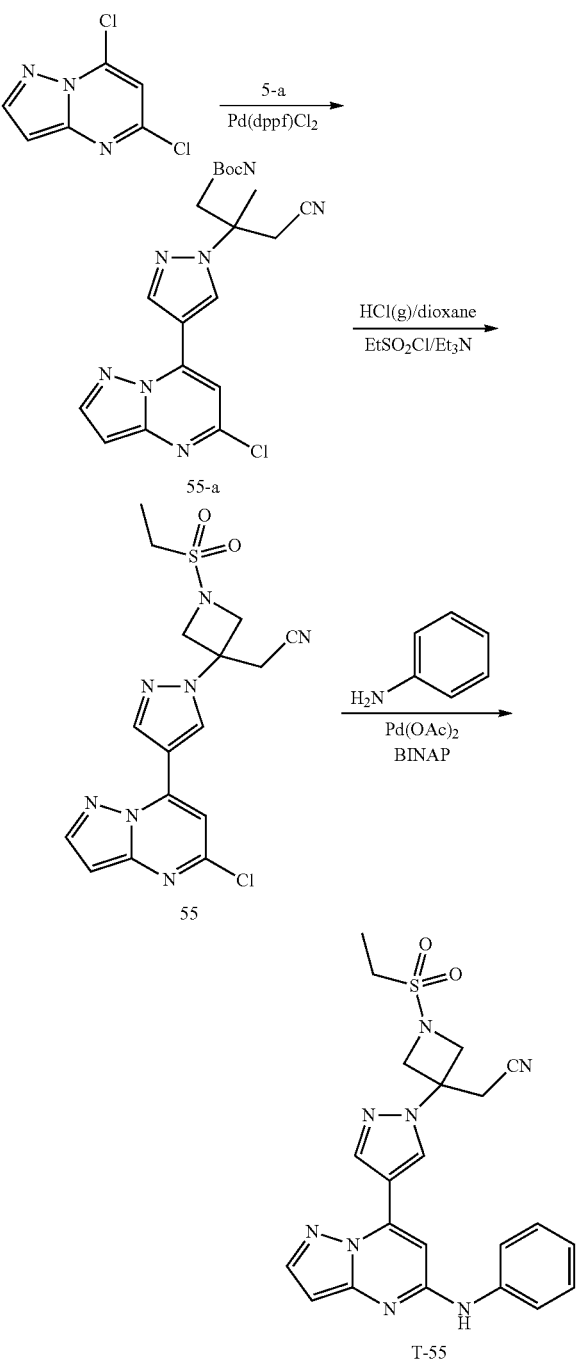

Preparation of Compound 55-a

Under nitrogen, compound 5-a (400 mg, 1.04 mmol), 5,7-dichloropyrazolo[1,5-a]pyrimidine (200 mg, 1.04 mmol) and sodium carbonate (331 mg, 3.12 mmol) were suspended in 1,4-dioxane (2 mL) and water (2 mL), Pd(dppf)Cl$_2$ (100 mg, 0.1 mmol) was added. The mixture was heated to 80° C. and stirred for 16 hours. The mixture was concentrated under reduced pressure, the residue was treated with dichloromethane (20 mL), washed with water (10 mL×3) and saturated brine (10 mL) in sequence. The mixture was dried over anhydrous sodium sulfate, then filtrated, the filtrate was concentrated under reduced pressure, the residue was purified by preparation TLC (dichloromethane: ethyl acetate=30:1) to give compound 55-a (230 mg, yield: 54%). LC-MS (ESI): m/z=414 [M+H]$^+$.

Preparation of Compound 55

To a solution of compound 55-a (230 mg, 0.56 mmol) in THF (2 mL) was added a solution of hydrochloride in 1,4-dioxane (4 N, 1.5 mL), the mixture was stirred at room temperature for 16 hours, then concentrated under reduced pressure and the residue was treated with dichloromethane (5 mL) and triethylamine (0.3 mL, 2.2 mmol). The mixture was then cooled to 0° C., ethylsulfonyl chloride (0.15 mL, 0.84 mmol) was added dropwise, and the mixture was stirred at 0° C. for further 30 minutes after completion of dropping. Water (5 mL) was added, and the mixture was extracted with dichloromethane (10 mL×3). The organic layers were combined, washed with water (10 mL×3) and saturated brine (10 mL) in sequence, dried over anhydrous sodium sulfate, then filtrated, the filtrate was concentrated under reduced pressure. The residue was purified by column chromatography (petroleum ether:ethyl acetate=1:1) to give compound 55 (102 mg, yield: 45%). LC-MS (ESI): m/z=406 [M+H]$^+$.

Preparation of Compound T-55

Under nitrogen, to a suspension of compound 55 (70 mg, 0.17 mmol), aniline (25 mg, 0.26 mmol) and cesium carbonate (102 mg, 0.32 mmol) in 1,4-dioxane (4 mL) were added Pd(OAc)$_2$ (15 mg, 0.07 mmol) and BINAP (40 mg, 0.07 mmol), the mixture was heated to 125° C. by microwave and stirred for 40 minutes. After cooled to room temperature, the mixture was diluted with ethyl acetate (10 mL), washed with water (5 mL×3) and saturated brine (5 mL) in sequence, dried over anhydrous sodium sulfate, then filtrated, the filtrate was concentrated under reduced pressure. The residue was purified by preparation HPLC (mobile phase:acetonitrile, water (0.05% trifluoroacetic acid); gradient: 40%-70%-10%) to give compound T-55 (10 mg, yield: 13%). LC-MS (ESI): m/z=463 [M+H]$^+$.

$^1$H-NMR (400 MHz, CDCl$_3$) δ: 9.12 (s, 1H), 8.15 (s, 1H), 8.01 (d, J=2 Hz, 114), 7.46 (m, 4H), 7.26 (m, 1H), 6.61 (s, 1H), 6.39 (d, J-=2 Hz, 1H), 4.63 (d, J=9 Hz, 2H), 4.24 (d, J=9 Hz, 2H), 3.42 (s, 2H), 3.09 (q, J=7 Hz, 2H), 1.42 (t, J=7 Hz, 3H) ppm Example 56

2-Fluoro-4-(2-(phenylamino)thieno[3,2-d]pyrimidin-4-yl)benzonitrile T-56

Synthetic Route:

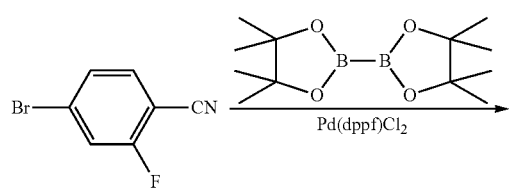

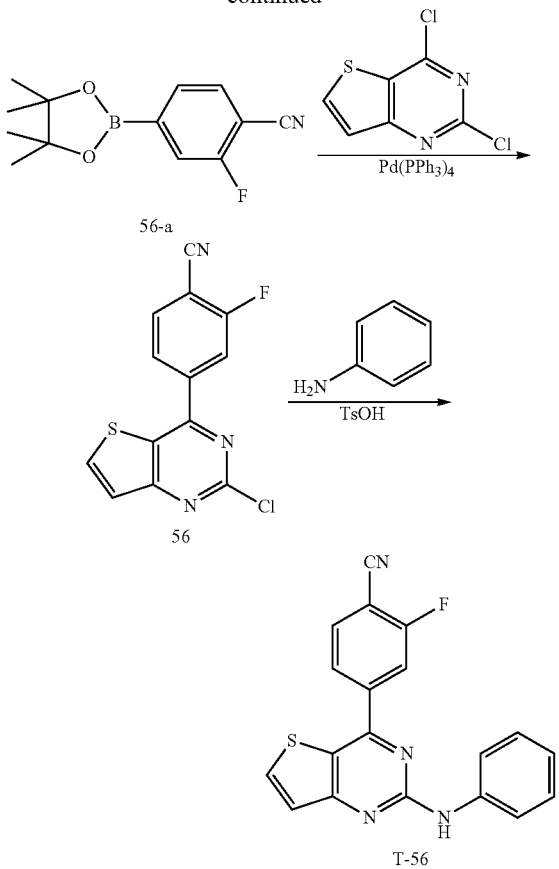

Preparation of Compound 56-a

Under nitrogen, 4-bromo-2-fluorobenzonitrile (4.0 g, 20 mmol), bis(pinacolato)diboron (3.8 g, 30 mmol) and potassium acetate (6.1 g, 60 mmol) were suspended in DMSO (50 mL), Pd(dppf)Cl$_2$ (1.5 g, 0.2 mmol) was added. The mixture was stirred at 80° C. for 4 hours. The mixture was diluted with water (100 mL), extracted with ethyl acetate (100 mL×3). The organic layers were combined, washed with water (50 mL×3) and saturated brine (50 mL) in sequence, dried over anhydrous sodium sulfate, then filtrated, the filtrate was concentrated under reduced pressure. The residue was purified by silica column chromatography (petroleum ether:ethyl acetate=50:1 to 10:1) to give compound 56-a (3.6 g, yield: 73%).

$^1$H-NMR (400 MHz, CD$_3$OD) δ: 7.62 (m, 3H), 1.35 (s, 12H) ppm

Preparation of Compound 56

Under nitrogen, compound 56-a (1.0 g, 4 mmol), 2,4-dichlorotheino[3,2-d]pyrimidine (1.0 g, 4.9 mmol) and potassium carbonate (1.38 g, 10 mmol) were suspended in 1,4-dioxane (20 mL) and water (4 mL), Pd(PPh$_3$)$_4$ (490 mg, 0.6 mmol) was added. The mixture was heated to 100° C. and stirred for 2 hours. The mixture was concentrated under reduced pressure, the residue was treated with water (20 mL), extracted with dichloromethane (20 mL×3). The organic layers were combined, washed with water (10 mL×3) and saturated brine (10 mL) in sequence, dried over anhydrous sodium sulfate, then filtrated, the filtrate was concentrated under reduced pressure. The residue was purified by silica column chromatography (petroleum ether: ethyl acetate=3:1) to give light yellow solid 56 (1.0 g, yield: 87.5%). LC-MS (ESI): m/z=290 [M+H]$^+$.

Preparation of Compound T-56

Compound 56 (290 mg, 1.0 mmol) and aniline (140 mg, 1.5 mmol) were dissolved in n-butanol (10 mL), p-toluene sulfonic acid monohydrate (260 mg, 1.5 mmol) was added. The mixture was heated to 120° C. and stirred for 6 hours, then cooled to room temperature. The mixture was treated with saturated aqueous NaHCO$_3$ solution (10 mL), extracted with dichloromethane (10 mL×3). The organic layers were combined, washed with water (10 mL×3) and saturated brine (10 mL) in sequence, dried over anhydrous sodium sulfate, then filtered. The residue was purified by silica column chromatography (petroleum ether:ethyl acetate=3:1 to 1:1) to give compound T-56 (120 mg, yield: 35%). LC-MS (ESI): m/z=347 [M+H]$^+$.

$^1$H-NMR (400 MHz, DMSO-d$_6$) δ: 9.89 (s, 1H), 8.48 (d, J=5.2, 1H), 8.29 (m, 3H), 7.87 (d, J=7.6, 1H), 7.51 (d, J=5.2 Hz, 1H), 7.33 (t, J=7.2 Hz, 2H), 6.98 (t, J=7.2 Hz, 1H) ppm Example 57

2-(3-(4-(2-((1H-Indazol-5-yl)amino)thieno[3,2-d]pyrimidin-4-yl)-1H-pyrazol-1-yl)-1-(ethylsulfonyl)azetidin-3-yl)acetonitrile T-57

Synthetic Route:

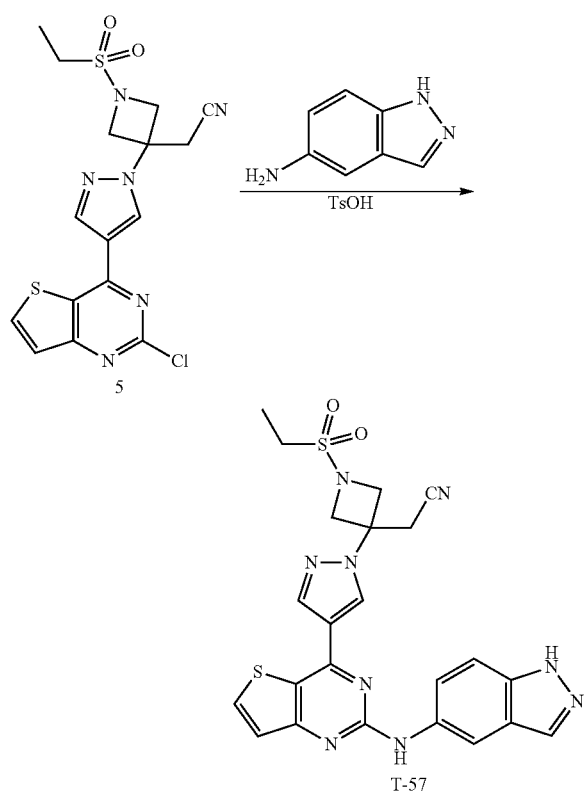

5-Aminoindazole (47 mg, 0.36 mmol) and compound 5 (50 mg, 0.12 mmol) were dissolved in n-butanol (0.5 mL), p-toluene sulfonic acid monohydrate (43 mg, 0.24 mmol) was added. The mixture was heated to 110° C. and stirred for 18 hours, then cooled to room temperature. The mixture was treated with saturated aqueous NaHCO$_3$ solution (10 mL), extracted with dichloromethane (5 mL×3). The organic layers were combined, washed with water (5 mL×3) and saturated brine (5 mL) in sequence, dried over anhydrous sodium sulfate, then filtrated. The residue was purified by preparation HPLC (mobile phase:methanol, water (0.05% trifluoroacetic acid); gradient: 70%-95%-10%) to give yellow solid T-57 (20 mg, yield: 33%). LC-MS (ESI): m/z=520 [M+H]$^+$.

$^1$H-NMR (400 MHz, CDCl$_3$) δ: 11.1 (br, 1H), 8.53 (s, 1H), 8.36 (s, 1H), 8.15 (d, J=1.2 Hz, 1H), 8.09 (d, J=9 Hz, 2H), 7.52 (d, J=1.2 Hz, 1H), 7.48 (d, J=9 Hz, 1H), 4.62 (d, J=9 Hz, 2H), 4.23 (d, J=9 Hz, 2H), 3.41 (s, 2H), 3.09 (q, J=7 Hz, 2H), 1.42 (t, J=7 Hz, 3H) ppm Example 58

2-(3-(4-(2-((1H-Benzo[d]imidazol-5-yl)amino)thieno[3,2-d]pyrimidin-4-yl)-1H-pyrazol-1-yl)-1-(ethylsulfonyl)azetidin-3-yl)acetonitrile T-58

Synthetic Route:

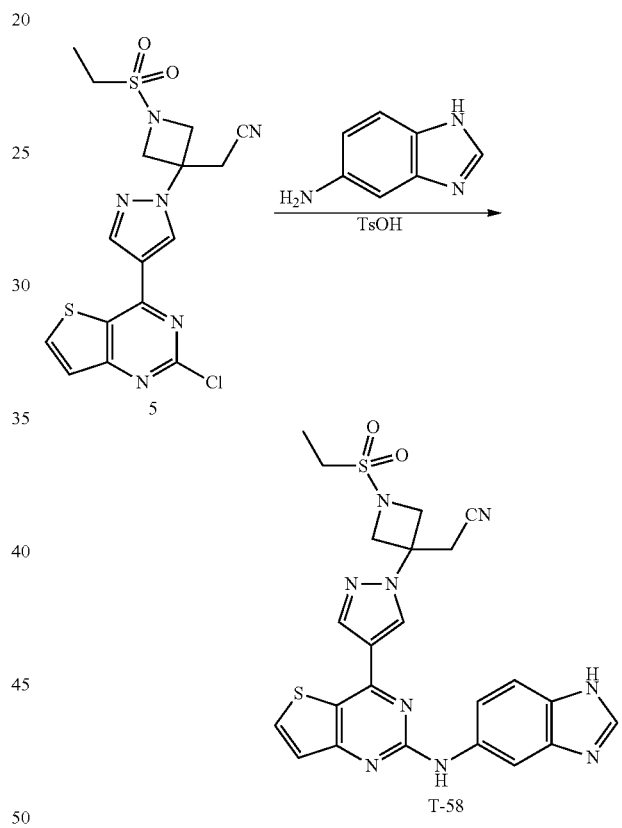

5-Aminobenzimidazole (47 mg, 0.36 mmol) and compound 5 (50 mg, 0.12 mmol) were dissolved in n-butanol (0.5 mL), p-toluene sulfonic acid monohydrate (43 mg, 0.24 mmol) was added. The mixture was heated to 110° C. and stirred for 18 hours, then cooled to room temperature. The mixture was treated with saturated aqueous NaHCO$_3$ solution (10 mL), extracted with dichloromethane (5 mL×3). The organic layers were combined, washed with water (5 mL×3) and saturated brine (5 mL), dried over anhydrous sodium sulfate, then filtrated. The residue was purified by preparation HPLC (mobile phase:methanol, water (0.05% trifluoroacetic acid); gradient: 50%-80%-10%) to give yellow solid T-58 (20 mg, yield: 33%). LC-MS (ESI): m/z=520 [M+H]$^+$.

$^1$H-NMR (500 MHz, DMSO-d6) δ: 10.11 (s, 1H), 9.45 (s, 1H), 8.88 (s, 1H), 8.76 (d, J=1.5 Hz, 1H), 8.52 (s, 2H), 8.47

(d, J=1.5 Hz, 1H), 7.85 (dd, J=10 Hz, J=1.5 Hz, 1H), 7.44 (d, J=5.5 Hz, 1H), 4.59 (d, J=9 Hz, 2H), 4.29 (d, J=9 Hz, 2H), 3.75 (s, 2H), 3.25 (q, J=7 Hz, 2H), 1.26 (t, J=7 Hz, 3H) ppm

Example 59

2-(3-(4-(2-((4-(1H-Tetrazol-1-yl)phenyl)amino)thieno[3,2-d]pyrimidin-4-yl)-1H-pyrazol-1-yl)-1-(ethylsulfonyl)azetidin-3-yl)acetonitrile T-59

Synthetic Route:

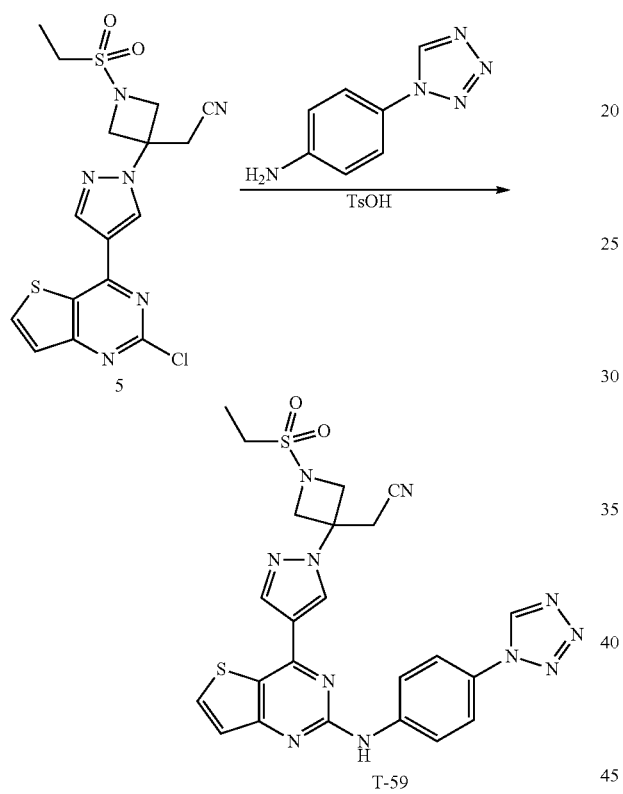

4-(1H-Tetrazol-1-yl)aniline (77 mg, 0.47 mmol) and compound 5 (100 mg, 0.26 mmol) were dissolved in n-butanol (2 mL), p-toluene sulfonic acid monohydrate (68 mg, 0.36 mmol) was added. The mixture was heated to 110° C. and stirred for 18 hours, then cooled to room temperature. The mixture was treated with saturated aqueous NaHCO$_3$ solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:acetonitrile, water (0.05% trifluoroacetic acid); gradient: 50%-80%-10%) to give yellow solid T-59 (44 mg, yield: 34%). LC-MS (ESI): m/z=548 [M+H]$^+$.

$^1$H-NMR (400 MHz, DMSO-d6) δ: 10.07 (s, 1H), 10.00 (s, 1H), 8.88 (s, 1H), 8.45 (d, =9 Hz, 1H), 8.16 (d, J=9 Hz, 2H), 7.84 (d, J=1.2 Hz, 1H), 7.49 (d, J=10 Hz, J=1.6 Hz, 1H), 4.58 (d, J=9 Hz, 2H), 4.28 (d, J=9 Hz, 2H), 3.74 (s, 2H), 3.25 (q, J=7 Hz, 2H), 1.26 (t, J=7 Hz, 3H) ppm

Example 60

2-(1-(Ethylsulfonyl)-3-(4-(2-((1-(3-morpholinopropyl)-1H-pyrazol-4-yl)amino)thieno[3,2-d]pyrimidin-4-yl)-1H-pyrazol-1-yl)azetidin-3-yl)acetonitrile T-60

Synthetic Route:

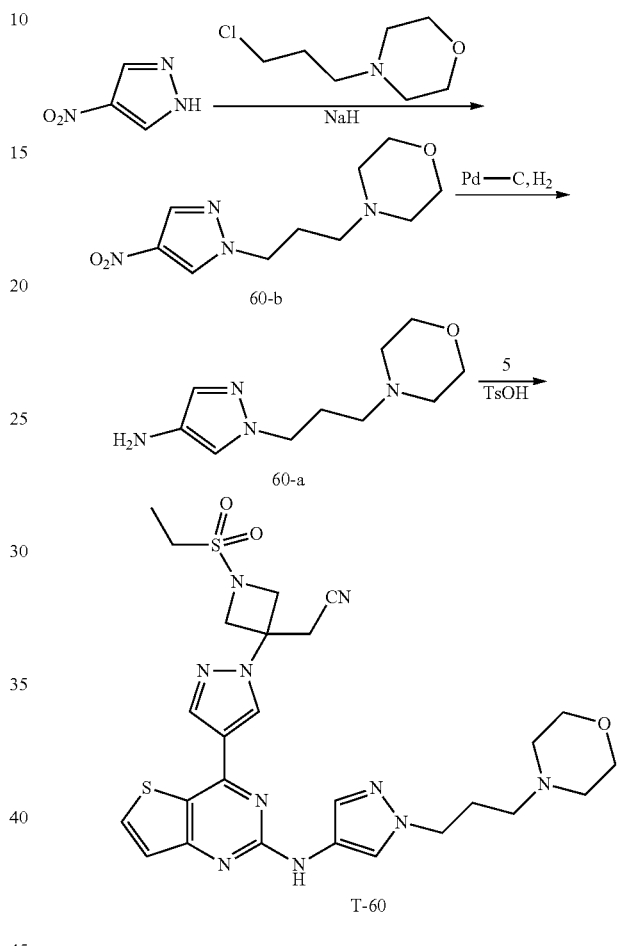

Preparation of Compound 60-b

At 0° C., 60% NaH in mineral oil (530 mg, 13.27 mmol) was added to a solution of 4-nitropyrazole (1.0 g, 8.85 mmol) in THF (10 mL), stirred for 30 minutes, N-(3-chloropropyl)morpholine (1.73 g, 10.62 mmol) was added. The mixture was warmed to room temperature and stirred for further 16 hours. The mixture was diluted with water (25 mL), extracted with ethyl acetate (50 mL×3). The organic layers were combined, dried over anhydrous sodium sulfate, then filtrated, the filtrate was concentrated under reduced pressure. The residue was purified by silica column chromatography (petroleum ether:ethyl acetate=1:1) to give yellow oil 60-b (1.2 g, yield: 56.6%). LC-MS (ESI): m/z=241 [M+H]$^+$.

Preparation of Compound 60-a

Under hydrogen (1 atm), to a solution of compound 60-b (300 mg, 1.25 mmol) in ethanol (5 mL) was added 10% Pd—C (0.1 g). The mixture was stirred at 25° C. for 16 hours, and then filtrated, the filtrate was concentrated under reduced pressure to give red brown oil 60-a (180 mg, yield: 69%), which was used directly for the next step without purification. LC-MS (ESI): m/z=211 [M+H]$^+$.

Preparation of Compound T-60

Compound 60-a (100 mg, 0.48 mmol) and compound 5 (100 mg, 0.24 mmol) were dissolved in n-butanol (2 mL), p-toluene sulfonic acid monohydrate (68 mg, 0.36 mmol) was added. The mixture was heated to 110° C. and stirred for 18 hours, then cooled to room temperature. The mixture was treated with saturated aqueous NaHCO$_3$ solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:acetonitrile, water (0.05% trifluoroacetic acid); gradient: 25%-55%-10%) to give yellow solid T-60 (60 mg, yield: 43%). LC-MS (ESI): m/z=597 [M+H]$^+$.

$^1$H-NMR (400 MHz, CD$_3$OD) δ: 8.78 (s, 1H), 8.44 (s, 1H), 8.25 (s, 1H), 8.21 (d, J=5.2 Hz, 1H), 8.18 (s, 1H), 7.72 (s, 1H), 7.35 (d, J=5.6 Hz, 1H), 4.66 (d, J=9 Hz, 2H), 4.33 (m, 4H), 4.06 (m, 2H), 3.77 (m, 2H), 3.65 (s, 2H), 3.50 (m, 2H), 3.20 (m, 6H), 2.36 (m, 2H), 1.38 (d, J=7 Hz, 2H) ppm Example 61

2-(3-(4-(2-((1-(3-(2H-Tetrazol-5-yl)propyl)-1H-pyrazol-4-yl)amino)thieno[3,2-d]pyrimidin-4-yl)-1H-pyrazol-1-yl)-1-(ethylsulfonyl)azetidin-3-yl) acetonitrile T-61

Synthetic Route:

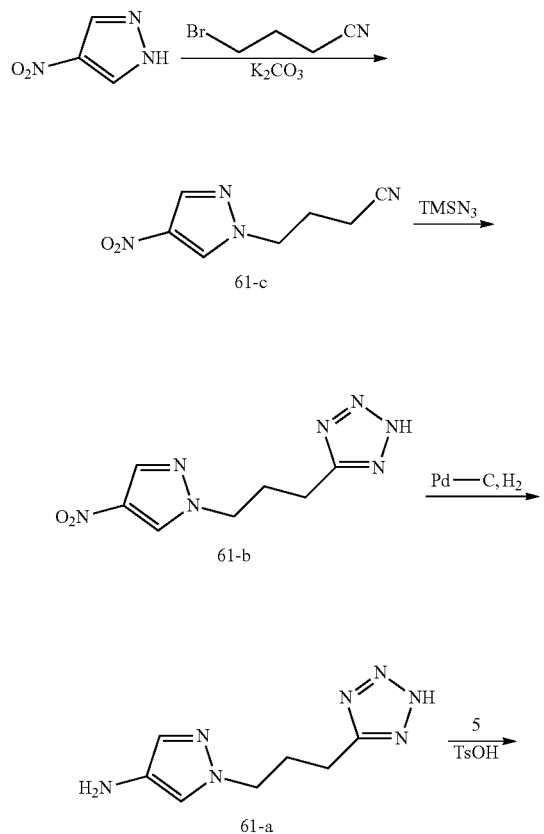

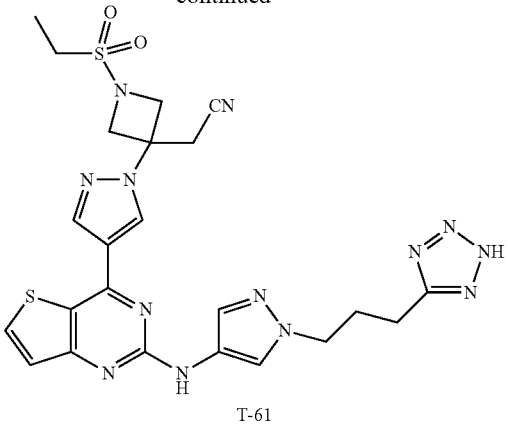

T-61

Preparation of Compound 61-c

4-Bromobutyronitrile (4.27 g, 26.55 mmol) was added to a solution of 4-nitropyrazole (2.0 g, 17.69 mmol) and potassium carbonate (5.0 g, 35.39 mmol) in acetonitrile (20 mL), the mixture was refluxed for 16 hours. After cooled to room temperature, the mixture was treated with water (60 mL), extracted with ethyl acetate (50 mL×3). The organic layers were combined, dried over anhydrous sodium sulfate, then filtrated, the filtrate was concentrated under reduced pressure. The residue was purified by silica column chromatography (petroleum ether:ethyl acetate=5:1) to give compound 61-c (2.5 g, yield: 79%).

Preparation of Compound 61-b

A solution of 1.0 M tetrabutylammonium fluoride in THF (12 mL, 12 mmol) was added to a solution of compound 61-c (2.0 g, 11.1 mmol) and azidotrimethylsilane (2.0 g, 17.39 mmol) in toluene (20 mL), the mixture was refluxed for 16 hours. An additional portion of azidotrimethylsilane (2.0 g, 17.39 mmol) was added, the mixture was refluxed for further 16 hours. The mixture was then concentrated, the residue was purified by silica column chromatography (dichloromethane:methanol=10:1) to give compound 61-b (2.1 g, yield: 85%). LC-MS (ESI): m/z=224 [M+H]$^+$.

Preparation of Compound 61-a

Under hydrogen (1 atm), to a solution of compound 61-b (1.0 g, 4.48 mmol) in ethanol (20 mL) was added 10% Pd—C (0.1 g). The mixture was stirred at 25° C. for 16 hours, and then filtrated, the filtrate was concentrated under reduced pressure to give red brown oil 61-a (750 mg, yield: 86%), which was used directly for the next step without purification. LC-MS (ESI): m/z=194 [M+H]$^+$.

Preparation of Compound T-61

Compound 61-a (137 mg, 0.71 mmol) and compound 5 (100 mg, 0.24 mmol) were dissolved in n-butanol (2 mL), p-toluene sulfonic acid monohydrate (91 mg, 0.47 mmol) was added. The mixture was heated to 110° C. and stirred for 18 hours, then cooled to room temperature. The mixture was treated with saturated aqueous NaHCO$_3$ solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:acetonitrile, water (0.05% trifluoroacetic acid); gradient: 25%-55%-10%) to give yellow solid T-61 (19 mg, yield: 13.6%). LC-MS (ESI): m/z=580 [M+H]$^+$.

$^1$H-NMR (400 MHz, CDCl$_3$) δ: 8.49 (s, 1H), 8.37 (s, 1H), 8.03 (s, 1H), 7.91 (d, J=5.6 Hz, 1H), 7.69 (s, 1H), 7.35 (d,

J=5.6 Hz, 1H), 6.97 (s, 1H), 4.66 (d, J=9 Hz, 2H), 4.25 (d, J=9 Hz, 4H), 4.17 (t, J=6 Hz, 4H), 3.44 (s, 2H), 3.11 (q, J=7 Hz, 2H), 2.91 (m, 2H), 2.28 (m, 2H), 1.42 (t, J=7 Hz, 3H) ppm Example 62

2-(1-(Ethylsulfonyl)-3-(4-(2-((6-morpholinopyridin-3-yl)amino)thieno[3,2-d]pyrimidin-4-yl)-1H-pyrazol-1-yl)azetidin-3-yl)acetonitrile T-62

Synthetic Route:

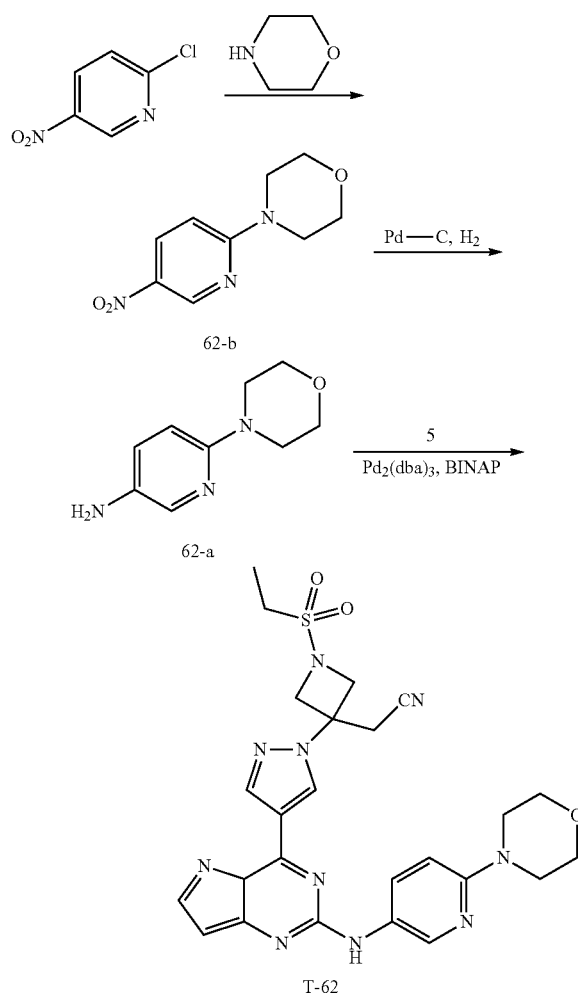

Preparation of Compound 62-b

Morpholine (2.0 g, 31.7 mmol) was added to a solution of 2-chloro-5-nitropyridine (2.0 g, 12.7 mmol) in acetonitrile (20 mL), the mixture was stirred at room temperature for 16 hours. After water (50 mL) was added, there was solid precipitated. After filtration, the solid was dried in vacuum for 6 hours to give compound 62-b (2 g, yield: 75.6%), which was directly for the next step without purification.

Preparation of Compound 62-a

Under hydrogen (1 atm), to a solution of compound 62-b (2.0 g, 9.62 mmol) in ethanol (20 mL) was added 10% Pd—C (0.2 g). The mixture was stirred at 25° C. for 16 hours, and then filtrated, the filtrate was concentrated under reduced pressure to give brown solid 62-a (1.5 g, yield: 87%), which was used directly for the next step without purification. LC-MS (ESI): m/z=180 [M+H]$^+$.

Preparation of Compound T-62

Under nitrogen, Pd$_2$(dba)$_3$ (28 mg, 0.03 mmol) and BINAP (20 mg, 0.03 mmol) were added to a suspension of compound 5 (100 mg, 0.24 mmol), compound 62-a (85 mg, 0.47 mmol) and cesium carbonate (155 mg, 0.48 mmol) in 1,4-dioxane (2 mL), the mixture was heated to 110° C. by microwave and stirred for 30 minutes. After cooled to room temperature, the mixture was diluted with dichloromethane (15 mL), washed with water (10 mL×3) and saturated brine (10 mL) in sequence, dried over anhydrous sodium sulfate, then filtrated, the filtrate was concentrated under reduced pressure. The residue was purified by preparation HPLC (mobile phase:acetonitrile, water (0.05% trifluoroacetic acid); gradient: 35%-65%-10%) to give compound T-62 (10 mg, yield: 8%). LC-MS (ESI): m/z=566 [M+H]$^+$.

$^1$H-NMR (500 MHz, CDCl$_3$) δ: 12.45 (br, 1H), 9.22 (br, 2H), 8.43 (s, 1H), 8.23 (d, J=5.2 Hz, 1H), 8.04 (dd, J=9.6 Hz, J=2.8 Hz, 1H), 7.55 (d, J=9.6 Hz, 1H), 7.03 (d, J=9.6 Hz, 1H), 4.77 (d, J=9 Hz, 2H), 4.30 (d, J=9 Hz, 2H), 3.93 (m, 4H), 3.73 (m, 4H), 3.59 (s, 2H), 3.15 (q, J=7 Hz, 2H), 1.42 (t, J=7 Hz, 3H) ppm Example 63

2-(1-(Ethylsulfonyl)-3-(4-(2-((2-morpholinopyrimidin-5-yl)amino)thieno[3,2-d]pyrimidin-4-yl)-1H-pyrazol-1-yl)azetidin-3-yl)acetonitrile T-63

Synthetic Route:

135

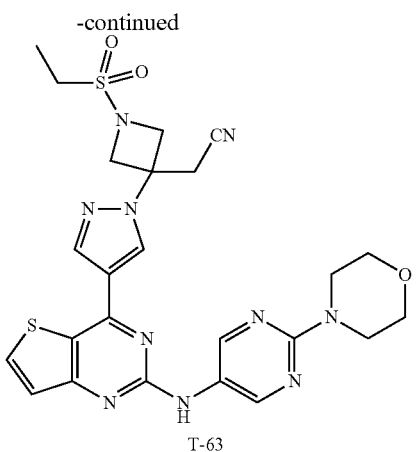

T-63

Preparation of Compound 63-b

Morpholine (492 mg, 6.07 mmol) was added to a solution of 2-chloro-5-nitropyrimidine (440 mg, 2.76 mmol) in acetonitrile (5 mL), the mixture was stirred at room temperature for 3 hours, then concentrated under reduced pressure. The residue was diluted with ethyl acetate (50 mL) and IN aqueous HCl solution (20 mL). The organic layer was washed with water (10 mL×3) and saturated brine (10 mL) in sequence, dried over anhydrous sodium sulfate, then filtrated, the filtrate was concentrated under reduced pressure to give compound 63-b (350 mg, yield: 61%), which was used directly for the next step without purification. LC-MS (ESI): m/z=211 [M+H]$^+$.

Preparation of Compound 63-a

Under hydrogen (1 atm), to a solution of compound 63-b (350 mg, 1.67 mmol) in ethanol (10 mL) was added 10% Pd—C (0.1 g). The mixture was stirred at 25° C. for 16 hours, and then filtrated, the filtrate was concentrated under reduced pressure to give brown solid 63-a (230 mg, yield: 77%), which was used directly for the next step without purification. LC-MS (ESI): m/z=181 [M+H]$^+$.

Preparation of Compound T-63

Compound 63-a (52 mg, 0.28 mmol) and compound 5 (80 mg, 0.19 mmol) were dissolved in n-butanol (2 mL), p-toluene sulfonic acid monohydrate (44 mg, 0.23 mmol) was added. The mixture was heated to 110° C. and stirred for 18 hours, then cooled to room temperature. The mixture was concentrated under reduced pressure, then treated with saturated aqueous NaHCO$_3$ solution (5 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:acetonitrile, water (0.05% trifluoroacetic acid); gradient: 40%-70%-10%) to give brown solid T-63 (12 mg, yield: 12%). LC-MS (ESI): m/z=567 [M+H]$^+$.

$^1$H-NMR (400 MHz, CDCl$_3$) δ: 8.70 (d, J=2.4 Hz, 1H), 8.48 (s, 1H), 8.37 (s, 1H), 7.97 (d, J=5.6 Hz, 1H), 7.36 (d, J=5.21 Hz, 1H), 4.63 (d, J=9.2 Hz, 2H), 4.25 (d, J=9.2 Hz, 2H), 3.81 (s, 8H), 3.43 (s, 2H), 3.15 (q, J=7 Hz, 2H), 1.42 (t, J=7 Hz, 3H) ppm

136

Example 64

2-(1-(Ethylsulfonyl)-3-(4-(2-((1-(1-methylpiperidin-4-yl)-1H-pyrazol-4-yl)amino)thieno[3,2-d]pyrimidin-4-yl)-1H-pyrazol-1-yl)azetidin-3-yl)acetonitrile T-64

Synthetic Route:

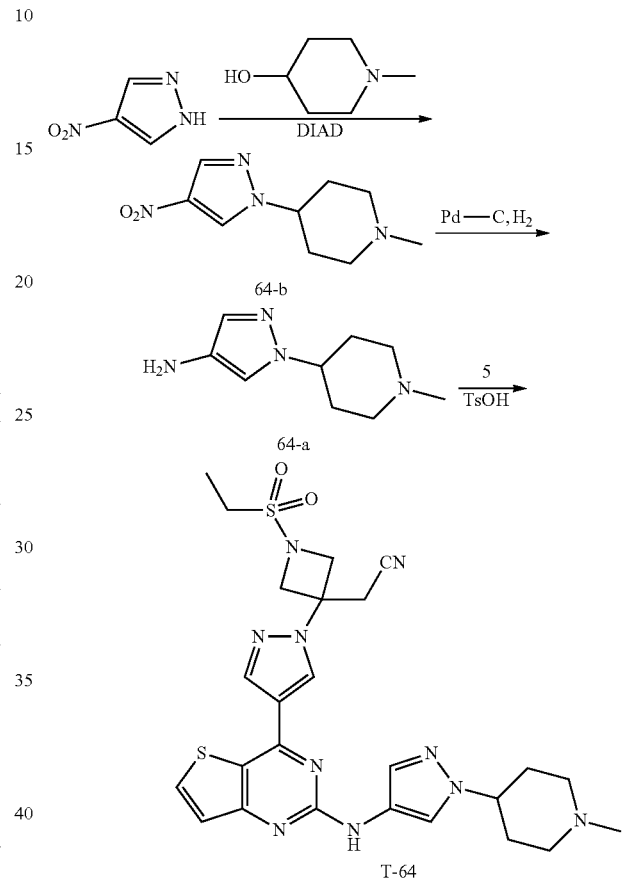

T-64

Preparation of Compound 64-b

At 0° C., DIAD (5.4 g, 26.54 mmol) was added slowly to a solution of 4-nitropyrazole (2.0 g, 17.69 mmol), PPh$_3$ (6.95 g, 26.54 mmol) and N-methyl-4-hydroxypiperidine (2.4 g, 21.23 mmol) in anhydrous THF (50 mL). The mixture was warmed to room temperature and stirred for 16 hours. After the mixture was concentrated under reduced pressure, the residue was diluted with ethyl acetate (50 mL) and 3N aqueous HCl solution (50 mL) in sequence. The aqueous layer was treated with saturated aqueous K$_2$CO$_3$ solution to adjust pH=9, then extracted with ethyl acetate (50 mL×3). The organic layers were combined, washed with water (50 mL×3) and saturated brine (50 mL) in sequence, dried over anhydrous sodium sulfate, then filtrated, the filtrate was concentrated under reduced pressure to give yellow oil 64-b (2.1 g, yield: 57%), which was used directly for the next step without purification.

Preparation of Compound 64-a

Under hydrogen (1 atm), to a solution of compound 64-b (500 mg, 2.38 mmol) in ethanol (10 mL) was added 10% Pd—C (0.1 g). The mixture was stirred at 25° C. for 16 hours, and then filtrated, the filtrate was concentrated under reduced pressure to give red brown oil 64-a (420 mg, yield:

98%), which was used directly for the next step without purification. LC-MS (ESI): m/z=181 [M+H]$^+$.

Preparation of Compound T-64

Compound 64-a (128 mg, 0.71 mmol) and compound 5 (100 mg, 0.24 mmol) were dissolved in n-butanol (2 mL), p-toluene sulfonic acid monohydrate (135 mg, 0.71 mmol) was added. The mixture was heated to 110° C. and stirred for 18 hours, then cooled to room temperature. The mixture was concentrated under reduced pressure, the residue was treated with saturated aqueous NaHCO$_3$ solution (5 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:acetonitrile, water (0.05% trifluoroacetic acid); gradient: 25%-55%-10%) to give brown solid T-64 (62 mg, yield: 47%). LC-MS (ESI): m/z=567 [M+H]$^+$.

$^1$H-NMR (400 MHz, CDCl$_3$) δ: 8.43 (s, 1H), 8.35 (s, 1H), 8.03 (s, 1H), 7.87 (d, J=5.6 Hz, 1H), 7.58 (s, 1H), 7.31 (d, J=5.2 Hz, 1H), 7.18 (s, 1H), 4.63 (d, J=9.2 Hz, 2H), 4.25 (d, J=9.2 Hz, 2H), 4.18 (m, 1H), 3.40 (s, 2H), 3.09 (q, J=7 Hz, 2H), 3.01 (m, 2H), 2.35 (s, 3H), 2.15 (m, 6H), 1.41 (t, J=7 Hz, 3H) ppm Example 65

2-(3-(4-(2-((1-(Azetidin-3-yl)-1H-pyrazol-4-yl)amino)thieno[3,2-d]pyrimidin-4-yl)-1H-pyrazol-1-yl)-1-(ethylsulfonyl)azetidin-3-yl)acetonitrile T-65

Synthetic Route:

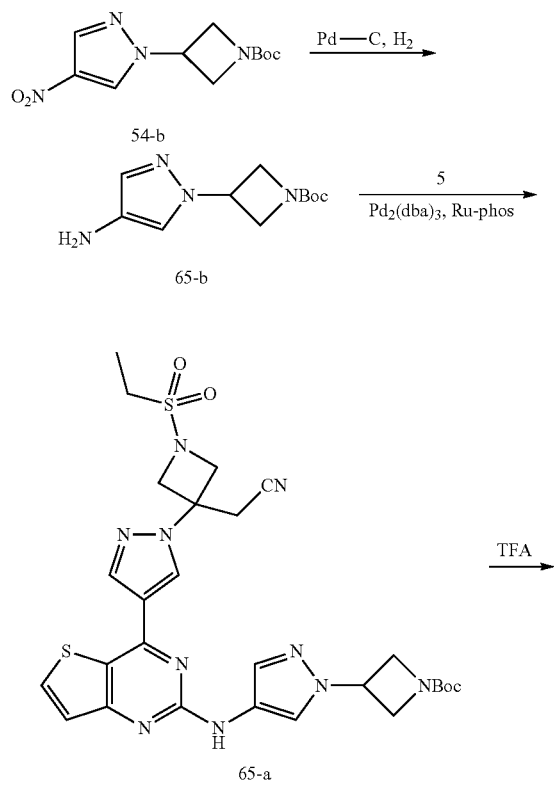

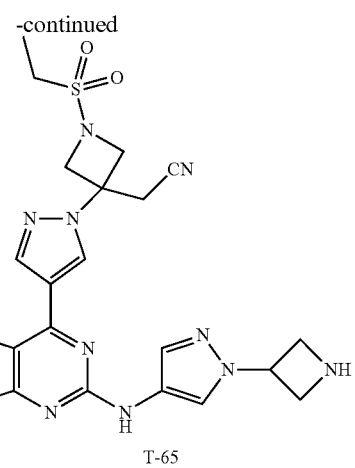

T-65

Preparation of Compound 65-b

Under hydrogen (1 atm), to a solution of compound 54-b (1.33 g, 5 mmol) in methanol (10 mL) was added 10% Pd—C (0.1 g). The mixture was stirred at 25° C. for 12 hours, and then filtrated, the filtrate was concentrated under reduced pressure to give compound 65-b (940 mg, yield: 79%), which was used directly for the next step without purification. LC-MS (ESI): m/z=261 [M+Na]$^+$.

Preparation of Compound 65-a

Under nitrogen, to a suspension of compound 5 (422 mg, 1.0 mmol), compound 65-b (357 mg, 1.5 mmol) and potassium carbonate (276 mg, 2.0 mmol) in 1,4-dioxane (10 mL) were added Pd$_2$(dba)$_3$ (15 mg, 0.017 mmol) and Ruphos (10 mg, 0.07 mmol), the mixture was heated to 120° C. by microwave and stirred for 40 minutes. After cooled to room temperature, the mixture was diluted with ethyl acetate (10 mL), then filtrated, the filtrate was concentrated under reduced pressure. The residue was purified by silica column chromatography (petroleum ether:ethyl acetate=2:1 to 1:1) to give compound 65-a (374 mg, yield: 60%). LC-MS (ESI): m/z=625 [M+H]$^+$.

Preparation of Compound T-65

Trifluoroacetic acid (2 mL) was added to a solution of compound 65-a (370 mg, 0.6 mmol) in dichloromethane (6 mL) and stirred for 3 hours. The mixture was concentrated under reduced pressure, the residue was treated with saturated aqueous NaHCO$_3$ solution (10 mL), extracted with dichloromethane (10 mL×3). The organic layers were combined, dried over anhydrous sodium sulfate, then filtrated, the filtrate was concentrated under reduced pressure. The residue was purified by silica column chromatography (petroleum ether:ethyl acetate=1:1 to 1:3) to give compound T-65 (160 mg, yield: 50%). LC-MS (ESI): m/z=525 [M+H]$^+$.

$^1$H-NMR (400 MHz, DMSO-d6) δ: 9.56 (s, 1H), 8.84 (s, 1H), 8.41 (s, 1H), 8.37 (d, J=5.6 Hz, 1H), 8.22 (s, 1H), 7.74 (s, 1H), 7.81 (d, J=5.6 Hz, 1H), 5.35 (m, 1H), 4.59 (d, J=9.6 Hz, 2H), 4.27 (d, J=9.6 Hz, 2H), 4.18 (m, 4H), 3.73 (s, 2H), 3.27 (q, J=7.2 Hz, 2H), 1.25 (t, J=7.2 Hz, 3H) ppm

Example 66

2-(3-(4-(2-((1-(1-(Cyclopropylmethyl)azetidin-3-yl)-1H-pyrazol-4-yl)amino)thieno[3,2-d]pyrimidin-4-yl)-1H-pyrazol-1-yl)-1-(ethylsulfonyl)azetidin-3-yl)acetonitrile T-66

Synthetic Route:

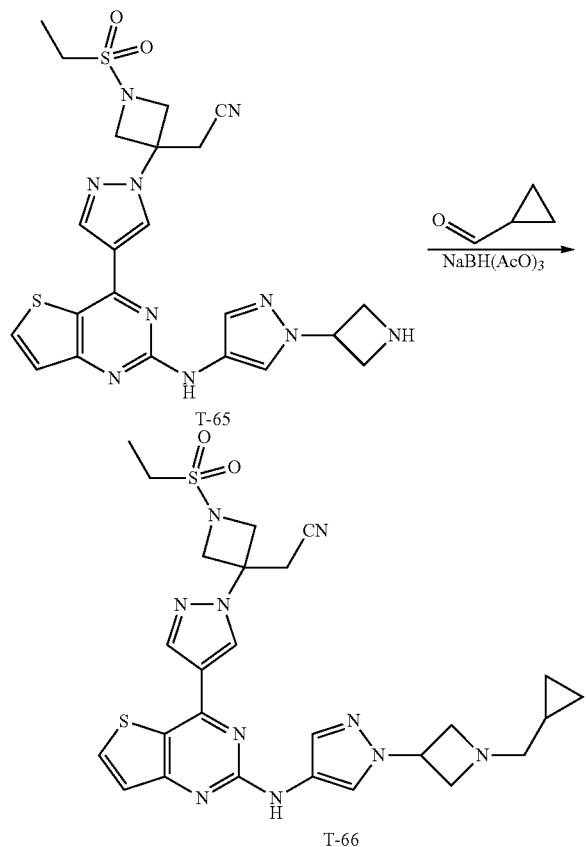

At 0° C., NaBH(AcO)₃ (212 mg, 1.0 mmol) was added to a solution of compound T-65 (120 mg, 0.23 mmol) and cyclopropanecarbaldehyde (70 mg, 1.0 mmol) in a component solvent of methanol (6 mL) and dichloromethane (6 mL), stirred for 2 hours, then warmed to room temperature, and stirred for further 16 hours. The mixture was concentrated under reduced pressure, the residue was treated with saturated aqueous NaHCO₃ solution (10 mL), extracted with dichloromethane (10 mL×3). The organic layers were combined, dried over anhydrous sodium sulfate, then filtrated, the filtrate was concentrated under reduced pressure. The residue was purified by silica column chromatography (petroleum ether:ethyl acetate=1:1 to 1:3) to give compound T-66 (60 mg, yield: 43%). LC-MS (ESI): m/z=579 [M+H]⁺.

¹H-NMR (400 MHz, DMSO-d6) δ: 9.49 (s, 1H), 8.83 (s, 1H), 8.40 (s, 1H), 8.36 (d, J=5.2 Hz, 1H), 8.20 (s, 1H), 7.65 (s, 1H), 7.38 (d, J=5.2 Hz, 1H), 4.98 (m, 1H), 4.59 (d, J=9.2 Hz, 2H), 4.27 (d, J=9.2 Hz, 2H), 3.72 (m, 4H), 3.37 (t, J=7.2 Hz, 2H), 3.25 (q, J=7.2 Hz, 2H), 2.36 (d, J=7.2 Hz, 2H), 1.25 (t, J=7.2 Hz, 3H), 0.79 (m, 1H), 0.41 (m, 2H), 0.11 (m, 2H) ppm

Example 67

2-(1-(Ethylsulfonyl)-3-(4-(2-((1-(3-(4-methylpiperazin-1-yl)propyl)-1H-pyrazol-4-yl)amino)thieno[3,2-d]pyrimidin-4-yl)-1H-pyrazol-1-yl)azetidin-3-yl)acetonitrile Synthetic Route:

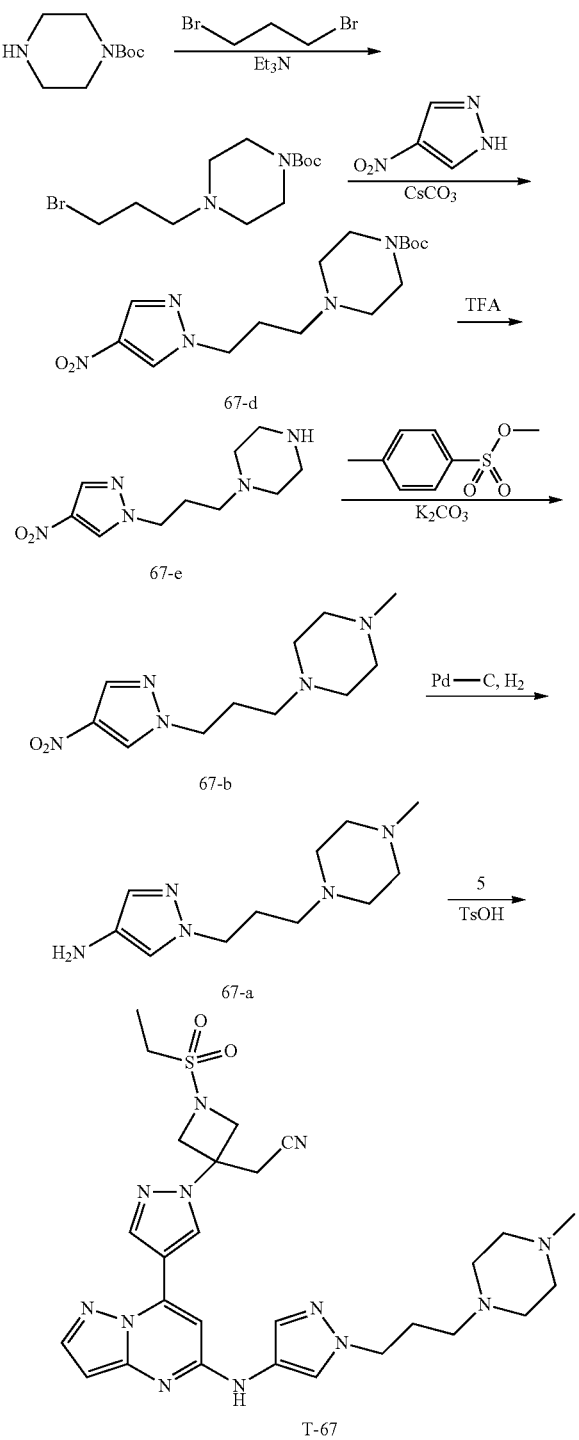

Preparation of Compound 67-e 1,3-Dibromopropane (4.0 g, 20 mmoL) was added slowly to a solution of 1-boc piperazine (1.86 g, 10 mmol) and triethylamine (4.0 g, 40 mmol) in dichloromethane (200 mL). The mixture was stirred for 16 hours, concentrated under reduced pressure, the residue was treated with saturated aqueous NaHCO$_3$ solution (100 mL), extracted with dichloromethane (100 mL×3). The organic layers were combined, dried over anhydrous sodium sulfate, then filtrated, the filtrate was concentrated under reduced pressure. The residue was purified by silica column chromatography (petroleum ether:ethyl acetate=1:1 to 1:3) to give compound 67-e (1.25 g, yield: 41%).

$^1$H-NMR (400 MHz, CDCl$_3$) δ: 3.60 (t, J=6.6 Hz, 2H), 3.43 (t, J=5.0 Hz, 4H), 2.49 (t, J=7.0 Hz, 2H), 2.38 (t, J=5.0 Hz, 4H), 1.94 (m, 2H), 1.46 (s, 9H) ppm Preparation of Compound 67-d Compound 67-e (1.23 g, 4.1 mmol) was added to a solution of 4-nitropyrazole (650 mg, 5.0 mmol) and cesium carbonate (3.25 g, 10.0 mmol) in DMF (15 mL), the mixture was heated to 90° C. and stirred for 6 hours. After cooled to room temperature, the mixture was treated with water (60 mL), extracted with ethyl acetate (20 mL×3). The organic layers were combined, dried over anhydrous sodium sulfate, then filtrated, the filtrate was concentrated under reduced pressure. The residue was purified by silica column chromatography (petroleum ether:ethyl acetate=1:1) to give compound 67-d (910 mg, yield: 66%). LC-MS (ESI): m/z=340 [M+H]$^+$.

Preparation of Compound 67-c

Trifluoroacetic acid (2 mL) was added to a solution of compound 67-d (560 mg, 1.66 mmol) in dichloromethane (6 mL) and stirred for 3 hours. The mixture was concentrated under reduced pressure, the residue was treated with saturated aqueous NaHCO$_3$ solution (10 mL), extracted with dichloromethane (10 mL×3). The organic layers were combined, dried over anhydrous sodium sulfate, then filtrated, the filtrate was concentrated under reduced pressure to give compound 67-c (360 mg, yield: 90%), which was used directly for the next step without purification. LC-MS (ESI): m/z=240 [M+H]$^+$.

Preparation of Compound 67-b

Methyl p-toluenesulfonate (190 mg, 1.0 mmol) was added slowly to a solution of compound 67-c (239 mg, 1.0 mmol) and potassium carbonate (1.38 g, 10.0 mmol) in THF. After stirred for 2 hours, the mixture was treated with saturated aqueous NaHCO$_3$ solution (10 mL), extracted with dichloromethane (15 mL×3). The organic layers were combined, dried over anhydrous sodium sulfate, then filtrated, the filtrate was concentrated under reduced pressure to give compound 67-b (255 mg, yield: 100%), which was used directly for the next step without purification. LC-MS (ESI): m/z=254 [M+H]$^+$.

Preparation of Compound 67-a

Under hydrogen (1 atm), to a solution of compound 67-b (255 mg, 1.0 mmol) in methanol (10 mL) was added 10% Pd—C (0.1 g). The mixture was stirred at 25° C. for 12 hours, and then filtrated, the filtrate was concentrated under reduced pressure to give compound 67-a (180 mg, yield: 80%), which was used directly for the next step without purification. LC-MS (ESI): m/z=224 [M+Na]$^+$.

Preparation of Compound T-67

Compound 67-a (180 mg, 0.8 mmol) and compound 5 (221 mg, 0.5 mmol) were dissolved in n-butanol (10 mL), p-toluene sulfonic acid monohydrate (258 mg, 1.5 mmol) was added. The mixture was heated to 120° C. and stirred for 3 hours, then cooled to room temperature. The mixture was treated with saturated aqueous NaHCO$_3$ solution (10 mL), extracted with dichloromethane (10 mL×3). The organic layers were combined, washed with water (10 mL×3) and saturated brine (10 mL) in sequence, dried over anhydrous sodium sulfate, then filtrated. The residue was purified by preparation HPLC (mobile phase:acetonitrile, water (0.05% trifluoroacetic acid); gradient: 20%-50%-10%) to give compound T-67 (15 mg, yield: 4.9%). LC-MS (ESI): m/z=610 [M+H]$^+$.

$^1$H-NMR (400 MHz, DMSO-d$_6$) δ: 8.75 (s, 1H), 8.38 (s, 1H), 8.25 (d, J=5.2 Hz, 1H), 8.09 (s, 1H), 7.89 (s, 1H), 7.32 (d, J=5.2 Hz, 1H), 4.67 (d, J=9.2 Hz, 2H), 4.33 (s, 2H), 4.30 (d, J=9.2 Hz, 2H), 3.65 (s, 2H), 3.53 (s, 4H), 3.37 (s, 2H), 3.20 (q, J=7.6 Hz, 2H), 3.06 (m, 2H), 2.95 (s, 3H), 2.29 (m, 2H), 1.39 (t, J=7.6 Hz, 3H) ppm Example 68

2-(3-(4-(6-Chloro-2-((1-methyl-1H-pyrazol-4-yl)amino)thieno[3,2-d]pyrimidin-4-yl)-1H-pyrazol-1-yl)-1-(ethylsulfonyl)azetidin-3-yl)acetonitrile T-68

Synthetic Route:

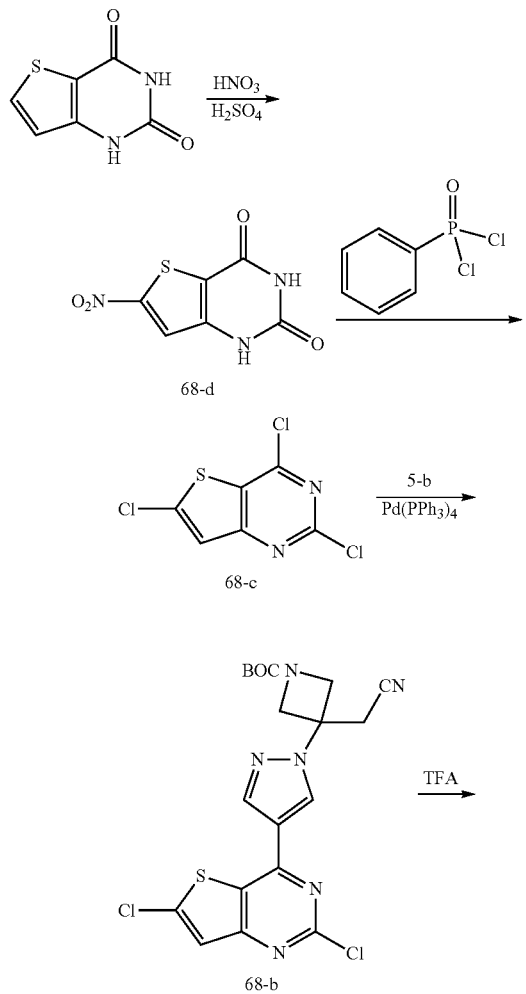

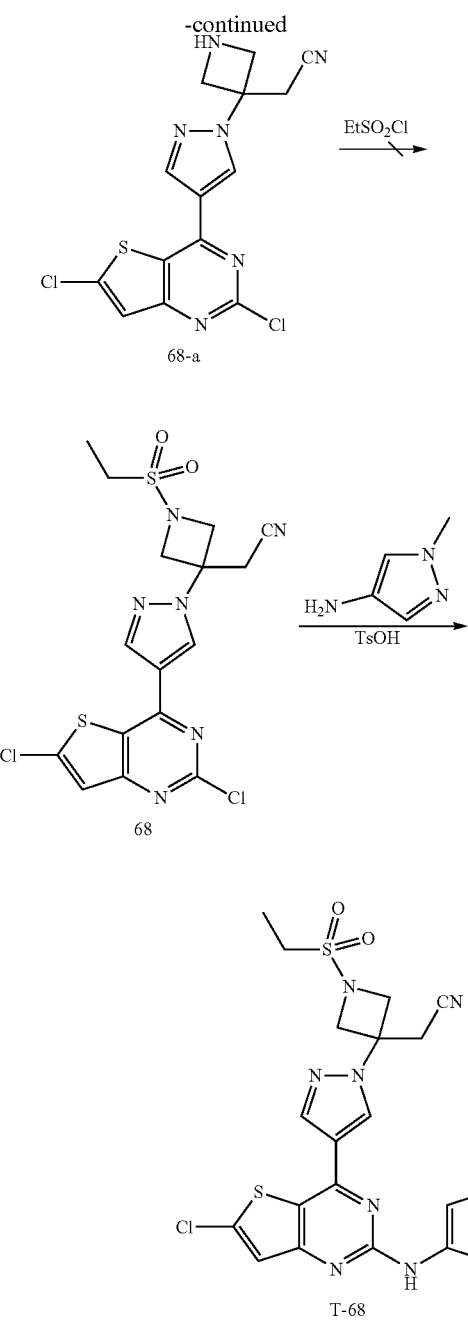

Preparation of Compound 68-d

At 0° C., 1,3-dihydrothiopheno[3,2-d]pyrimidine-2,4-dione (1.68 g, 10 mmol) was added slowly to a component solvent of con. HNO₃ (15 mL) and con. H₂SO₄ (15 mL), stirred for 1 hour, ice water (30 mL) was added, and the mixture was stirred for further 3 hours. The mixture was filtrated, the filter cake was washed with ice water (5 mL×3), dried in vacuum for 8 hours to give yellow solid 68-d (1.36 g, yield: 63.8%), which was used directly for the next step without purification. LC-MS (ESI): m/z=214 [M+H]⁺.

Preparation of Compound 68-c

A mixture of compound 68-d (1.36 g, 6.4 mmol) and phenylphosphonic dichloride (15 mL) was heated to 180° C., stirred for 4 hours, the mixture was cooled to 90° C. Water (200 mL) was added slowly. The mixture was cooled slowly to 25° C., and stirred for further 16 hours. The mixture was filtrated, the filter cake was washed with water (15 mL×3), dried in vacuum for 8 hours to give white solid 68-c (1.1 g, yield: 72%), which was used directly for the next step without purification. LC-MS (ESI): m/z=239 [M+H]⁺.

Preparation of Compound 68-b

Under nitrogen, compound 5-b (390 mg, 1.0 mmol), compound 68-c (240 Ing, 1.0 mmol) and potassium carbonate (280 mg, 2.0 mmol) were suspended in 1,4-dioxane (8 mL) and water (2 mL), Pd(PPh₃)₄ (48 mg, 0.04 mmol) was added, the mixture was stirred at 80° C. for 4 hours. The mixture was concentrated under reduced pressure, the residue was diluted with water (10 mL), extracted with ethyl acetate (10 mL×3). The organic layers were combined, washed with water (10 mL×3) and saturated brine (10 mL) in sequence, dried over anhydrous sodium sulfate, then filtrated, the filtrate was concentrated under reduced pressure. The residue was purified by silica column chromatography (petroleum ether:ethyl acetate=3:1) to give compound 68-b (230 mg, yield: 49.6%). LC-MS (ESI): m/z=465 [M+H]⁺.

Preparation of Compound 68-a

Trifluoroacetic acid (3 mL) was added to a solution of compound 68-b (230 mg, 0.5 mmoL) in dichloromethane (6 mL) and stirred for 3 hours at room temperature. The mixture was concentrated under reduced pressure to give compound 68-a (160 mg, yield: 88%), which was used directly for the next step without purification. LC-MS (ESI): m/z=365 [M+H]⁺.

Preparation of Compound 68

At room temperature, to a solution of compound 68-a (160 mg, 0.44 mmoL) and triethylamine (90 mg, 0.88 mmol) in dichloromethane (6 mL) was added slowly dropwise ethylsulfonyl chloride (65 mg, 0.5 mmoL). After stirred for 3 hours, the mixture was concentrated under reduced pressure, the residue was treated with saturated aqueous sodium bicarbonate solution (10 mL), extracted with dichloromethane (10 mL×3). The organic layers were combined, washed with water (10 mL×3) and saturated brine (20 mL) in sequence, dried over anhydrous sodium sulfate, then filtrated, the filtrate was concentrated under reduced pressure to give compound 68 (150 mg, yield: 74.5%), which was used directly for the next step without purification. LC-MS (ESI): m/z=459 [M+H]⁺.

Preparation of Compound T-68

Compound 68 (150 mg, 0.33 mmol) and 1-methyl-4-aminopyrazole (97 mg, 1.0 mmol) were dissolved in n-butanol (10 mL), p-toluene sulfonic acid monohydrate (190 mg, 1.0 mmol) was added. The mixture was heated to 108° C. and stirred for 3 hours, then cooled to room temperature. The mixture was concentrated under reduced pressure to remove the solvent, the residue was treated with saturated aqueous sodium bicarbonate solution (10 mL), extracted with dichloromethane (10 mL×3). The organic layers were combined, dried over anhydrous sodium sulfate, then filtrated, the filtrate was concentrated under reduced pressure. The residue was purified by silica column chromatography (petroleum ether:ethyl acetate=3:1 to 1:1) to give compound T-68 (36 mg, yield: 21%). LC-MS (ESI): m/z=518 [M+H]⁺.

¹H-NMR (400 MHz, CD₃OD) δ: 8.57 (s, 1H), 8.22 (s, 1H), 7.95 (s, 1H), 7.49 (s, 1H), 7.19 (s, 1H), 4.50 (d, J=9.2 Hz, 2H), 4.20 (d, J=9.2 Hz, 2H), 3.80 (s, 3H), 3.51 (s, 2H), 3.08 (q, J=7.6 Hz, 2H), 1.27 (t, J=7.6 Hz, 3H) ppm

Example 69

2-(1-(Ethylsulfonyl)-3-(4-(2-((1-(2,2,2-trifluoro-ethyl)-1H-pyrazol-4-yl)amino)thieno[3,2-d]pyrimidin-4-yl)-1H-pyrazol-1-yl)azetidin-3-yl)acetonitrile T-69

Synthetic Route:

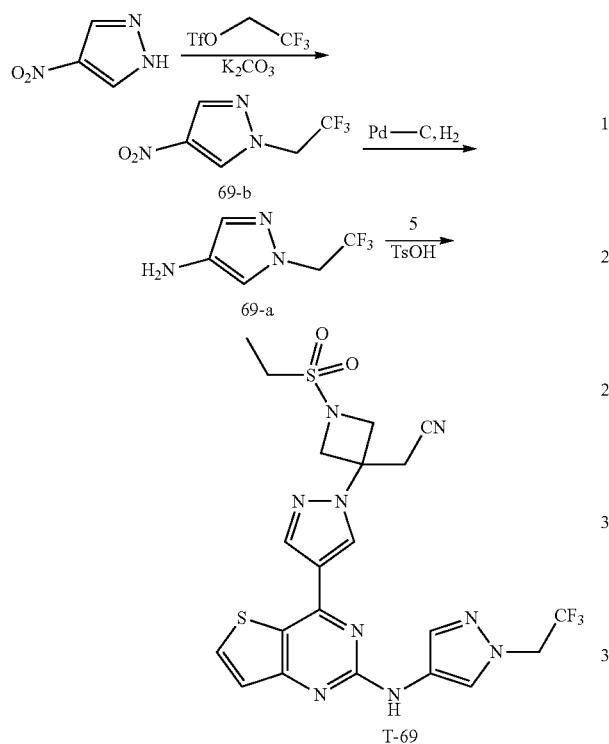

Preparation of Compound 69-b

4-Nitropyrazole (1.13 g, 10 mmol) was added to a solution of 2,2,2-trifluoroethyl methanesulfonate (3.48 g, 15 mmol) and potassium carbonate (2.76 g, 20 mmol) in DMF (10 mL), the mixture was warmed to 40° C. and stirred for 6 hours. After cooled to room temperature, the mixture was treated with water (100 mL), extracted with ethyl acetate (50 mL×2). The organic layers were combined, dried over anhydrous sodium sulfate, then filtrated, the filtrate was concentrated under reduced pressure. The residue was washed with petroleum ether (20 mL) to give white solid 69-b (1.6 g, yield: 82%), which was used directly for the next step without purification. LC-MS (ESI): m/z=196 [M+H]$^+$.

Preparation of Compound 69-a

Under hydrogen (1 atm), to a solution of compound 69-b (1.5 g, 7.69 mmol) in ethanol (5 mL) was added 10% Pd—C (0.15 g). The mixture was stirred at 25° C. for 16 hours, and then filtrated, the filtrate was concentrated under reduced pressure to give red brown oil 69-a (1.2 g, yield: 95%), which was used directly for the next step without purification. LC-MS (ESI): m/z=166 [M+H]$^+$.

Preparation of Compound T-69

Compound 69-a (176 mg, 1.07 mmol) and compound 5 (150 mg, 0.36 mmol) were dissolved in n-butanol (0.5 mL), p-toluene sulfonic acid monohydrate (170 mg, 0.89 mmol) was added. The mixture was heated to 110° C. and stirred for 18 hours, then cooled to room temperature. The mixture was concentrated under reduced pressure to remove the solvent, the residue was treated with saturated aqueous sodium bicarbonate solution (50 mL), extracted with dichloromethane (50 mL×2). The organic layers were combined, dried over anhydrous sodium sulfate, then filtrated, the filtrate was concentrated under reduced pressure. The residue was purified by preparation TLC (chromatographic solution:ethyl acetate) to give yellow solid T-69 (73 mg, yield: 38%). LC-MS (ESI): m/z=552 [M+H]$^+$.

$^1$H-NMR (400 MHz, CDCl$_3$) δ: 8.47 (s, 1H), 8.35 (s, 1H), 8.18 (s, 1H), 7.91 (d, J=5.2 Hz, 1H), 7.63 (s, 1H), 7.34 (d, J=5.2 Hz, 1H), 7.22 (s, 1H), 4.74 (dd, J=16.8 Hz, J=8.4 Hz, 2H), 4.64 (d, J=9 Hz, 2H), 4.24 (d, J=9 Hz, 2H), 3.41 (s, 2H), 3.10 (q, J=7 Hz, 2H), 1.42 (t, J=7 Hz, 3H) ppm

Example 70

2-(1-(Ethylsulfonyl)-3-(4-(2-((1-(2-methoxyethyl)-1H-pyrazol-4-yl)amino)thieno[3,2-d]pyrimidin-4-yl)-1H-pyrazol-1-yl)azetidin-3-yl)acetonitrile T-70

Synthetic Route:

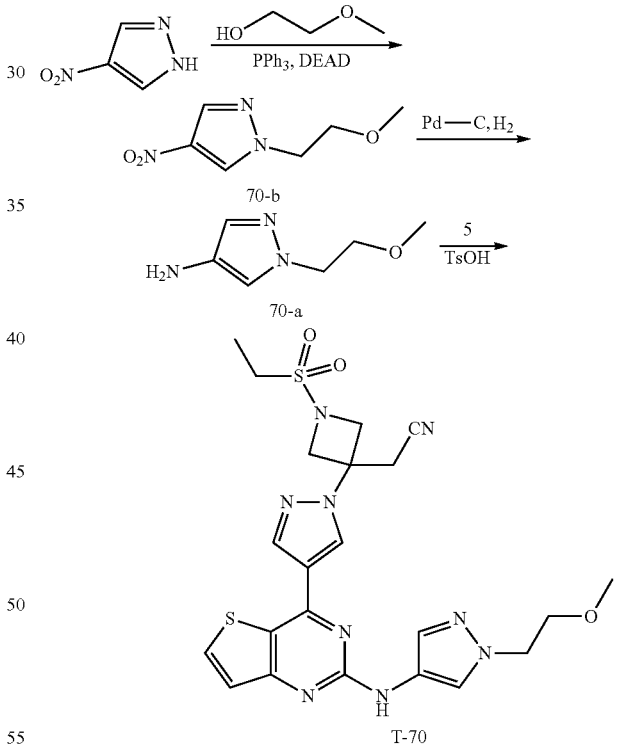

Preparation of Compound 70-b

At 0° C., DEAD (4.1 g, 19.91 mmol) was added slowly to a solution of 4-nitropyrazole (1.5 g, 13.27 mmol), 2-methoxyethanol (1.5 g, 19.91 mmol) and PPh$_3$ (5.2 g, 19.91 mmol) in anhydrous TH-IF (25 mL). The mixture was warmed to room temperature and stirred for 3 hours, then concentrated under reduced pressure, the residue was purified by silica column chromatography (petroleum ether: ethyl acetate=5:1) to give white solid 70-b (1.72 g, yield: 76.1%). LC-MS (ESI): m/z=198 [M+H]$^+$.

Preparation of Compound 70-a

Under hydrogen (1 atm), to a solution of compound 70-b (1.7 g, 10 mmol) in ethanol (20 mL) was added 10% Pd—C (0.2 g). The mixture was stirred at 25° C. for 16 hours, and then filtrated, the filtrate was concentrated under reduced pressure to give red brown oil 70-a (1.3 g, yield: 93%), which was used directly for the next step without purification. LC-MS (ESI): m/z=142 [M+H]$^+$.

Preparation of Compound T-70

Compound 70-a (151 mg, 1.07 mmol) and compound 5 (150 mg, 0.36 mmol) were dissolved in n-butanol (3 mL), p-toluene sulfonic acid monohydrate (170 mg, 0.89 mmol) was added. The mixture was heated to 110° C. and stirred for 18 hours, then cooled to room temperature. The mixture was concentrated under reduced pressure to remove the solvent, the residue was treated with saturated aqueous sodium bicarbonate solution (50 mL), extracted with dichloromethane (50 mL×2). The organic layers were combined, dried over anhydrous sodium sulfate, then filtrated, the filtrate was concentrated under reduced pressure. The residue was purified by preparation TLC (chromatographic solution:ethyl acetate) to give yellow solid T-70 (55 mg, yield: 30%). LC-MS (ESI): m/z=528 [M+H]$^+$.

$^1$H-NMR (400 MHz, CDCl$_3$) δ: 8.41 (s, 1H), 8.32 (s, 1H), 8.03 (s, 1H), 7.84 (d, J=5.2 Hz, 1H), 7.58 (s, 1H), 7.45 (s, 1H), 7.27 (d, J=5.2 Hz, 1H), 4.62 (d, J=9 Hz, 2H), 4.30 (t, J=5.2 Hz, 2H), 4.24 (d, J=9 Hz, 2H), 3.79 (t, J=5.2 Hz, 2H), 3.39 (s, 2H), 3.37 (s, 3H), 3.09 (q, J=7 Hz, 2H), 1.41 (t, J=7 Hz, 3H) ppm Example 71

3-(4-((4-(1-(3-(Cyanomethyl)-1-(ethylsulfonyl)azetidin-3-yl)-1H-pyrazol-4-yl)thieno[3,2-d]pyrimidin-2-yl)amino)-1H-pyrazol-1-yl)propanenitrile T-71

Synthetic Route:

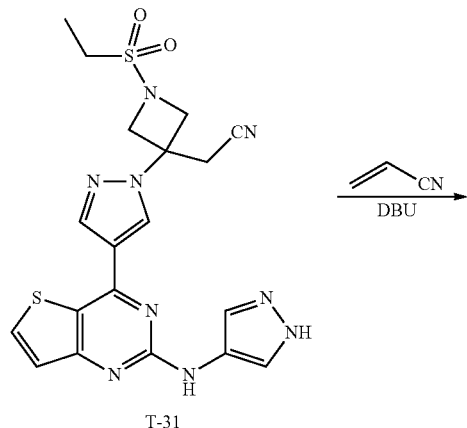

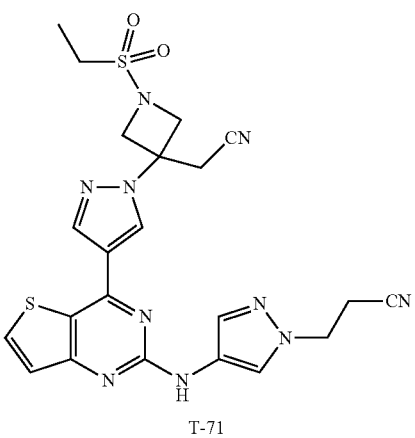

Preparation of Compound T-71

At room temperature, DBU (0.1 mL) was added to a solution of compound T-31 (235 mg, 0.5 mmol) and acrylonitrile (50 mg, 1 mmol) in acetonitrile (8 mL). After stirred for 3 hours, the mixture was concentrated under reduced pressure, the residue was purified by silica column chromatography (petroleum ether:ethyl acetate=5:1) to give light yellow solid T-71 (38 mg, yield: 14.6%). LC-MS (ESI): m/z=523 [M+H]$^+$.

$^1$H-NMR (400 MHz, DMSO-d$_6$) δ: 9.54 (s, 1H), 8.83 (s, 1H), 8.38 (s, 1H), 8.36 (s, 1H), 8.20 (s, 1H), 7.65 (s, 1H), 4.58 (d, J=9.2 Hz, 2H), 4.40 (t, J=6.0 Hz, 2H), 4.27 (d, J=9.2 Hz, 2H), 3.73 (s, 2H), 3.25 (q, J=7.6 Hz, 2H), 3.07 (t, J=6.4 Hz, 2H), 1.25 (t, J=7.6 Hz, 3H) ppm Example 72

2-(1-(Ethylsulfonyl)-3-(4-(2-((5-methyl-1H-pyrazol-3-yl)amino)thieno[3,2-d]pyrimidin-4-yl)-1H-pyrazol-1-yl)azetidin-3-yl)acetonitrile T-72

Synthetic Route:

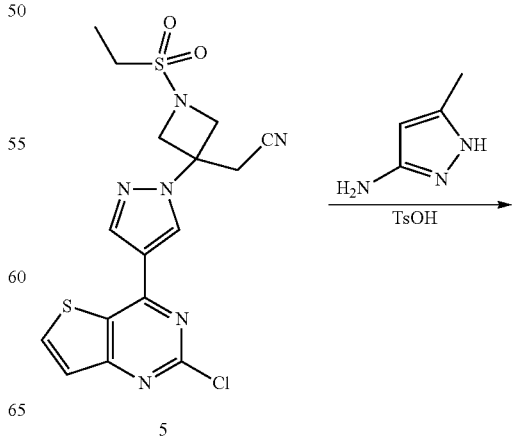

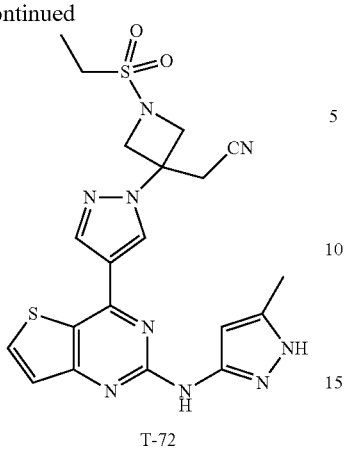

T-72

Preparation of Compound T-72

5-Methyl-3-aminopyrazole (69 mg, 0.72 mmol) and compound 5 (100 mg, 0.24 mmol) were dissolved in n-butanol (2 mL), p-toluene sulfonic acid monohydrate (91 mg, 0.48 mmol) was added. The mixture was heated to 110° C. and stirred for 48 hours, then cooled to room temperature. The mixture was concentrated under reduced pressure, the residue was treated with saturated aqueous NaHCO$_3$ solution (50 mL), extracted with dichloromethane (50 mL×2). The organic layers were combined, dried over anhydrous sodium sulfate, then filtrated, the filtrate was concentrated under reduced pressure. The residue was purified by preparation HPLC (mobile phase:water (10 mmol/mL ammonium bicarbonate), acetonitrile; gradient: 22%-55%) to give yellow solid T-72 (10 mg, yield: 9%). LC-MS (ESI): m/z=484 [M+H]$^+$.

$^1$H-NMR (400 MHz, CDCl$_3$) δ: 8.71-8.45 (2×s, 1H), 8.37-8.33 (2×s, 1H), 8.04-7.90 (2×d, J=5.6 Hz, 1H), 7.90-7.57 (2×d, J=5.6 Hz, 1H), 7.34 (d, J=5.6 Hz, 1H), 6.21-5.93 (2×br, 1H), 5.44 (s, 1H), 4.64 (dd, J=3.6H, J=9.2 Hz, 2H), 4.26 (dd, J=9 Hz, J=3.6 Hz, 2H), 3.41 (s, 2H), 3.10 (m, 2H), 2.31 (s, 3H), 1.42 (m, 3H) ppm

Example 73

2-(1-(4-(2-((1-(3-(Methylsulfonyl)propyl)-1H-pyrazol-4-yl)amino)thieno[3,2-d]pyrimidin-4-yl)-1H-pyrazol-1-yl)cyclobutyl)acetonitrile T-73

Synthetic Route:

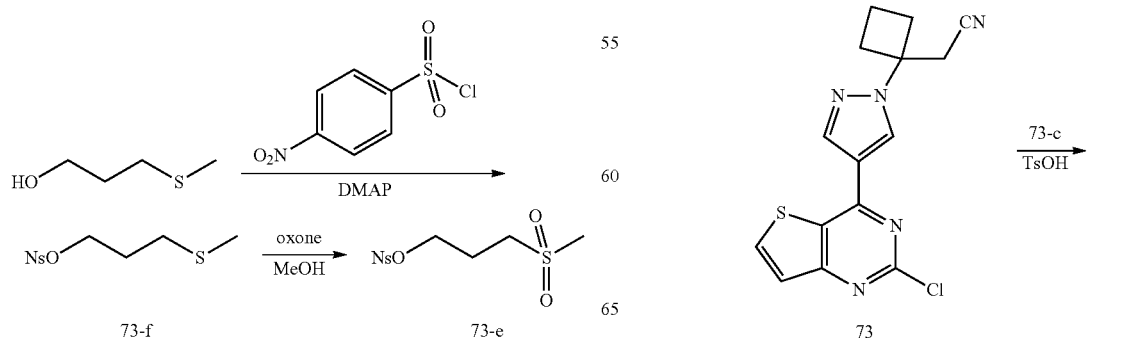

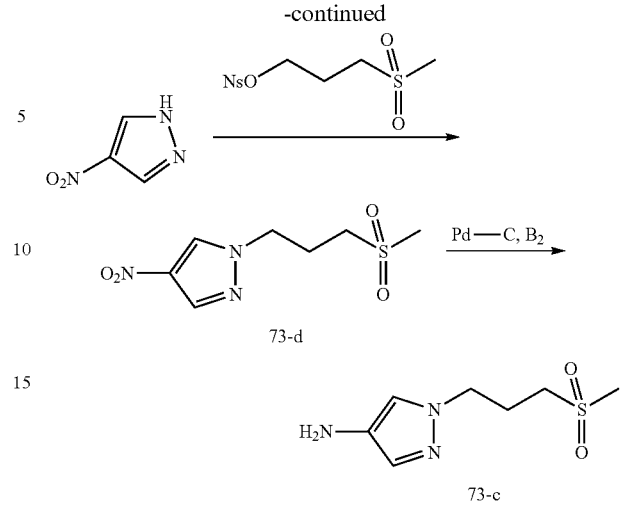

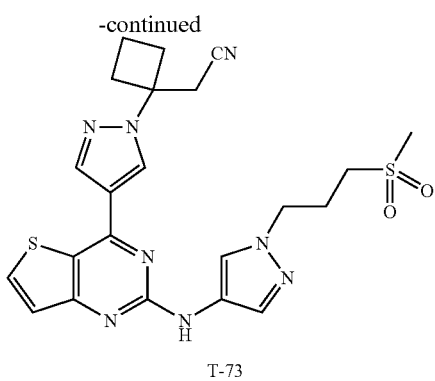

T-73

Preparation of Compound 73-f

At 0° C., a solution of p-nitrobenzenesulfonyl chloride (2.43 g, 11 mmol) in toluene (20 mL) was added dropwise to a solution of 3-(methylthio)propan-1-ol (1.06 g, 10 mmol) and DMAP (1.46 g, 12 mmol) in toluene (20 mL). The mixture was warmed to 25° C. and stirred for 16 hours. The mixture was treated with water (100 mL), extracted with ethyl acetate (100 mL×2). The organic layers were combined, washed with saturated brine (100 mL), dried over anhydrous sodium sulfate, then filtrated, the filtrate was concentrated under reduced pressure. The residue was purified by silica column chromatography (petroleum ether:ethyl acetate=3:1) to give white solid 73-f (2 g, yield: 69°%). LC-MS (ESI): m/z=292 [M+H]$^+$.

Preparation of Compound 73-e

At 0° C., a solution of oxone (9.3 g, 15.12 mmol) in water (50 mL) was added dropwise to a solution of compound 73-f (2 g, 6.87 mmol) in methanol (50 mL). The mixture was warmed to room temperature and stirred for 2 hours. The mixture was concentrated under reduced pressure to remove the solvent, the residue was treated with water (50 mL), extracted with ethyl acetate (100 mL×3). The organic layers were combined, washed with saturated brine (100 mL), dried over anhydrous sodium sulfate, then filtrated, the filtrate was concentrated under reduced pressure to give compound 73-e (1.7 g, yield: 77%), which was used directly for the next step without purification. LC-MS (ESI): m/z=346 [M+Na]$^+$.

Preparation of Compound 73-d

4-Nitropyrazole (250 mg, 2.21 mmol) was added to a solution of compound 73-e (790 mg, 2.45 mmol) and anhydrous potassium carbonate (765 mg, 5.54 mmol) in acetonitrile (10 mL), the mixture was refluxed for 18 hours. After cooled to room temperature, the mixture was concentrated under reduced pressure, the residue was treated with water (20 mL), extracted with ethyl acetate (50 mL×2). The organic layers were combined, dried over anhydrous sodium sulfate, then filtrated, the filtrate was concentrated under reduced pressure to give yellow solid 73-d (485 mg, yield: 94%). LC-MS (ESI): m/z=234 [M+H]$^+$.

Preparation of Compound 73-c

Under hydrogen (1 atm), to a solution of compound 73-d (210 mg, 0.91 mmol) in ethanol (5 mL) was added 10% Pd—C (0.2 g). The mixture was stirred at 25° C. for 16 hours, and then filtrated, the filtrate was concentrated under reduced pressure to give red brown oil 73-c (171 mg, yield: 93%), which was used directly for the next step without purification. LC-MS (ESI): m/z=204 [M+H]$^+$.

Preparation of Compound 73-b

At room temperature, cyclobutanone (2.5 g, 35.7 mmol) was added to a solution of cyanomethylene triphenylphosphorane (16.2 g, 53.57 mmol) in dichloromethane (30 mL), the mixture was stirred for 3 hours. The mixture was concentrated under reduced pressure to removed the solvent, the residue was purified by silica column chromatography (petroleum ether:ethyl acetate=10:1) to give yellow oil 73-b (3 g, yield: 90.3%).

Preparation of Compound 73-a

Compound 73-b (1.5 g, 15.79 mmol) and 4-(4,4,5,5-tetramethyl-1,3,2-dioxaborolan-2-yl)-1H-pyrazole (4.6 g, 23.68 mmol) were dissolved in anhydrous acetonitril (50 mL), 1,8-diazabicyclo[5.4.0]undec-7-ene (6.1 g, 40 mmol) was added. The mixture was stirred at 80° C. for 18 hours, then concentrated under reduced pressure. The residue was treated with water (50 mL), extracted with ethyl acetate (50 mL×2). The aqueous layer was adjusted to pH=3 with aqueous HCl solution (3 N), then extracted with ethyl acetate (50 mL×2). The organic layers were combined, washed with water (60 mL×3) and saturated brine (60 mL) in sequence, dried over anhydrous sodium sulfate, then filtrated, the filtrate was concentrated under reduced pressure to give colorless oil 73-a (2.6 g, yield: 58%), which was used directly for the next step without purification. LC-MS (ESI): m/z=288 [M+H]$^+$.

Preparation of Compound 73

Under nitrogen, compound 73-a (2.6 g, 9.06 mmol), 2,4-dichlorotheino[3,2-d]pyrimidine (1.85 g, 9.06 mmol) and sodium carbonate (2.9 g, 27.18 mmol) were suspended in 1,4-dioxane (15 mL) and water (15 mL), Pd(dppf)Cl$_2$ (733 mg, 0.9 mmol) was added. The mixture was heated to 80° C. and stirred for 16 hours. After cooled to room temperature, the mixture was concentrated under reduced pressure, the residue was treated with water (20 mL), extracted with dichloromethane (20 mL×3). The organic layers were combined, washed with water (60 mL×3) and saturated brine (60 mL) in sequence, dried over anhydrous sodium sulfate, then filtrated, the filtrate was concentrated under reduced pressure. The residue was purified by silica column chromatography (dicholormethane:methanol=100:1) to give light yellow solid 73 (1.6 g, yield: 53.6%). LC-MS (ESI): m/z=330 [M+H]$^+$.

Preparation of Compound T-73

Compound 73-c (46 mg, 0.227 mmol) and compound 73 (50 mg, 0.152 mmol) were dissolved in n-butanol (5 mL), p-toluene sulfonic acid monohydrate (43 mg, 0.227 mmol) was added. The mixture was heated to 110° C. and stirred for 48 hours, then cooled to room temperature. The mixture was concentrated under reduced pressure, the residue was treated with saturated aqueous sodium bicarbonate solution (50 mL), extracted with dichloromethane (50 mL×3). The organic layers were combined, dried over anhydrous sodium sulfate, then filtrated, the filtrate was concentrated under reduced pressure, the residue was purified by preparation TLC (chromatographic solution:ethyl acetate) to give yellow solid T-73 (27 mg, yield: 36%). LC-MS (ESI): m/z=497 [M+H]$^+$.

$^1$H-NMR (400 MHz, CDCl$_3$) δ: 8.39 (s, 1H), 8.34 (s, 1H), 8.09 (s, 1H), 7.88 (d, J=5.2 Hz, 1H), 7.56 (s, 1H), 7.32 (d, J=5.2 Hz, 1H), 7.14 (s, 1H), 4.32 (t, J=6.4 Hz, 2H), 3.16 (s, 2H), 3.05 (t, J=6.4 Hz, 2H), 2.91 (s, 3H), 2.86 (m, 2H), 2.58 (m, 2H), 2.47 (m, 2H), 2.12 (m, 2H) ppm

Example 74

2-(3-(4-(2-((1-Methyl-1H-pyrazol-4-yl)amino)thieno[3,2-d]pyrimidin-4-yl)-1H-pyrazol-1-yl)-1-(methylsulfonyl)azetidin-3-yl)acetonitrile T-74

Synthetic Route:

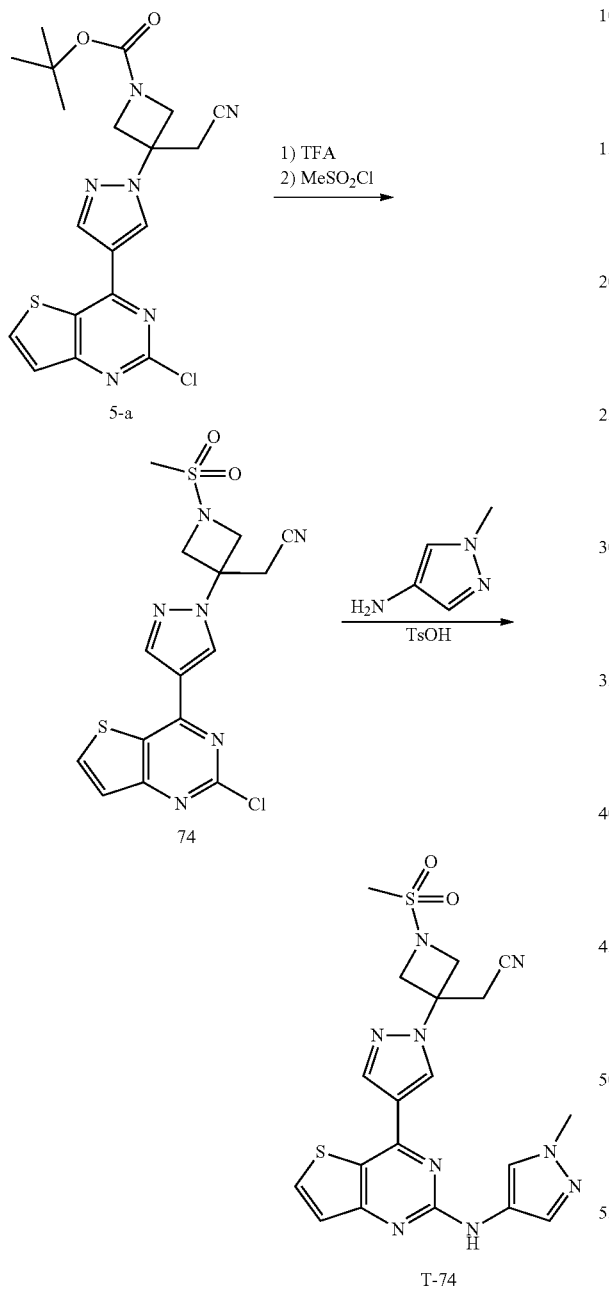

Preparation of Compound 74

At room temperature, trifluoroacetic acid (3 mL) was added to a solution of compound 5-a (250 mg, 0.58 mmol) in dichloromethane (3 mL) and stirred for 3 hours, then concentrated under reduced pressure and the residue was treated with dichloromethane (10 mL) and triethylamine (2 mL). The mixture was then cooled to 0° C., methylsulfonyl chloride (100 mg, 0.87 mmol) was added dropwise, and the resultant mixture was stirred for further 30 minutes, then treated with water (5 mL), extracted with dichloromethane (5 mL×3). The organic layers were combined, dried over anhydrous sodium sulfate, then filtrated, the filtrate was concentrated under reduced pressure. The residue was purified by silica column chromatography (petroleum ether:ethyl acetate=3:1) to give compound 74 (135 mg, yield: 57%). LC-MS (ESI): m/z=409 [M+H]$^+$.

Preparation of Compound T-74

Compound 74 (100 mg, 0.25 mmol) and 1-methyl-4-aminopyrazole (71 mg, 0.74 mmol) were dissolved in n-butanol (2 mL), p-toluene sulfonic acid monohydrate (117 mg, 0.62 mmol) was added. The mixture was heated to 110° C. and stirred for 18 hours, then cooled to room temperature, concentrated under reduced pressure to remove the solvent, the residue was treated with saturated aqueous sodium bicarbonate solution (50 mL), extracted with dichloromethane (50 mL×3). The organic layers were combined, dried over anhydrous sodium sulfate, then filtrated, the filtrate was concentrated under reduced pressure. The residue was purified by preparation TLC (chromatographic solution:ethyl acetate) to give yellow solid T-74 (25 mg, yield: 22%). LC-MS (ESI): m/z:=470 [M+H]$^+$.

$^1$H-NMR (400 MHz, CDCl$_3$) δ: 8.45 (s, 1H), 8.36 (s, 1H), 7.96 (s, 1H), 7.88 (d, J=5.2 Hz, 1H), 7.55 (s, 1H), 7.32 (d, J=5.2 Hz, 1H), 7.12 (s, 1H), 4.60 (d, J=9.2 Hz, 2H), 4.26 (d, J=9.6 Hz, 2H), 3.93 (s, 3H), 3.42 (s, 2H), 3.01 (s, 3H) ppm

Example 75

2-(1-(4-(2-((1-Methyl-1H-pyrazol-4-yl)amino)thieno[3,2-d]pyrimidin-4-yl)-1H-pyrazol-1-yl)cyclopropyl)acetonitrile T-75

Synthetic Route:

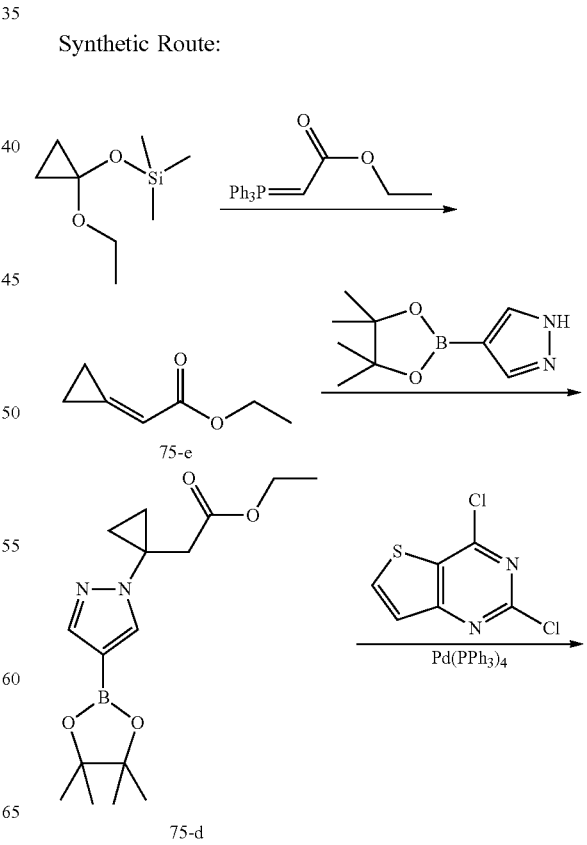

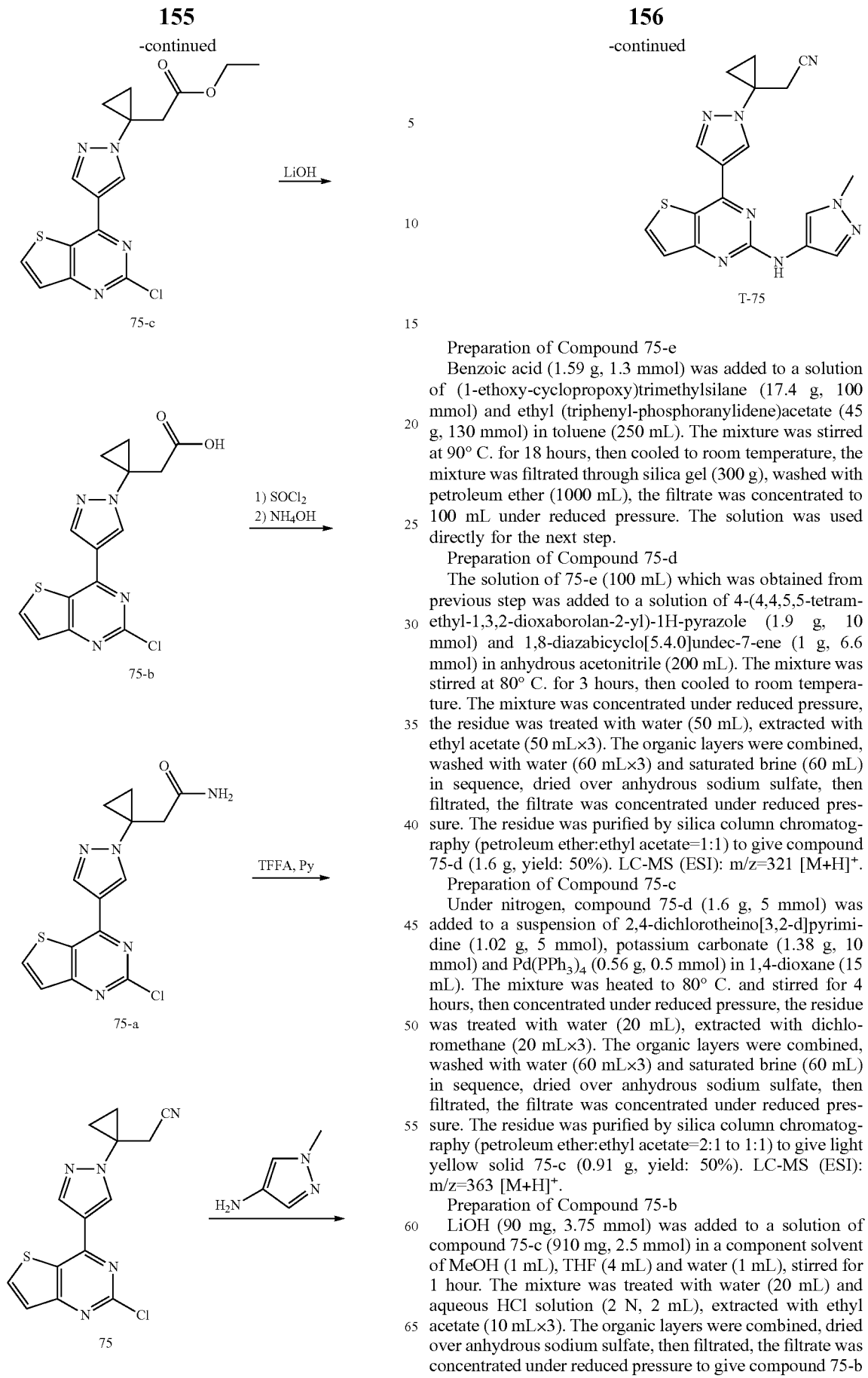

Preparation of Compound 75-e

Benzoic acid (1.59 g, 1.3 mmol) was added to a solution of (1-ethoxy-cyclopropoxy)trimethylsilane (17.4 g, 100 mmol) and ethyl (triphenyl-phosphoranylidene)acetate (45 g, 130 mmol) in toluene (250 mL). The mixture was stirred at 90° C. for 18 hours, then cooled to room temperature, the mixture was filtrated through silica gel (300 g), washed with petroleum ether (1000 mL), the filtrate was concentrated to 100 mL under reduced pressure. The solution was used directly for the next step.

Preparation of Compound 75-d

The solution of 75-e (100 mL) which was obtained from previous step was added to a solution of 4-(4,4,5,5-tetramethyl-1,3,2-dioxaborolan-2-yl)-1H-pyrazole (1.9 g, 10 mmol) and 1,8-diazabicyclo[5.4.0]undec-7-ene (1 g, 6.6 mmol) in anhydrous acetonitrile (200 mL). The mixture was stirred at 80° C. for 3 hours, then cooled to room temperature. The mixture was concentrated under reduced pressure, the residue was treated with water (50 mL), extracted with ethyl acetate (50 mL×3). The organic layers were combined, washed with water (60 mL×3) and saturated brine (60 mL) in sequence, dried over anhydrous sodium sulfate, then filtered, the filtrate was concentrated under reduced pressure. The residue was purified by silica column chromatography (petroleum ether:ethyl acetate=1:1) to give compound 75-d (1.6 g, yield: 50%). LC-MS (ESI): m/z=321 [M+H]$^+$.

Preparation of Compound 75-c

Under nitrogen, compound 75-d (1.6 g, 5 mmol) was added to a suspension of 2,4-dichlorotheino[3,2-d]pyrimidine (1.02 g, 5 mmol), potassium carbonate (1.38 g, 10 mmol) and Pd(PPh$_3$)$_4$ (0.56 g, 0.5 mmol) in 1,4-dioxane (15 mL). The mixture was heated to 80° C. and stirred for 4 hours, then concentrated under reduced pressure, the residue was treated with water (20 mL), extracted with dichloromethane (20 mL×3). The organic layers were combined, washed with water (60 mL×3) and saturated brine (60 mL) in sequence, dried over anhydrous sodium sulfate, then filtered, the filtrate was concentrated under reduced pressure. The residue was purified by silica column chromatography (petroleum ether:ethyl acetate=2:1 to 1:1) to give light yellow solid 75-c (0.91 g, yield: 50%). LC-MS (ESI): m/z=363 [M+H]$^+$.

Preparation of Compound 75-b

LiOH (90 mg, 3.75 mmol) was added to a solution of compound 75-c (910 mg, 2.5 mmol) in a component solvent of MeOH (1 mL), THF (4 mL) and water (1 mL), stirred for 1 hour. The mixture was treated with water (20 mL) and aqueous HCl solution (2 N, 2 mL), extracted with ethyl acetate (10 mL×3). The organic layers were combined, dried over anhydrous sodium sulfate, then filtrated, the filtrate was concentrated under reduced pressure to give compound 75-b (0.79 g, yield: 94.6%), which was used directly for the next step without purification. LC-MS (ESI): m/z=335 [M+H]⁺.

Preparation of Compound 75-a

Thionyl chloride (2 mL) was added to a solution of compound 75-b (800 mg, 2.3 mmol) in toluene (5 mL), the mixture was heated to 100° C. and stirred for 3 hours, then cooled to room temperature, concentrated under reduced pressure. The residue was treated with ammonium hydroxide (3 mL), stirred for 1 hour, then saturated aqueous NaHCO₃ solution (10 mL) was added. The mixture was extracted with dichloromethane (20 mL×3). The organic layers were combined, dried over anhydrous sodium sulfate, then filtrated, the filtrate was concentrated under reduced pressure. The residue was purified by silica column chromatography (petroleum ether:ethyl acetate=3:1) to give gray compound 75-a (0.68 g, yield: 88.8%). LC-MS (ESI): m/z=334 [M+H]⁺.

Preparation of Compound 75

At 0° C., trifluoroacetic anhydride (430 mg, 2.1 mmol) was added slowly to a solution of compound 75-a (680 mg, 2.1 mmol) and pyridine (320 mg, 4.2 mmol) in dichloromethane (10 mL). The mixture was warmed to room temperature, stirred for further 1 hour. Saturated aqueous NaHCO₃ solution (10 mL) was added, the mixture was extracted with dichloromethane (20 mL×3). The organic layers were combined, dried over anhydrous sodium sulfate, then filtrated, the filtrate was concentrated under reduced pressure. The residue was purified by silica column chromatography (petroleum ether:ethyl acetate=3:1) to give compound 75 (510 mg, yield: 77%). LC-MS (ESI): m/z=316 [M+H]⁺.

Preparation of Compound T-75

1-Methyl-4-aminopyrazole (37 mg, 0.38 mmol) and compound 75 (100 mg, 0.32 mmol) were dissolved in n-butanol (10 mL), p-toluene sulfonic acid monohydrate (72 mg, 0.38 mmol) was added. The mixture was heated to 108° C. and stirred for 3 hours, then cooled to room temperature, concentrated under reduced pressure to remove the solvent. The residue was treated with saturated aqueous NaHCO₃ solution (10 mL), extracted with dichloromethane (10 mL×3). The organic layers were combined, dried over anhydrous sodium sulfate, then filtrated, the filtrate was concentrated under reduced pressure. The residue was purified by preparation HPLC (mobile phase:water (10 mmol/mL ammonium bicarbonate), acetonitrile; gradient: 26%-78%) to give compound T-75 (32 mg, yield: 26.6%). LC-MS (ESI): m/z=377 [M+H]⁺.

¹H-NMR (400 MHz, CD₃OD) δ: 8.60 (s, 1H), 8.35 (s, 1H), 8.11 (d, J=5.6 Hz, 1H), 8.07 (s, 1H), 7.63 (s, 1H), 7.33 (d, J=5.6 Hz, 1H), 3.92 (s, 3H), 3.18 (s, 2H), 1.55 (t, J=5.6 Hz, 2H), 1.36 (t, J=5.6 Hz, 2H) ppm Example 76

2-(1-(4-(2-((1-Cyclopropyl-1H-pyrazol-4-yl)amino) thieno[3,2-d]pyrimidin-4-yl)-1H-pyrazol-1-yl)cyclopropyl)acetonitrile T-76

Synthetic Route:

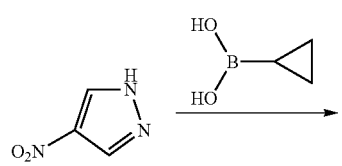

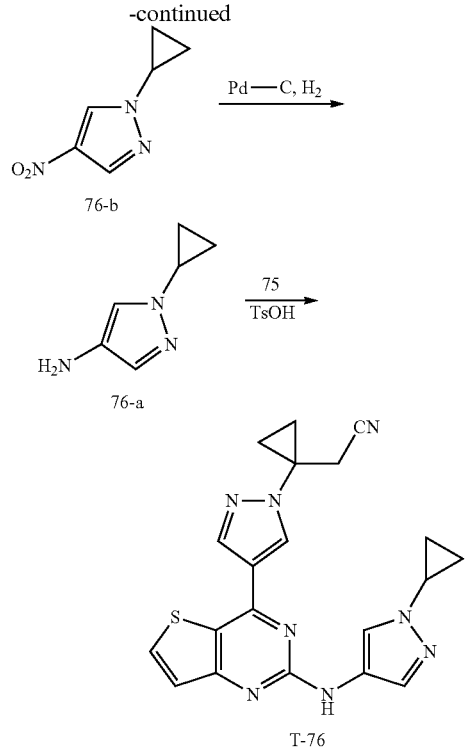

Preparation of Compound 76-b

Under nitrogen, 4-nitropyrazole (1.0 g, 8.45 mmol) was added to a solution of cyclopropyl boronic acid (1.45 g, 16.9 mmol), anhydrous CuSO₄ (1.55 g, 8.45 mmol), 4,4'-di-tert-butyl-2,2'-dipyridyl (2.26 g, 8.45 mmol) and Na₂CO₃ (1.87 g, 16.9 mmol) in 1,2-dichloroethane (30 mL). The mixture was stirred at 70° C. for 16 hours, then cooled to room temperature, concentrated under reduced pressure to remove there solvent, the residue was purified by silica column chromatography (petroleum ether:ethyl acetate=8:1) to give compound 76-b (740 mg, yield: 55%). LC-MS (ESI): m/z=154 [M+H]⁺.

Preparation of Compound 76-a

Under hydrogen (1 atm), to a solution of compound 76-b (100 mg, 0.65 mmol) in methanol (10 mL) was added 10% Pd—C (30 mg). The mixture was stirred at 25° C. for 1 hour, and then filtrated, the filtrate was treated with p-toluene sulfonic acid monohydrate (124 mg, 0.65 mmol). The mixture was concentrated under reduced pressure to give a p-tosylate of compound 76-a, which was used directly for the next step without purification. LC-MS (ESI): m/z=124 [M+H]⁺.

Preparation of Compound T-76

The p-tosylate of compound 76-a (94 mg, 0.3 mmol) obtained from previous step was added to a solution of compound 75 (100 mg, 0.32 mmol) in n-butanol (3 mL), the mixture was heated to 108° C. and stirred for 3 hours, then cooled to room temperature, concentrated under reduced pressure to remove the solvent. The residue was treated with saturated aqueous sodium bicarbonate solution (10 mL), extracted with dichloromethane (10 mL×3). The organic layers were combined, dried over anhydrous sodium sulfate, then filtrated, the filtrate was concentrated under reduced pressure. The residue was purified by silica column chromatography (petroleum ether:ethyl acetate=1:1) to give compound T-76 (23 mg, yield: 19%). LC-MS (ESI): m/z=403 [M+H]⁺.

$^1$H-NMR (400 MHz, CD$_3$OD) δ: 8.68 (s, 1H), 8.41 (s, 1H), 8.28 (d, J=5.6 Hz, 1H), 8.10 (s, 1H), 7.68 (s, 1H), 7.38 (d, J=5.6 Hz, 1H), 3.72 (m, 3H), 3.20 (s, 2H), 1.56 (t, J=5.6 Hz, 2H), 1.37 (t, J=5.6 Hz, 2H), 1.19 (m, 2H), 1.11 (m, 2H) ppm Example 77

2-(3-Fluoro-1-(4-(2-((1-methyl-1H-pyrazol-4-yl)amino)thieno[3,2-d]pyrimidin-4-yl)-1H-pyrazol-1-yl)cyclobutyl)acetonitrile T-77

Synthetic Route:

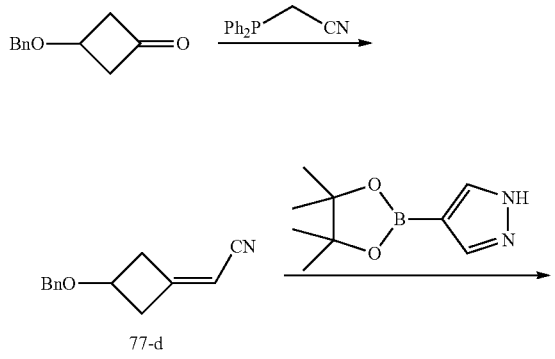

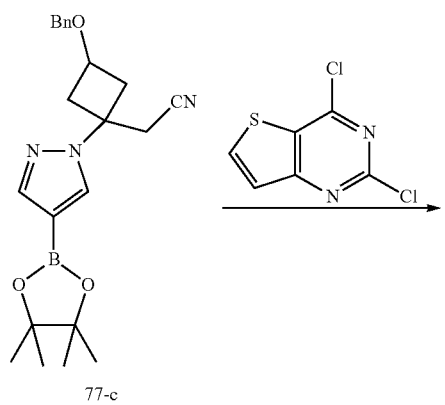

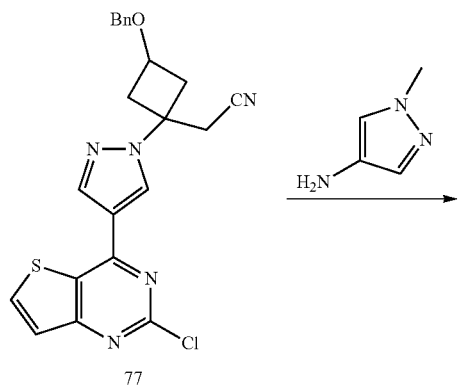

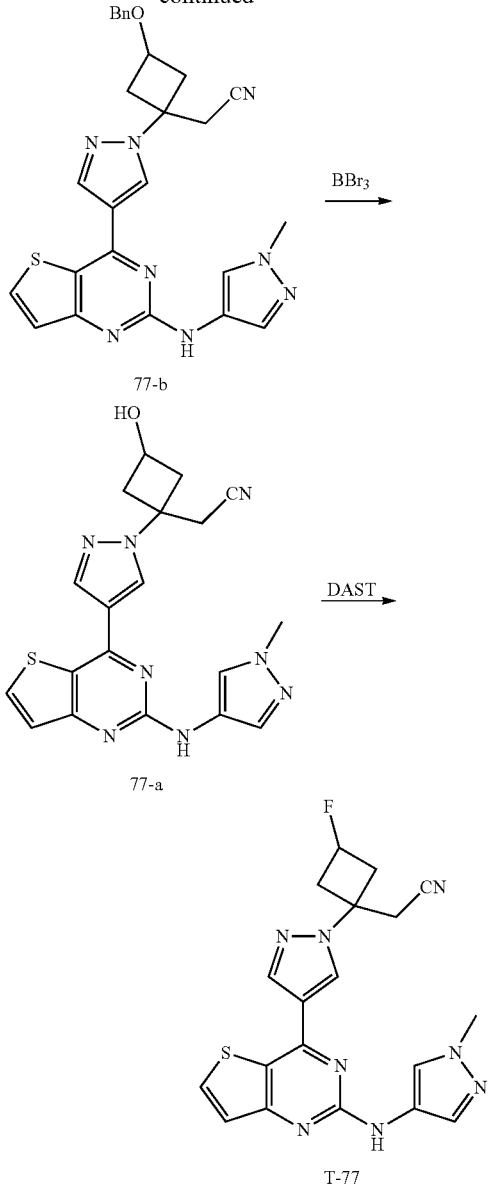

Preparation of Compound 77-d 3-(Benzyloxy)cyclobutanone (1.0 g, 5.68 mmol) was added to a solution of (cyanomethylene)triphenylphosphorane (2.6 g, 8.52 mmol) in toluene, the mixture was refluxed for 16 hours. After cooled to room temperature, the mixture was concentrated under reduced pressure, the residue was purified by silica column chromatography (petroleum ether:ethyl acetate=10:1) to give colorless oil 77-d (1.1 g, yield: 97%). LC-MS (ESI): m/z=200 [M+H]$^+$.

$^1$H-NMR (400 MHz, CDCl$_3$) δ: 7.25~7.38 (m, 5H), 5.22 (m, 1H), 4.47 (s, 2H), 4.17 (m, 1H), 3.05 (m, 1H), 2.96 (m, 1H), 2.91 (m, 2H) ppm Preparation of Compound 77-c Compound 77-d (1.0 g, 5 mmol) and 4-(4,4,5,5-tetramethyl-1,3,2-dioxaborolan-2-yl)-1H-pyrazole (1.16 g, 6 mmol) were dissolved in anhydrous acetonitrile (10 mL), 1,8-diazabicyclo[5.4.0]undec-7-ene (5 g, 33 mmol) was added. The mixture was stirred at 55° C. for 18 hours. The mixture was concentrated under reduced pressure, the residue was treated with water (50 mL), extracted with ethyl acetate (50 mL×2). The aqueous layer was treated with aqueous HCl solution (1 N) to adjust pH=5, extracted with ethyl acetate (50 mL×2). The organic layers were combined, washed with water (50 mL×3) and saturated brine (50 mL) in sequence, dried over anhydrous sodium sulfate, then filtrated, the filtrate was concentrated under reduced pressure to give light, yellow oil compound 77-c (1.15 g, yield: 58%), which was used directly for the next step without purification. LC-MS (ESI): m/z=394 [M+H]⁺.

Preparation of Compound 77

Under nitrogen, compound 77-c (1.1 g, 2.8 mmol), 2,4-dichlorotheino[3,2-d]pyrimidine (0.571 g, 8.51 mmol) and sodium carbonate (0.902 g, 8.51 mmol) were suspended in a component solvent of 1,4-dioxane (10 mL) and water (10 mL), Pd(dppf)Cl₂ (228 mg, 0.28 mmol) was added. The mixture was stirred at 80° C. for 16 hours, then concentrated under reduced pressure. The residue was treated with water (20 mL), extracted with dichloromethane (20 mL×3). The organic layers were combined, washed with water (20 mL×3) and saturated brine (20 mL) in sequence, dried over anhydrous sodium sulfate, then filtrated, the filtrate was concentrated under reduced pressure. The residue was purified by silica column chromatography (dichloromethane:methanol=100:1) to give light yellow solid 77 (1.05 g, yield: 94%). LC-MS (ESI): m/z=436 [M+H]⁺.

Preparation of Compound 77-b

1-Methyl-4-aminopyrazole (0.667 g, 6.87 mmol) and compound 77 (1.0 g, 2.29 mmol) were dissolved in n-butanol (20 mL), p-toluene sulfonic acid monohydrate (1.31 g, 6.87 mmol) was added. The mixture was heated to 100° C. and stirred for 18 hours, then cooled to room temperature, concentrated under reduced pressure to remove the solvent. The residue was treated with saturated aqueous NaHCO₃ solution (100 mL), extracted with dichloromethane (100 mL×3). The organic layers were combined, dried over anhydrous sodium sulfate, then filtrated, the filtrate was concentrated under reduced pressure. The residue was purified by preparation TLC (chromatographic solution:dichloromethane:methanol=100:1) to give light yellow solid 77-b (0.515 g, yield: 45%). LC-MS (ESI): m/z=497 [M+H]⁺.

Preparation of Compound 77-a

At −78° C., a solution of boron tribromide in dichloromethane (4 N, 2 mL) was added slowly dropwise to a solution of compound 77-b (510 mg, 1.03 mmol) in dichloromethane (20 mL), then warmed to room temperature, and stirred for 30 minutes. The mixture was added slowly to saturated aqueous NaHCO₃ solution (50 mL), extracted with dichloromethane (50 mL×2). The organic layers were combined, dried over anhydrous sodium sulfate, then filtrated, the filtrate was concentrated under reduced pressure. The residue was purified by silica column chromatography (dichloromethane:methanol=100:1) to give light yellow solid 77-a (98 mg, yield: 24%). LC-MS (ESI): m/z=407 [M+H]⁺.

Preparation of Compound T-77

At 0° C., DAST (360 mg, 1.62 mmol) was added slowly to a solution of compound 77-a (98 mg, 0.24 mmol) in dichloromethane (10 mL), the mixture was warmed to room temperature and stirred for further 30 minutes. The mixture was diluted with water (10 mL), adjusted to pH=10 with saturated aqueous NaHCO₃ solution, then extracted with dichloromethane (50 mL×2). The organic layers were combined, dried over anhydrous sodium sulfate, then filtrated, the filtrate was concentrated under reduced pressure. The residue was purified by preparation HPLC (mobile phase: water (0.05% trifluoroacetic acid), acetonitrile; gradient: 15%-50%) to give compound T-77 (7 mg, yield: 12%). LC-MS (ESI): m/z=409 [M+H]⁺.

¹H-NMR (400 MHz, CD₃OD) δ: 8.74 (d, J=0.4 Hz, 1H), 8.44 (d, J=6.0 Hz, 1H), 8.31 (d, J:=5.6 Hz, 1H), 8.04 (s, 1H), 7.68 (s, 1H), 7.38 (d, J=5.2 Hz, 1H), 5.13-5.34 (m, 1H), 3.91 (s, 3H), 3.44 (s, 2H), 3.37 (m, 2H), 2.88 (m, 2H) ppm Example 78

2-(3-(4-(2-((1-(2-Hydroxy-2-methylpropyl)-1H-pyrazol-4-yl)amino)thieno[3,2-d]pyrimidin-4-yl)-1H-pyrazol-1-yl)-1-(methylsulfonyl)azetidin-3-yl)acetonitrile T-78

Synthetic Route:

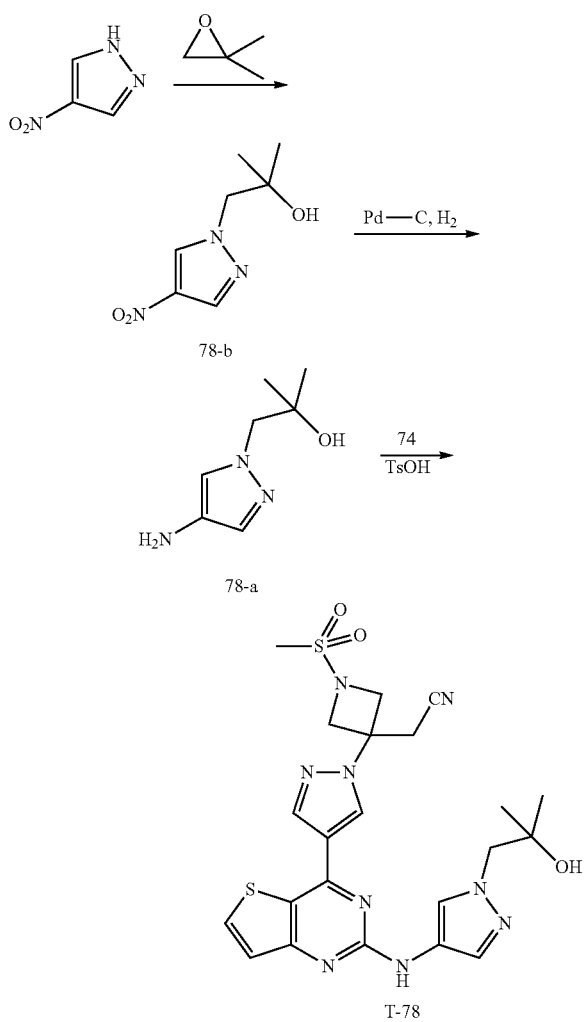

Preparation of Compound 78-b

4-Nitropyrazole (1.13 g, 10 mmol) was added to a solution of 2,2-dimethyloxirane (20 mL) and cesium carbonate (2 g, 6 mmol) in acetonitrile (65 mL), the mixture was heated to 80° C. and stirred for 12 hours. After cooled to room temperature, the mixture was treated with water (100 mL), extracted with ethyl acetate (100 mL×3). The organic layers were combined, dried over anhydrous sodium sulfate, then filtrated, the filtrate was concentrated under reduced pressure. The residue was purified by silica column chromatography (petroleum ether:ethyl acetate=1:1) to give compound 78-b (0.99 g, yield: 54%). LC-MS (ESI): m/z=186 [M+H]⁺.

Preparation of Compound 78-a

Under hydrogen (1 atm), to a solution of compound 78-b (99 mg, 5.4 mmol) in methanol (10 mL) was added 10% Pd—C (0.3 g). The mixture was stirred at 25° C. for 12 hours, and then filtrated, the filtrate was concentrated under reduced pressure to give compound 78-a (0.8 g, yield: 95%), which was used directly for the next step without purification. LC-MS (ESI): m/z=156 [M+H]$^+$.

Preparation of Compound T-78

Compound 78-a (116 mg, 0.75 mmol) and compound 74 (210 mg, 0.5 mmol) were dissolved in n-butanol (5 mL), p-toluene sulfonic acid monohydrate (140 mg, 0.75 mmol) was added. The mixture was heated to 100° C. and stirred for 6 hours, then cooled to room temperature. The mixture was concentrated under reduced pressure to remove the solvent, the residue was treated with saturated aqueous NaHCO$_3$ solution (10 mL), extracted with dichloromethane (10 mL×3). The organic layers were combined, dried over anhydrous sodium sulfate, then filtrated, the filtrate was concentrated under reduced pressure. The residue was purified by silica column chromatography (petroleum ether: ethyl acetate=1:1) to give compound T-78 (61 mg, yield: 23%). LC-MS (ESI): m/z=528 [M+H]$^+$.

$^1$H-NMR (400 MHz, CD$_3$OD) δ: 8.73 (s, 1H), 8.43 (s, 1H), 8.20 (s, 1H), 8.11 (d, J=5.6 Hz, 2H), 7.64 (s, 1H), 7.30 (d, J=5.6 Hz, 1H), 4.67 (d, J=9.6 Hz, 2H), 4.34 (d, J=9.6 Hz, 2H), 4.12 (s, 2H), 3.65 (s, 2H), 3.09 (s, 3H), 1.23 (s, 6H) ppm

Example 79

2-(3-(4-(2-((1-(1-Hydroxy-2-methylpropan-2-yl)-1H-pyrazol-4-yl)amino)thieno[3,2-d]pyrimidin-4-yl)-1H-pyrazol-1-yl)-1-(methylsulfonyl)azetidin-3-yl)acetonitrile T-79

Synthetic Route:

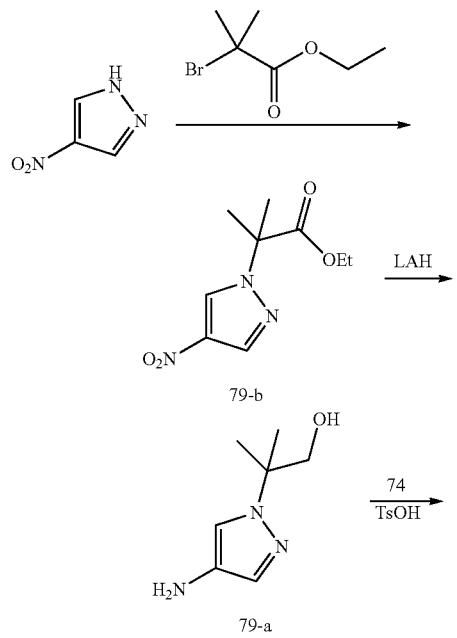

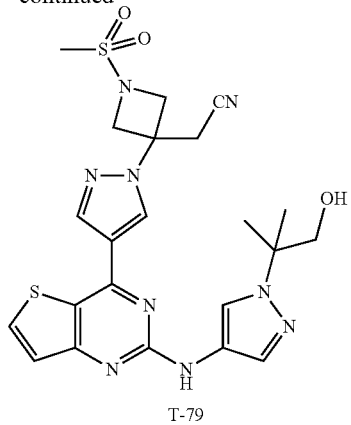

Preparation of Compound 79-b

4-Nitropyrazole (1.13 g, 10 mmol) was added to a solution of ethyl 2-bromo isobutyrate (3.88 g, 20 mmol) and cesium carbonate (6.5 g, 20 mmol) in DMF (50 mL), the mixture was heated to 80° C. and stirred for 4 hours. After cooled to room temperature, the mixture was treated with water (100 mL), extracted with ethyl acetate (100 mL×3). The organic layers were combined, dried over anhydrous sodium sulfate, then filtrated, the filtrate was concentrated under reduced pressure. The residue was purified by silica column chromatography (petroleum ether:ethyl acetate=3:1) to give compound 79-b (1.7 g, yield: 75%). LC-MS (ESI): m/z=228 [M+H]$^+$.

Preparation of Compound 79-a

At room temperature, a solution of compound 79-b (1.15 g, 5 mmol) in anhydrous 11-IF (30 mL) was added slowly dropwise to a solution of LiAlH$_4$ in THF (1 N, 15 mL, 15 mmol). The mixture was stirred for 2 hours, then treated portionwise with NaSO$_4$.10H$_2$O (3 g). The mixture was filtrated, the filtrate was concentrated under reduced pressure to give compound 79-a (0.6 g, yield: 77%), which was used directly for the next step without purification. LC-MS (ESI): m/z=156 [M+H]$^+$.

Preparation of Compound T-79

Compound 79-a (116 mg, 0.75 mmol) and compound 74 (210 mg, 0.5 mmol) were dissolved in n-butanol (5 mL), p-toluene sulfonic acid monohydrate (140 mg, 0.75 mmol) was added. The mixture was heated to 110° C. and stirred for 6 hours, then cooled to room temperature, concentrated under reduced pressure to remove the solvent, the residue was treated with saturated aqueous NaHCO$_3$ solution (10 mL), extracted with dichloromethane (10 mL×3). The organic layers were combined, dried over anhydrous sodium sulfate, then filtrated, the filtrate was concentrated under reduced pressure. The residue was purified by silica column chromatography (petroleum ether:ethyl acetate=1:1) to give compound T-79 (76 mg, yield: 28%). LC-MS (ESI): m/z=528 [M+H]$^+$.

$^1$H-NMR (400 MHz, CD$_3$OD) δ: 8.75 (s, 1H), 8.45 (s, 1H), 8.21 (s, 1H), 8.13 (d, J=5.6 Hz, 2H), 7.71 (s, 1H), 7.32 (d, J=5.6 Hz, 1H), 4.67 (d, J=9.6 Hz, 2H), 4.31 (d, J=9.6 Hz, 2H), 3.79 (s, 2H), 3.65 (s, 2H), 3.09 (s, 3H), 1.62 (s, 6H) ppm

Example 80

(R)-2-(3-(4-(2-((1-(2-Hydroxypropyl)-1H-pyrazol-4-yl)amino)thieno[3,2-d]pyrimidin-4-yl)-1H-pyrazol-1-yl)oxetan-3-yl)acetonitrile T-80

Synthetic Route:

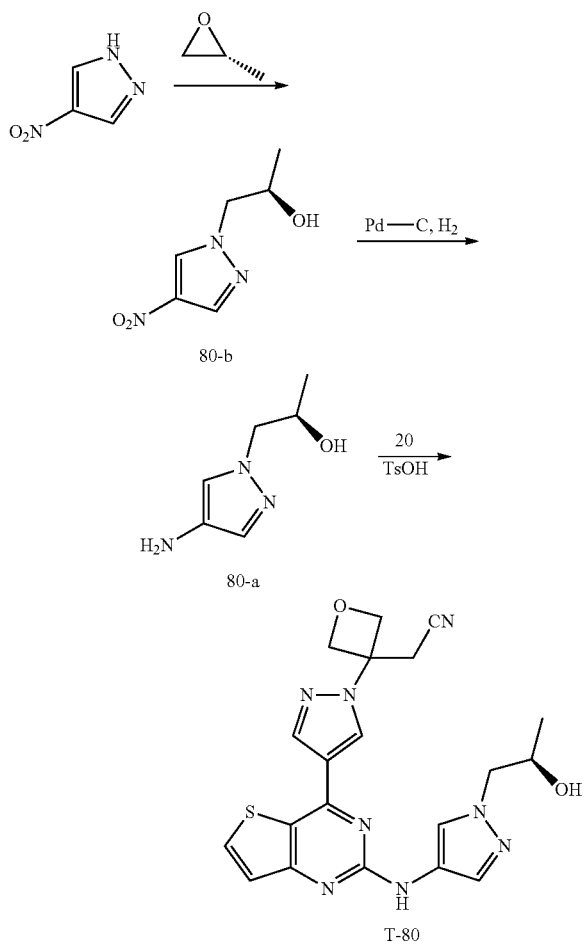

Preparation of Compound 80-b

4-Nitropyrazole (2.5 g, 22.12 mmol) was added to a mixture of (R)-epoxypropane (30 mL) and cesium carbonate (2 g, 6 mmol), the mixture was stirred at room temperature for 18 hours. Water (50 mL) was added, the mixture was extracted with ethyl acetate (50 mL×3). The organic layers were combined, dried over anhydrous sodium sulfate, then filtered, the filtrate was concentrated under reduced pressure to give light yellow oil 80-b (2.5 g, yield: 66%), which was used directly for the next step without purification. LC-MS (ESI): m/z=172 [M+H]$^+$.

Preparation of Compound 80-a

Under hydrogen (1 atm), to a solution of compound 80-b (1.0 g, 5.85 mmol) in ethanol (25 mL) was added 10% Pd—C (0.2 g). The mixture was stirred at 25° C. for 18 hours, and then filtered, the filtrate was concentrated to give red brown oil 80-a (0.78 g, yield: 95%), which was used directly for the next step without purification.

Preparation of Compound T-80

Compound 80-a (179 mg, 1.27 mmol) and compound 20 (140 mg, 0.43 mmol) were dissolved in n-butanol (5 mL), p-toluene sulfonic acid monohydrate (242 mg, 1.27 mmol) was added. The mixture was heated to 110° C. and stirred for 16 hours, then cooled to room temperature, concentrated under reduced pressure to remove the solvent, the residue was treated with saturated aqueous NaHCO$_3$ solution (100 mL), extracted with dichloromethane (100 mL×3). The organic layers were combined, dried over anhydrous sodium sulfate, then filtered, the filtrate was concentrated under reduced pressure. The residue was purified by preparation HPLC (mobile phase:water (0.05% trifluoroacetic acid), acetonitrile; gradient: 20%-55%) to give light yellow solid T-80 (25 mg, yield: 14%). LC-MS (ESI): m/z=437 [M+H]$^+$.

$^1$H-NMR (400 MHz, CDCl$_3$) δ: 8.46 (s, 1H), 8.36 (s, 1H), 8.06 (s, 1H), 7.88 (d, J=5.6 Hz, 1H), 7.56 (s, 1H), 7.32 (d, J=5.6 Hz, 1H), 7.04 (s, 1H), 5.19 (d, J=7.6 Hz, 2H), 4.87 (d, J=7.6 Hz, 2H), 4.24 (br, 1H), 4.17-4.21 (m, 1H), 3.97-4.03 (m, 1H), 3.56 (s, 1H), 3.45 (s, 2H), 1.25 (d, J=6.4 Hz, 3H) ppm

Example 81

(S)-2-(3-(4-(2-((1-(2-Hydroxypropyl)-1H-pyrazol-4-yl)amino)thieno[3,2-d]pyrimidin-4-yl)-1H-pyrazol-1-yl)oxetan-3-yl)acetonitrile T-81

Synthetic Route:

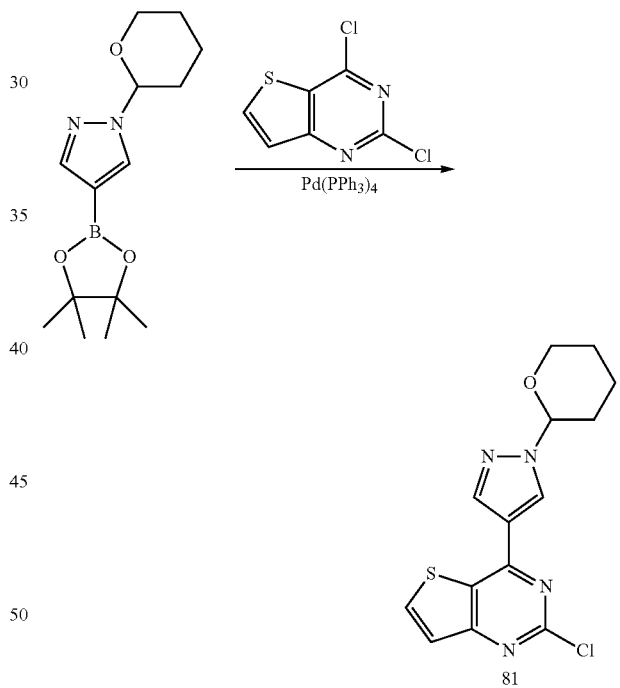

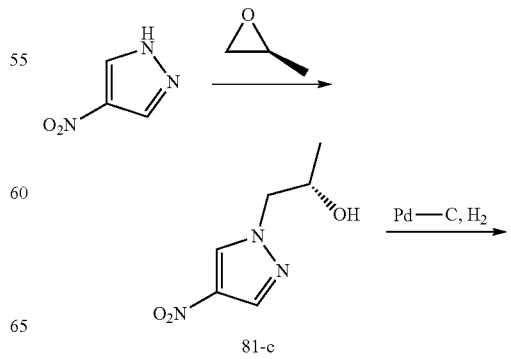

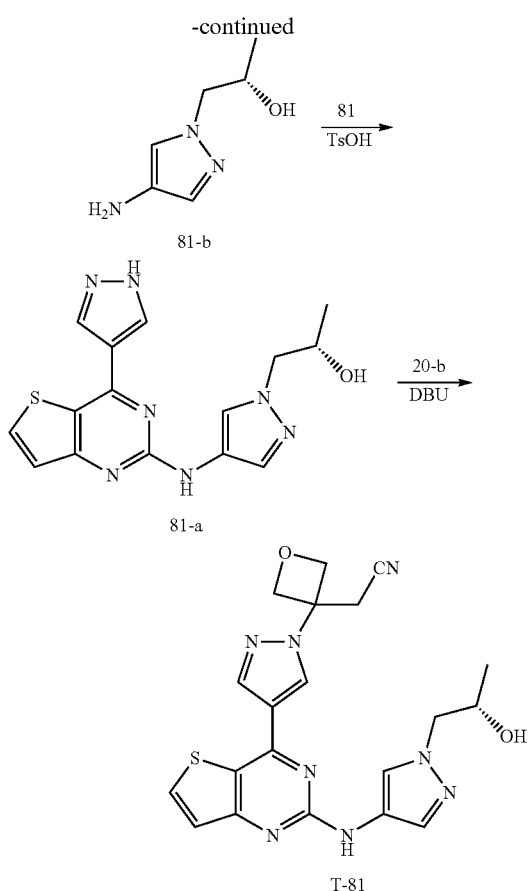

Preparation of Compound 81

Under nitrogen, Pd(PPh₃)₄ (0.56 g, 0.5 mmol) was added to a suspension of 1-(tetrahydro-2H-pyran-2-yl)-4-(4,4,5,5-tetramethyl-1,3,2-dioxaborolan-2-yl)-1H-pyrazole (2.8 g, 10 mmol), 2,4-dichlorotheino[3,2-d]pyrimidine (2.05 g, 10 mmol) and potassium carbonate (2.76 g, 20 mmol) in 1,4-dioxane (30 mL). The mixture was stirred at 80° C. for 4 hours, then cooled to room temperature. The mixture was concentrated under reduced pressure, the residue was treated with water (100 mL), extracted with ethyl acetate (100 mL×3). The organic layers were combined, dried over anhydrous sodium sulfate, then filtrated, the filtrate was concentrated under reduced pressure. The residue was purified by silica column chromatography (petroleum ether:ethyl acetate=3:1 to 2:1) to give light yellow solid 81 (2.8 g, yield: 87.5%). LC-MS (ESI): m/z=321 [M+H]⁺.

Preparation of Compound 81-c

4-Nitropyrazole (1.0 g, 8.85 mmol) was added to a mixture of (S)-epoxypropane (3 mL) and cesium carbonate (1.73 g, 5.31 mmol), the mixture was stirred at room temperature for 18 hours. Water (50 mL) was added, the mixture was extracted with ethyl acetate (50 mL×3). The organic layers were combined, dried over anhydrous sodium sulfate, then filtrated, the filtrate was concentrated under reduced pressure to give light yellow oil 81-c (1 g, yield: 66%), which was used directly for the next step without purification. LC-MS (ESI): m/z=172 [M+H]⁺.

Preparation of Compound 81-b

Under hydrogen (1 atm), to a solution of compound 81-c (1.0 g, 5.85 mmol) in ethanol (25 mL) was added 10% Pd—C (0.2 g). The mixture was stirred at 25° C. for 18 hours, and then filtrated, the filtrate was concentrated under reduced pressure to give red brown oil 81-b (0.7 g, yield: 85%), which was used directly for the next step without purification.

Preparation of Compound 81-a

Compound 81-b (397 mg, 2.82 mmol) and compound 81 (300 mg, 0.94 mmol) were dissolved in n-butanol (5 mL), p-toluene sulfonic acid monohydrate (555 mg, 2.82 mmol) was added. The mixture was heated to 110° C. and stirred for 16 hours, then cooled to room temperature. The mixture was concentrated under reduced pressure, the residue was treated with saturated aqueous NaHCO₃ solution (50 mL), extracted with dichloromethane (50 mL×3). The organic layers were combined, dried over anhydrous sodium sulfate, then filtrated, the filtrate was concentrated under reduced pressure. The residue was purified by silica column chromatography (dichloromethane:methanol=100:1) to give yellow solid 81-a (67 mg, yield: 21%). LC-MS (ESI): m/z=341 [M+H]⁺.

Preparation of Compound T-81

Compound 81-a (67 mg, 0.29 mmol) and compound 20-b (31 mg, 0.32 mmol) were dissolved in anhydrous acetonitrile (1 mL), DBU (0.1 g, 0.6 mmol) was added, the mixture was stirred at room temperature for 1 hour. After the mixture was concentrated under reduced pressure, the residue was treated with water (50 mL), extracted with dichloromethane (50 mL×2). The organic layers were combined, dried over anhydrous sodium sulfate, then filtrated, the filtrate was concentrated under reduced pressure. The residue was purified by preparation TLC (chromatographic solution:ethyl acetate) to give light yellow solid T-81 (21 mg, yield: 26%). LC-MS (ESI): m/z=437 [M+H]⁺.

¹H-NMR (400 MHz, CDCl₃) δ: 8.44 (s, 1H), 8.36 (s, 1H), 8.06 (s, 1H), 7.87 (d, J=5.6 Hz, 1H), 7.54 (d, J=0.4 Hz, 1H), 7.31 (d, J=5.6 Hz, 1H), 7.15 (s, 1H), 5.19 (d, J=7.6 Hz, 2H), 4.87 (d, J=7.6 Hz, 2H), 4.16-4.21 (m, 2H), 3.97-4.02 (m, 2H), 3.55 (br, 1H), 3.45 (s, 3H), 1.26 (d, J=6.4 Hz, 3H) ppm Example 82

(R)-2-(3-(4-(2-((1-(1-Hydroxypropan-2-yl)-1H-pyrazol-4-yl)amino)thieno[3,2-d]pyrimidin-4-yl)-1H-pyrazol-1-yl)oxetan-3-yl)acetonitrile T-82

Synthetic Route:

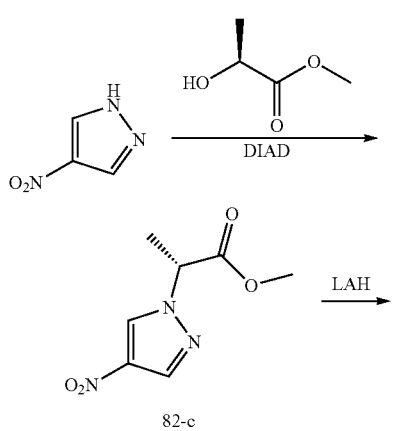

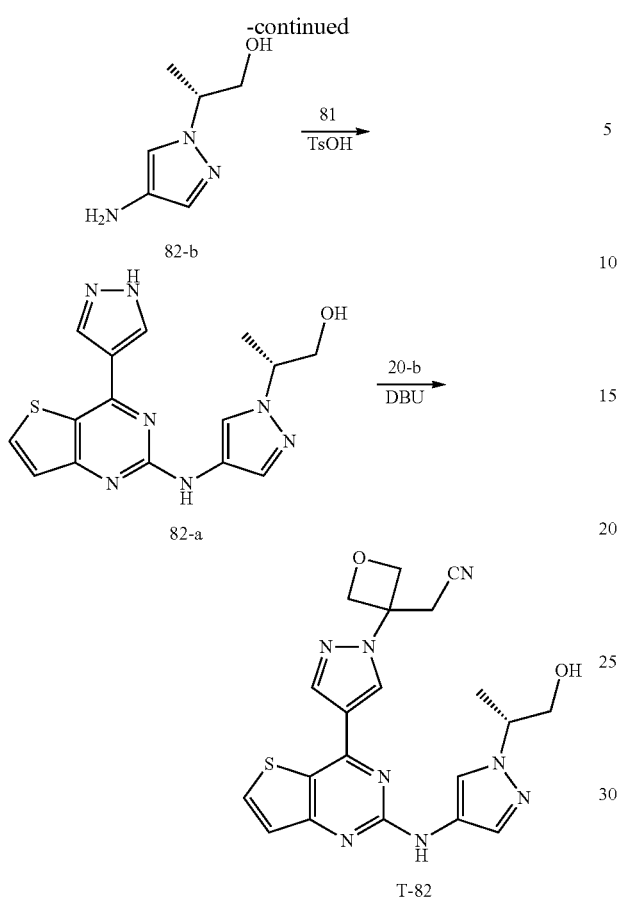

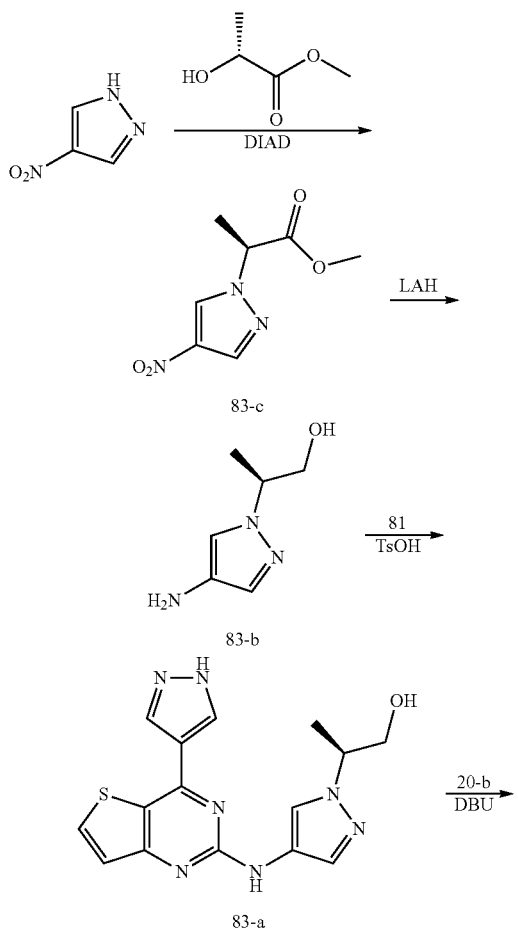

Preparation of Compound T-82

Compound 82-a (38 mg, 0.106 mmol) and compound 20-b (11 mg, 0.106 mmol) were dissolved in anhydrous acetonitrile (3 mL), DBU (100 mg, 0.6 mmol) was added. The mixture was stirred at room temperature for 1 hour, then concentrated under reduced pressure. The residue was treated with water (50 mL), extracted with dichloromethane (50 mL×2). The organic layers were combined, dried over anhydrous sodium sulfate, then filtrated, the filtrate was concentrated under reduced pressure. The residue was purified by preparation HPLC (mobile phase:water (10 mmol/mL ammonium bicarbonate), acetonitrile; gradient: 15%-45%) to give light yellow solid T-82 (13 mg, yield: 28%). LC-MS (ESI): m/z=437 [M+H]$^+$.

$^1$H-NMR (400 MHz, CD$_3$OD) δ: 8.72 (s, 1H), 8.43 (s, 1H), 8.16 (s, 1H), 8.13 (d, J=5.6 Hz, 1H), 7.69 (s, 1H), 7.32 (d, J=5.6 Hz, 1H), 5.24 (d, J=8.4 Hz, 2H), 4.95 (d, J=8.4 Hz, 2H), 4.43 (m, 1H), 3.86 (m, 2H), 3.64 (s, 2H), 1.53 (d, J=6.8 Hz, 3H) ppm Example 83

(S)-2-(3-(4-(2-((1-(1-Hydroxypropan-2-yl)-1H-pyrazol-4-yl)amino)thieno[3,2-d]pyrimidin-4-yl)-1H-pyrazol-1-yl)oxetan-3-yl)acetonitrile T-83

Synthetic Route:

Preparation of Compound 82-c

At 25° C., DIAD (10.8 g, 53.1 mmol) was added slowly to a solution of 4-nitropyrazole (5 g, 44.2 mmol), methyl L-lactate (5.1 g, 48.6 mmol) and PPh$_3$ (13.9 g, 53.1 mmol) in anhydrous THF (100 mL). After stirred for 3 hours, the mixture was concentrated under reduced pressure, the residue was purified by silica column chromatography (petroleum ether:ethyl acetate=10:1) to give compound 82-c (6.6 g, yield: 74%). LC-MS (ESI): m/z=200 [M+H]$^+$.

Preparation of Compound 82-b

At room temperature, compound 82-c (2.0 g, 10 mmol) was added slowly dropwise to a solution of LiAlH$_4$ in THF (1 N, 26.3 mL, 26.3 mmol). The mixture was stirred for 2 hours, then treated portionwise with Na$_2$SO$_4$.10H$_2$O (3 g). The mixture was filtrated, the filtrate was concentrated under reduced pressure to give compound 82-b (1.1 g, yield: 78%), which was used directly for the next step without purification. LC-MS (ESI): m/z=142 [M+H]$^+$.

Preparation of Compound 82-a

Compound 82-b (140 mg, 1 mmol) and compound 81 (320 mg, 1 mmol) were dissolved in n-butanol (5 mL), p-toluene sulfonic acid monohydrate (190 mg, 1 mmol) was added. The mixture was heated to 110° C. and stirred for 6 hours, then cooled to room temperature, concentrated under reduced pressure to remove the solvent. The residue was treated with saturated aqueous NaHCO$_3$ solution (10 mL), extracted with dichloromethane (10 mL×3). The organic layers were combined, dried over anhydrous sodium sulfate, then filtrated, the filtrate was concentrated under reduced pressure. The residue was purified by silica column chromatography (petroleum ether:ethyl acetate=1:1) to give yellow solid 82-a (38 mg, yield: 10.6%). LC-MS (ESI): m/z=342 [M+H]$^+$.

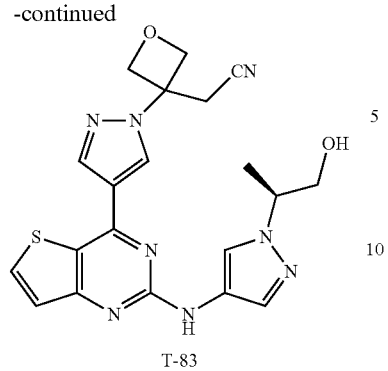

T-83

Preparation of Compound 83-c

At 25° C., DIAD (10.8 g, 53.1 mmol) was added slowly to a solution of 4-nitropyrazole (5 g, 44.2 mmol), methyl D-lactate (5.1 g, 48.6 mmol) and PPh$_3$ (13.9 g, 53.1 mmol) in anhydrous THF (100 mL). After stirred for 3 hours, the mixture was concentrated under reduced pressure, the residue was purified by silica column chromatography (petroleum ether:ethyl acetate=10:1) to give compound 83-c (6.2 g, yield: 70%). LC-MS (ESI): m/z=200 [M+H]$^+$.

Preparation of Compound 83-b

At room temperature, compound 83-c (2.0 g, 10 mmol) was added slowly to a solution of LiAlH$_4$ in THF (1 N, 26.3 mL, 26.3 mmol). The mixture was stirred for 2 hours, then treated portionwise with Na$_2$SO$_4$.10H$_2$O (3 g). The mixture was filtered, the filtrate was concentrated under reduced pressure to give compound 83-b (1.0 g, yield: 71%), which was used directly for the next step without purification. LC-MS (ESI): m/z=142 [M+H]$^+$.

Preparation of Compound 83-a

Compound 83-b (140 mg, 1 mmol) and compound 81 (320 mg, 1 mmol) were dissolved in n-butanol (5 mL), p-toluene sulfonic acid monohydrate (190 mg, 1 mmol) was added. The mixture was heated to 110° C. and stirred for 6 hours, then cooled to room temperature, concentrated under reduced pressure to remove the solvent. The residue was treated with saturated aqueous NaHCO$_3$ solution (10 mL), extracted with dichloromethane (10 mL×3). The organic layers were combined, dried over anhydrous sodium sulfate, then filtrated, the filtrate was concentrated under reduced pressure. The residue was purified by silica column chromatography (petroleum ether:ethyl acetate=1:1) to give yellow solid 83-a (76 mg, yield: 22.3%). LC-MS (ESI): m/z=342 [M+H]$^+$.

Preparation of Compound T-83

Compound 83-a (76 mg, 0.223 mmol) and compound 20-b (21 mg, 0.223 mmol) were dissolved in anhydrous acetonitrile (5 mL), DBU (100 mg, 0.6 mmol) was added. The mixture was stirred at room temperature for 1 hour, then concentrated under reduced pressure. The residue was treated with water (50 mL), extracted with dichloromethane (50 mL×2). The organic layers were combined, dried over anhydrous sodium sulfate, then filtrated, the filtrate was concentrated under reduced pressure. The residue was purified by preparation TLC (chromatographic solution:ethyl acetate) to give yellow solid T-83 (56 mg, yield: 57.6%). LC-MS (ESI): m/z=437 [M+H]$^+$.

$^1$H-NMR (400 MHz, CD$_3$OD) δ: 8.72 (s, 1H), 8.43 (s, 1H), 8.16 (s, 1H), 8.13 (d, J=5.6 Hz, 1H), 7.69 (s, 1H), 7.33 (d, J=5.6 Hz, 1H), 5.24 (d, J=7.2 Hz, 2H), 4.95 (d, J=7.2 Hz, 2H), 4.44 (m, 1H), 3.33 (m, 2H), 1.55 (d, J=6.8 Hz, 3H) ppm

Example 84

(R)-2-(3-(4-(2-((1-(1-Hydroxypropan-2-yl)-1H-pyrazol-4-yl)amino)thieno[3,2-d]pyrimidin-4-yl)-1H-pyrazol-1-yl)-1-(methylsulfonyl)azetidin-3-yl)acetonitrile T-84

Synthetic Route:

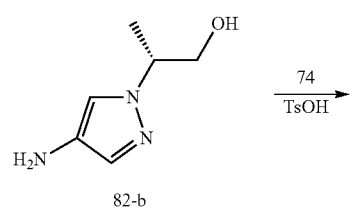

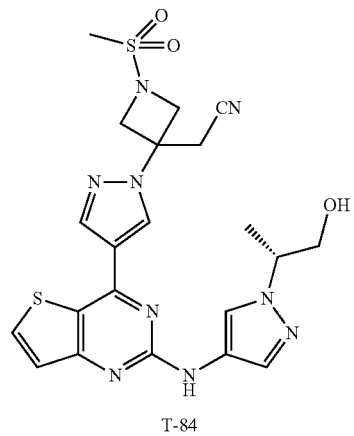

T-84

Preparation of Compound T-84

Compound 74 (210 mg, 0.5 mmol) and compound 82-b (70 mg, 0.5 mmol) were dissolved in n-butanol (5 mL), p-toluene sulfonic acid monohydrate (100 mg, 0.5 mmol) was added. The mixture was heated to 110° C. and stirred for 6 hours, then cooled to room temperature, concentrated under reduced pressure to remove the solvent. The residue was treated with saturated aqueous NaHCO$_3$ solution (10 mL), extracted with dichloromethane (10 mL×3). The organic layers were combined, dried over anhydrous sodium sulfate, then filtrated, the filtrate was concentrated under reduced pressure. The residue was purified by silica column chromatography (petroleum ether:ethyl acetate=1:1) to give compound T-84 (100 mg, yield: 38%). LC-MS (ESI): m/z=514 [M+H]$^+$.

$^1$H-NMR (400 MHz, CD$_3$OD) δ: 8.83 (s, 1H), 8.50 (s, 1H), 8.27 (d, J=5.6 Hz, 2H), 8.15 (s, 1H), 7.72 (s, 1H), 7.37 (d, J=5.6 Hz, 2H), 4.68 (d, J=9.6 Hz, 2H), 4.46 (m, 1H), 4.37 (d, J=9.6 Hz, 2H), 3.87 (m, 1H), 3.66 (s, 2H), 3.09 (s, 3H), 1.54 (d, J=6.8 Hz, 3H) ppm

Example 85

(S)-2-(3-(4-(2-((1-(1-Hydroxypropan-2-yl)-1H-pyrazol-4-yl)amino)thieno[3,2-d]pyrimidin-4-yl)-1H-pyrazol-1-yl)-1-(methylsulfonyl)azetidin-3-yl)acetonitrile T-85

Synthetic Route:

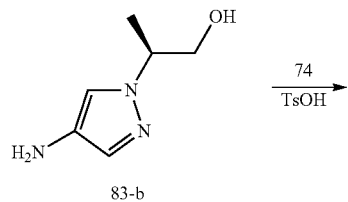

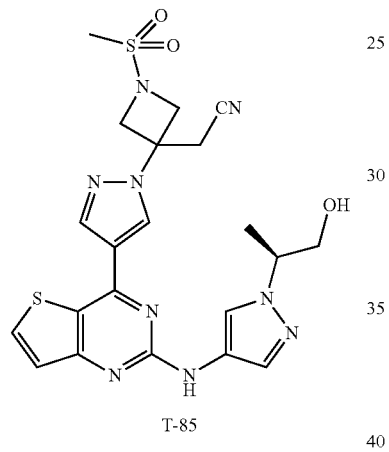

Preparation of Compound T-85

Compound 74 (210 mg, 0.5 mmol) and compound 83-b (70 mg, 0.5 mmol) were dissolved in n-butanol (5 mL), p-toluene sulfonic acid monohydrate (100 mg, 0.5 mmol) was added. The mixture was heated to 110° C. and stirred for 6 hours, then cooled to room temperature, concentrated under reduced pressure to remove the solvent. The residue was treated with saturated aqueous NaHCO$_3$ solution (10 mL), extracted with dichloromethane (10 mL×3). The organic layers were combined, dried over anhydrous sodium sulfate, then filtrated, the filtrate was concentrated under reduced pressure. The residue was purified by preparation HPLC (mobile phase:water (0.05% trifluoroacetic acid), acetonitrile; gradient: 15%-65%) to give compound T-85 (80 mg, yield: 32%). LC-MS (ESI): m/z=514 [M+H]$^+$.

$^1$H-NMR (400 MHz, CD$_3$OD) δ: 8.82 (s, 1H), 8.49 (s, 1H), 8.26 (d, J=5.6 Hz, 2H), 8.15 (s, 1H), 7.71 (s, 1H), 7.37 (d, J=5.6 Hz, 2H), 4.68 (d, J=9.6 Hz, 2H), 4.47 (m, 1H), 4.36 (d, J=9.6 Hz, 2H), 3.88 (m, 1H), 3.66 (s, 2H), 3.09 (s, 3H), 1.54 (d, J=6.8 Hz, 3H) ppm

Example 86

(R)-2-(3-(4-(2-((1-(2-Hydroxypropyl)-1H-pyrazol-4-yl)amino)thieno[3,2-d]pyrimidin-4-yl)-1H-pyrazol-1-yl)-1-(methylsulfonyl)azetidin-3-yl)acetonitrile T-86

Synthetic Route:

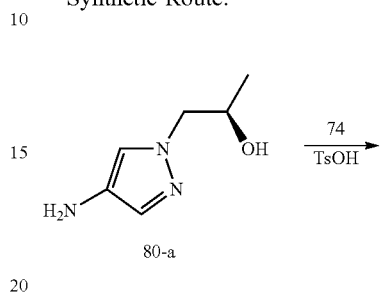

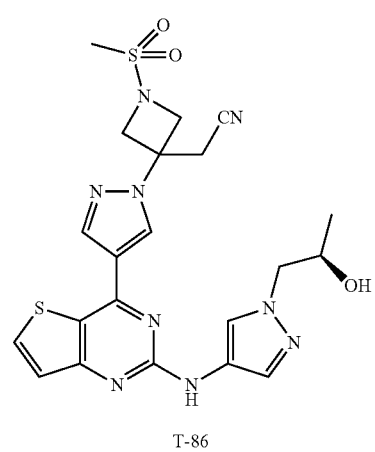

Preparation of Compound T-86

Compound 80-a (311 mg, 2.21 mmol) and compound 74 (300 mg, 0.74 mmol) were dissolved in n-butanol (10 mL), p-toluene sulfonic acid monohydrate (349 mg, 1.84 mmol) was added. The mixture was heated to 110° C. and stirred for 16 hours, then cooled to room temperature, concentrated under reduced pressure to remove the solvent. The residue was treated with saturated aqueous NaHCO$_3$ solution (50 mL), extracted with dichloromethane (50 mL×3). The organic layers were combined, dried over anhydrous sodium sulfate, then filtrated, the filtrate was concentrated under reduced pressure. The residue was purified by silica column chromatography (ethyl acetate) to give yellow solid T-86 (115 mg, yield: 31%). LC-MS (ESI): m/z=514 [M+H]$^+$.

$^1$H-NMR (400 MHz, CDCl$_3$) δ: 8.47 (d, J=0.4 Hz, 1H), 8.36 (s, 1H), 8.04 (s, 1H), 7.88 (d, J=5.6 Hz, 1H), 7.57 (d, J=0.4 Hz, 1H), 7.31 (d, J=5.6 Hz, 1H), 6.96 (s, 1H), 4.61 (d, J=7.6 Hz, 2H), 4.26 (d, J=7.6 Hz, 2H), 4.03-4.18 (m, 3H), 3.43 (s, 2H), 3.02 (s, 3H), 1.26 (d, J=6.4 Hz, 3H) ppm

Example 87

(S)-2-(3-(4-(2-((1-(2-Hydroxypropyl)-1H-pyrazol-4-yl)amino)thieno[3,2-d]pyrimidin-4-yl)-1H-pyrazol-1-yl)-1-(methylsulfonyl)azetidin-3-yl)acetonitrile T-87

Synthetic Route:

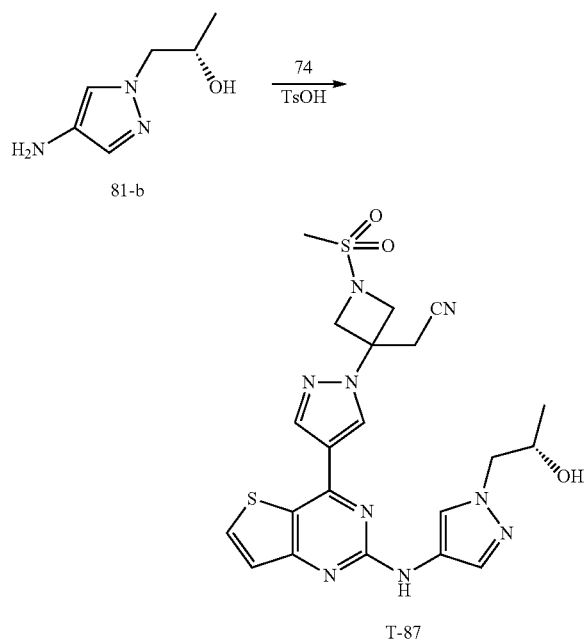

T-87

Preparation of Compound T-87

Compound 81-b (311 mg, 2.21 mmol) and compound 74 (300 mg, 0.74 mmol) were dissolved in n-butanol (10 mL), p-toluene sulfonic acid monohydrate (349 mg, 1.84 mmol) was added. The mixture was heated to 110° C. and stirred for 16 hours, then cooled to room temperature, concentrated under reduced pressure to remove the solvent. The residue was treated with saturated aqueous NaHCO$_3$ solution (50 mL), extracted with dichloromethane (50 mL×3). The organic layers were combined, dried over anhydrous sodium sulfate, then filtrated, the filtrate was concentrated under reduced pressure. The residue was purified by silica column chromatography (ethyl acetate) to give yellow oil T-87 (65 mg, yield: 17%). LC-MS (ESI): m/z=514 [M+H]$^+$.

$^1$H-NMR (400 MHz, CDCl$_3$) δ: 8.47 (d, J=0.4 Hz, 1H), 8.36 (s, 1H), 8.04 (s, 1H), 7.88 (d, J=5.6 Hz, 1H), 7.57 (d, J=0.4 Hz, 1H), 7.31 (d, J=5.6 Hz, 1H), 6.96 (s, 1H), 4.61 (d, J=7.6 Hz, 2H), 4.26 (d, J=7.6 Hz, 2H), 4.03-4.18 (m, 3H), 3.43 (s, 2H), 3.02 (s, 3H), 1.26 (d, J=6.4 Hz, 3H) ppm

Effect Experiment

Biological effect: intracytoplasmic JAK 1,2,3 enzymatic inhibitory activity IC$_{50}$ assay Experimental Steps:

1. Buffer Preparation

JAK1 buffer solution: 25 mM HEPES, pH 7.5, 0.01% Brij-35, 0.01 M Triton. JAK2,3 buffer solution: 50 mM HEPES, pH 7.5, 0.0015% Brij-35.

2. Compound was formulated in 100% DMSO in a concentration gradient, deposited to a 384-well plate with a final concentration of 2% of DMSO.

3. JAK2,3 enzymes were diluted to having an optimum concentration with the following buffer: 50 mM HEPES, pH 7.5, 0.0015% Brij-35, 2 mM DTT. JAK1 enzyme was diluted to having an optimum concentration with the following buffer: 25 mM HEPES, pH 7.5, 0.01% Brij-35, 2 mM DTT, 0.01M Triton. Then they were transferred to a 384-well plate and incubated with the compound for a certain time.

4. JAK2,3 substrate was diluted to having an optimum concentration with the following buffer: 50 mM HEPES, pH 7.5, 0.0015% Brij-35, 10 mM MgCl$_2$, Km adenosine triphosphate. JAK1 substrate was diluted to having an optimum concentration with the following buffer: 25 mM HEPES, pH 7.5, 0.01% Brij-35, 10 mM MgCl$_2$, 0.01 M Triton. Km adenosine triphosphate was added into 384-well plates to initiate reactions, and the reaction were carried out at 28° C. for 1 hour.

5. Read the conversion rate by Caliper Reader, and the inhibition rate are calculated according to the average of two tests.

Results

The biological activity for the compounds of the present invention was test according to the method described above, the results are listed below (table 1):

TABLE 1

The results for JAK 1, 2, 3 enzymatic inhibitory activity assay of the compounds in the present invetion

| Compound | JAK 1 | JAK 2 | JAK 3 |
|---|---|---|---|
| T-01 | n.d. | D | D |
| T-02 | n.d. | B | D |
| T-03 | n.d. | A | D |
| T-04 | n.d. | A | D |
| T-05 | B | A | B |
| T-06 | n.d. | D | D |
| T-07 | A | A | B |
| T-08 | n.d. | A | B |
| T-09 | B | A | B |
| T-10 | A | A | B |
| T-11 | B | A | D |
| T-12 | A | A | B |
| T-13 | C | B | C |
| T-14 | C | A | D |
| T-15 | A | A | B |
| T-16 | D | D | D |
| T-17 | D | D | D |
| T-18 | B | A | C |
| T-19 | B | A | B |
| T-20 | B | A | C |
| T-21 | B | A | B |
| T-22 | D | A | D |
| T-23 | D | D | D |
| T-24 | n.d. | A | D |
| T-25 | A | A | B |
| T-26 | A | A | B |
| T-27 | n.d. | D | D |
| T-28 | D | D | D |
| T-29 | B | A | D |
| T-30 | B | A | B |
| T-31 | A | A | B |
| T-32 | A | A | A |
| T-33 | A | A | B |
| T-34 | B | A | B |
| T-35 | A | A | B |
| T-36 | B | A | A |
| T-37 | A | A | A |
| T-38 | A | A | A |
| T-39 | B | A | A |
| T-40 | A | A | A |
| T-41 | A | A | A |
| T-42 | C | B | D |
| T-43 | B | A | B |
| T-44 | B | A | B |

TABLE 1-continued

The results for JAK 1, 2, 3 enzymatic inhibitory activity assay of the compounds in the present invetion

| Compound | JAK 1 | JAK 2 | JAK 3 |
|---|---|---|---|
| T-45 | A | A | B |
| T-46 | B | A | C |
| T-47 | C | C | D |
| T-48 | D | B | D |
| T-49 | C | A | C |
| T-50 | C | A | C |
| T-51 | A | A | A |
| T-52 | A | A | B |
| T-53 | B | A | A |
| T-54 | B | A | B |
| T-55 | D | D | D |
| T-56 | D | D | D |
| T-57 | B | A | B |
| T-58 | A | A | B |
| T-59 | A | A | B |
| T-60 | A | A | A |
| T-61 | A | A | A |
| T-62 | B | A | B |
| T-63 | C | A | C |
| T-64 | A | A | A |
| T-65 | A | A | B |
| T-66 | A | A | A |
| T-67 | B | A | A |
| T-68 | D | B | D |
| T-69 | A | A | B |
| T-70 | A | A | A |
| T-71 | A | A | A |
| T-72 | A | A | A |
| T-73 | B | A | B |
| T-74 | A | A | A |
| T-75 | B | A | B |
| T-76 | B | A | B |
| T-77 | B | A | B |
| T-78 | A | A | A |
| T-79 | A | A | A |
| T-80 | B | A | B |
| T-81 | B | A | B |
| T-82 | B | A | B |
| T-83 | A | A | B |
| T-84 | A | A | A |
| T-85 | A | A | A |
| T-86 | A | A | A |
| T-87 | A | A | A |

In table 1,
"n.d." indicated: not detected,
"A" indicated: $IC_{50} \leq 50$ nM,
"B" indicated: 50 nM < $IC_{50} \leq 500$ nM,
"C" indicated: 500 nM < $IC_{50} \leq 1000$ nM,
"D" indicated: 1000 nM < $IC_{50}$.

What is claimed is:

1. A five-and-six-membered heterocyclic compound represented by formula IV-1-1 or a pharmaceutically acceptable salt thereof,

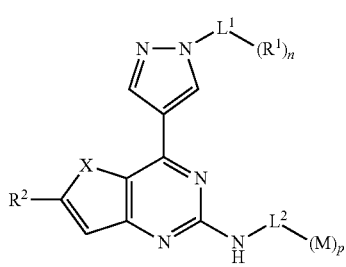

IV-1-1 wherein:
X is O or S;
L$^1$ is a chemical bond, an alkyl, an alkylene, a cycloalkyl or a heterocycloalkyl; wherein the alkyl, alkylene, cycloalkyl or heterocycloalkyl can be independently substituted by the substituents selected from the group consisting of: a halogen, a cyano,

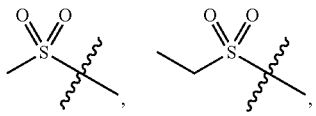

an acyl, a cycloalkyl and a heterocycloalkyl;
L$^2$ is an alkyl, an acyl, a cycloalkyl, a heterocycloalkyl, an aryl or a heteroaryl;
M is a halogen, an alkyl, an alkylene, a cycloalkyl, an alkoxy, a heterocycloalkyl, an aryl, a heteroaryl, a cyano or an acyl; wherein the alkyl, alkylene, alkoxy, heterocycloalkyl, aryl, heteroaryl or acyl can be independently substituted by the substituents selected from the group consisting of: a halogen, a hydroxyl, a cyano, an amino, an acylamino, a nitro, a carboxyl, an acyl, an alkoxy, a cycloalkyl, a heterocycloalkyl, an aryl and a heteroaryl;
each R$^1$ is independently a hydrogen, a halogen, a cyano, an alkyl, a cycloalkyl, an "alkyl-NH—CO—" or an "alkyl-NHSO$_2$—"; wherein the alkyl can be substituted by the substituents selected from the group consisting of: a halogen, a hydroxyl, a cyano, an amino, a nitro, a carboxyl, an acyl, an alkoxy, a cycloalkyl, an alkenyl and an alkynyl;
R$^2$ is a hydrogen, a halogen or an alkyl;
n is 1, 2, 3 or 4; and
p is 0, 1, 2, 3, 4 or 5.

2. The five-and-six-membered heterocyclic compound represented by formula IV-1-1 or a pharmaceutically acceptable salt thereof as defined in claim 1, wherein:
X is O or S;
R$^1$ is a hydrogen, an alkyl or a halogen; wherein the alkyl is substituted by the substituents selected from the group consisting of: a halogen, a hydroxyl, a cyano, an amino, a nitro, a carboxyl and an acyl;
R$^2$ is a hydrogen, a halogen or an alkyl;
n is 1 or 2; and
p is 0 or 1.

3. The five-and-six-membered heterocyclic compound represented by formula IV-1-1 or a pharmaceutically acceptable salt thereof as defined in claim 1, wherein:
when R$^1$ is a halogen, the halogen is F, Cl, Br or I;
when R$^2$ is a halogen, the halogen is F, Cl, Br or I;
when L$^1$ is an alkyl, the alkyl is a C$_{1-4}$ alkyl;
when L$^1$ is a cycloalkyl, the cycloalkyl is a C$_{3-6}$ cycloalkyl;
when L$^1$ is a heterocycloalkyl, the heterocycloalkyl is a C$_{3-6}$ heterocycloalkyl containing 1 to 3 nitrogen atoms or a C$_{3-6}$ heterocycloalkyl containing 1 to 3 oxygen atoms;
when the alkyl, alkylene, cycloalkyl or heterocycloalkyl defined in L$^1$ is substituted by the substituents selected from the group consisting of a cycloalkyl, the cycloalkyl is a C$_{3-6}$ cycloalkyl;
when the alkyl, alkylene, cycloalkyl or heterocycloalkyl defined in L$^1$ is substituted by the substituents selected from the group consisting of an acyl, the acyl is a formyl or a C$_{1-4}$ alkylacyl;

when the alkyl, alkylene, cycloalkyl or heterocycloalkyl defined in $L^1$ is substituted by the substituents selected from the group consisting of a halogen, the halogen is F, Cl, Br or I;

the alkyl defined in $R^1$ is a $C_{1-4}$ alkyl; and when $R^2$ is selected from an alkyl, the alkyl is a $C_{1-4}$ alkyl.

4. The five-and-six-membered heterocyclic compound represented by formula IV-1-1 or a pharmaceutically acceptable salt thereof as defined in claim 1, wherein:

when $L^2$ is an alkyl, the alkyl is a $C_{1-4}$ alkyl;

when $L^2$ is a cycloalkyl, the cycloalkyl is a $C_{3-6}$ cycloalkyl;

when $L^2$ is a heterocycloalkyl, the heterocycloalkyl is a $C_{3-6}$ heterocycloalkyl containing 1 to 4 oxygen and/or nitrogen atoms;

when $L^2$ is an aryl, the aryl is a $C_{6-10}$ aryl; and when $L^2$ is a heteroaryl, the heteroaryl is a $C_{3-10}$ heteroaryl containing 1 to 4 nitrogen atoms.

5. The five-and-six-membered heterocyclic compound represented by formula IV-1-1 or a pharmaceutically acceptable salt thereof as defined in claim 1, wherein:

when M is a halogen, the halogen is fluorine;

when M is an alkyl, the alkyl is a $C_{1-6}$ alkyl;

when M is a cycloalkyl, the cycloalkyl is a $C_{3-6}$ cycloalkyl;

when M is an alkoxy, the alkoxy is a $C_{1-4}$ alkoxy substituted by a heterocycloalkyl; the heterocycloalkyl is not further substituted; or the heterocycloalkyl is a $C_{2-10}$ heterocycloalkyl containing 1 to 4 oxygen and/or nitrogen atoms; and when M is a heterocycloalkyl, the heterocycloalkyl is a $C_{3-8}$ heterocycloalkyl containing 1 to 4 oxygen and/or nitrogen atoms.

6. The five-and-six-membered heterocyclic compound represented by formula IV-1-1 or a pharmaceutically acceptable salt thereof as defined in claim 1, wherein:

when M is an aryl, the aryl is a $C_{6-10}$ aryl;

when M is an alkyl, an alkylene, a cycloalkyl, an alkoxy, a heterocycloalkyl, a heteroaryl or an acyl substituted by a halogen, the halogen is F, Cl, Br or I;

when M is an alkyl, an alkylene, a cycloalkyl, an alkoxy, a heterocycloalkyl, a heteroaryl or an acyl substituted by an alkoxy, the alkoxy is a $C_{1-6}$ alkoxy;

when M is an alkyl, an alkylene, a cycloalkyl, an alkoxy, a heterocycloalkyl, a heteroaryl or an acyl substituted by a cycloalkyl, the cycloalkyl is a $C_{3-6}$ cycloalkyl; and when M is an alkyl, an alkylene, a cycloalkyl, an alkoxy, a heterocycloalkyl, a heteroaryl or an acyl substituted by a heterocycloalkyl, the heterocycloalkyl is a $C_{3-8}$ heterocycloalkyl containing 1 to 4 oxygen and/or nitrogen atoms.

7. The five-and-six-membered heterocyclic compound represented by formula IV-1-1 or a pharmaceutically acceptable salt thereof as defined in claim 3, wherein:

when the alkyl, alkylene, cycloalkyl or heterocycloalkyl defined in $L^1$ is substituted by the substituents selected from the group consisting of a cycloalkyl, the $C_{3-6}$ cycloalkyl is a cyclopentyl;

when the alkyl, alkylene, cycloalkyl or heterocycloalkyl defined in $L^1$ is substituted by the substituents selected from the group consisting of a $C_{1-4}$ alkylacyl, the $C_{1-4}$ alkylacyl is a $C_2$ alkylacyl; and when $L^1$ is a $C_{3-6}$ cycloalkyl, the $C_{3-6}$ cycloalkyl is a cyclopropyl.

8. The five-and-six-membered heterocyclic compound represented by formula IV-1-1 or a pharmaceutically acceptable salt thereof as defined in claim 4, wherein:

when $L^2$ is a $C_{1-4}$ alkyl, the $C_{1-4}$ alkyl is a methyl;

when $L^2$ is a $C_{3-6}$ cycloalkyl, the $C_{3-6}$ cycloalkyl is a cyclopropyl or a cyclohexyl;

when $L^2$ is a heterocycloalkyl, the heterocycloalkyl is a $C_{3-6}$ heterocycloalkyl containing 1 to 3 oxygen atoms;

when $L^2$ is a $C_{6-10}$ aryl, the $C_{6-10}$ aryl is a phenyl; and when $L^2$ is a $C_{3-10}$ heteroaryl, the $C_{3-10}$ heteroaryl is a $C_{4-8}$ heteroaryl containing 1 to 4 nitrogen atoms.

9. The five-and-six-membered heterocyclic compound represented by formula IV-1-1 or a pharmaceutically acceptable salt thereof as defined in claim 5, wherein:

when M is a $C_{1-6}$ alkyl, the $C_{1-6}$ alkyl is a methyl, an ethyl, a propyl or an isopropyl;

when M is a $C_{1-6}$ alkyl substituted by a halogen, the $C_{1-6}$ alkyl substituted by a halogen is a trifluoromethyl or

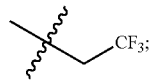

when M is a $C_{1-6}$ alkyl substituted by a hydroxyl, the $C_{1-6}$ alkyl substituted by a hydroxyl is

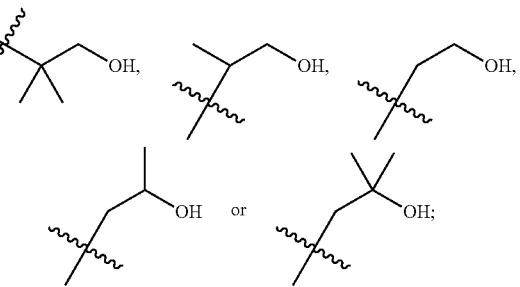

when M is a $C_{1-6}$ alkyl substituted by a cyano, the $C_{1-6}$ alkyl substituted by a cyano is

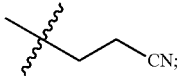 [SMILES: *CCC#N]

when M is an alkyl, an alkylene, a cycloalkyl, an alkoxy, a heterocycloalkyl, a heteroaryl or an acyl substituted by a $C_{1-6}$ alkoxy, the $C_{1-6}$ alkoxy is a $C_{1-3}$ alkoxy;

when M is a $C_{1-4}$ alkoxy substituted by a $C_{2-10}$ heterocycloalkyl, the $C_{1-4}$ alkoxy is a $C_2$ alkoxy;

when M is a $C_{1-4}$ alkoxy substituted by a $C_{2-10}$ heterocycloalkyl, the $C_{2-10}$ heterocycloalkyl is a $C_{3-8}$ heterocycloalkyl containing 1 to 3 oxygen and/or nitrogen atoms; and when M is a $C_{3-8}$ heterocycloalkyl, the $C_{3-8}$ heterocycloalkyl is a $C_{4-6}$ heterocycloalkyl containing 1 to 4 oxygen and/or nitrogen atoms.

10. The five-and-six-membered heterocyclic compound represented by formula IV-1-1 or a pharmaceutically acceptable salt thereof as defined in claim 6, wherein:

when M is a $C_{6-10}$ aryl, the $C_{6-10}$ aryl is a phenyl;

when M is an alkyl, an alkylene, an alkoxy, a heterocycloalkyl, a heteroaryl or an acyl substituted by a $C_{3-6}$ cycloalkyl, the $C_{3-6}$ cycloalkyl is a cyclopropyl; and when M is a $C_{1-4}$ alkoxy substituted by a $C_{2-10}$ heterocycloalkyl, the $C_{2-10}$ heterocycloalkyl is a $C_{4-6}$ heterocycloalkyl containing 1 to 3 oxygen and/or nitrogen atoms.

11. The five-and-six-membered heterocyclic compound represented by formula IV-1-1 or a pharmaceutically acceptable salt thereof as defined in claim 8, wherein:

when $L^2$ is a $C_{3-6}$ heterocycloalkyl, the $C_{3-6}$ heterocycloalkyl is a tetrahydropyranyl; and when $L^2$ is a $C_{4-8}$ heteroaryl, the $C_{4-8}$ heteroaryl is a pyrazolyl, an imidazolyl, a pyridyl, a benzimidazolyl, a benzopyrazolyl, a pyridazinyl or a pyrimidinyl.

12. The five-and-six-membered heterocyclic compound represented by formula IV-1-1 or a pharmaceutically acceptable salt thereof s defined in claim 9, wherein:

when M is a $C_2$ alkoxy substituted by a $C_{2-10}$ heterocycloalkyl, the $C_{2-10}$ heterocycloalkyl is a $C_{3-8}$ heterocycloalkyl containing 1 to 3 oxygen and/or nitrogen atoms;

when M is a $C_{4-6}$ heterocycloalkyl, the $C_{4-6}$ heterocycloalkyl is a morpholinyl, a tetrahydropyranyl, an azetidinyl, a piperidyl, an oxetanyl, a tetrazolyl, a piperazinyl or a pyrrolidinyl; and when M is a $C_{1-6}$ alkyl substituted by a $C_{1-3}$ alkoxy, the $C_{1-6}$ alkyl substituted by a $C_{1-3}$ alkoxy is

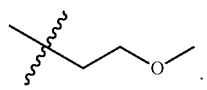

13. The five-and-six-membered heterocyclic compound represented by formula IV-1-1 or a pharmaceutically acceptable salt thereof as defined in claim 12, wherein:

when M is a $C_2$ alkoxy substituted by a $C_{2-10}$ heterocycloalkyl, the $C_{2-10}$ heterocycloalkyl is a $C_{3-8}$ heterocycloalkyl containing 1 to 3 oxygen and/or nitrogen atoms.

14. The five-and-six-membered heterocyclic compound represented by formula IV-1-1 or a pharmaceutically acceptable salt thereof as defined in claim 13, wherein:

when a $C_2$ alkoxy defined in M is substituted by a $C_{4-6}$ heterocycloalkyl, the $C_{4-6}$ heterocycloalkyl is a morpholinyl or a pyrrolidinyl.

15. The five-and-six-membered heterocyclic compound represented by formula IV-1-1 or a pharmaceutically acceptable salt thereof defined in claim 13, wherein:

when M is a $C_2$ alkoxy substituted by a $C_{4-6}$ heterocycloalkyl, the $C_{4-6}$ heterocycloalkyl is a morpholinyl, a tetrahydropyranyl, an azetidinyl, a piperidyl, an oxetanyl, a piperazinyl or a pyrrolidinyl.

16. The five-and-six-membered heterocyclic compound represented by formula IV-1-1 or a pharmaceutically acceptable salt thereof as defined in claim 1, wherein the compound represented by formula IV-1-1 has the structure represented by formula V-1-1,

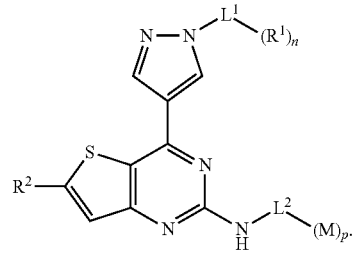

V-1-1

17. The five-and-six-membered heterocyclic compound represented by formula IV-1-1 or a pharmaceutically acceptable salt thereof as defined in claim 1, wherein the compound represented by formula IV-1-1 is selected from the group consisting of:

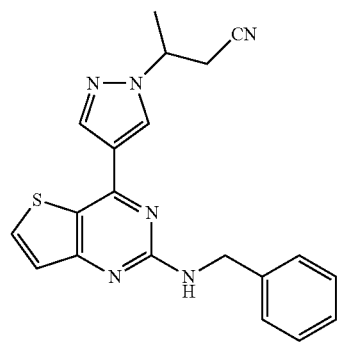

T-01

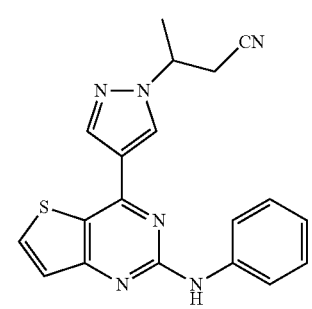

T-02

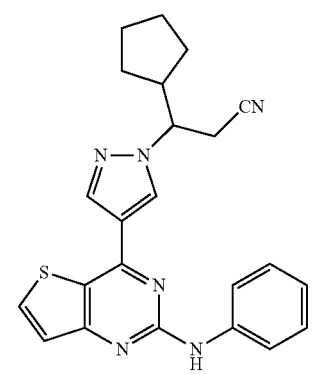

T-03

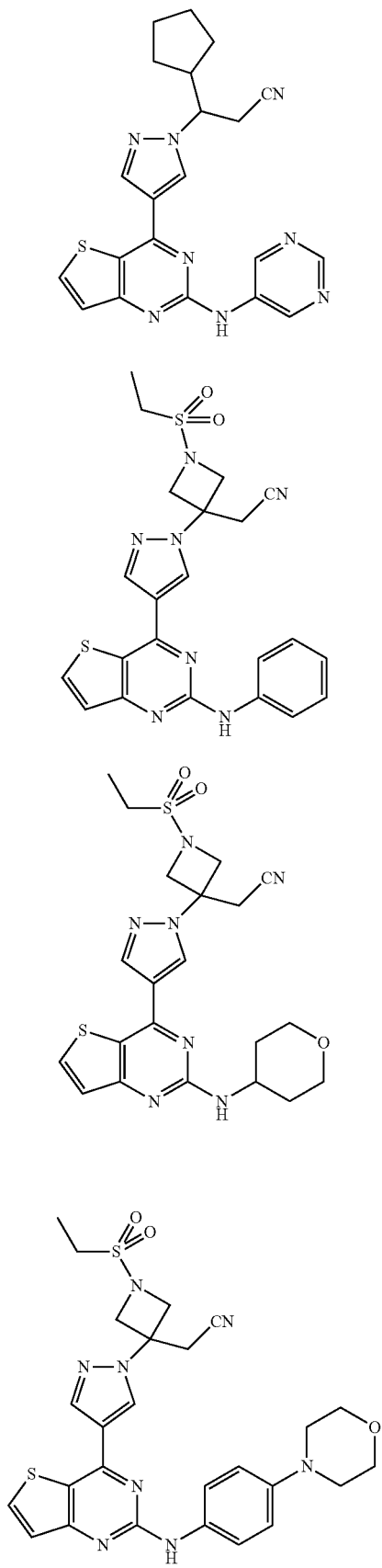
T-04
T-05
T-06
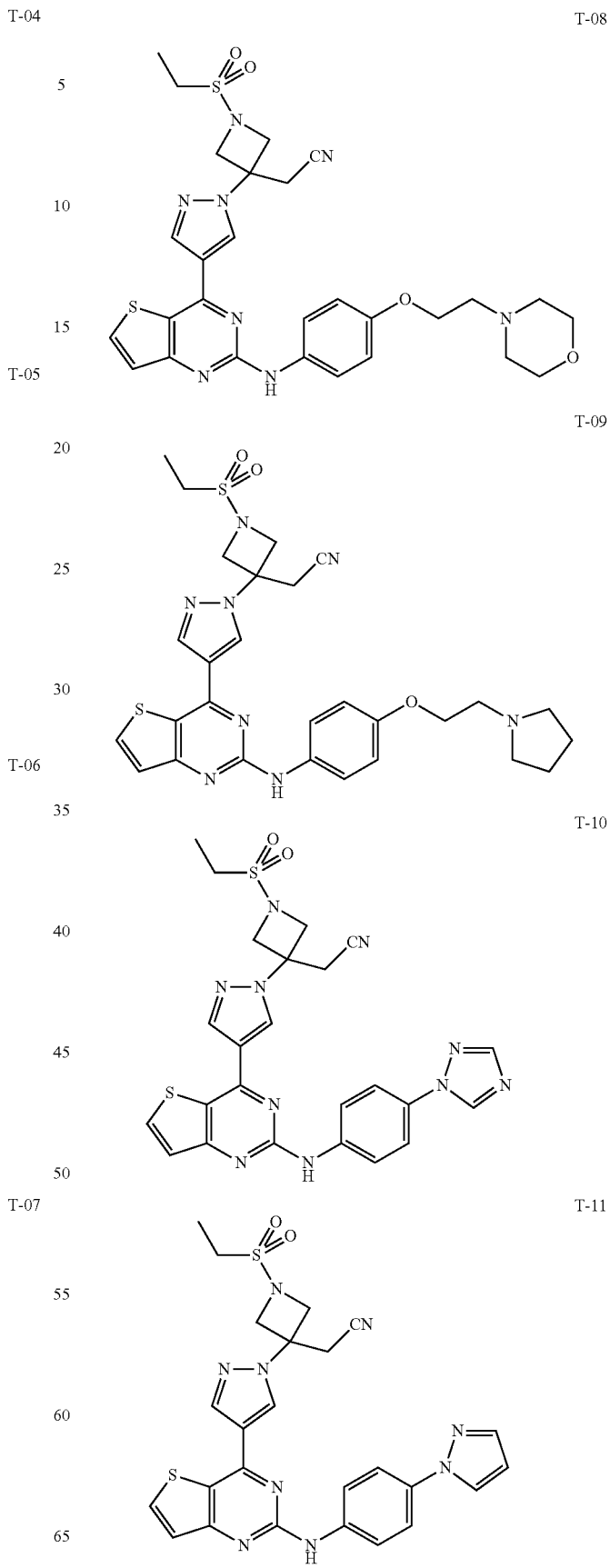
T-08
T-09
T-10
T-11

T-12 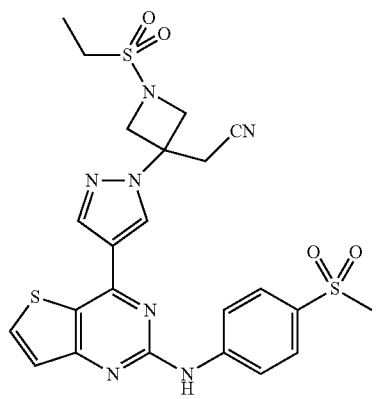
T-13 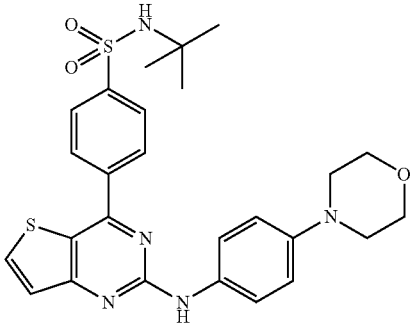
T-14 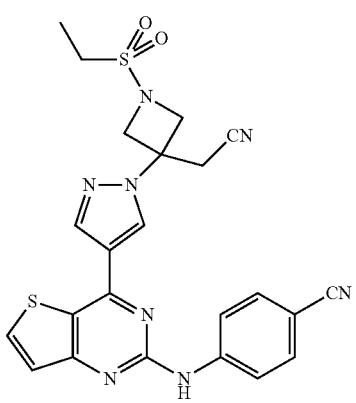
T-15 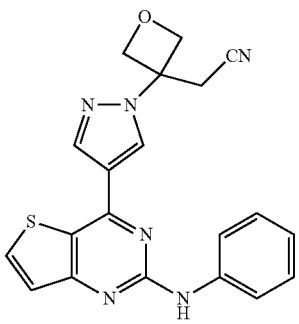
T-17 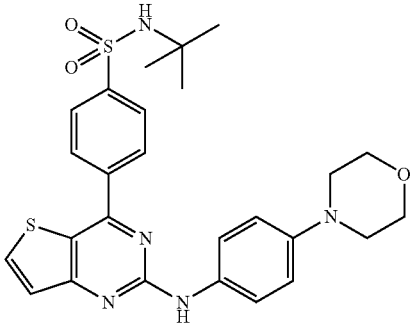
T-19 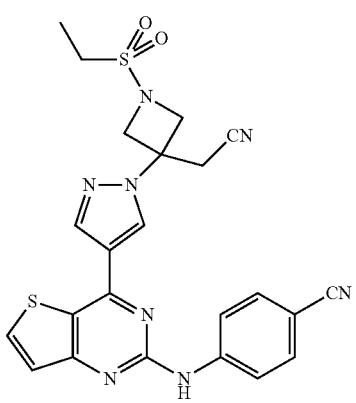
T-20 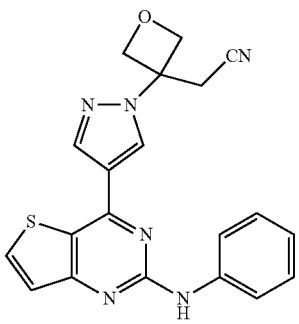
T-21 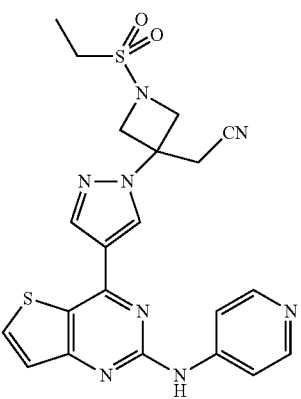

T-22
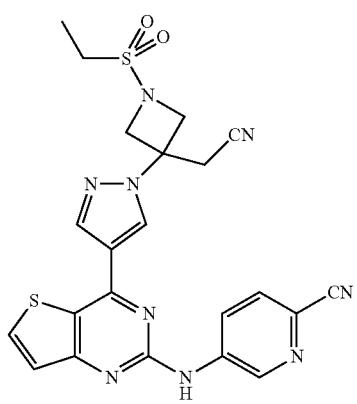
T-23
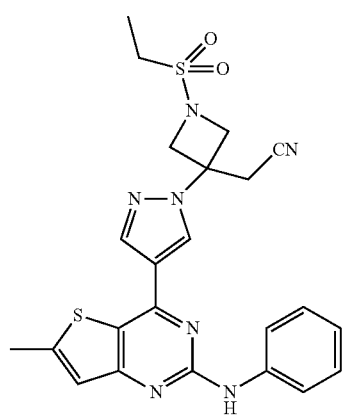
T-24
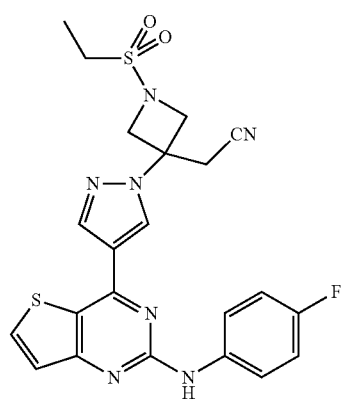
T-25
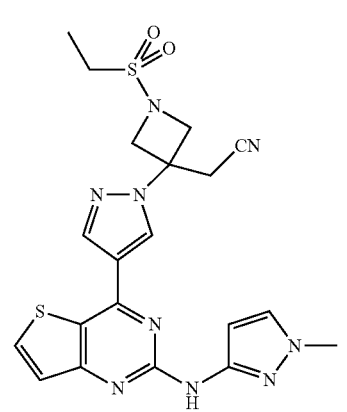
T-26
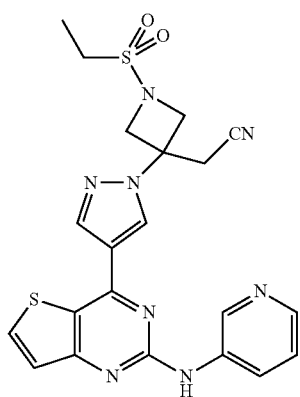
T-27
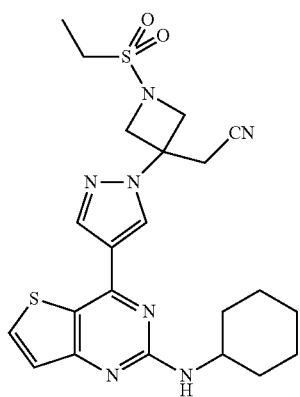
T-28
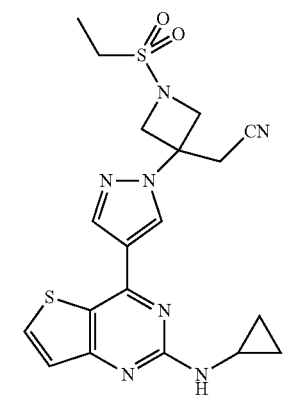
T-29
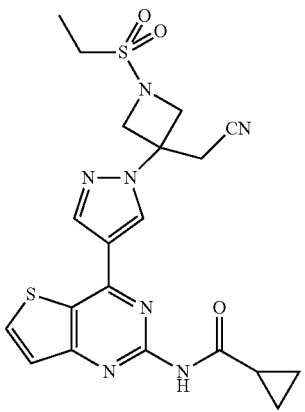

T-30 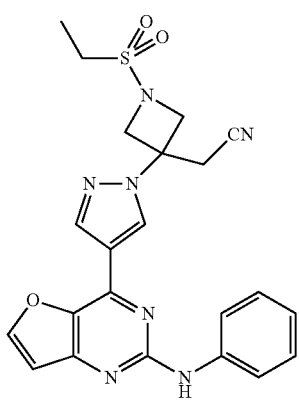
T-31 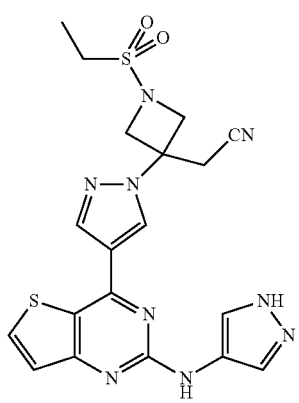
T-32 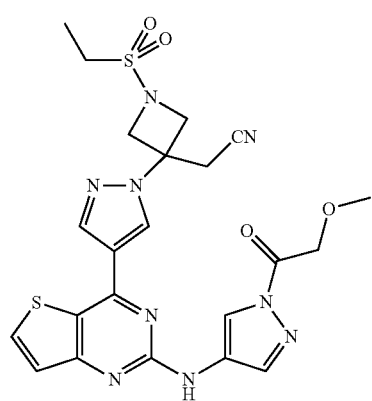
T-33 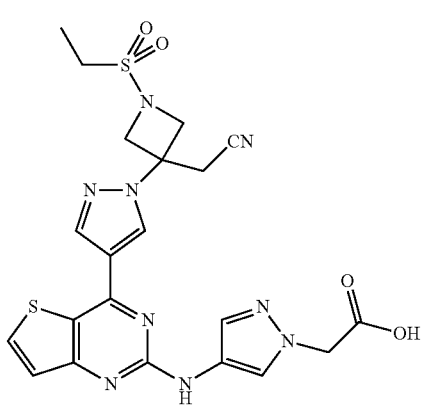
T-34 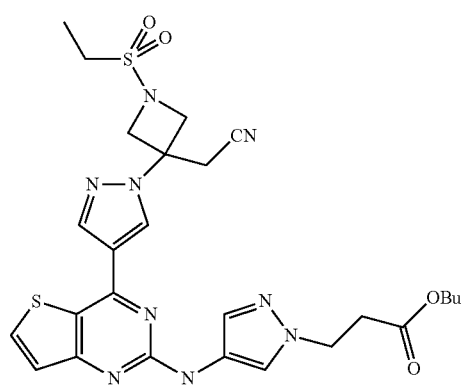
T-35 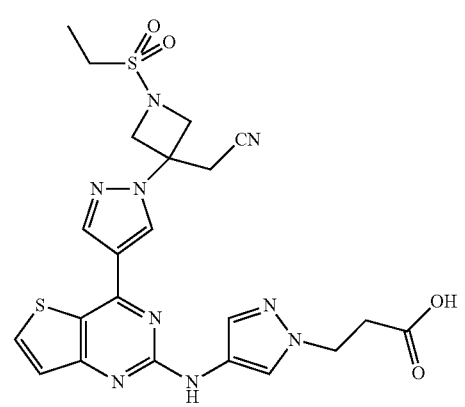
T-36 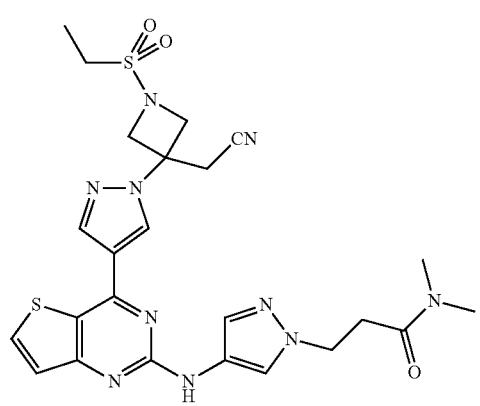
T-37 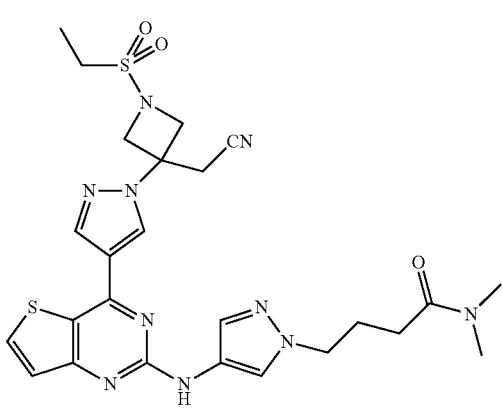

T-38
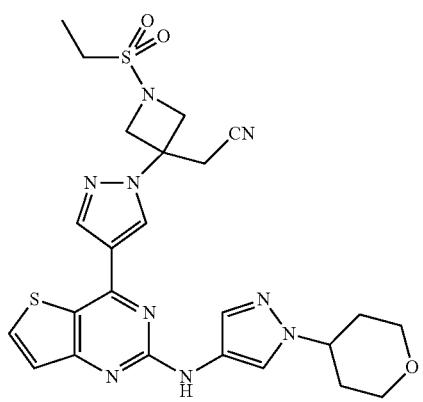
T-39
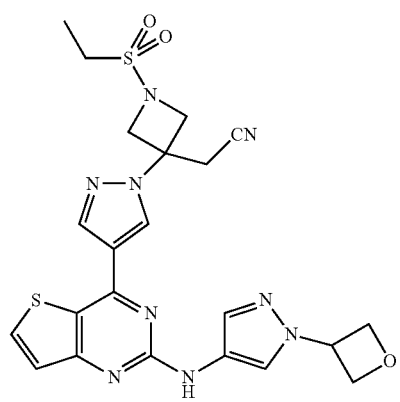
T-40
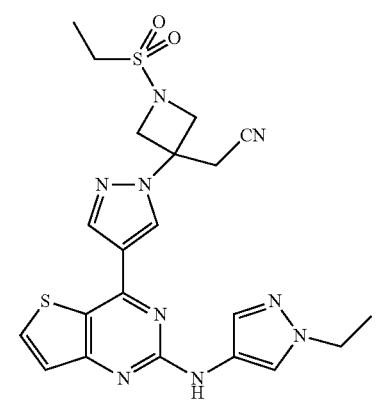
T-41
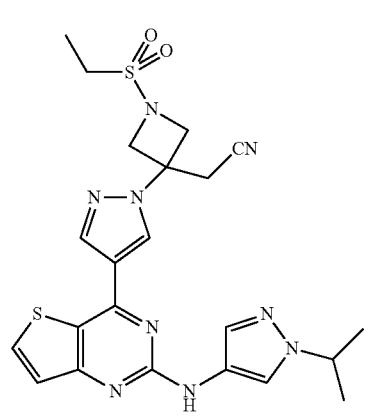
T-43
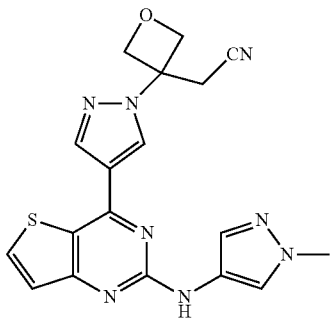
T-44
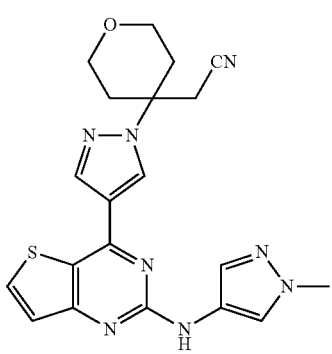
T-45
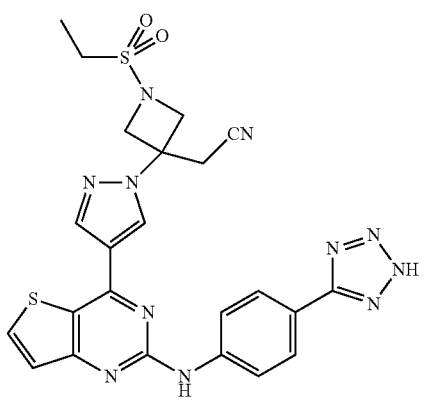
T-46
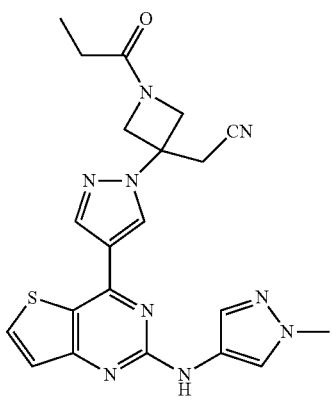

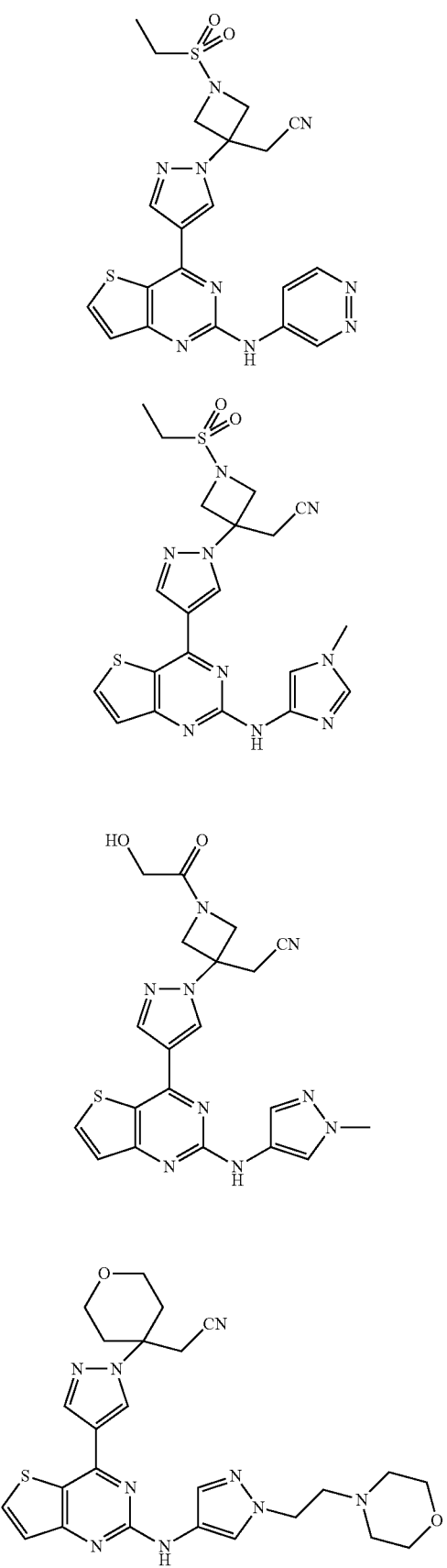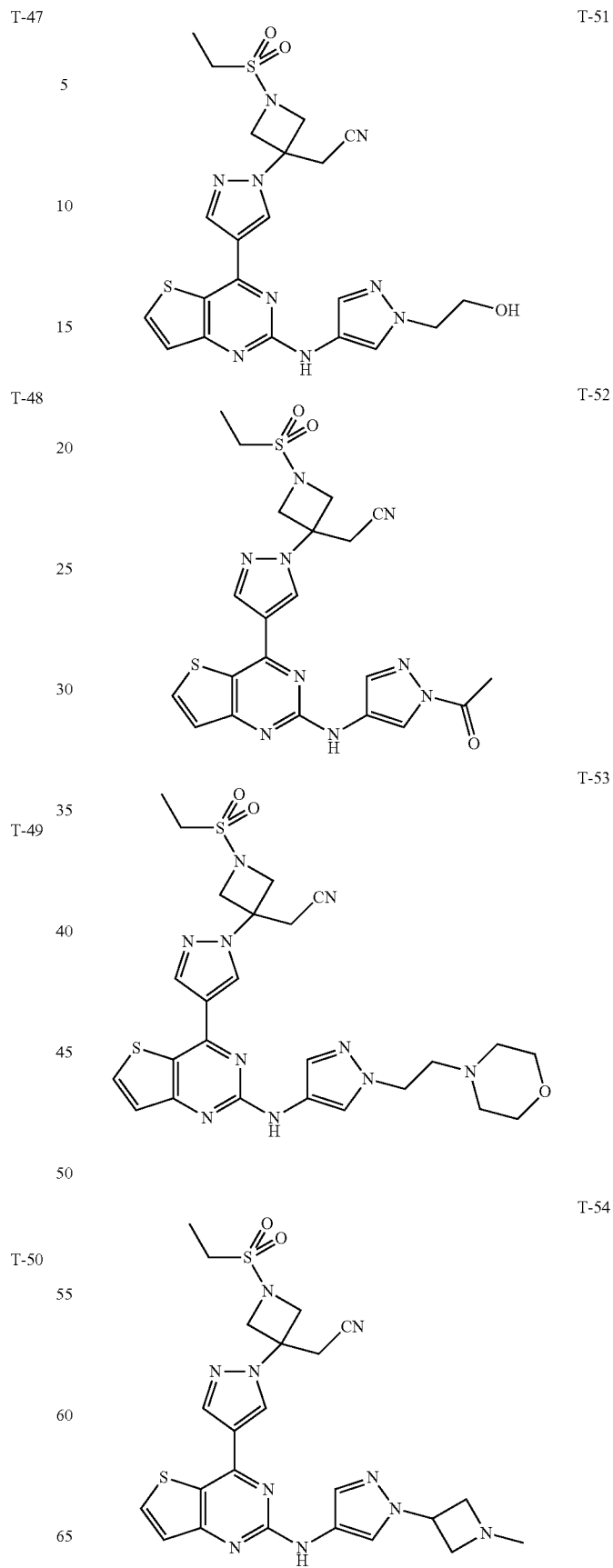

T-57
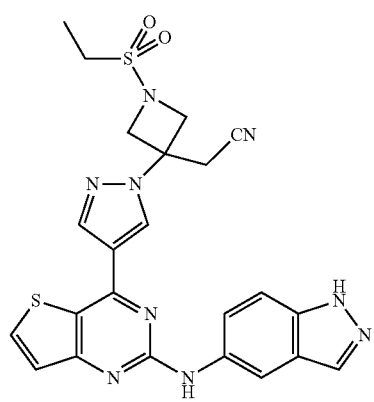
T-58
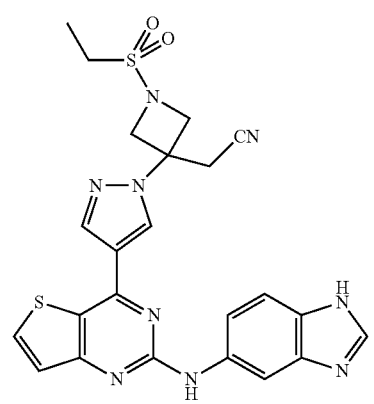
T-59
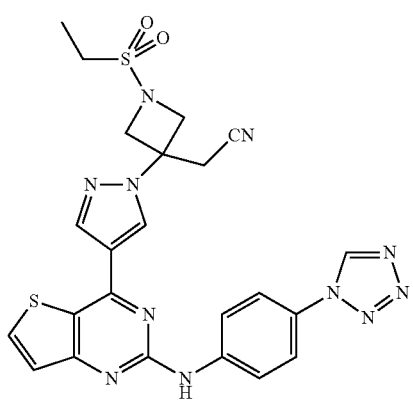
T-60
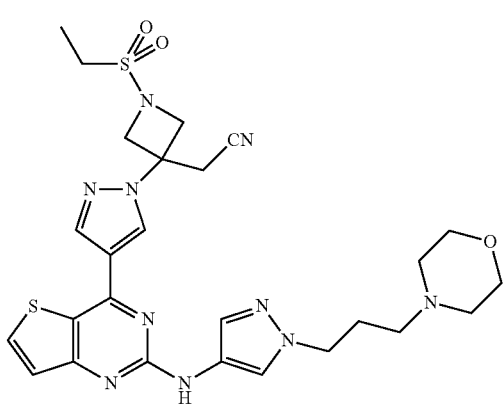
T-61
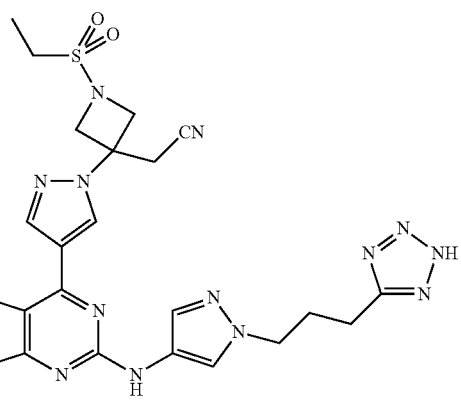
T-62
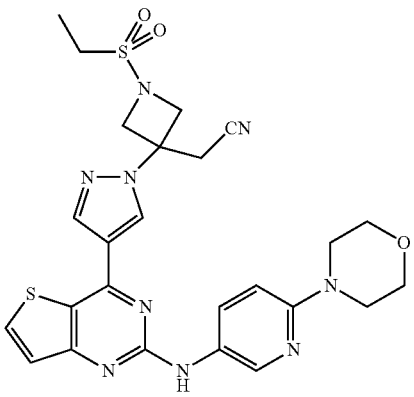
T-63
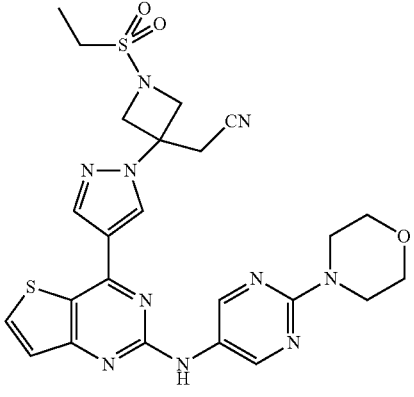
T-64
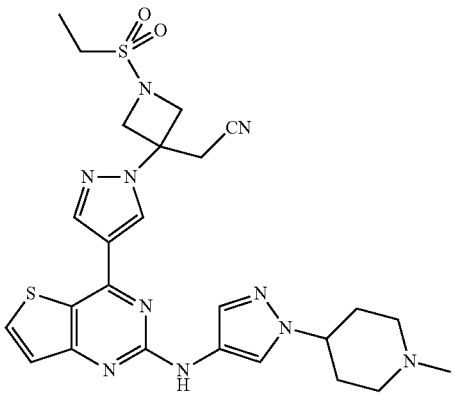

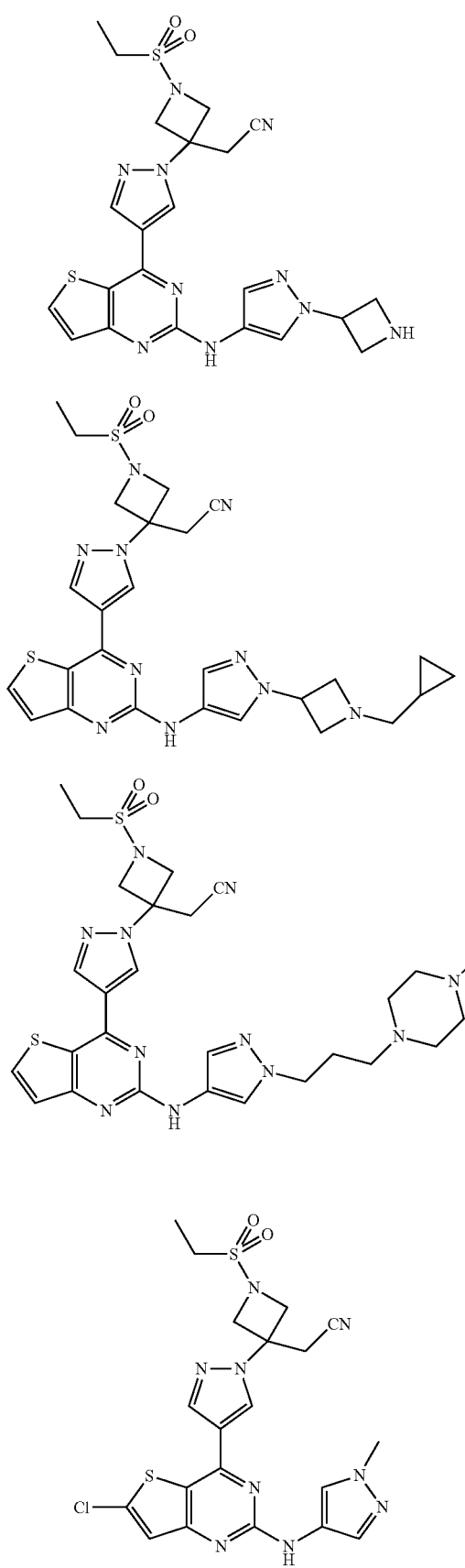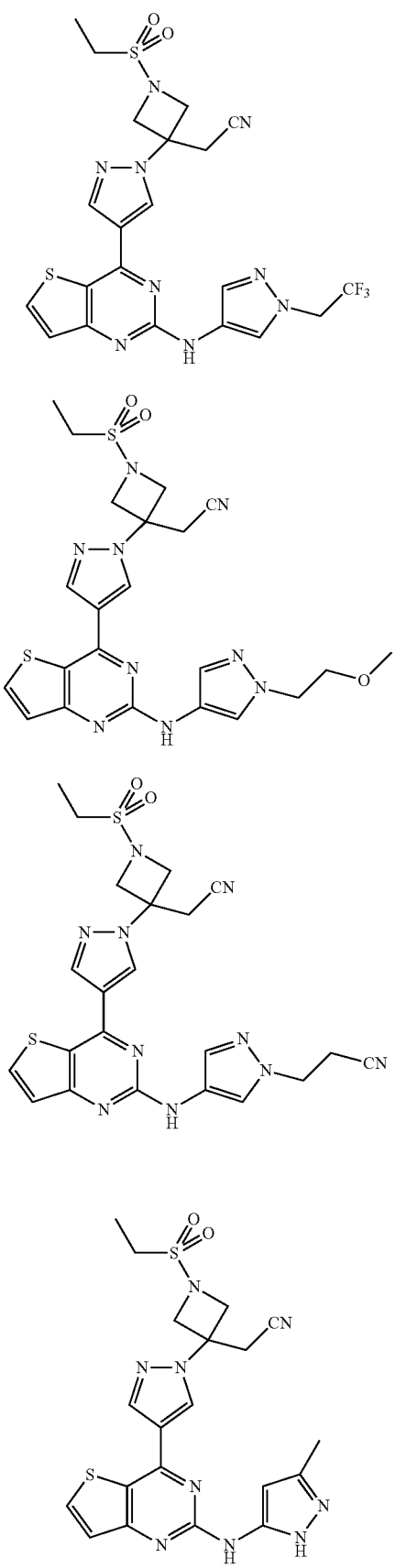

T-73 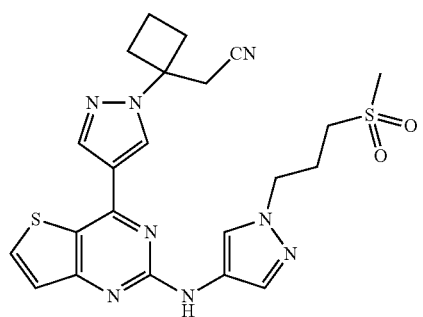
T-74 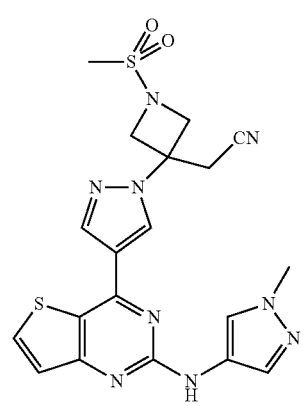
T-75 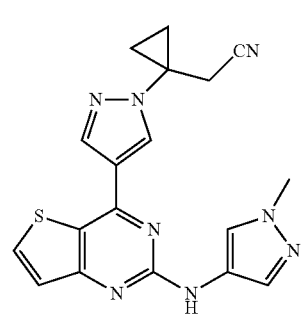
T-76 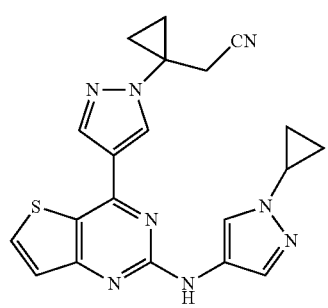
T-77 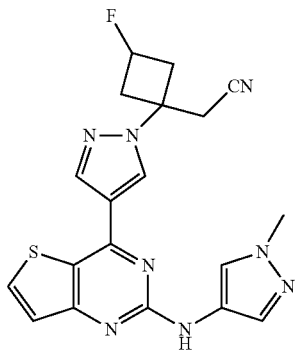
T-78 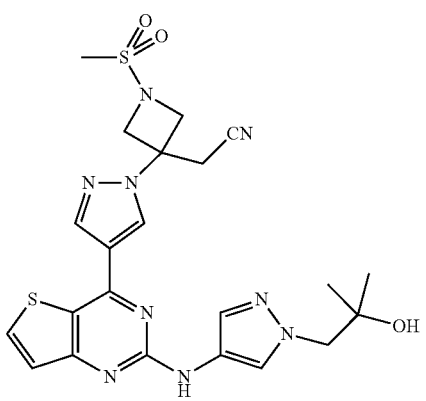
T-79 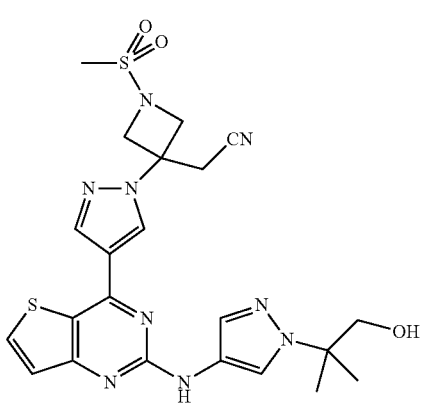
T-80 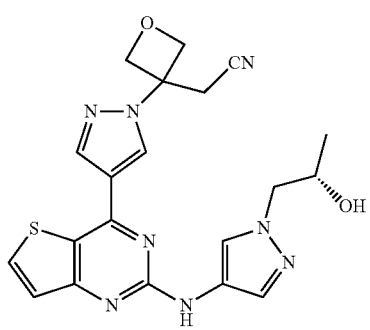

T-81

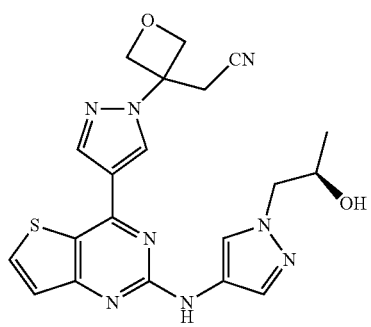

T-82

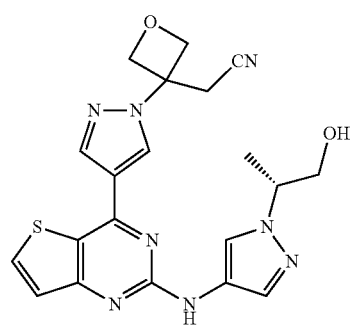

T-83

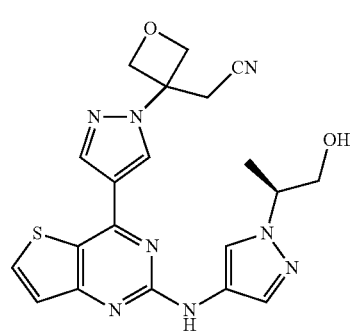

T-84

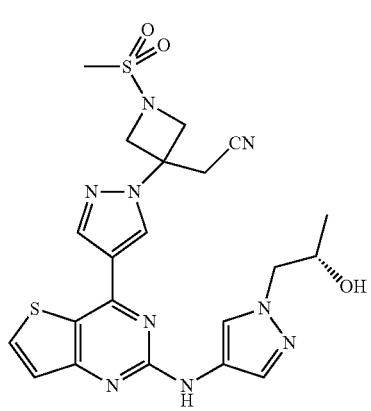

T-85

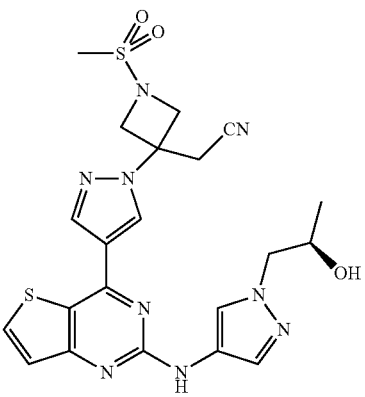

T-86

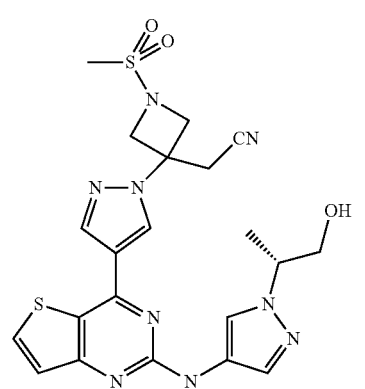

T-87

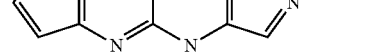

18. A method of treating rheumatoid arthritis or inflammatory bowel disease in a subject in need thereof, comprising: administering a medicament comprising an effective amount of the five-and-six-membered heterocyclic compound represented by formula IV-1-1 or a pharmaceutically acceptable salt thereof as defined in claim 1 to the subject.

19. A pharmaceutical composition, comprising a therapeutically effective amount of the five-and-six-membered heterocyclic compound represented by formula IV-1-1 or a pharmaceutically acceptable salt thereof as defined in claim 1, and at least one further component selected from the group consisting of pharmaceutically acceptable carriers and diluents.

* * * * *